(12) United States Patent
Leftheris et al.

(10) Patent No.: US 11,396,506 B2
(45) Date of Patent: Jul. 26, 2022

(54) AMINO ACID COMPOUNDS WITH UNBRANCHED LINKERS AND METHODS OF USE

(71) Applicant: Pliant Therapeutics, Inc., South San Francisco, CA (US)

(72) Inventors: Katerina Leftheris, South San Francisco, CA (US); Maureen Reilly, Burlingame, CA (US); Darren Finkelstein, Palo Alto, CA (US); Nicole Cooper, Oakland, CA (US); Christopher Bailey, Mountain View, CA (US); Jacob Cha, San Bruno, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/455,490

(22) Filed: Jun. 27, 2019

(65) Prior Publication Data

US 2020/0123151 A1 Apr. 23, 2020

Related U.S. Application Data

(60) Provisional application No. 62/690,939, filed on Jun. 27, 2018.

(51) Int. Cl.
| | | |
|---|---|---|
| *C07D 471/02* | (2006.01) | |
| *C07D 471/04* | (2006.01) | |
| *C07D 519/00* | (2006.01) | |

(52) U.S. Cl.
CPC ......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS

| | | |
|---|---|---|
| 6,048,861 A | 4/2000 | Askew |
| 9,572,801 B2 | 2/2017 | Askew |
| 10,131,658 B2 | 11/2018 | Degrado |
| 10,214,552 B2 | 2/2019 | Fu |
| 10,604,520 B2 | 3/2020 | Jiang |
| 10,696,672 B2 | 6/2020 | Morgans, Jr. |
| 10,793,564 B2 | 10/2020 | Cha |
| 11,180,494 B2 | 11/2021 | Cha et al. |
| 2002/0010176 A1 | 1/2002 | Askew |
| 2002/0035127 A1 | 3/2002 | Head |
| 2008/0045521 A1 | 2/2008 | Arnould |
| 2009/0104116 A1 | 4/2009 | Zischinsky et al. |
| 2016/0264566 A1 | 9/2016 | Degrado |
| 2016/0280705 A1 | 9/2016 | Anderson |
| 2016/0376266 A1 | 12/2016 | Degrado |
| 2018/0093984 A1 | 4/2018 | Jiang |
| 2019/0276449 A1 | 9/2019 | Cha |
| 2019/0322663 A1 | 10/2019 | Morgans, Jr. et al. |
| 2020/0109141 A1 | 4/2020 | Cha |
| 2021/0017171 A1 | 1/2021 | Cha et al. |
| 2021/0024516 A1 | 1/2021 | Jiang |
| 2021/0122747 A1 | 4/2021 | Morgans, Jr. et al. |

FOREIGN PATENT DOCUMENTS

| | | |
|---|---|---|
| WO | 199931061 A1 | 6/1999 |
| WO | 2015048819 A1 | 4/2015 |
| WO | 2016145258 A1 | 9/2016 |

(Continued)

OTHER PUBLICATIONS

International Search Report and Written Opinion, dated Sep. 13, 2019, for PCT Application No. PCT/US19/39624, 15 pages.
Kim, D.S. et al. (2006). "Classification and Natural History of the Idiopathic Interstitial Pneumonias," Proc. Am. Thorac. Soc. 3:285-292.
Kinder, B.W. et al. (Jun. 2007) "Idiopathic Nonspecific Interstitial Pneumonia. Lung Manifestation of Undifferentiated Connective Tissue Disease?," Am. J. Respir. Crit. Care Med. 176:691-697.
Remington: The Science and Practice of Pharmacy, 21st Edition , Journal of Pharmacy Technology, (2006) March-April, 22:133-135.
U.S. Appl. No. 16/843,824, filed Apr. 8, 2020, Cha et al. (U.S. Patent Application is not submitted herewith pursuant to the waiver of 37 C.F.R. § 1.98(a)(2)(iii) issued by the Office on Sep. 21, 2004.).
Ullman, E.F. et al. (Jun. 7, 1994). "Luminescent Oxygen Channeling Immunoassay: Measurement of Particle Binding Kinetics by Chemiluminescence," Proc. Natl. Acad. Sci. USA 91(12):5426-5430.
Whitman, D.B. et al. (2004) "Nonpeptide αvβ3 Antagonists. Part 9: Improved Pharmacokinetic Profile Through the Use of an Aliphatic, Des-Amide Backbone," Bioorganic & Medicinal Chemistry Letters 14:4411-4415.

(Continued)

*Primary Examiner* — Patrick T Lewis

(74) *Attorney, Agent, or Firm* — Morrison & Foerster LLP; Kraig Anderson; Johannes Hull

(57) ABSTRACT

The invention relates to compounds of formula (A):

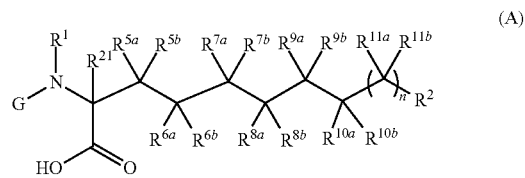

or a salt thereof, wherein $R^1$, $R^2$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{21}$, n, and G are as described herein. Compounds of formula (I) and pharmaceutical compositions thereof are $\alpha_v\beta_6$ integrin inhibitors that are useful for treating fibrosis such as idiopathic pulmonary fibrosis (IPF) and nonspecific interstitial pneumonia (NSIP).

33 Claims, 12 Drawing Sheets

(56) References Cited

FOREIGN PATENT DOCUMENTS

| WO | 2018009501 A1 | 1/2018 |
| WO | 2018049068 A1 | 3/2018 |
| WO | 2018119087 A1 | 6/2018 |
| WO | 2019173653 A1 | 9/2019 |
| WO | 2020076862 A1 | 4/2020 |
| WO | 2020210404 A1 | 10/2020 |
| WO | 2021225912 A1 | 11/2021 |

OTHER PUBLICATIONS

Patsenker, E. et al. (2011, e-pub. Jun. 9, 2011). "Role of Integrins in Fibrosing Liver Diseases," American Journal of Physiology-Gastrointestinal and Liver Physiology 301(3):G425-G434.

| # | Solid phase assay | | Proximity-based assay | |
|---|---|---|---|---|
| | $\alpha_V\beta_1$ | $\alpha_V\beta_6$ | $\alpha_V\beta_1$ | $\alpha_V\beta_6$ |
| 1 | <50 | 50-<250 | 250-<1000 | <50 |
| 2 | <50 | <50 | 250-<1000 | <50 |
| 3 | <50 | <50 | ≥1000 | <50 |
| 4 | <50 | 50-<250 | <50 | <50 |
| 5 | <50 | 50-<250 | 250-<1000 | <50 |
| 6 | <50 | <50 | 250-<1000 | <50 |
| 7 | <50 | <50 | 250-<1000 | <50 |
| 8 | <50 | <50 | 50-<250 | <50 |
| 9 | <50 | <50 | ≥1000 | <50 |
| 10 | <50 | <50 | ≥1000 | <50 |
| 11 | <50 | 250-<1000 | 50-<250 | <50 |
| 12 | <50 | <50 | ≥1000 | <50 |
| 13 | <50 | <50 | ≥1000 | <50 |
| 14 | <50 | <50 | 50-<250 | <50 |
| 15 | <50 | <50 | 250-<1000 | <50 |
| 16 | <50 | 50-<250 | 250-<1000 | <50 |
| 17 | <50 | <50 | ≥1000 | <50 |
| 18 | <50 | ≥1000 | ≥1000 | <50 |
| 19 | <50 | 250-<1000 | ≥1000 | <50 |
| 20 | <50 | <50 | ≥1000 | <50 |
| 21 | <50 | 250-<1000 | ≥1000 | <50 |
| 22 | <50 | 50-<250 | ≥1000 | <50 |
| 23 | <50 | 50-<250 | 250-<1000 | <50 |
| 24 | <50 | 250-<1000 | ≥1000 | <50 |
| 25 | <50 | 250-<1000 | ≥1000 | <50 |
| 26 | <50 | 250-<1000 | ≥1000 | <50 |
| 27 | <50 | <50 | 250-<1000 | <50 |
| 28 | <50 | 250-<1000 | ≥1000 | <50 |
| 29 | <50 | 250-<1000 | 250-<1000 | <50 |
| 30 | <50 | 250-<1000 | 250-<1000 | <50 |
| 31 | <50 | <50 | 250-<1000 | <50 |
| 32 | <50 | <50 | 50-<250 | <50 |
| 33 | 250-<1000 | <50 | ≥1000 | <50 |
| 34 | <50 | 50-<250 | 250-<1000 | <50 |
| 35 | <50 | <50 | 250-<1000 | <50 |
| 36 | <50 | 50-<250 | ≥1000 | <50 |

Fig. 2

| # | Solid phase assay | | Proximity-based assay | |
|---|---|---|---|---|
| | $\alpha_V\beta_1$ | $\alpha_V\beta_6$ | $\alpha_V\beta_1$ | $\alpha_V\beta_6$ |
| 37 | <50 | <50 | 50-<250 | <50 |
| 38 | <50 | 250-<1000 | ≥1000 | <50 |
| 39 | <50 | <50 | ≥1000 | <50 |
| 40 | <50 | <50 | ≥1000 | <50 |
| 41 | <50 | <50 | 50-<250 | <50 |
| 42 | <50 | <50 | <50 | <50 |
| 43 | <50 | <50 | 50-<250 | <50 |
| 44 | <50 | <50 | 250-<1000 | <50 |
| 45 | <50 | <50 | 50-<250 | <50 |
| 46 | <50 | 50-<250 | ≥1000 | <50 |
| 47 | <50 | 50-<250 | 250-<1000 | <50 |
| 48 | <50 | <50 | <50 | <50 |
| 49 | 50-<250 | ≥1000 | 50-<250 | <50 |
| 50 | <50 | ≥1000 | 250-<1000 | 50-<250 |
| 51 | 250-<1000 | ≥1000 | ≥1000 | 50-<250 |
| 52 | <50 | 50-<250 | 50-<250 | 50-<250 |
| 53 | <50 | 50-<250 | <50 | 50-<250 |
| 54 | <50 | <50 | ≥1000 | 50-<250 |
| 55 | <50 | <50 | 250-<1000 | 50-<250 |
| 56 | <50 | <50 | 250-<1000 | 50-<250 |
| 57 | <50 | <50 | 250-<1000 | 50-<250 |
| 58 | <50 | <50 | 250-<1000 | 50-<250 |
| 59 | <50 | <50 | 250-<1000 | 50-<250 |
| 60 | <50 | 50-<250 | ≥1000 | 50-<250 |
| 61 | <50 | <50 | <50 | 50-<250 |
| 62 | <50 | <50 | ≥1000 | 50-<250 |
| 63 | <50 | 50-<250 | ≥1000 | 50-<250 |
| 64 | 50-<250 | 250-<1000 | ≥1000 | 50-<250 |
| 65 | <50 | ≥1000 | ≥1000 | 50-<250 |
| 66 | <50 | ≥1000 | ≥1000 | 50-<250 |
| 67 | 250-<1000 | 250-<1000 | ≥1000 | 50-<250 |
| 68 | 250-<1000 | 250-<1000 | ≥1000 | 50-<250 |
| 69 | 50-<250 | 50-<250 | 250-<1000 | 50-<250 |
| 70 | ≥1000 | ≥1000 | ≥1000 | 50-<250 |
| 71 | ≥1000 | ≥1000 | ≥1000 | 50-<250 |
| 72 | ≥1000 | ≥1000 | ≥1000 | 50-<250 |

Fig. 2 (Cont.)

| # | Solid phase assay | | Proximity-based assay | |
|---|---|---|---|---|
| | $\alpha_V\beta_1$ | $\alpha_V\beta_6$ | $\alpha_V\beta_1$ | $\alpha_V\beta_6$ |
| 73 | ≥1000 | ≥1000 | ≥1000 | 50-<250 |
| 74 | ≥1000 | ≥1000 | ≥1000 | 50-<250 |
| 75 | ≥1000 | ≥1000 | ≥1000 | 50-<250 |
| 76 | ≥1000 | ≥1000 | ≥1000 | 50-<250 |
| 77 | - | - | - | - |
| 78 | <50 | <50 | <50 | 50-<250 |
| 79 | <50 | 250-<1000 | <50 | 50-<250 |
| 80 | <50 | 250-<1000 | 250-<1000 | 50-<250 |
| 81 | <50 | ≥1000 | 50-<250 | 50-<250 |
| 82 | <50 | <50 | 250-<1000 | 50-<250 |
| 83 | <50 | <50 | 250-<1000 | 50-<250 |
| 84 | <50 | <50 | 50-<250 | 50-<250 |
| 85 | <50 | <50 | 50-<250 | 50-<250 |
| 86 | <50 | <50 | 250-<1000 | 50-<250 |
| 87 | <50 | <50 | 50-<250 | 50-<250 |
| 88 | <50 | <50 | 250-<1000 | 50-<250 |
| 89 | <50 | <50 | ≥1000 | 50-<250 |
| 90 | <50 | <50 | 250-<1000 | 50-<250 |
| 91 | <50 | <50 | 250-<1000 | 50-<250 |
| 92 | ≥1000 | ≥1000 | ≥1000 | 50-<250 |
| 93 | <50 | <50 | ≥1000 | 50-<250 |
| 94 | <50 | <50 | ≥1000 | 50-<250 |
| 95 | <50 | <50 | ≥1000 | 50-<250 |
| 96 | <50 | <50 | <50 | 50-<250 |
| 97 | <50 | <50 | <50 | 50-<250 |
| 98 | <50 | <50 | 50-<250 | 50-<250 |
| 99 | <50 | <50 | <50 | 50-<250 |
| 100 | <50 | <50 | <50 | 50-<250 |
| 101 | <50 | <50 | 50-<250 | 50-<250 |
| 102 | <50 | <50 | <50 | 50-<250 |
| 103 | <50 | <50 | 250-<1000 | 50-<250 |
| 104 | <50 | <50 | 50-<250 | 50-<250 |
| 105 | <50 | <50 | <50 | 50-<250 |
| 106 | <50 | <50 | 250-<1000 | 50-<250 |
| 107 | <50 | <50 | <50 | 50-<250 |
| 108 | <50 | <50 | 50-<250 | 50-<250 |

Fig. 2 (Cont.)

| # | Solid phase assay | | Proximity-based assay | |
|---|---|---|---|---|
| | $\alpha_V\beta_1$ | $\alpha_V\beta_6$ | $\alpha_V\beta_1$ | $\alpha_V\beta_6$ |
| 109 | <50 | <50 | 50-<250 | 50-<250 |
| 110 | <50 | <50 | <50 | 50-<250 |
| 111 | <50 | <50 | 50-<250 | 50-<250 |
| 112 | <50 | <50 | 250-<1000 | 50-<250 |
| 113 | <50 | <50 | ≥1000 | 50-<250 |
| 114 | <50 | <50 | <50 | 50-<250 |
| 115 | <50 | 250-<1000 | 50-<250 | 50-<250 |
| 116 | <50 | <50 | 50-<250 | 50-<250 |
| 117 | <50 | <50 | <50 | 50-<250 |
| 118 | <50 | <50 | 250-<1000 | 50-<250 |
| 119 | <50 | <50 | 250-<1000 | 50-<250 |
| 120 | <50 | <50 | ≥1000 | 50-<250 |
| 121 | <50 | <50 | 250-<1000 | 50-<250 |
| 122 | <50 | <50 | ≥1000 | 50-<250 |
| 123 | <50 | <50 | ≥1000 | 50-<250 |
| 124 | <50 | - | <50 | <50 |

Fig. 2 (Cont.)

AMINO ACID COMPOUNDS WITH UNBRANCHED LINKERS AND METHODS OF USE

RELATED APPLICATIONS

This application claims the benefit of priority to U.S. Provisional Pat. App. No. 62/690,939, filed Jun. 27, 2018. The preceding application is entirely incorporated by reference herein.

BACKGROUND OF THE INVENTION

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Primary biliary cholangitis (PBC), also known as primary biliary cirrhosis, is a chronic disease of the liver that causes damage and fibrosis in the liver. It results from a slow, progressive destruction of the small bile ducts of the liver, causing bile and other toxins to build up in the liver, a condition called cholestasis. Over time, this leads to scarring and fibrosis in both the liver and biliary tract.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. (Kim et al., Proc. Am. Thorac. Soc. (2006) 3:285-292; Lynch, D., Radiology (2001) 221:583-584; Kinder et al., Am. J. Respir. Crit. Care Med. (2007) 176: 691-697)

Available courses of treatment are scarce, as there are currently no options on the market proven to have an effect on long-term patient survival or symptomatology. There remains a need for treatment of fibrotic diseases.

The $\alpha_v\beta_6$ integrin is expressed in epithelial cells, and binds to the latency-associated peptide of transforming growth factor-$\beta 1$ (TGF$\beta 1$) and mediates TGF$\beta 1$ activation. The expression level of $\alpha_v\beta_6$ integrin is significantly increased after injury to lung and cholangiocytes, and plays a critical in vivo role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of $\alpha_v\beta_6$ is elevated in liver and bile duct of PSC patients.

The present disclosure provides for $\alpha_v\beta_6$ integrin inhibitors that may be useful for treatment of fibrosis.

BRIEF SUMMARY OF THE INVENTION

Disclosed are amino acid compounds that are $\alpha_v\beta_6$ integrin inhibitors, compositions containing these compounds and methods for treating diseases mediated by $\alpha_v\beta_6$ integrin such as a fibrotic disease.

In one aspect, provided is a compound of formula (I), or any variation thereof, or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

In another aspect, provided is a method of treating a fibrotic disease in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In another aspect, provided is a method of delaying the onset and/or development of a fibrotic disease in an individual (such as a human) who is at risk for developing a fibrotic disease comprising administering to the individual a therapeutically effective amount of a compound of formula (I), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or PBC. In some embodiments, the individual at risk of developing a fibrotic disease has or is suspected of having NAFLD, NASH, CKD, scleroderma, Crohn's Disease, NSIP, PSC, PBC, or is an individual who has had or is suspected of having had a myocardial infarction.

Also provided is a compound of formula (I), or any variation thereof detailed herein, or a pharmaceutical composition thereof, for the treatment of a fibrotic disease.

Also provided is use of a compound of formula (I), or any variation thereof detailed herein, or a pharmaceutically acceptable salt thereof, or a pharmaceutical composition comprising any of the foregoing, in the manufacture of a medicament for the treatment of a fibrotic disease.

Further provided is a kit comprising a compound of formula (I), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (I) or any variation thereof, or a pharmaceutically acceptable salt thereof. Also provided are compound intermediates useful in synthesis of a compound of formula (I), or any variation thereof.

BRIEF DESCRIPTION OF THE FIGURES

FIG. 2 Table B-2 shows biological data for various compounds disclosed herein.

DETAILED DESCRIPTION OF THE INVENTION

Figure 1:
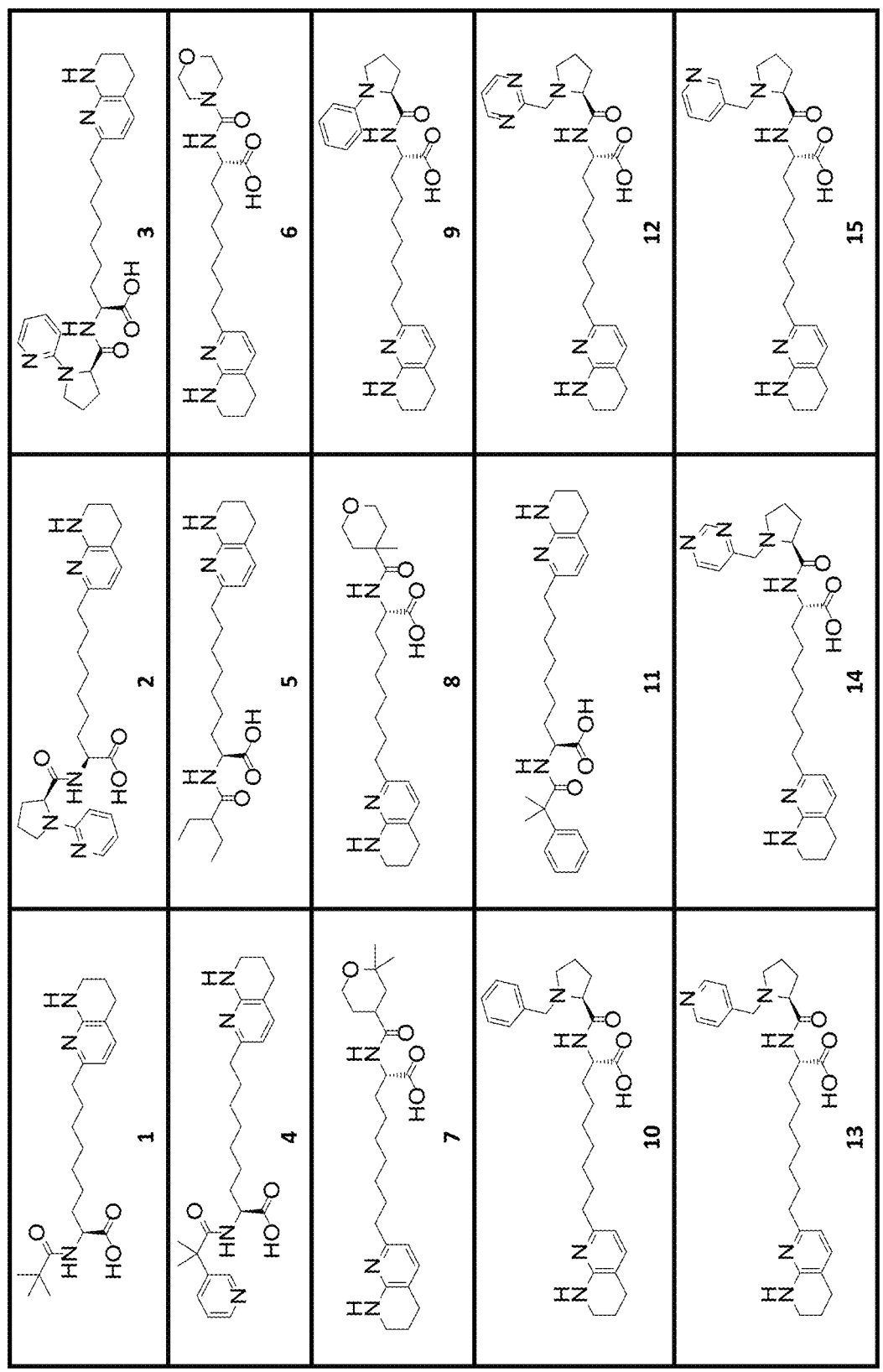
FIG. 1, Table 1 shows the chemical structures of Compound Nos. 1-124.
Figure 1:
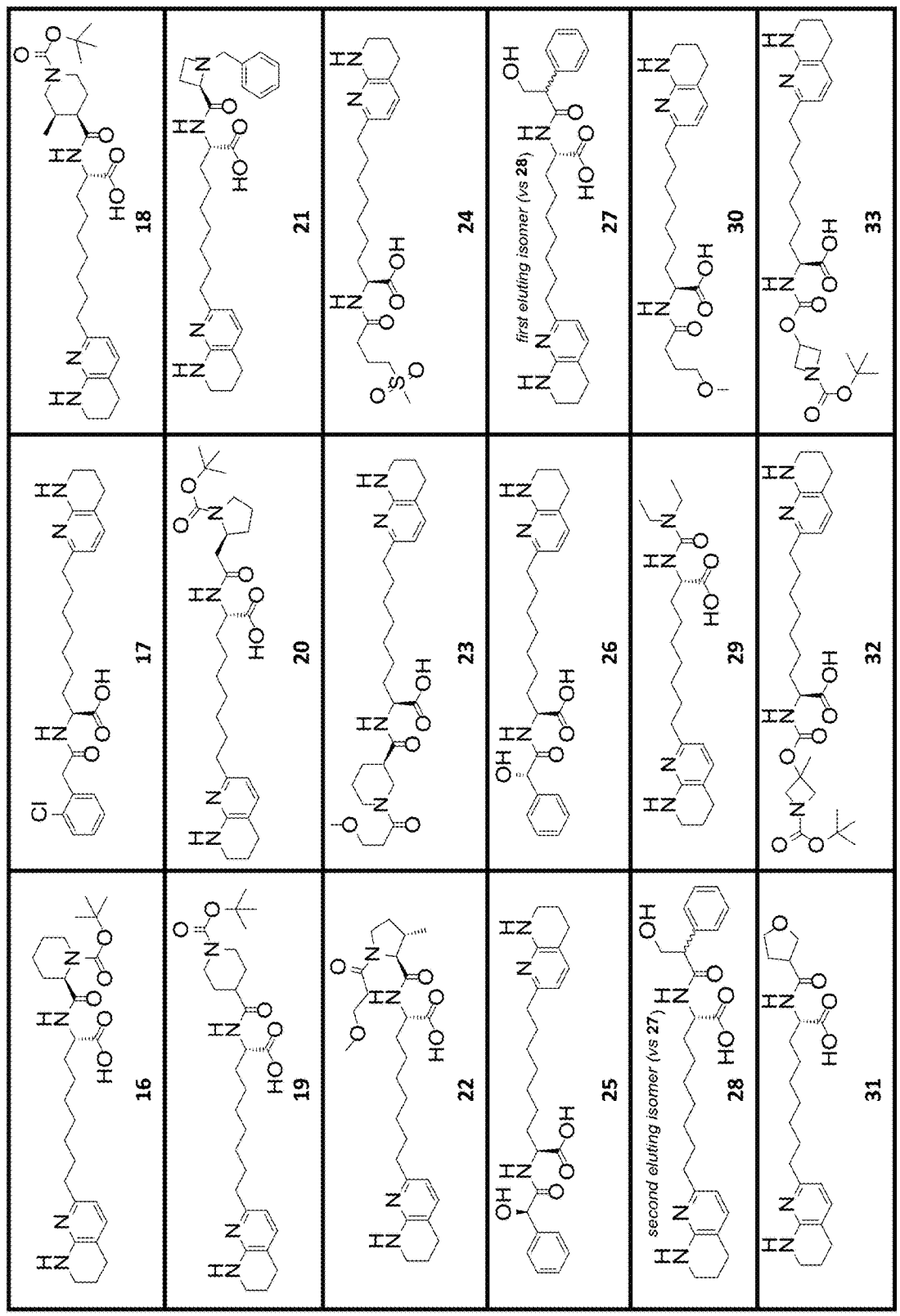
Figure 1:
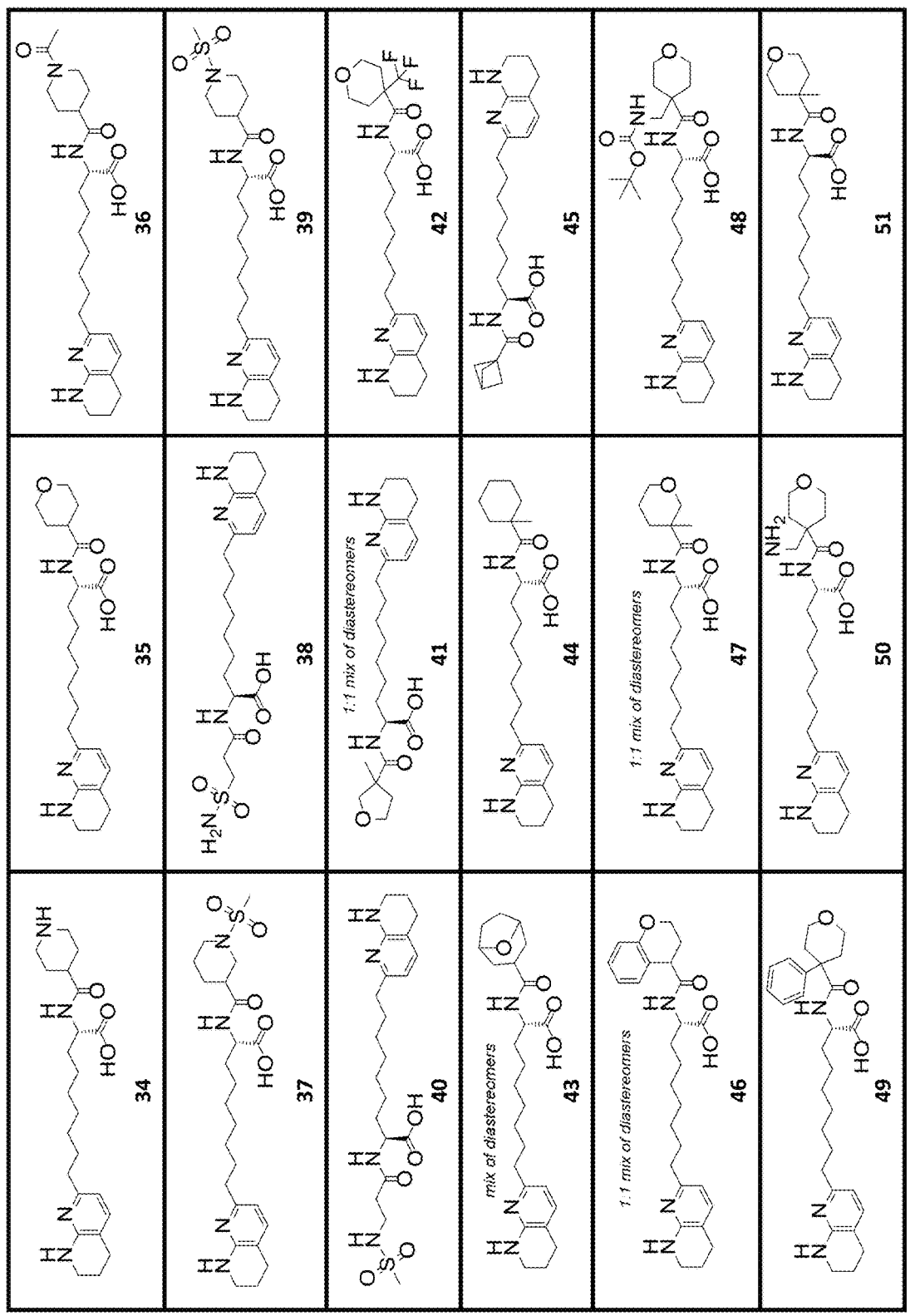
Figure 1:
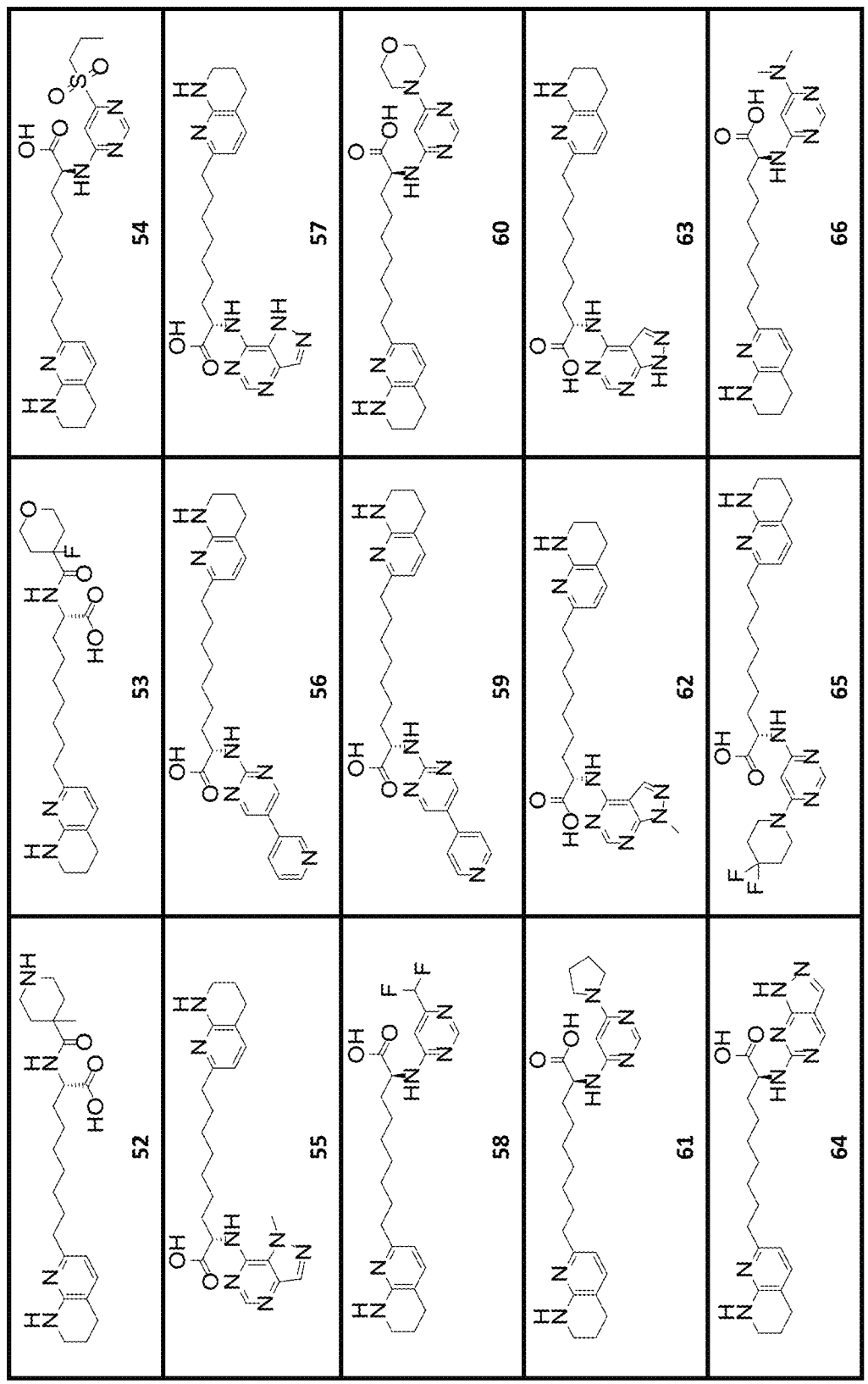
Figure 1:
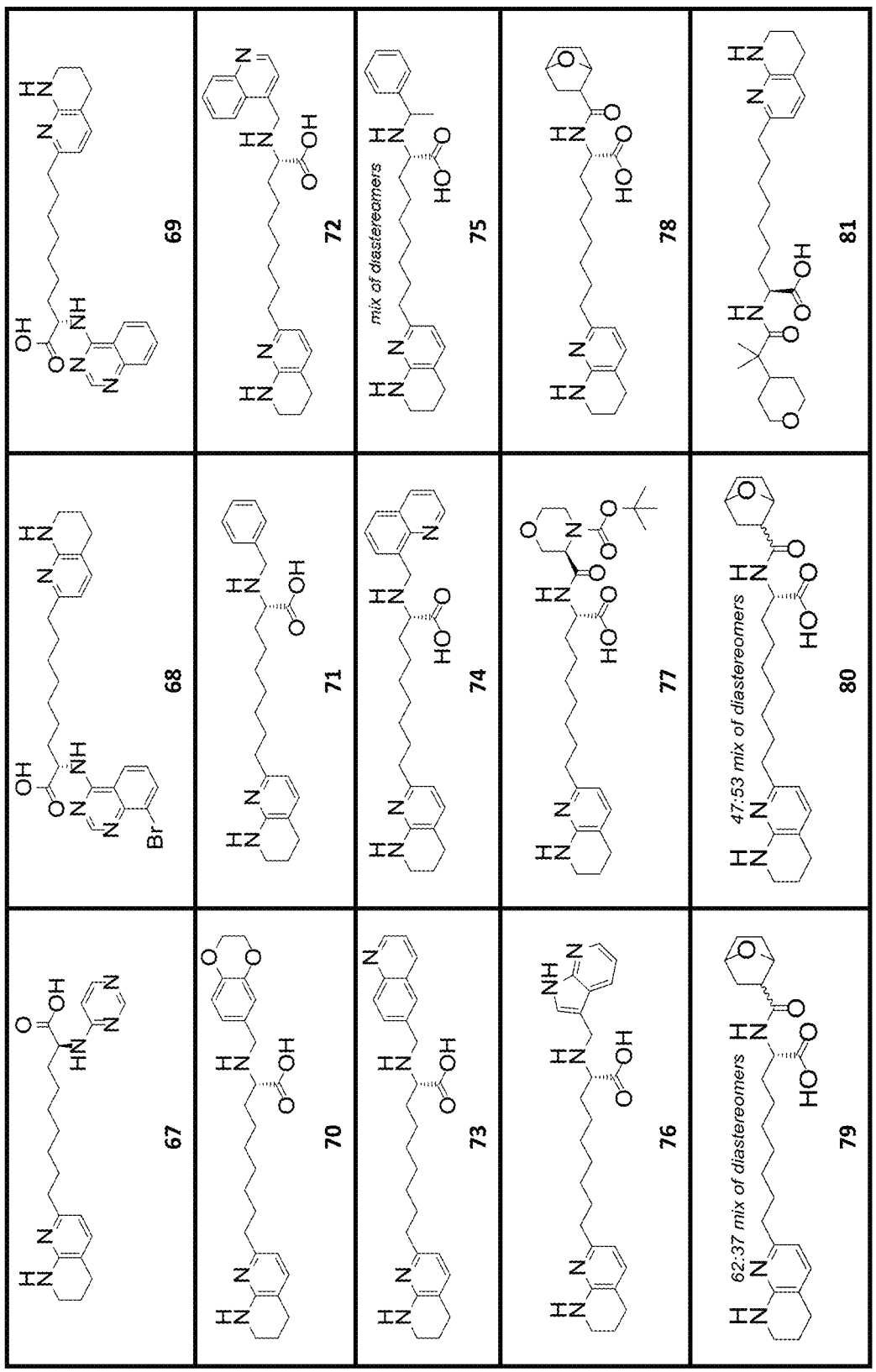
Figure 1:
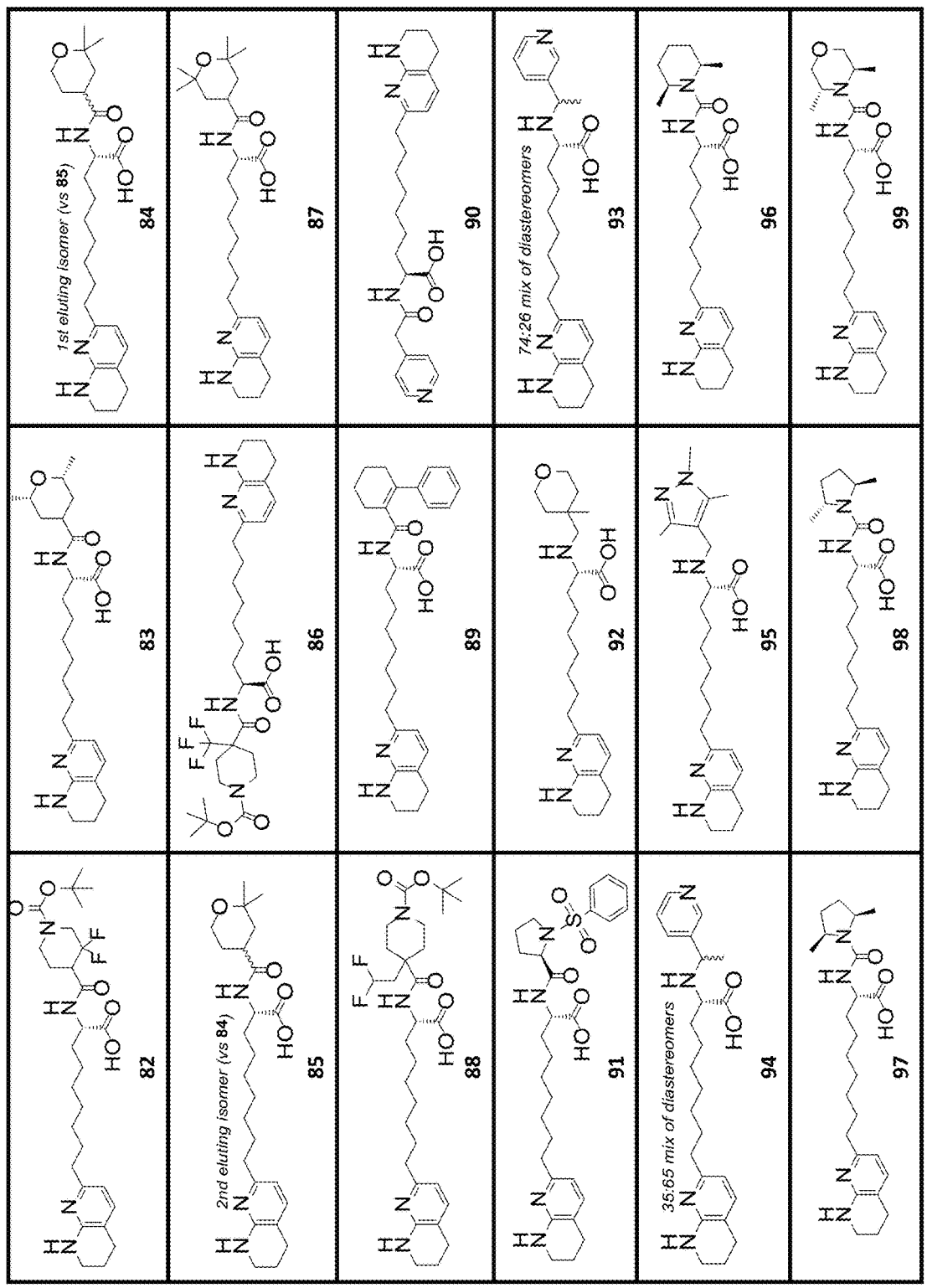
Figure 1:
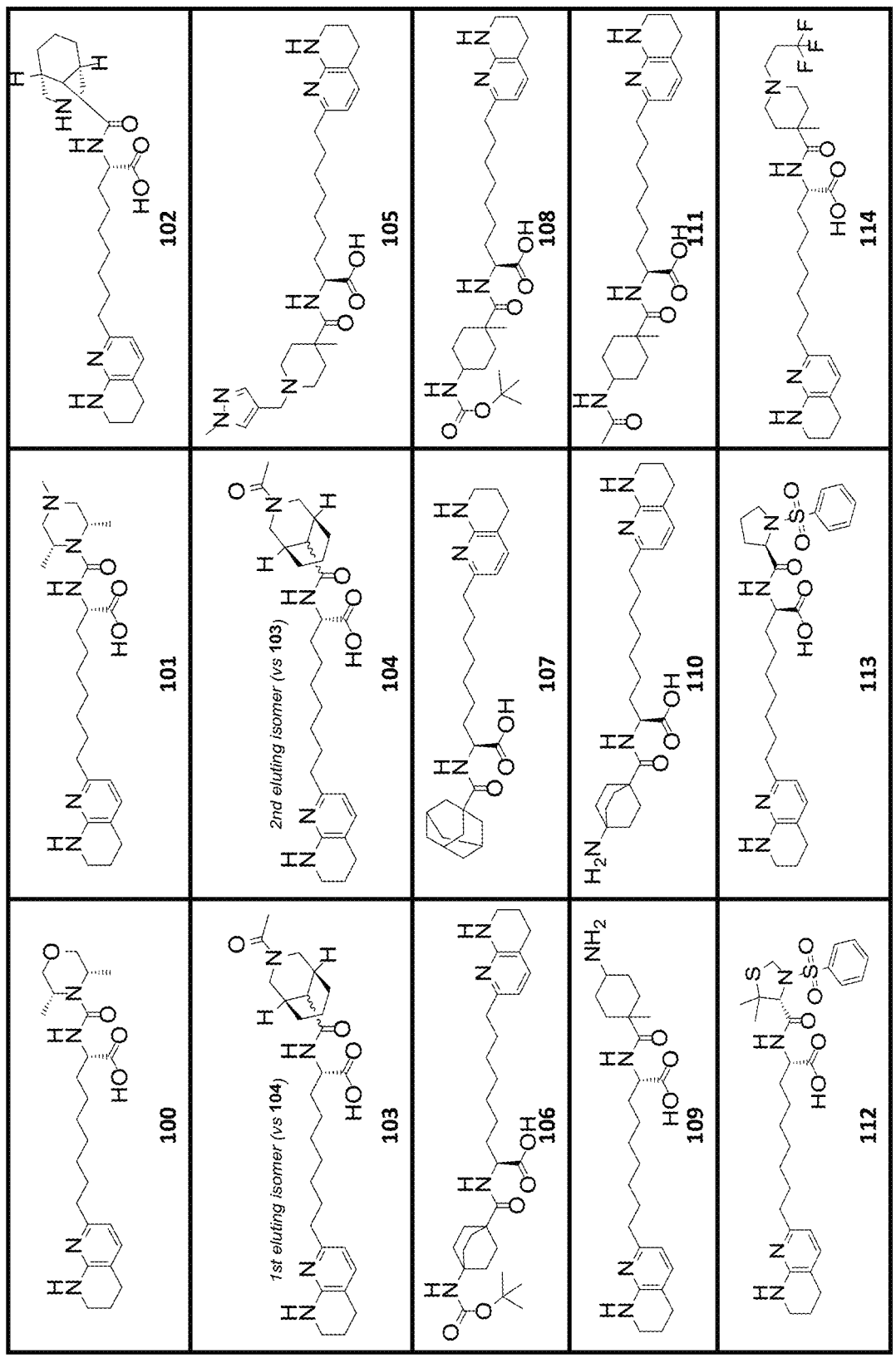
Figure 1:
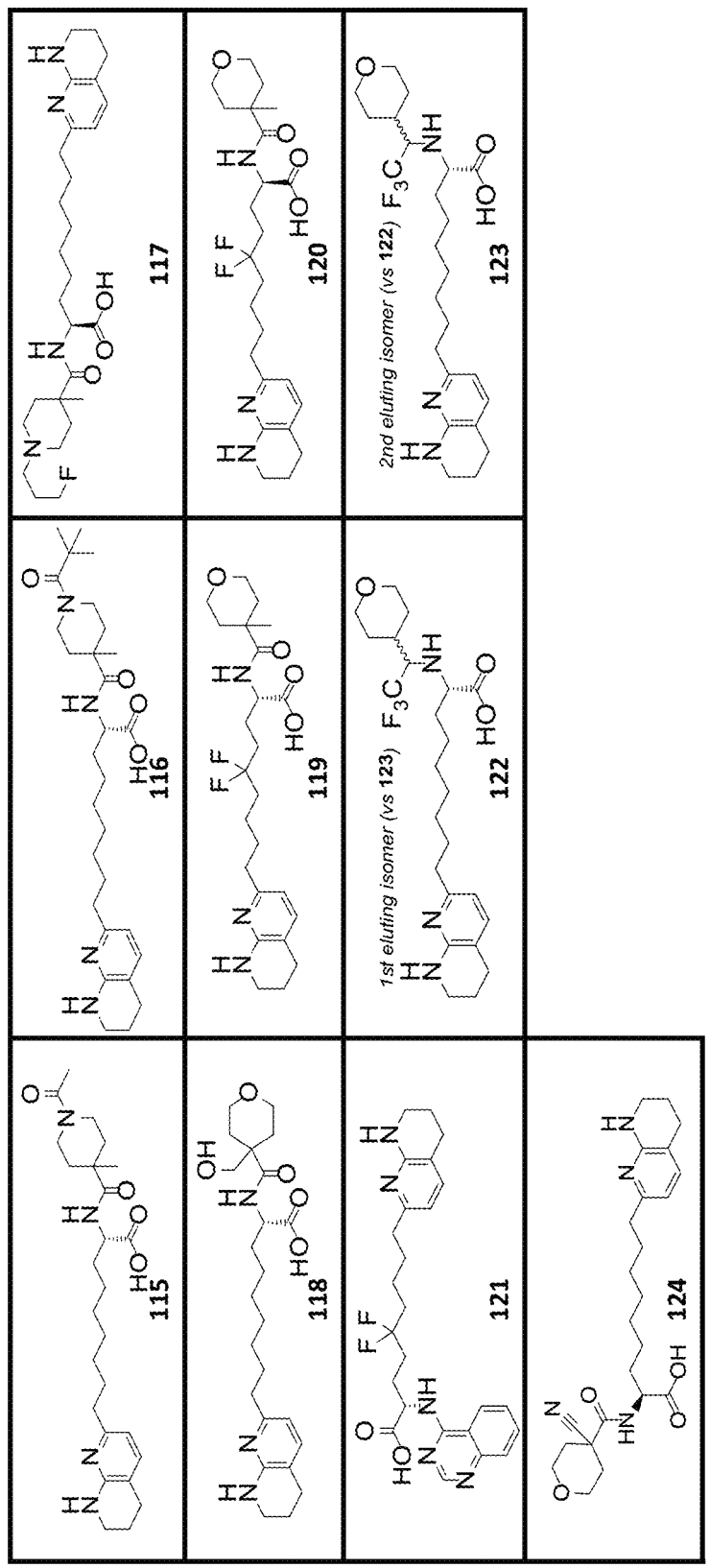

The present disclosure provides, inter alia, compounds of formula (I), and variations thereof, or a salt thereof, pharmaceutical compositions comprising compounds of formula (I) or a salt thereof, and methods of using such compounds and compositions in treating fibrotic diseases.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH$_2$—), 1,4-but-1-enylene (—CH=CH—CH$_2$CH$_2$—), 1,4-but-2-enylene (—CH$_2$CH=CHCH$_2$—), 1,6-hex-1-enylene (—CH=CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 annular carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof. In fused ring systems, one or more of the fused rings can be cycloalkyl or aryl, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"D" refers to deuterium ($^2$H).

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. Beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless otherwise stated, "substantially pure" intends a composition that contains no more than 10% impurity, such as a composition comprising less than 9%, 7%, 5%, 3%, 1%, or 0.5% impurity.

It is understood that aspects and embodiments described herein as "comprising" include "consisting of" and "consisting essentially of" embodiments.

The following abbreviations may be used herein: AcOH for acetic acid; ACN, acetonitrile; anhyd, anhydrous; aq, aqueous; tBoc or BOC, tert-butoxycarbonyl; br, broad (spectral); ° C., degrees Celsius; calcd, calculated; CBZ, benzyloxycarbonyl; compd, compound; concd, concentrated; concn, concentration; δ, NMR chemical shift in ppm downfield of SiMe$_4$; d, day(s); doublet (spectral); DCE, 1,2-dichloroethane; DCM, dichloromethane; DMA, dimethylacetamide; DMAP, 4-(N,N-dimethylamino)pyridine; DME, 1,2-dimethoxyethane; DMF, dimethylformamide; DMSO, dimethyl sulfoxide; EA, ethyl acetate; equiv, equivalent; Et, ethyl; g, gram(s); GC, gas chromatography; h, hour(s); Hz, hertz; IR, infrared; J, NMR coupling constant; K, kelvin(s); L, liter(s); µ, micro; m, multiplet (spectral); milli; M, molar (moles per liter), mega; M+, parent molecular ion; max, maximum; Me, methyl; MHz, megahertz; min, minute(s), minimum; mM, millimolar (millimoles per liter); mol, mole(s); MOM, methoxymethyl; mp, melting point; MS, mass spectrometry; MW, molecular weight; m/z, mass-to-charge ratio; N, normal (equivalents per liter); nm, nanometer(s); NMP, N-methylpyrrolidone; NMR, nuclear magnetic resonance; PE, petroleum ether; Ph, phenyl; ppm, part(s) per million; Pr, propyl; iPr, isopropyl; PSI, pounds per square inch; q, quartet (spectral); redox, reduction-oxidation; rel, relative; Rf, chromatography retention factor; rt, room temperature; s, singlet (spectral), second(s); t, triplet (spectral); TEA, triethylamine; THF, tetrahydrofuran; TLC, thin-layer chromatography; UV, ultraviolet; vis, visible; vol, volume; v/v, ratio of volume per unit volume; wt, and weight; w/w, ratio of weight per unit weight.

Compounds

Provided is a compound of formula (A):

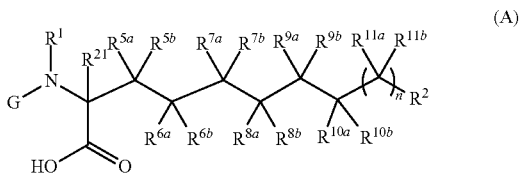

or a salt thereof, wherein:

$R^1$ is hydrogen;

$R^2$ is 5,6,7,8-tetrahydro-1,8-naphthyridin-2-yl optionally substituted by $R^{12}$, 1,2,3,4-tetrahydro-1,8-naphthyridin-2-yl optionally substituted by $R^{12}$, 6-aminopyridin-2-yl optionally substituted by $R^{12}$, or (pyridin-2-yl)amino optionally substituted by $R^{12}$;

G is —C(O)R$^3$ or R$^4$;

$R^3$ is —OR$^{3a}$, —NR$^{3b}$R$^{3c}$, $C_1$-$C_6$ alkyl optionally substituted by R$^{3d}$, $C_3$-$C_{12}$ cycloalkyl optionally substituted by R$^{3e}$, 3- to 12-membered heterocyclyl optionally substituted by R$^{3f}$, $C_3$-$C_8$ cycloalkenyl optionally substituted by R$^{3i}$;

$R^4$ is $C_1$-$C_6$ alkyl optionally substituted by R$^{4a}$, $C_3$-$C_8$ cycloalkyl optionally substituted by R$^{4b}$, 3- to 12-membered heterocyclyl optionally substituted by R$^{4c}$, $C_6$-$C_{14}$ aryl optionally substituted by R$^{4d}$, or 5- to 10-membered heteroaryl optionally substituted by R$^{4e}$;

$R^{3a}$ is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R$^{3a}$ are independently optionally substituted by R$^{3g}$;

$R^{3b}$ and R$^{3c}$ are each independently hydrogen, deuterium, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R$^{3b}$ and R$^{3c}$ are independently optionally substituted by R$^{3h}$;

$R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, and $R^{10b}$ are each independently hydrogen, deuterium, or halogen;

each $R^{11a}$ and $R^{11b}$ are independently hydrogen, deuterium, or halogen;

n is 0, 1, or 2;

each $R^{3d}$, $R^{3e}$, $R^{3f}$, $R^{3g}$, $R^{3h}$, $R^{3i}$, $R^{4a}$, $R^{4b}$, $R^{4c}$, $R^{4d}$, and $R^{4e}$ is independently oxo or R$^{12}$;

each $R^{12}$ is independently $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, $C_6$-$C_{14}$ aryl, halogen, deuterium, —CN, —OR$^{13}$, —SR$^{13}$, —NR$^{14}$R$^{15}$, —NO$_2$, —C≡NH(OR$^{13}$), —C(O)R$^{13}$, —OC(O)R$^{13}$, —C(O)OR$^{13}$, —C(O)NR$^{14}$R$^{15}$, —NR$^{13}$C(O)R$^{14}$, —NR$^{13}$C(O)OR$^{14}$, —NR$^{13}$C(O)NR$^{14}$R$^{15}$, —S(O)R$^{13}$, —S(O)$_2$R$^{13}$, —NR$^{13}$S(O)R$^{14}$, —NR$^{13}$S(O)$_2$R$^{14}$, —S(O)NR$^{14}$R$^{15}$, —S(O)$_2$NR$^{14}$R$^{15}$, or —P(O)(OR$^{13}$)(OR$^{14}$), wherein the C$_1$-C$_6$ alkyl, C$_2$-C$_6$ alkenyl, C$_2$-C$_6$ alkynyl, C$_3$-C$_8$ cycloalkyl, 3- to 12-membered heterocyclyl, 5- to 10-membered heteroaryl, and C$_6$-C$_{14}$ aryl of R$^{12}$ are independently optionally substituted by R$^{12a}$;

each R$^{12a}$ is independently deuterium, halogen, oxo, —OR$^{16}$, —NR$^{16}$R$^{17}$, —C(O)R$^{16}$, —C(O)OR$^{16}$, —NR$^{16}$C(O)OR$^{18}$, —CN, —S(O)R$^{16}$, —S(O)$_2$R$^{16}$, —P(O)(OR$^{16}$)(OR$^{17}$), C$_3$-C$_8$ cycloalkyl, 3- to 12-membered heterocyclyl, 5- to 10-membered heteroaryl, C$_6$-C$_{14}$ aryl, or C$_1$-C$_6$ alkyl, wherein the 3- to 12-membered heterocyclyl, 5- to 10-membered heteroaryl, C$_6$-C$_{14}$ aryl, and C$_1$-C$_6$ alkyl of R$^{12a}$ are independently optionally substituted by R$^{12b}$;

each R$^{12b}$ is independently deuterium, oxo, —OH, or halogen;

each R$^{13}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, and 3- to 6-membered heterocyclyl of R$^{13}$ are each independently optionally substituted by R$^{13a}$;

each R$^{13a}$ is independently halogen, deuterium, oxo, —CN, —OR$^{18}$, —NR$^{19}$R$^{20}$, —P(O)(OR$^{19}$)(OR$^{20}$), 3- to 12-membered heterocyclyl, or C$_1$-C$_6$ alkyl optionally substituted by deuterium, halogen, —OH, or oxo;

each R$^{14}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, and 3- to 6-membered heterocyclyl of R$^{14}$ and R$^{15}$ are independently optionally substituted by deuterium, halogen, oxo, —CN, —OR$^{18}$, —NR$^{19}$R$^{20}$, or C$_1$-C$_6$ alkyl optionally substituted by deuterium, halogen, —OH, or oxo;

each R$^{15}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 10-membered heteroaryl, and 3- to 6-membered heterocyclyl of R$^{14}$ and R$^{15}$ are independently optionally substituted by deuterium, halogen, oxo, —CN, —OR$^{18}$, —NR$^{19}$R$^{20}$, or C$_1$-C$_6$ alkyl optionally substituted by deuterium, halogen, —OH, or oxo;

or R$^{14}$ and R$^{15}$ are taken together with the atom to which they attached to form a 3- to 6-membered heterocyclyl optionally substituted by deuterium, halogen, oxo, —OR$^{18}$, —NR$^{19}$R$^{20}$, or C$_1$-C$_6$ alkyl optionally substituted by deuterium, halogen, oxo, or —OH;

each R$^{16}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{17}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{18}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{19}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo; and each R$^{20}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

or R$^{19}$ and R$^{20}$ are taken together with the atom to which they attached to form a 3-6 membered heterocyclyl optionally substituted by deuterium, halogen, oxo or C$_1$-C$_6$ alkyl optionally substituted by deuterium, oxo, or halogen; and R$^{21}$ is hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_3$-C$_6$ cycloalkyl optionally substituted by deuterium, halogen, or oxo, provided that the compound is other than a compound in Table IX or a salt thereof.

In various embodiments of formula (A), R$^{21}$ is hydrogen or deuterium. R$^{21}$ is C$_1$-C$_6$ alkyl optionally substituted by deuterium or halogen, C$_2$-C$_6$ alkenyl optionally substituted by deuterium or halogen, or C$_2$-C$_6$ alkynyl optionally substituted by deuterium or halogen. R$^{21}$ is C$_1$-C$_6$ alkyl optionally substituted by deuterium, C$_2$-C$_6$ alkenyl optionally substituted by deuterium, or C$_2$-C$_6$ alkynyl optionally substituted by deuterium. R$^{21}$ is C$_1$-C$_4$ alkyl, C$_1$-C$_4$ alkenyl, or C$_1$-C$_4$ alkynyl optionally substituted by deuterium. R$^{21}$ is C$_1$-C$_2$ alkyl, C$_1$-C$_2$ alkenyl, or C$_1$-C$_2$ alkynyl optionally substituted by deuterium. R$^{21}$ is methyl optionally substituted by deuterium. The carbon to which R$^{21}$ is bonded is in the R configuration, or the S configuration. For example, R$^{21}$ is methyl, ethyl, 1-propyl, or 2-propyl, and the carbon to which R$^{21}$ is bonded is in the R configuration. R$^{21}$ is methyl, ethyl, 1-propyl, or 2-propyl, and the carbon to which R$^{21}$ is bonded is in the S configuration.

In various embodiments, R$^{21}$ is hydrogen and R$^3$ is —OR$^{3a}$, —NR$^{3b}$R$^{3c}$, C$_1$-C$_6$ alkyl optionally substituted by R$^{3d}$, C$_3$-C$_8$ cycloalkyl optionally substituted by R$^{3e}$, 3- to 12-membered heterocyclyl optionally substituted by R$^{3f}$.

In one embodiment, disclosed herein is a compound of formula (I):

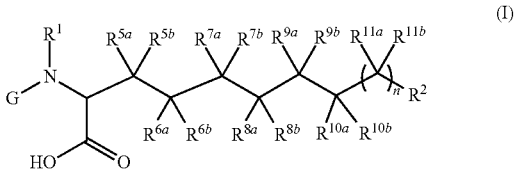

or a salt thereof, wherein:

R$^1$ is hydrogen;

R$^2$ is 5,6,7,8-tetrahydro-1,8-naphthyridin-2-yl optionally substituted by R$^{12}$, 1,2,3,4-tetrahydro-1,8-naphthyridin-2-yl optionally substituted by R$^{12}$, 6-aminopyridin-2-yl optionally substituted by R$^{12}$, or (pyridin-2-yl)amino optionally substituted by R$^{12}$;

G is —C(O)R³ or R⁴;

R³ is —OR³ᵃ, —NR³ᵇR³ᶜ, $C_1$-$C_6$ alkyl optionally substituted by R³ᵈ, $C_3$-$C_8$ cycloalkyl optionally substituted by R³ᵉ, or 3- to 12-membered heterocyclyl optionally substituted by R³ᶠ;

R⁴ is $C_1$-$C_6$ alkyl optionally substituted by R⁴ᵃ, $C_3$-$C_8$ cycloalkyl optionally substituted by R⁴ᵇ, 3- to 12-membered heterocyclyl optionally substituted by R⁴ᶜ, $C_6$-$C_{14}$ aryl optionally substituted by R⁴ᵈ, or 5- to 10-membered heteroaryl optionally substituted by R₄ₑ;

R³ᵃ is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R³ᵃ are independently optionally substituted by R³ᵍ;

R³ᵇ and R³ᶜ are each independently hydrogen, deuterium, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R³ᵇ and R³ᶜ are independently optionally substituted by R³ʰ;

R⁵ᵃ, R⁵ᵇ, R⁶ᵃ, R⁶ᵇ, R⁷ᵃ, R⁷ᵇ, R⁸ᵃ, R⁹ᵇ, R⁹ᵃ, R⁹ᵇ, R¹⁰ᵃ, and R¹⁰ᵇ are each independently hydrogen, deuterium, or halogen;

each R¹¹ᵃ and R¹¹ᵇ are independently hydrogen, deuterium, or halogen;

n is 0, 1, or 2;

each R³ᵈ, R³ᵉ, R³ᶠ, R³ᵍ, R³ʰ, R⁴ᵃ, R⁴ᵇ, R⁴ᶜ, R⁴ᵈ, and R⁴ᵉ is independently oxo or R¹²;

each R¹² is independently $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, $C_6$-$C_{14}$ aryl, halogen, deuterium, —CN, —OR¹³, —SR¹³, —NR¹⁴R¹⁵, —NO₂, —C=NH(OR¹³), —C(O)R¹³, —OC(O)R¹³, —C(O)OR¹³, —C(O)NR¹⁴R¹⁵, —NR¹³C(O)R¹⁴, —NR¹³C(O)OR¹⁴, —NR¹³C(O)NR¹⁴R¹⁵, —S(O)R¹³, —S(O)₂R¹³, —NR¹³S(O)R¹⁴, —NR¹³S(O)₂R¹⁴, —S(O)NR¹⁴R¹⁵, —S(O)₂NR¹⁴R¹⁵, or —P(O)(OR¹³)(OR¹⁴), wherein the $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, 5- to 10-membered heteroaryl, and $C_6$-$C_{14}$ aryl of R¹² are independently optionally substituted by R¹²ᵃ;

each R¹²ᵃ is independently deuterium, halogen, oxo, —OR¹⁶, —NR¹⁶R¹⁷, —C(O)R¹⁶, —C(O)OR¹⁶, —NR¹⁶C(O)OR¹⁸, —CN, —S(O)R¹⁶, —S(O)₂R¹⁶, —P(O)(OR¹⁶)(OR¹⁷), $C_3$-$C_8$ cycloalkyl, 3- to 12-membered heterocyclyl, 5- to 10-membered heteroaryl, $C_6$-$C_{14}$ aryl, or $C_1$-$C_6$ alkyl, wherein the 3- to 12-membered heterocyclyl, 5- to 10-membered heteroaryl, $C_6$-$C_{14}$ aryl, and $C_1$-$C_6$ alkyl of R¹²ᵃ are independently optionally substituted by R¹²ᵇ;

each R¹²ᵇ is independently deuterium, oxo, —OH, or halogen;

each R¹³ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of R¹³ are each independently optionally substituted by R¹³ᵃ;

each R¹³ᵃ is independently halogen, deuterium, oxo, —CN, —OR¹⁸, —NR¹⁹R²⁰, —P(O)(OR¹⁹)(OR²⁰), 3- to 12-membered heterocyclyl, or $C_1$-$C_6$ alkyl optionally substituted by deuterium, halogen, —OH, or oxo;

each R¹⁴ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of R¹⁴ and R¹⁵ are independently optionally substituted by deuterium, halogen, oxo, —CN, —OR¹⁸, —NR¹⁹R²⁰, or $C_1$-$C_6$ alkyl optionally substituted by deuterium, halogen, —OH, or oxo;

each R¹⁵ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of R¹⁴ and R¹⁵ are independently optionally substituted by deuterium, halogen, oxo, —CN, —OR¹⁸, —NR¹⁹R²⁰, or $C_1$-$C_6$ alkyl optionally substituted by deuterium, halogen, —OH, or oxo;

or R¹⁴ and R¹⁵ are taken together with the atom to which they attached to form a 3- to 6-membered heterocyclyl optionally substituted by deuterium, halogen, oxo, —OR¹⁸, —NR¹⁹R²⁰, or $C_1$-$C_6$ alkyl optionally substituted by deuterium, halogen, oxo, or —OH;

each R¹⁶ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each R¹⁷ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each R¹⁸ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

each R¹⁹ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo; and each R²⁰ is independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

or R¹⁹ and R²⁰ are taken together with the atom to which they attached to form a 3-6 membered heterocyclyl optionally substituted by deuterium, halogen, oxo or $C_1$-$C_6$ alkyl optionally substituted by deuterium, oxo, or halogen;

provided that the compound is other than a compound in Table IX or a salt thereof.

In one variation is provided a compound of the formula (I), or a salt thereof, wherein the carbon bearing the CO₂H and N(R¹)G moieties is in the "S" configuration. In another variation is provided a compound of the formula (I), or a salt thereof, wherein the carbon bearing the CO₂H and N(R¹))G moieties is in the "R" configuration. Mixtures of a compound of the formula (I) are also embraced, including racemic or non-racemic mixtures of a given compound, and mixtures of two or more compounds of different chemical formulae. The description above of embodiments for formula (I) also apply equally to formula (A) to provide the corresponding embodiments of formula (A).

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^2$ of formula (I) may be combined with every description, variation, embodiment or aspect of G the same as if each and every combination were specifically and individually listed. The description above of embodiments for formula (I) also apply equally to formula (A) to provide the corresponding embodiments of formula (A).

In some embodiments, the compound is other than a compound in Table IX and salts thereof. In some embodiments, the compound herein, such as a compound of formula (I), is other than a compound selected from one or more of Compound Nos. 1x-4x in Table 1X. In some embodiments, the compounds of the disclosure, and methods of using the compounds detailed herein, encompass any of the compounds of formula (I), including those listed Table 1X and salts thereof. The description above of embodiments for formula (I) also apply equally to formula (A) to provide the corresponding embodiments of formula (A).

In one variation, in any of the embodiments disclosed herein, the compounds can exclude compounds in Table 1X or salts thereof.

TABLE 1X

| No. | Structure | Name |
|---|---|---|
| 1x | 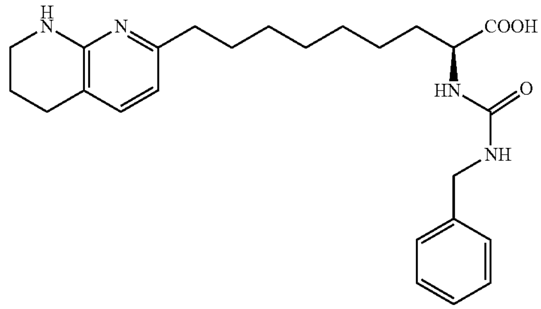 [SMILES: O=C(NCc1ccccc1)N[C@@H](CCCCCCCc1ccc2c(n1)NCCC2)C(=O)O] | (S)-2-(3-benzylureido)-9-(5,6,7,8-tetrahydro-1,8-naphthyridin-2-yl) nonanoic acid |
| 2x | 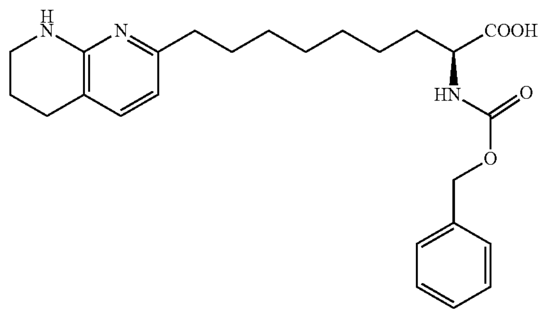 [SMILES: O=C(N[C@@H](CCCCCCCc1ccc2c(n1)NCCC2)C(=O)O)OCc1ccccc1] | (S)-2-(((benzyloxy)carbonyl)amino)-9-(5,6,7,8-tetrahydro-1,8-naphthyridin-2-yl) nonanoic acid |
| 3x | 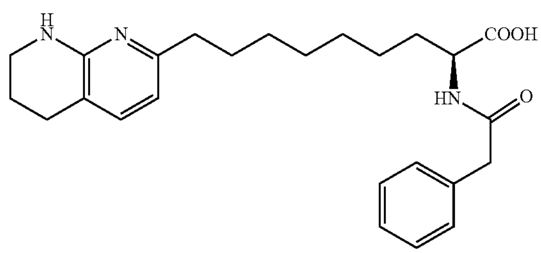 [SMILES: O=C(Cc1ccccc1)N[C@@H](CCCCCCCc1ccc2c(n1)NCCC2)C(=O)O] | (S)-2-(2-phenylacetamido)-9-(5,6,7,8-tetrahydro-1,8-naphthyridin-2-yl) nonanoic acid |
| 4x | 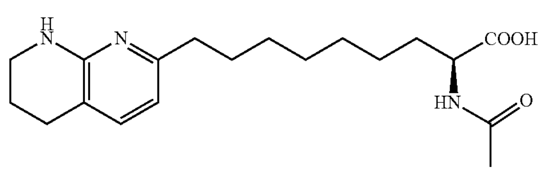 [SMILES: CC(=O)N[C@@H](CCCCCCCc1ccc2c(n1)NCCC2)C(=O)O] | (S)-2-acetamido-9-(5,6,7,8-tetrahydro-1,8-naphthyridin-2-yl) nonanoic acid |

In some embodiments of the compound of formula (I), or a salt thereof, $R^3$ is $C_3$-$C_8$ cycloalkyl optionally substituted by $R^{3e}$ or 3- to 12-membered heterocyclyl optionally substituted by $R^{3f}$. The description above of embodiments for formula (I) also apply equally to formula (A) to provide the corresponding embodiments of formula (A), where additionally $R^3$ is $C_3$-$C_{12}$ cycloalkyl optionally substituted by $R^{3e}$.

Also provided is a compound of formula (I), or a salt thereof, wherein:

a. when G is —C(O)$R^3$ and $R^3$ is $C_1$-$C_6$ alkyl optionally substituted by $R^{3d}$, then:

i. $R^3$ is $C_2$-$C_6$ alkyl optionally substituted by $R^{3d}$; or
ii. $R^3$ is $C_1$ alkyl substituted by 2-5 $R^{3d}$; or
iii. $R^3$ is $C_1$ alkyl substituted by at least one $R^{3d}$, which is further substituted by $R^{12a}$; and
b. when G is —C(O)$R^3$ and $R^3$ is —OR$^{3a}$, then $R^{3a}$ is unsubstituted $C_1$-$C_6$ alkyl; and
c. when G is —C(O)$R^3$ and $R^3$ is —NR$^{3b}$R$^{3c}$, then:
i. $R^{3b}$ and $R^{3c}$ are other than hydrogen; or
ii. at least one of $R^{3b}$ or $R^{3c}$ is unsubstituted $C_1$-$C_6$ alkyl.

The description above of embodiments for formula (I) also apply equally to formula (A) to provide the corresponding embodiments of formula (A).

In some embodiments of formula (I), or formula (A), G is —C(O)$R^3$. In such embodiments, when $R^3$ is $C_1$-$C_6$ alkyl optionally substituted by $R^{3d}$, $R^3$ is one of: (1) $C_2$-$C_6$ alkyl optionally substituted by $R^{3d}$; (2) $C_1$ alkyl substituted by 2 or 3 $R^{3d}$; or (3) $C_1$ alkyl substituted by at least one $R^{3d}$, the at least one $R^{3d}$ being further substituted by at least one $R^{12}$. Further in such embodiments, when $R^3$ is —NR$^{3b}$R$^{3c}$, $R^{3b}$ and $R^{3c}$ are any value described herein for $R^{3b}$ and $R^{3c}$ other than hydrogen, or at least one of $R^{3b}$ or $R^{3c}$ is unsubstituted $C_1$-$C_6$ alkyl. Also in such embodiments, when $R^3$ is —OR$^{3a}$, $R^{3a}$ is unsubstituted $C_1$-$C_6$ alkyl. In some such embodiments of the compound of formula (A) or (I), or a salt thereof: n is 1; $R^1$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen; in the case of formula (A), $R^{21}$ is hydrogen; the carbon to which the depicted —CO$_2$H group is bonded is in the S configuration; and $R^2$ is unsubstituted 5,6,7,8-tetrahydro-1,8-naphthyridin-2-yl.

In various embodiments of the compound of formula (A) or (I), or a salt thereof: n is 1; $R^1$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen; in the case of formula (A), $R^{21}$ is hydrogen; the carbon to which the depicted —CO$_2$H group is bonded is in the S configuration; $R^2$ is unsubstituted 5,6,7,8-tetrahydro-1,8-naphthyridin-2-yl; and G is —C(O)$R^3$. In such embodiments, when $R^3$ is $C_1$-$C_6$ alkyl optionally substituted by $R^{3d}$, $R^3$ is one of: (1) $C_2$-$C_6$ alkyl optionally substituted by $R^{3d}$; (2) $C_1$ alkyl substituted by 2 or 3 $R^{3d}$; or (3) $C_1$ alkyl monosubstituted by a single $R^{3d}$, wherein when the single $R^{3d}$ is phenyl, $R^{3d}$ is substituted with at least one $R^{12}$. Further in such embodiments, when $R^3$ is —NR$^{3b}$R$^{3c}$, one of $R^{3b}$ and $R^{3c}$ is $C_1$-$C_6$ alkyl, and the other of $R^{3b}$ and $R^{3c}$ is H, such that the one of $R^{3b}$ and $R^{3c}$ that is $C_1$-$C_6$ alkyl is one of: (1) $C_2$-$C_6$ alkyl optionally substituted by $R^{3h}$; (2) $C_1$ alkyl substituted by 0, 2, or 3 $R^{3h}$; or (3) $C_1$ alkyl monosubstituted by a single $R^{3h}$, wherein when the single $R^{3h}$ is phenyl, the single $R^{3h}$ is substituted with at least one $R^{2a}$. In some embodiments, the at least one $R^{12a}$ substituting the single $R^{3h}$ is any value described herein for $R^{12a}$ other than deuterium or oxo. Also in such embodiments, when $R^3$ is —OR$^{3a}$ and $R^{3a}$ is $C_1$-$C_6$ alkyl, $R^{3a}$ is one of: (1) $C_2$-$C_6$ alkyl optionally substituted by $R^{3g}$; (2) $C_1$ alkyl substituted by 0, 2, or 3 $R^{3g}$; or (3) $C_1$ alkyl monosubstituted by a single $R^{3g}$, wherein when the single $R^{3g}$ is phenyl, the single $R^{3g}$ is substituted with at least one $R^{12a}$. In some embodiments, the at least one $R^{12a}$ substituting the single $R^{3g}$ is any value described herein for $R^{12a}$ other than deuterium or oxo.

In some embodiments of the preceding paragraph, where the single $R^{3d}$ is phenyl, the at least one $R^{12}$ is any value described herein for $R^{12}$ other than one of: methyl; $C_1$-$C_2$ alkyl; $C_1$-$C_3$ alkyl; $C_1$-$C_4$ alkyl; $C_1$-$C_5$ alkyl; or $C_1$-$C_6$ alkyl. For example, the single $R^{3d}$ may be phenyl substituted with at least one value described herein for $R^{12}$ other than methyl or ethyl. In several embodiments of the preceding paragraph where the single $R^{3g}$ is phenyl, or the single $R^{3h}$ is phenyl, the at least one $R^{12a}$ is any value described herein for $R^{12a}$ other than one of: deuterium and methyl; deuterium and $C_1$-$C_2$ alkyl; deuterium and $C_1$-$C_3$ alkyl; deuterium and $C_1$-$C_4$ alkyl; deuterium and $C_1$-$C_5$ alkyl; or deuterium and $C_1$-$C_6$ alkyl. For example, the single $R^{3g}$ may be phenyl substituted by at least one value described for $R^{12a}$ herein other than deuterium, methyl, or ethyl. Further, for example, the single $R^{3h}$ may be phenyl substituted by at least one value described for $R^{12a}$ herein other than deuterium, methyl, or ethyl.

In various embodiments of the compound of formula (A) or (I), or a salt thereof: n is 1; $R^1$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen; in the case of formula (A), $R^{21}$ is hydrogen; the carbon to which the depicted —CO$_2$H group is bonded is in the S configuration; $R^2$ is unsubstituted 5,6,7,8-tetrahydro-1,8-naphthyridin-2-yl; and G is —C(O)$R^3$. In such embodiments, when $R^3$ is $C_1$-$C_6$ alkyl optionally substituted by $R^{3d}$, $R^3$ is one of: (1) $C_3$-$C_6$ alkyl optionally substituted by $R^{3d}$; (2) $C_1$ alkyl substituted by 2 $R^{3d}$ in which at least one $R^{3d}$ is any value described for $R^{3d}$ herein other than methyl, or $C_1$ alkyl substituted by 3 $R^{3d}$; or (3) $C_1$ alkyl monosubstituted by a single $R^{3d}$, the single $R^{3d}$ being any value of $R^{3d}$ described herein other than phenyl optionally substituted with at least one $R^{12}$. Further in such embodiments, when $R^3$ is —NR$^{3b}$R$^{3c}$, one of $R^{3b}$ and $R^{3c}$ is $C_1$-$C_6$ alkyl, and the other of $R^{3b}$ and $R^{3c}$ is H, such that the one of $R^{3b}$ and $R^{3c}$ that is $C_1$-$C_6$ alkyl is one of: (1) $C_3$-$C_6$ alkyl optionally substituted by $R^{3h}$; (2) $C_1$ alkyl substituted by 0, 2, or 3 $R^{3h}$; or (3) $C_1$ alkyl monosubstituted by a single $R^{3h}$, the single $R^{3h}$ being any value described herein for $R^{3h}$ other than phenyl optionally substituted by $R^{12a}$. Also in such embodiments, when $R^3$ is —OR$^{3a}$ and $R^{3a}$ is $C_1$-$C_6$ alkyl, $R^{3a}$ is one of: (1) $C_2$-$C_6$ alkyl optionally substituted by $R^{3g}$; (2) $C_1$ alkyl substituted by 0, 2, or 3 $R^{3g}$; or (3) $C_1$ alkyl monosubstituted by a single $R^{3g}$, the single $R^{3g}$ being any value described herein for $R^{3g}$ other than phenyl optionally substituted by $R^{2a}$.

In various embodiments of the compound of formula (A) or (I), or a salt thereof: n is 1; $R^1$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen; in the case of formula (A), $R^{21}$ is hydrogen; the carbon to which the depicted —CO$_2$H group is bonded is in the S configuration; $R^2$ is unsubstituted 5,6,7,8-tetrahydro-1,8-naphthyridin-2-yl; and G is —C(O)$R^3$. In such embodiments, when $R^3$ is $C_1$-$C_6$ alkyl optionally substituted by $R^{3d}$, $R^3$ is one of: (1) $C_3$-$C_6$ alkyl optionally substituted by $R^{3d}$; (2) $C_1$ alkyl substituted by 2 $R^{3d}$ in which at least one $R^{3d}$ is any value described herein for $R^{3d}$ other than methyl, or $C_1$ alkyl substituted by 3 $R^{3d}$; or (3) $C_1$ alkyl monosubstituted by a single $R^{3d}$, the single $R^{3d}$ being any value described herein for $R^{3d}$ other than $C_6$-$C_{14}$ aryl optionally substituted with at least one $R^{12}$. Further in such embodiments, when $R^3$ is —NR$^{3b}$R$^{3c}$, one of $R^{3b}$ and $R^{3c}$ is $C_1$-$C_6$ alkyl, and the other of $R^{3b}$ and $R^{3c}$ is H, such that the one of $R^{3b}$ and $R^{3c}$ that is $C_1$-$C_6$ alkyl is one of: (1) $C_2$-$C_6$ alkyl optionally substituted by $R^{3h}$; (2) $C_1$ alkyl substituted by 0, 2, or 3 $R^{3h}$; or (3) $C_1$ alkyl monosubstituted by a single $R^{3h}$, the single $R^{3h}$ being any value described herein for $R^{3h}$ other than $C_6$-$C_{14}$ aryl optionally substituted by $R^{12a}$. Also in such embodiments, when $R^3$ is —OR$^{3a}$ and $R^{3a}$ is $C_1$-$C_6$ alkyl, $R^{3a}$ is one of: (1) $C_2$-$C_6$ alkyl optionally substituted by $R^{3g}$; (2) $C_1$ alkyl substituted by 0, 2, or 3 $R^{3g}$; or (3) $C_1$ alkyl monosubstituted by a single $R^{3g}$, the single $R^{3g}$ being any value described herein for $R^{3g}$ other than $C_6$-$C_{14}$ aryl optionally substituted by $R^{2a}$.

In some embodiments of the compound of formula (I), or a salt thereof, n is 0. In some embodiments of the compound of formula (I), or a salt thereof, n is 1. In some embodiments of the compound of formula (I), or a salt thereof, n is 2. The description above of embodiments for formula (I) also apply equally to formula (A) to provide the corresponding embodiments of formula (A).

In some embodiments of formula (A), or (I), or a salt thereof, $R^{7a}$ and $R^{7b}$ are each hydrogen. $R^{7a}$ and $R^{7b}$ are each deuterium. $R^{7a}$ and $R^{7b}$ are each halogen, e.g., $R^{7a}$ and $R^{7b}$ are each fluorine. $R^{7a}$ and $R^{7b}$ are each fluorine, and $R^{5a}$, $R^{5b}$, $R^{6a}$, $R^{6b}$, $R^{8a}$, $R^{8b}$, $R^{9a}$, $R^{9b}$, $R^{10a}$, $R^{10b}$, $R^{11a}$, and $R^{11b}$ are each hydrogen.

In some embodiments of formula (I), or a salt thereof, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen. The description above of embodiments for formula (I) also apply equally to formula (A) to provide the corresponding embodiments of formula (A).

In some embodiments of formula (I), or a salt thereof, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each deuterium. The description above of embodiments for formula (I) also apply equally to formula (A) to provide the corresponding embodiments of formula (A).

In some embodiments of the compound of formula (I), or a salt thereof, at least one of $R^{3b}$, $R^{3c}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12}$, $R^{12a}$, $R^{12b}$, $R^{13}$, $R^{13a}$, $R^{14}$, $R^{15}$, $R^{16}$, $R^{17}$, $R^{18}$, $R^{19}$, or $R^{20}$ is deuterium. The description above of embodiments for formula (I) also apply equally to formula (A) to provide the corresponding embodiments of formula (A), where additionally $R^{21}$ is deuterium.

In some embodiments of formula (I), or a salt thereof, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen, n is 1, and is represented by the compound of formula (I-A):

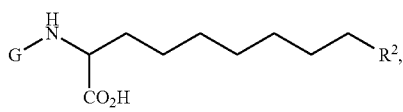

(I-A)

wherein $R^2$ and G are as defined for formula (I). The description above of embodiments for formula (I) also apply equally to formula (A) to provide the corresponding embodiments of formula (A), where additionally $R^{21}$ is hydrogen. For example, the compound is represented by formula (I-B) or (I-C):

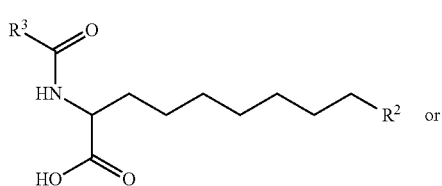

(I-B)

or

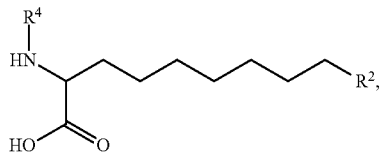

(I-C)

wherein $R^2$, $R^3$, and $R^4$ are as defined for formula (A) or (I).

In some embodiments of formula (I-A), or a salt thereof, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, and $R^{11b}$ are each hydrogen, n is 1, $R^2$ is 5,6,7,8-tetrahydro-1,8-naphthyridin-2-yl and is represented by the compound of formula (II):

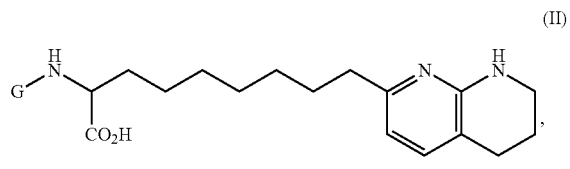

(II)

wherein G is as defined for formula (I). The description above of embodiments for formula (I) also apply equally to formula (A) to provide the corresponding embodiments of formula (A), where additionally $R^{21}$ is hydrogen.

In some embodiments of the compound of formula (II), wherein G is —C(O)$R^3$, the compound is of the formula (II-A):

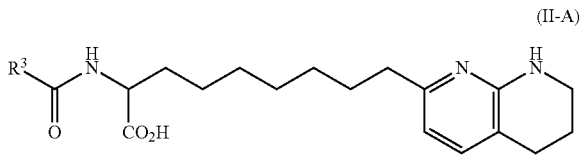

(II-A)

or a salt thereof, wherein $R^3$ is as defined for formula (I). The description above of embodiments for formula (I) also apply equally to formula (A) to provide the corresponding embodiments of formula (A).

In some embodiments of the compound of formula (II-A), the compound is of the formula (II-A-1):

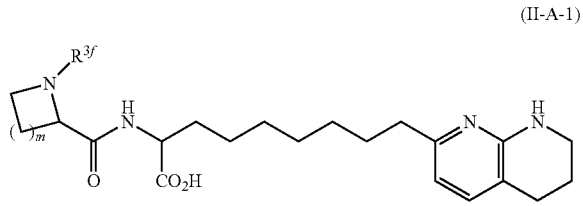

(II-A-1)

or a salt thereof, wherein $R^{3f}$ is as defined for formula (I), and m is 1, 2, or 3. The description above of embodiments for formula (I) also apply equally to formula (A) to provide the corresponding embodiments of formula (A).

In some embodiments of the compound represented by formula (II-A), the group represented by $R^3$ is —O$R^{3a}$ optionally substituted, where possible, by up to four $R^{3g}$, as described herein for formulas (I) or (A). For example, the compound is represented by any one of formulas (II-A-2) or (II-A-2a).

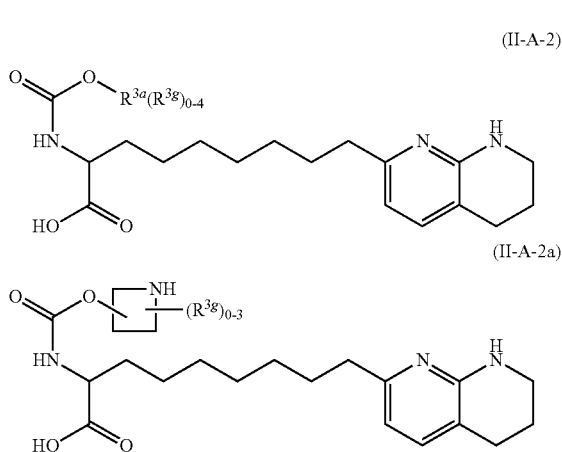

(II-A-2)

(II-A-2a)

Suitable values of $R^{3g}$ for the depicted azetidinyl group include $C_1$-$C_6$ alkyl, —C(O)O$R^3$, —S(O)$_2$$R^{13}$, and the like, wherein $R^{13}$ is as described herein for formulas (I) or (A). In several embodiments, the depicted azetidinyl group is substituted with: $C_1$-$C_3$ alkyl, —C(O)O—$C_1$-$C_6$ alkyl, and/or —S(O)$_2$—$C_1$-$C_6$ alkyl. For example, the azetidinyl group is substituted with N-t-Boc.

In some embodiments of the compound represented by formula (II-A), the group represented by $R^3$ is —N$R^{3b}R^{3c}$, wherein $R^{3b}$ and $R^{3c}$ are as described herein for formula (A) or (I) and $R^{3b}$ and $R^{3c}$ are further optionally substituted, where possible, by up to four $R^{3h}$ representing, where possible, oxo or $R^{12}$ as described herein for formulas (I) or (A), such as embodiments of formulas (II-A-3) or (II-A-3a):

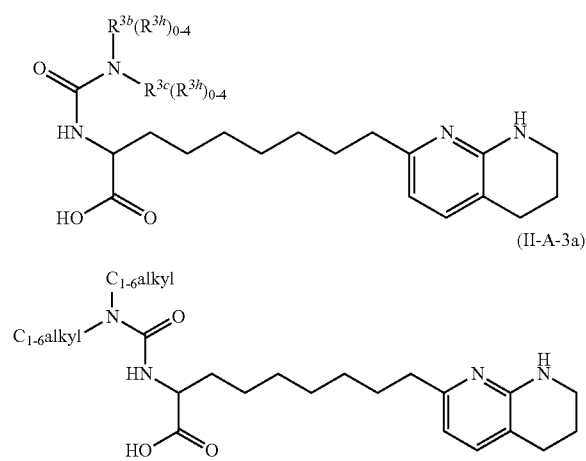

(II-A-3)

(II-A-3a)

Suitable values of $R^{3b}$ and $R^{3c}$ include $C_1$-$C_6$ alkyl and the like. For example, $R^{3b}$ and $R^{3c}$ each represent ethyl.

In some embodiments of the compound represented by formula (II-A), the group represented by $R^3$ is $C_1$-$C_6$ alkyl optionally substituted by $R^{3d}$, representing, where possible, oxo or $R^{12}$, of which $R^{12}$ is further optionally substituted, where possible, by or $R^{12a}$, as described herein for formulas (I) or (A). For example, in various embodiments, the compound is represented by any one of formulas (II-A-4), (II-A-4a), (II-A-4b), or (II-A-4c).

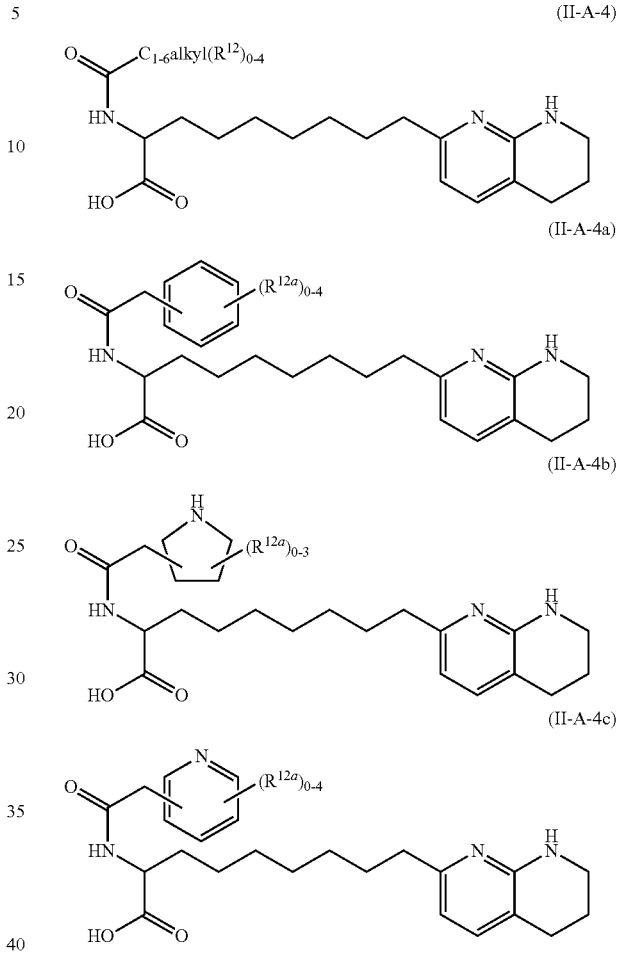

(II-A-4)

(II-A-4a)

(II-A-4b)

(II-A-4c)

Suitable values for the depicted $C_{1-6}$ alkyl group include, e.g., methyl, ethyl, prop-1-yl, prop-2-yl, pentan-3-yl, t-butyl, and the like. Such alkyl groups are optionally substituted by one or more, up to four $R^{12}$ groups such as hydroxy, $CH_3SO_2NH$—, $NH_2SO_2$—, and the depicted phenyl, pyrrolidinyl, and pyridyl groups. Each of the depicted phenyl, pyrrolidinyl, and pyridyl groups are further substituted, where possible, by up to four $R^{12a}$ groups. For example, in some embodiments, the depicted $C_{1-6}$ alkyl represent methyl substituted with up to three of: OH, phenyl, 2-chlorophenyl, pyrrolidine-2-yl, N-tBOC-pyrrolidin-2-yl, and/or pyridin-4-yl. In several embodiments, the depicted $C_{1-6}$ alkyl represent ethyl, optionally substituted by up to four of: 2-$CH_3SO_2NH$, 2-$NH_2SO_2$, 2-OH, 1-OH, and/or 1-phenyl. In various embodiments, the depicted $C_{1-6}$ alkyl represent prop-1-yl or prop-2-yl optionally substituted, where possible, with up to four of: 3-methoxy, 3-$CH_3SO_2$, 2-(pyridin-3-yl), 2-(tetrahydropyran-4-yl), and/or phenyl.

In some embodiments of the compound represented by formula (II-A), the group represented by $R^3$ is monocyclic, condensed bicyclic, or bridged bicyclic, and is, for example, $C_3$-$C_{12}$ cycloalkyl, e.g., $C_3$-$C_8$ cycloalkyl optionally substituted by $R^{3e}$, representing, where possible, $R^{12}$; or $C_3$-$C_{12}$, e.g., $C_3$-$C_8$ cycloalkenyl optionally substituted by $R^{3i}$, representing, where possible, oxo or $R^{12}$, as described herein for formulas (I) or (A). Such groups include, for example cyclohexanyl, e.g., cyclohexan-1-yl; cyclohexenyl, e.g., cyclohexen-1-yl; bicyclopentanyl, e.g., bicyclo[1.1.1]pentan-1-yl; bicyclooctanyl, e.g., bicyclo[2.2.2]octan-1-yl; and adamantanyl, e.g., adamantan-1-yl. For example, in various embodiments, the compound is represented by any one of formulas (II-A-5a), (II-A-5b), (II-A-5c), (II-A-5d), or (II-A-5e).

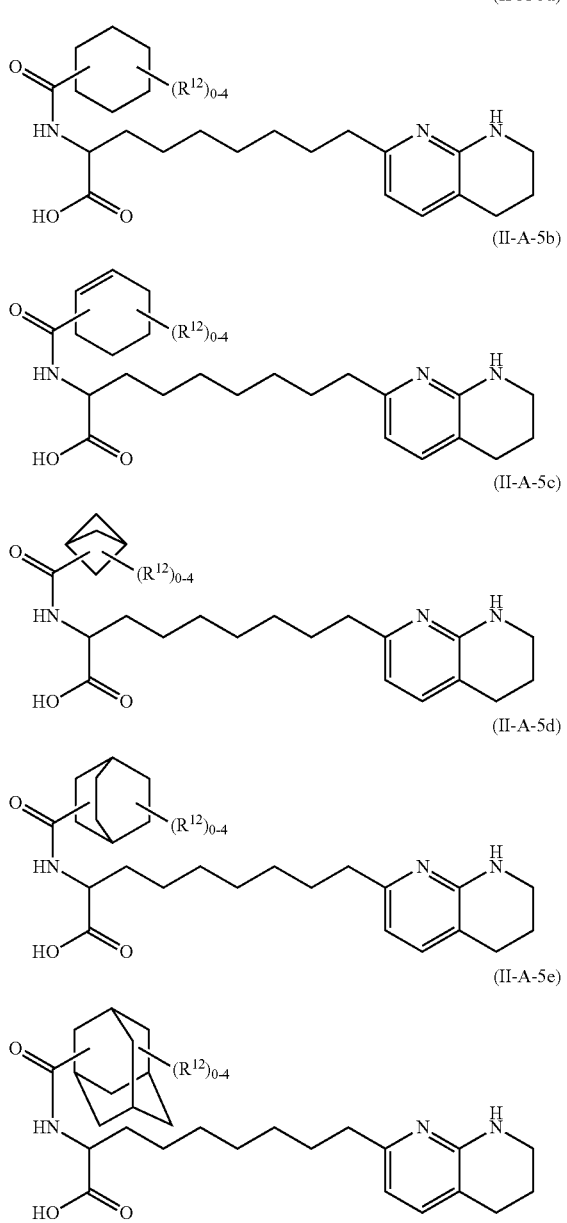

Such cycloalkyl or cycloalkenyl groups are substituted with any of the groups encompassed herein for $R^{12}$, for example, in some embodiments: $C_1$-$C_6$ alkyl, $C_6$-$C_{14}$ aryl, —$NR^{14}R^{15}$, —$NR^{13}C(O)R^{14}$, and/or —$NR^{13}C(O)OR^{14}$ groups, wherein $R^{13}$, $R^{14}$, and $R^{15}$ are as described herein for formulas (I) or (A). In several embodiments, such cycloalkyl or cycloalkenyl groups are substituted with: $C_1$-$C_3$ alkyl, —$NH_2$, —$NHC(O)$—$C_1$-$C_6$ alkyl, and/or —$NHC(O)O$—$C_1$-$C_6$ alkyl. In several embodiments, such cycloalkyl or cycloalkenyl groups include cyclohexanyl substituted with, where possible: 1-Me, 4-acetamido, 4-$NH_2$, and/or 4-tBOC—NH. In various embodiments, such cycloalkyl or cycloalkenyl groups include, e.g., cyclohexenyl substituted with 2-phenyl. In some embodiments, such cycloalkyl or cycloalkenyl groups include, e.g., bicyclooctanyl substituted with 4-$NH_2$ or 4-tBOC—NH.

For each generic structure herein where a point of attachment or a substituent of a multicyclic group, e.g., a bridged bicyclic or condensed bicyclic compound, is indicated generically in the chemical structure by a bond crossing one ring of the multicyclic group, it should be understood that attachment to any suitable ring atom of any ring of the multicyclic group is indicated. For example, in the indanyl group depicted above for II-A-6b, the indanyl group is considered as a cyclopentyl ring condensed with a phenyl ring. In various embodiments, the indanyl group is bonded to the depicted carbonyl group, where possible, to a position selected from the cyclopentyl ring, that is, one of positions 1, 2, or 3 of the indanyl group, or at the phenyl ring, that is, positions 4, 5, 6, or 7 of the indanyl group. Likewise, each $R^{12}$ is bonded, where possible, to a position selected from the cyclopentyl ring, that is, one of positions 1, 2, or 3 of the indanyl group, or at the phenyl ring, that is, positions 4, 5, 6, or 7 of the indanyl group.

In some embodiments of the compound represented by formula (II-A), the group represented by $R^3$ is monocyclic, condensed bicyclic, or bridged bicyclic, and is, for example, saturated or unsaturated 3- to 12-membered heterocyclyl optionally substituted by $R^{3f}$ representing, where possible, $R^{12}$, as described herein for formulas (I) or (A). For example, in various embodiments, $R^3$ represents: azetidinyl, e.g., azetidin-2-yl or azetidin-3-yl; pyrrolidinyl, e.g., pyrrolidin-1-yl, or pyrrolidin-2-yl; tetrahydrofuranyl, e.g., tetrahydrofuran-3-yl; thiazolidinyl, e.g., thiazolidin-4-yl; piperidinyl, e.g., piperidin-1-yl, piperidin-2-yl, piperidin-3-yl, or piperidin-4-yl; tetrahydropyranyl, e.g., tetrahydro-2H-pyran-3-yl or tetrahydro-2H-pyran-4-yl; piperazinyl, e.g., piperazin-1-yl; morpholinyl, e.g., morpholin-3-yl or morpholin-4-yl; dihydropyridinyl, e.g., 1,6-dihydropyridin-3-yl; chromanyl, e.g., chroman-4-yl; azabicyclononanyl, e.g., azabicyclo[3.3.1]nonan-9-yl; oxabicycloheptanyl, e.g., 7-oxabicyclo[2.2.1]heptan-2-yl; or oxabicyclooctanyl, e.g., 8-oxabicyclo[3.2.1]octan-3-yl. For example, in various embodiments, the compound is represented by any one of formulas (II-A-6a), (II-A-6b), (II-A-6c), (II-A-6d), (II-A-6e), (II-A-6f), (II-A-6g), (II-A-6h), (II-A-6i), (II-A-6j), (II-A-6k), (II-A-6l), or (II-A-6m).

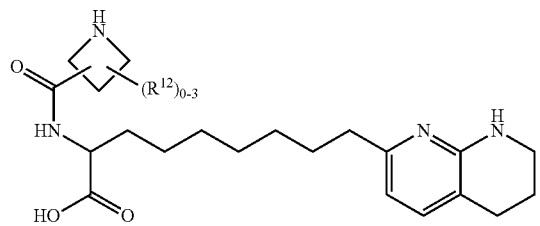

(II-A-6b)
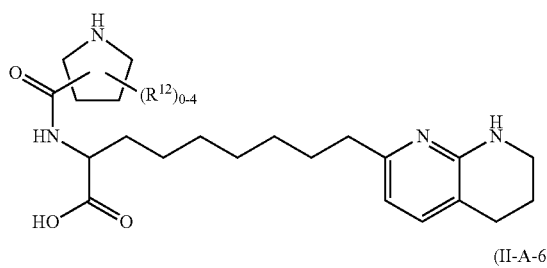
(II-A-6c)
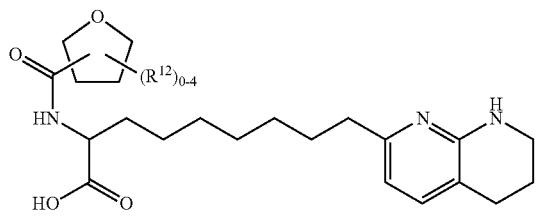
(II-A-6d)
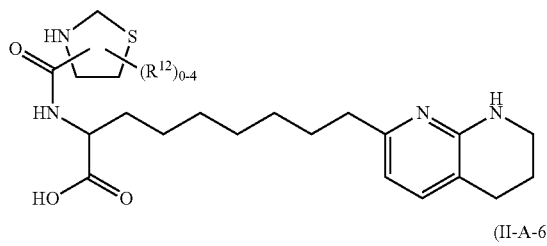
(II-A-6e)
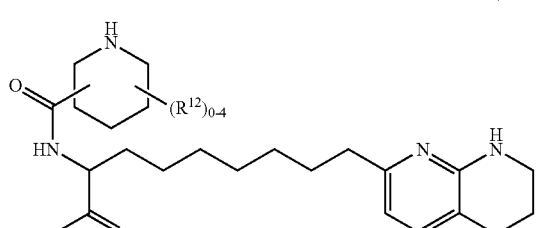
(II-A-6f)
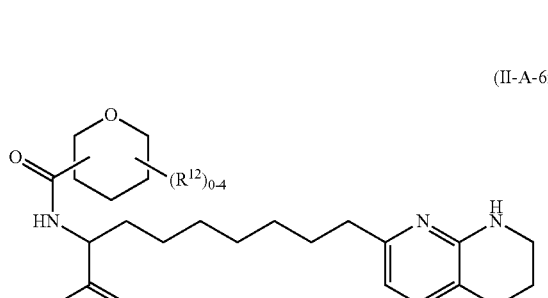
(II-A-6g)
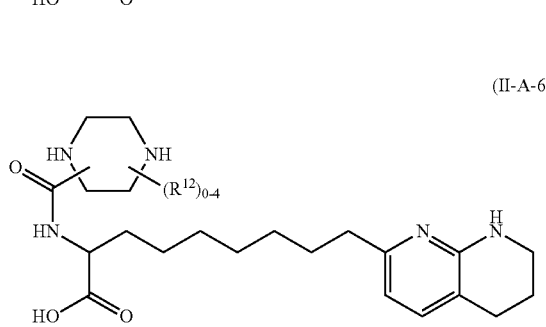
(II-A-6h)
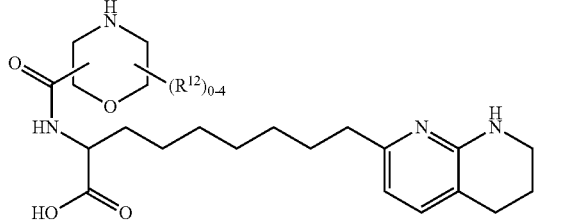
(II-A-6i)
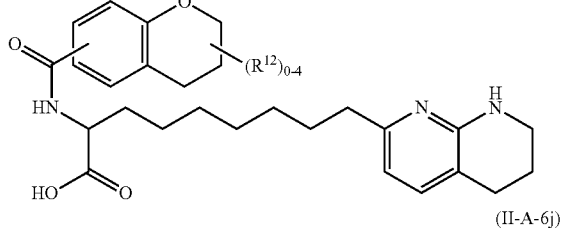
(II-A-6j)
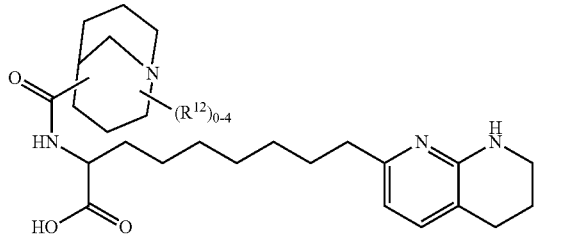
(II-A-6k)
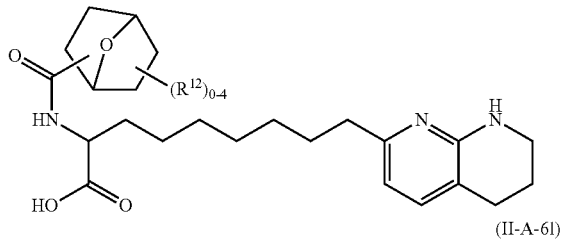
(II-A-6l)
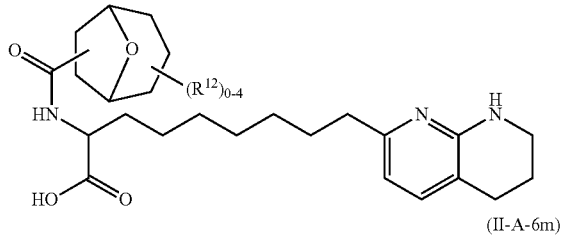
(II-A-6m)
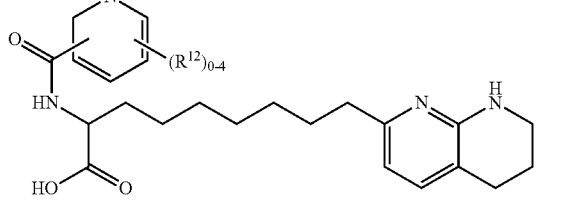
Such saturated or unsaturated 3- to 12-membered monocyclic heterocyclyl groups, are substituted with up to four of the groups encompassed herein for $R^{12}$, for example, in some embodiments: $C_1$-$C_6$ alkyl optionally substituted by halogen, —$OR^{16}$, $C_6$-$C_{14}$ aryl, 5- to 10-membered heteroaryl, —NR¹⁶R¹⁷, or —NR¹⁶C(O)OR¹⁸; —C(O)R¹³; —C(O)OR¹³; —S(O)₂R¹³; cyano; halogen; $C_6$-$C_{14}$ aryl; and/or 5- to 10-membered heteroaryl, wherein $R^{13}$, $R^{16}$, $R^{17}$, and $R^{18}$ are as described herein for formulas (I) or (A). In several embodiments, such saturated or unsaturated 3- to 12-membered monocyclic heterocyclyl groups are substituted with up to four of the groups encompassed herein for $R^{12}$, for example, in some embodiments: $C_1$-$C_6$ alkyl optionally substituted by halogen, —OH, phenyl, 5- to 10-membered heteroaryl, —NH₂, or —NH—C(O)O—$C_1$-$C_6$ alkyl; —C(O)—$C_1$-$C_6$ alkylene-O—$C_1$-$C_6$ alkyl; —C(O)—O—$C_1$-$C_6$ alkyl; —S(O)₂—$C_1$-$C_6$ alkyl; —S(O)₂—($C_6$-$C_{14}$ aryl); cyano; halogen; $C_6$-$C_{14}$ aryl; and/or 5- to 10-membered heteroaryl. In some embodiments, an azetidinyl group is substituted, where possible, with, e.g., N-benzyl, 3-methyl, and/or N-tBOC. In several embodiments, a pyrrolidinyl group is substituted, where possible, with up to four of: 2-Me, 3-Me, 5-Me, N-(3-methoxypropanoyl), N-phenyl, N-benzyl, N-pyridinyl, N-(pyridin-3-yl)methyl, N-(pyridin-4-yl)methyl, N-(pyrimidin-2-yl)methyl, N-(pyrimidin-4-yl)methyl, and/or N—SO₂Ph. In various embodiments, a tetrahydrofuranyl group is substituted with up to three Me, e.g., 3-Me. In some embodiments, a thiazolidinyl group is substituted with, e.g., 5,5-di-Me and/or N—SO₂Ph. In several embodiments, a piperidinyl group is substituted, where possible, with up to four of: 3-Me, 4-Me, 3,3-di-F, 2,6 di-Me, N-(3-methoxypropanoyl), N-acetyl, N-t-butylcarbonyl, N-tBOC, N—CH₃SO₂, 4-CF₃, N-(3-fluoropropyl), N-(3,3,3-trifluoropropyl), 4-(2,2-difluoroethyl), and/or N-(1-methyl pyrazol-4-yl)methyl). In some embodiments, a tetrahydropyranyl group is substituted, where possible, with up to four of: 2-Me, 3-Me, 4-Me, 6-Me, 4-HOCH₂—, 4-NH₂CH₂—, 4-CN, 4-CF₃, 4-F, 4-phenyl, and/or 4-tBoc-NHmethyl. In several embodiments, a tetrahydropyran-4-yl group is substituted according to one of: 2-Me, 2,2-di-Me, 2,2,6,6-tetra-Me, 3-Me, 4-Me, 6-Me, 4-HOCH₂—, 4-CF₃, 4-F, or 4-phenyl. In various embodiments, a morpholino group is substituted with alkyl, e.g., methyl, such as 3,5-dimethyl, and/or tBOC, e.g., N-tBOC.

In some embodiments of the compound of formula (II), wherein G is —R⁴, the compound is of the formula (II-B):

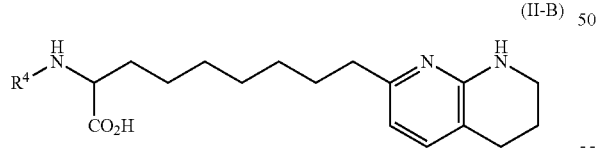

(II-B)

or a salt thereof, wherein $R^4$ is as defined for formula (I). The description above of embodiments for formula (I) also apply equally to formula (A) to provide the corresponding embodiments of formula (A).

For example, in various embodiments of the compound represented by formula (II-B), the group represented by $R^4$ is $C_1$-$C_6$ alkyl, optionally substituted by up to four $R^{4a}$ representing, where possible, oxo or $R^{12}$ as described herein for formulas (I) or (A). Suitable alkyl groups include, e.g., methyl or ethyl. For example, the compound is represented by any one of formulas (II-B-1a) or (II-B-1b).

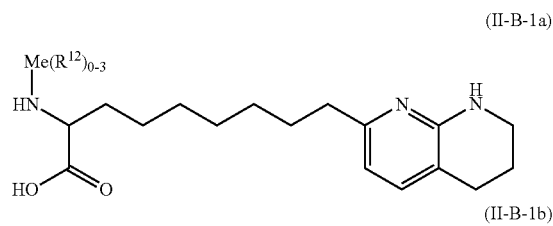

(II-B-1a)

(II-B-1b)

Suitable substituents for such alkyl groups include $C_6$-$C_{14}$ aryl, halogen, 3- to 12-membered heterocyclyl, and 5- to 10-membered heteroaryl. For example, ethyl is substituted with 1-Ph, 1-(tetrahydropyran-4-yl), F, e.g., 2,2,2-tri-F, and/or 1-(pyridin-3-yl). Methyl is substituted with, e.g., Ph, 4-methyltetrahydropyran-4-yl, 1H-pyrrolo[2,3-b]pyridin-3-yl, quinolin-4-yl, quinolin-6-yl, or quinolin-8-yl.

In some embodiments of the compound represented by formula (II-B), the group represented by $R^4$ is $C_3$-$C_8$ cycloalkyl, optionally substituted by up to four $R^{4b}$ representing, where possible, oxo or $R^{12}$ as described herein for formulas (I) or (A). Suitable cycloalkyl groups include, e.g., cyclopentyl or cyclohexyl. For example, the compound is represented by any one of formulas (II-B-2a) or (II-B-2b).

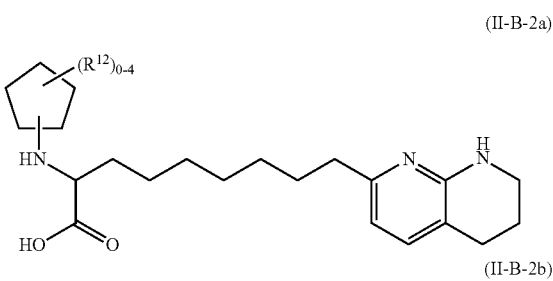

(II-B-2a)

(II-B-2b)

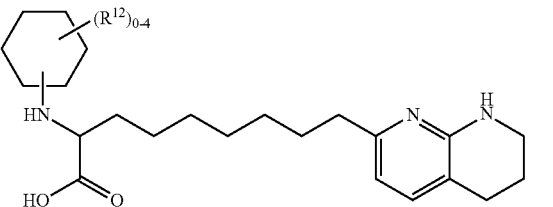

Suitable substituents for such cycloalkyl groups include oxo, $C_6$-$C_{14}$ aryl, halogen, 3- to 12-membered heterocyclyl, and 5- to 10-membered heteroaryl. For example, substituents include methyl, ethyl, Ph, tetrahydropyran-4-yl, F, Cl, pyridine-3-yl, 1H-pyrrolo[2,3-b]pyridin-3-yl, quinolin-4-yl, quinolin-6-yl, or quinolin-8-yl.

In several embodiments of the compound represented by formula (II-B), the group represented by $R^4$ is 3- to 12-membered heterocyclyl, optionally substituted by up to four $R^{4c}$ representing, where possible, oxo or $R^{12}$ as described herein for formulas (I) or (A). For example, the compound is represented by any one of formulas (II-B-3a) or (II-B-3b).

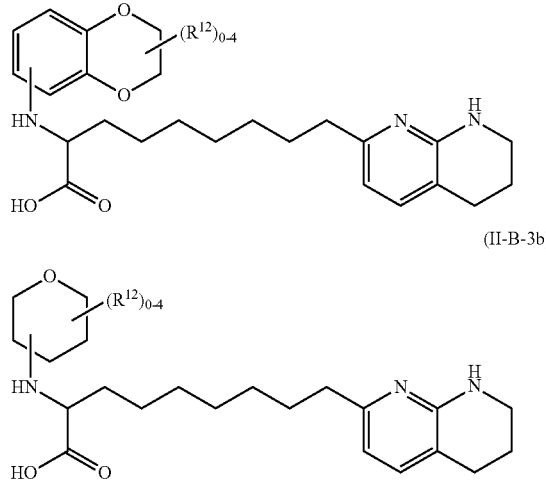

(II-B-3a)

(II-B-3b)

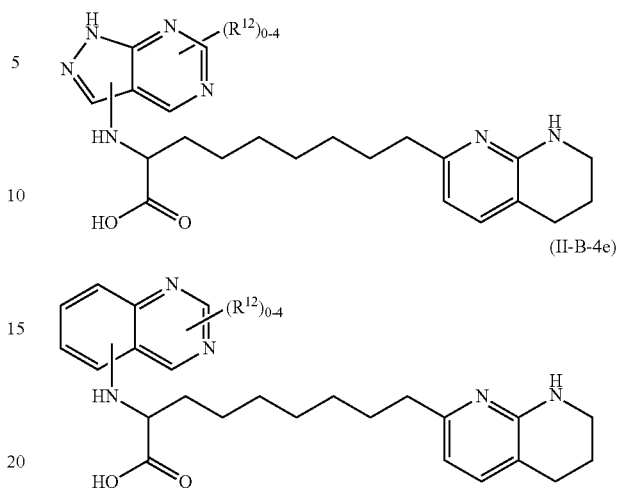

(II-B-4d)

(II-B-4e)

In some embodiments of the compound represented by formula (II-B), the group represented by $R^4$ is 5- to 10-membered heteroaryl, optionally substituted by up to four $R^{4e}$ representing, where possible, oxo or $R^{12}$ as described herein for formulas (I) or (A). Suitable heteroaryl groups include, e.g., pyrazolyl, e.g., pyrazol-4-yl; pyrimidinyl, e.g., pyrimidin-2-yl, pyrimidin-4-yl; quinazolinyl, e.g., quinazolin-4-yl; or pyrazolyl, e.g., pyrazol-4-yl. For example, the compound is represented by any one of formulas (II-B-4a), (II-B-4b), (II-B-4c), (II-B-4d), or (II-B-4e).

Suitable substituents for such heteroaryl groups include $C_1$-$C_6$ alkyl, —$NR^{14}R^{15}$, —$S(O)_2R^{13}$, halogen, 3- to 12-membered heterocyclyl, and/or 5- to 10-membered heteroaryl, wherein $R^{13}$, $R^{14}$, and $R^{15}$ are as described herein for formulas (I) or (A). In some embodiments, suitable substituents for such heteroaryl groups include $C_1$-$C_3$ alkyl, —NH—$C_1$-$C_6$ alkyl, —N($C_1$-$C_6$ alkyl)$_2$, —$S(O)_2$—$C_1$-$C_6$ alkyl, halogen, 3- to 10-membered heterocyclyl, and/or 5- to 10-membered heteroaryl. For example, substituents for pyrazolyl include, e.g., 1-Me (i.e., N-Me), 3-Me, or 5-Me. Substituents for pyrimidinyl include, e.g., 6-$NMe_2$, 6-$SO_2$propyl, 6-(pyrrolidin-1-yl), 6-(morpholin-1-yl), 4-(4,4-difluoropiperidin-1-yl), 5-(pyridin-3-yl), and/or 5-(pyridin-4-yl). Suitable substituents for quinolinyl include halo, e.g., 8-Br.

In various embodiments of the compound represented by formula (II-B), the group represented by $R^4$ is $C_6$-$C_{14}$ aryl, optionally substituted by up to four $R^{4d}$ representing, where possible, oxo or $R^{12}$ as described herein for formulas (I) or (A). Suitable aryl groups include, e.g., phenyl, indanyl, or indenyl. For example, the compound is represented by any one of formulas (II-B-5a) or (II-B-5b).

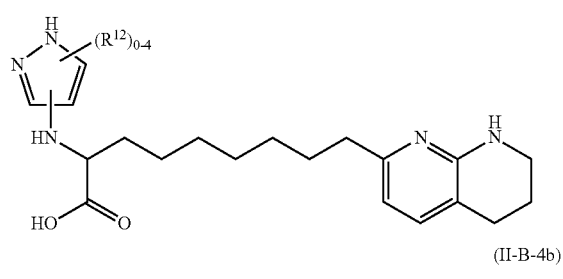

(II-B-4a)

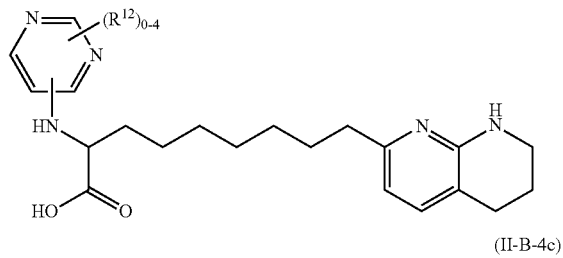

(II-B-4b)

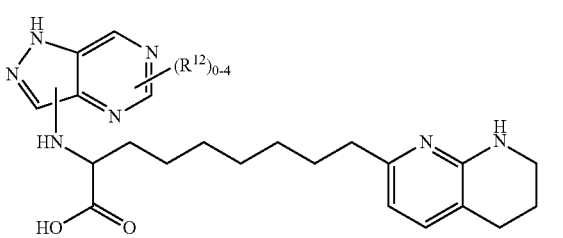

(II-B-4c)

(II-B-5a)

(II-B-5b)

Suitable substituents for such aryl groups include oxo (e.g., for the saturated indanyl or indenyl carbons), $C_6$-$C_{14}$ aryl, halogen, 3- to 12-membered heterocyclyl, and 5- to 10-membered heteroaryl. For example, substituents include methyl, ethyl, Ph, tetrahydropyran-4-yl, F, Cl, pyridine-3-yl, 1H-pyrrolo[2,3-b]pyridin-3-yl, quinolin-4-yl, quinolin-6-yl, or quinolin-8-yl.

Also provided is a compound of formula (I), or a salt thereof, wherein G is —C(O)$R^3$. In one variation, G is —C(O)$R^3$, wherein $R^3$ is $C_1$-$C_6$ alkyl substituted by 0-5 $R^{3d}$ (e.g., $R^3$ is unsubstituted $C_4$-$C_5$ alkyl or $C_1$-$C_3$ alkyl substituted by 0-5 $R^{3d}$). In another variation, G is —C(O)$R^3$, wherein $R^3$ is $C_1$-$C_3$ alkyl substituted by 1-5 $R^{3d}$. In another variation, G is —C(O)$R^3$, wherein $R^3$ is $C_1$-$C_3$ alkyl substituted by 1-5 $R^{3d}$, wherein at least one of the $R^{3d}$ is —O$R^3$ (e.g., $R^{13}$ is hydrogen or $C_1$-$C_6$ alkyl). In another variation, G is —C(O)$R^3$, wherein $R^3$ is $C_1$-$C_3$ alkyl substituted by 1-5 $R^{3d}$, wherein at least one of the $R^{3d}$ is $C_6$-$C_{14}$ aryl substituted by 0-5 halogen (e.g., $R^{3d}$ is unsubstituted phenyl or phenyl substituted by 1-4 halogen). In another variation, G is —C(O)$R^3$, wherein $R^3$ is $C_1$-$C_3$ alkyl substituted by 2-5 $R^{3d}$, wherein at least one $R^{3d}$ is unsubstituted phenyl and at least one $R^{3d}$ is O$R^{13}$. In another variation, G is —C(O)$R^3$, wherein $R^3$ is $C_1$-$C_3$ alkyl substituted by 1-5 $R^{3d}$, wherein at least one of the $R^{3d}$ is 3- to 12-membered heterocyclyl substituted by 0-5 —C(O)O$R^6$ (e.g., $R^{3d}$ is pyrrolidinyl substituted by at least one —C(O)O$R^6$). In another variation, G is —C(O)$R^3$, wherein $R^3$ is $C_1$-$C_3$ alkyl substituted by 1-5 $R^{3d}$, wherein at least one of the $R^{3d}$ is 3- to 12-membered heterocyclyl substituted by 0-5 —C(O)O$R^{16}$ (e.g., $R^3$ is pyrrolidinyl substituted by at least one —C(O)O$R^6$), wherein $R^{16}$ is $C_1$-$C_4$ alkyl. In another variation, G is —C(O)$R^3$, wherein $R^3$ is $C_1$-$C_3$ alkyl substituted by 1-5 $R^{3d}$, wherein at least one of the $R^{3d}$ is 5- to 10-membered heteroaryl substituted by 0-5 $R^{12a}$ (e.g., $R^{3d}$ is unsubstituted pyridinyl). In another variation, G is —C(O)$R^3$, wherein $R^3$ is $C_1$-$C_3$ alkyl substituted by 1-5 $R^{3d}$, wherein at least one of the $R^{3d}$ is —S(O)$_2R^{13}$, —N$R^{13}$S(O)$_2R^{14}$, or —S(O)$_2$N$R^{14}R^{15}$. The description above of embodiments for formula (I) also apply equally to formula (A) to provide the corresponding embodiments of formula (A).

Also provided is a compound of formula (I), or a salt thereof, wherein G is —C(O)$R^3$ and $R^3$ is $C_3$-$C_8$ cycloalkyl substituted by 0-5 $R^{3e}$ (e.g., $R^3$ is cyclohexanyl substituted by 0-5 $C_1$-$C_3$ alkyl or $R^3$ is bicyclo[1.1.1]pentanyl). The description above of embodiments for formula (I) also apply equally to formula (A) to provide the corresponding embodiments of formula (A).

Also provided in another embodiment is a compound of formula (I), or a salt thereof, wherein G is —C(O)$R^3$ and $R^3$ is 3- to 12-membered heterocyclyl (such as 4- to 6-membered heterocyclyl, e.g., azetidinyl, pyrrolidinyl, tetrahydrofuranyl, piperidinyl, tetrahydropyranyl, or morpholinyl), which is independently substituted by 0-5 $R^{3f}$. In another aspect of the foregoing embodiment, $R^3$ is substituted by 1-5 $R^{3f}$, wherein at least one $R^{3f}$ is $C_1$-$C_6$ alkyl substituted by 0-5 moieties selected from the group consisting of halogen, —N$R^{16}R^{17}$, —N$R^{16}$C(O)O$R^{18}$, 5- to 10-membered heteroaryl, and $C_6$-$C_{14}$ aryl, wherein the 5- to 10-membered heteroaryl and $C_6$-$C_{14}$ aryl of $R^{3f}$ are independently substituted by 0-5 $R^{12b}$. It is understood that in such embodiments wherein $R^3$ is substituted by 1-5 $R^{3f}$, wherein at least one $R^{3f}$ is $C_1$-$C_6$ alkyl substituted by 0-5 moieties selected from the group consisting of halogen, —N$R^{16}R^{17}$, —N$R^{16}$C(O)O$R^{18}$, 5- to 10-membered heteroaryl, and $C_6$-$C_{14}$ aryl, when $R^{3f}$ is $C_1$-$C_6$ alkyl substituted by 1-5 moieties selected from the group consisting of 5- to 10-membered heteroaryl and $C_6$-$C_{14}$ aryl, such 5- to 10-membered heteroaryl and $C_6$-$C_{14}$ aryl can be further independently substituted by 0-5 $R^{12b}$. In one aspect of the foregoing embodiment, at least one $R^{3f}$ is $C_1$-$C_2$ alkyl substituted by 0-5 fluoro, —NH$_2$, —NHC(O) O-t-butyl, pyridinyl, pyrimidinyl, or phenyl. In another aspect of the foregoing embodiment, $R^3$ is substituted by 1-5 $R^{3f}$, wherein at least one $R^{3f}$ is 5- to 10-membered heteroaryl or $C_6$-$C_{14}$ aryl, each of which is independently substituted by 0-5 $R^{12a}$. In one aspect of the foregoing embodiment, at least one $R^{3f}$ is unsubstituted 5- to 10-membered heteroaryl or unsubstituted $C_6$-$C_{14}$ aryl. In another aspect of the foregoing embodiment, at least one $R^{3f}$ is 5- to 10-membered heteroaryl or $C_6$-$C_{14}$ aryl, each of which is independently substituted by 1-5 $R^{12a}$. In another aspect of the foregoing embodiment, at least one $R^{3f}$ is pyridinyl or phenyl, each of which is independently optionally substituted. In another aspect of the foregoing embodiment, at least one $R^{3f}$ is substituted pyridinyl or substituted phenyl. In another aspect of the foregoing embodiment, at least one $R^{3f}$ is unsubstituted pyridinyl or unsubstituted phenyl. In another aspect of the foregoing embodiment, $R^3$ is substituted by 1-5 $R^{3f}$, wherein at least one $R^{3f}$ is —C(O)$R^{13}$, —C(O)O$R^{13}$, or —S(O)$_2R^{13}$. In one aspect of the foregoing embodiment, $R^{13}$ is independently $C_1$-$C_6$ alkyl substituted by 0-5 —O$R^{18}$, wherein $R^{18}$ is $C_1$-$C_6$ alkyl substituted by 0-5 deuterium, halogen, or oxo. In another aspect of the foregoing embodiment, $R^3$ is substituted by two or more $R^{3f}$, wherein each $R^{3f}$ is independently selected from the group consisting of $C_1$-$C_6$ alkyl, —C(O)$R^{13}$, and —C(O)O$R^{13}$. The description above of embodiments for formula (I) also apply equally to formula (A) to provide the corresponding embodiments of formula (A).

Also provided in another embodiment is a compound of formula (I), or a salt thereof, wherein G is —C(O)$R^3$ and $R^3$ is —O$R^{3a}$. In one aspect of the foregoing embodiment, $R^{3a}$ is $C_1$-$C_6$ alkyl or 3- to 12-membered heterocyclyl, each of which is independently substituted by 0-5 $R^{3g}$. In one aspect of the foregoing embodiment, $R^{3a}$ is $C_1$-$C_4$ alkyl (e.g., t-butyl) or 4- to 6-membered heterocyclyl (e.g., azetidinyl), each of which is independently substituted by 0-5 $R^{3g}$. In any of these aspects, in one variation, $R^{3g}$ is optionally substituted $C_1$-$C_6$ alkyl or —C(O)O$R^{13}$, wherein $R^{13}$ is $C_1$-$C_6$ alkyl. The description above of embodiments for formula (I) also apply equally to formula (A) to provide the corresponding embodiments of formula (A).

Also provided in another embodiment is a compound of formula (I), or a salt thereof, wherein G is —C(O)$R^3$ and $R^3$ is —N$R^{3b}R^{3c}$. In one aspect of the foregoing embodiment, $R^{3b}$ and $R^{3c}$ are independently $C_1$-$C_6$ alkyl. In another aspect of the foregoing embodiment, both $R^{3b}$ and $R^{3c}$ are $C_2$ alkyl. The description above of embodiments for formula (I) also apply equally to formula (A) to provide the corresponding embodiments of formula (A).

Also provided is a compound of formula (I), or a salt thereof, wherein G is —C(O)$R^3$ and $R^3$ is selected from the group consisting of:

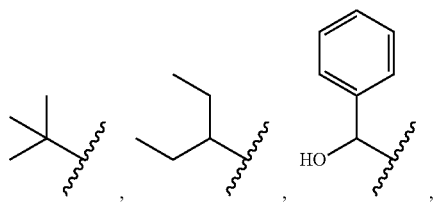

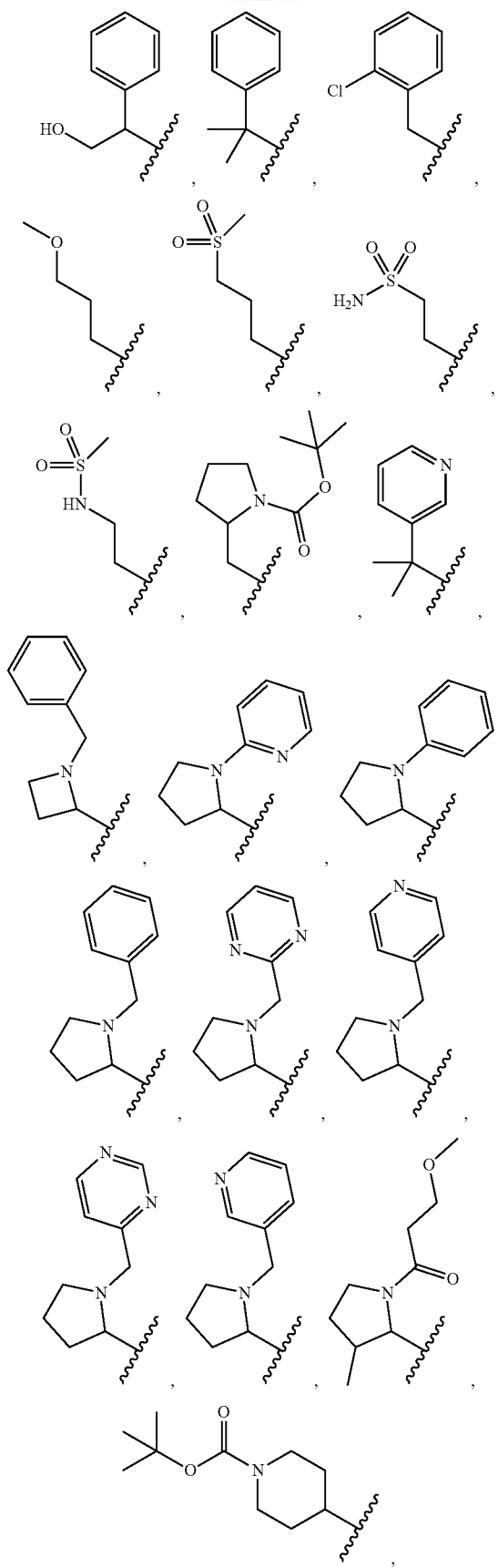
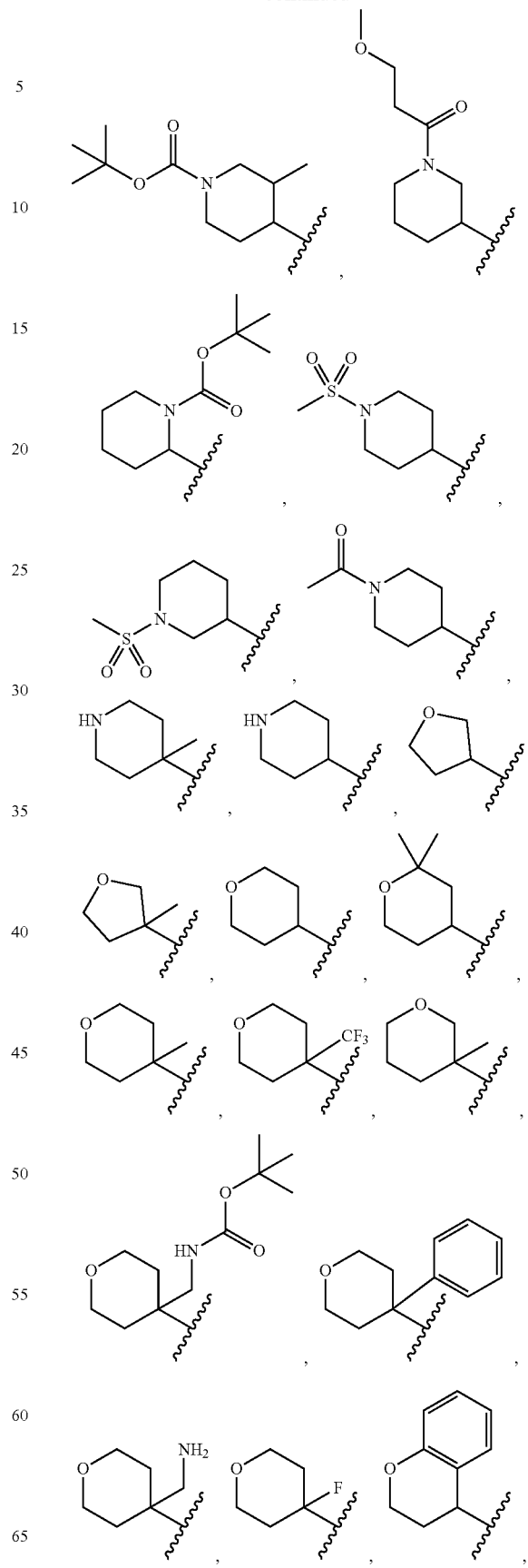

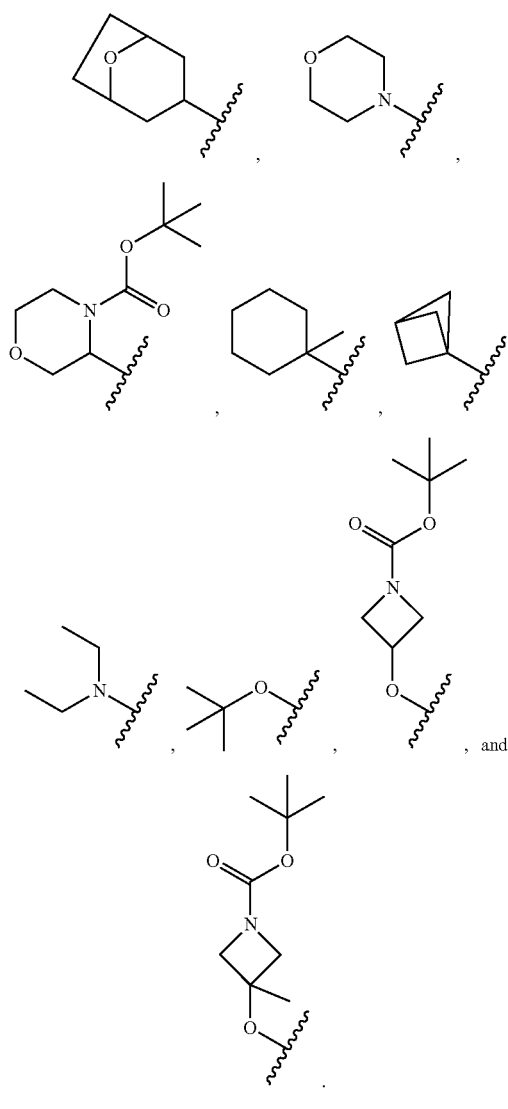
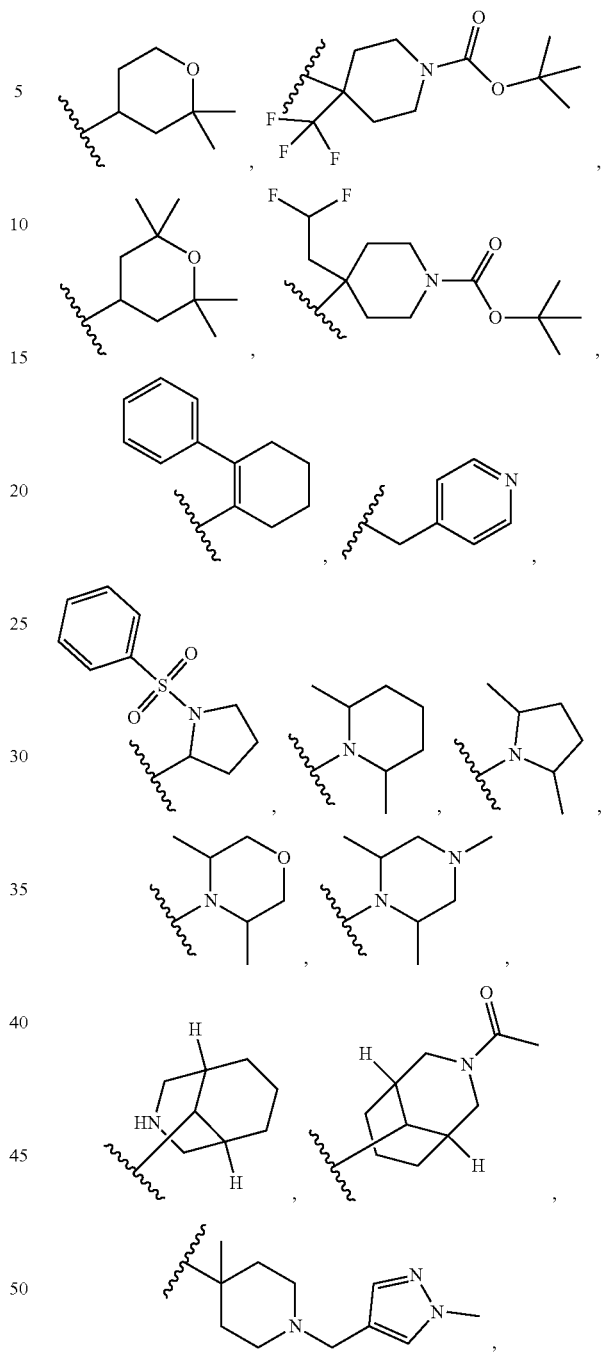
The description above of embodiments for formula (I) also apply equally to formula (A) to provide the corresponding embodiments of formula (A).
Also provided is a compound of formula (A), or (I), or a salt thereof, wherein G is —C(O)R$^3$ and R$^3$ is selected from the group consisting of

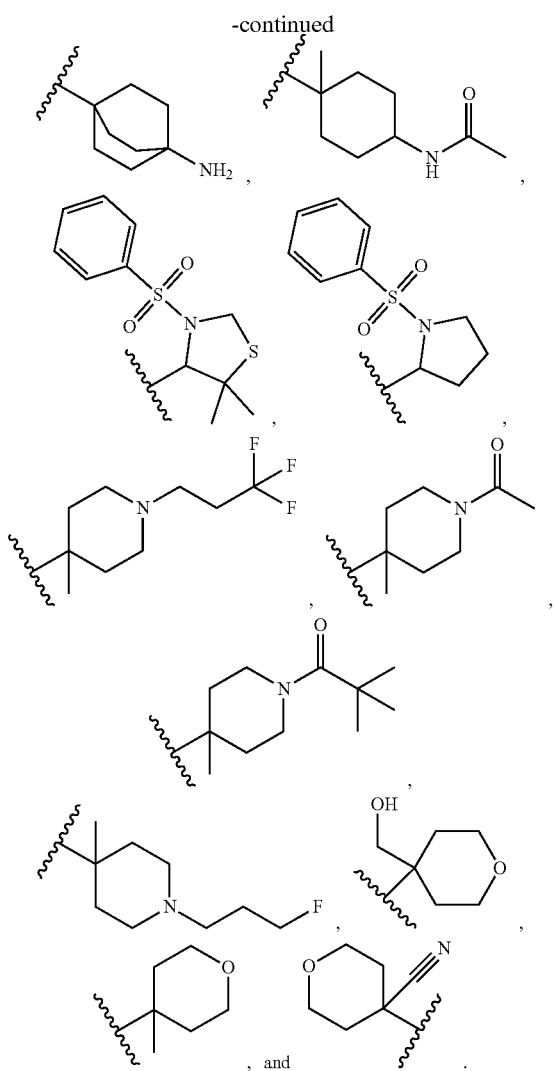

Also provided is a compound of formula (A), or (I), or a salt thereof, wherein G is —C(O)R³ and R³ is selected from the group consisting of all of the preceding structures depicted in this paragraph. Also provided are embodiments in any one or more hydrogen atom(s) in any of the preceding structures depicted in this paragraph is/are enriched, e.g., replaced with deuterium atom(s) or tritium atom(s). For example, in some embodiments, each hydrogen bonded to a ring carbon in the forgoing groups is replaced with a corresponding isotope, e.g., deuterium or tritium. Each hydrogen bonded to an acyclic carbon in the forgoing groups, e.g., methyl or methoxy carbons, is replaced with a corresponding isotope, e.g., deuterium or tritium. Further, for example, the forgoing groups are perdeuterated, in which every hydrogen is replaced with deuterium, or pertritiated, in which every hydrogen is replaced with tritium. In some embodiments, one or more ring carbons in the forgoing groups is/are replaced with $^{13}C$. For example, in polycyclic rings among the forgoing groups, one or more ring carbons in the ring directly bonded to the rest of the compound is/are replaced with $^{13}C$. In polycyclic rings among the forgoing groups, one or more ring carbons is/are replaced with $^{13}C$ in the ring that substitutes or is fused to the ring bonded to the rest of the compound. Further, for example, every ring carbon in the forgoing groups are replaced with $^{13}C$.

Also provided is a compound of formula (I), or a salt thereof, wherein G is $R^4$ and $R^4$ is $C_1$-$C_6$ alkyl (such as $C_1$-$C_2$ alkyl) substituted by 0-5 $R^{4a}$; wherein when $R^4$ is substituted by 1-5 $R^{4a}$, at least one $R^{4a}$ is 3- to 12-membered heterocyclyl (such as a 10-membered heterocyclyl, e.g., benzo-1,4-dioxanyl), 5- to 10-membered heteroaryl (such as 9- to 10-membered heteroaryl, e.g., quinolinyl or pyrrolopyridinyl), or $C_6$-$C_{14}$ aryl (such as $C_6$ aryl, e.g., phenyl), each of which is independently substituted by 0-5 (e.g., 0 or 1) $R^{12a}$. The description above of embodiments for formula (I) also apply equally to formula (A) to provide the corresponding embodiments of formula (A).

Also provided is a compound of formula (I), or a salt thereof, wherein G is $R^4$ and $R^4$ 5- to 10-membered heteroaryl (e.g., pyrimidinyl, such as pyrimidin-4-yl, or pyrimidin-2-yl) substituted by 0-5 (e.g., 0-3) $R^{4e}$. In one variation, the 5- to 10-membered heteroaryl (e.g., pyrimidinyl, such as pyrimidin-4-yl, or pyrimidin-2-yl) of $R^4$ is unsubstituted. In one variation, 5- to 10-membered heteroaryl of $R^4$ is substituted by 1-5 $R^{4e}$. In another variation, the 5- to 10-membered heteroaryl is substituted by 1-5 $R^{4e}$, wherein at least one $R^{4e}$ is $C_1$-$C_6$ alkyl, 3- to 12-membered heterocyclyl, 5- to 10-membered heteroaryl, —$NR^{14}R^{15}$, or —$S(O)_2R^{13}$, wherein the $C_1$-$C_6$ alkyl, 3- to 12-membered heterocyclyl, and 5- to 10-membered heteroaryl of $R^{4e}$ are independently substituted by 0-5 $R^{12a}$. In another variation, the 5- to 10-membered heteroaryl is substituted by 1-5 $R^{4e}$, wherein at least one $R^{4e}$ is $C_1$-$C_4$ alkyl, 5- to 6-membered heterocyclyl, or 6-membered heteroaryl, each of which is independently substituted by 0-5 halogen. In any of these aspects, $R^{4e}$, in one variation, is methyl, difluoromethyl, trifluoromethyl, t-butyl, pyrrolidinyl, morpholinyl, or optionally substituted piperidinyl. In another variation, the 5- to 10-membered heteroaryl of $R^4$ is substituted by 2-5 $R^{4e}$, wherein at least one $R^{4e}$ is methyl and at least one $R^{4e}$ is trifluoromethyl. In another variation, $R^4$ is quinazolinyl or pyrazolopyrimidinyl, each of which is independently substituted by 0-5 $R^{4e}$ (e.g., unsubstituted quinazolinyl, unsubstituted pyrazolopyrimidinyl, quinazolinyl substituted by 1-5 $R^{4e}$, or pyrazolopyrimidinyl substituted by 1-5 $R^{4e}$). In another variation, $R^4$ is quinazolinyl or pyrazolopyrimidinyl substituted by 1-5 $R^{4e}$, wherein at least one $R^{4e}$ is $C_1$-$C_6$ alkyl or halogen. The description above of embodiments for formula (I) also apply equally to formula (A) to provide the corresponding embodiments of formula (A).

When a moiety is contemplated, it is understood that the moiety can be attached to the rest of the structure at any available position. For example, 2-methylpyridinyl may be attached to the rest of the structure at the 3-, 4-, 5-, or 6-position (i.e., 2-methylpyridin-3-yl, 2-methylpyridin-4-yl, 2-methylpyridin-5-yl, or 2-methylpyridin-6-yl, respectively).

Also provided is a compound of formula (I), or a salt thereof, wherein G is $R^4$ and $R^4$ is selected from the group consisting of:

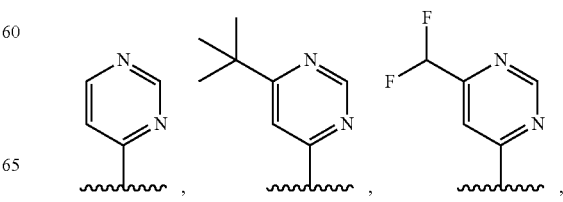

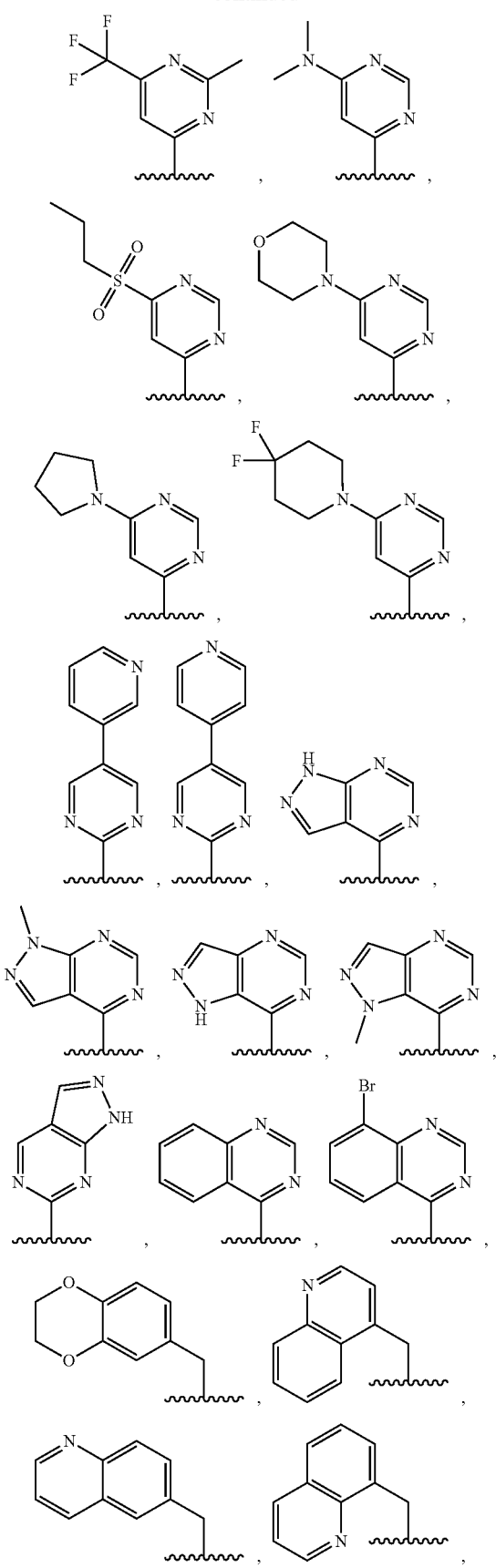

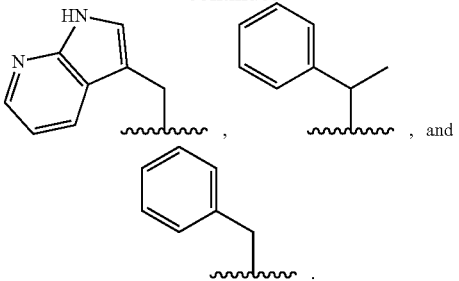

, and

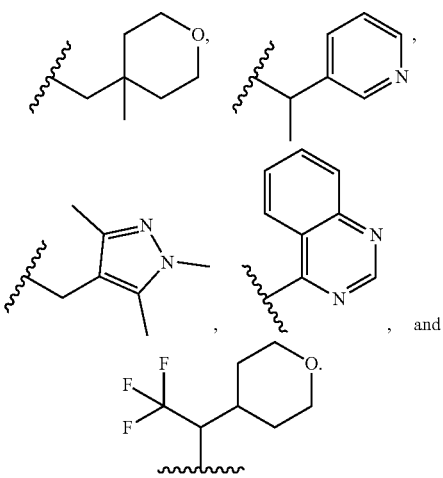

The description above of embodiments for formula (I) also apply equally to formula (A) to provide the corresponding embodiments of formula (A).

Also provided is a compound of formula (A), or (I), or a salt thereof, wherein G is $R^4$ and $R^4$ is selected from the group consisting of:

Also provided is a compound of formula (A), or (I), or a salt thereof, wherein G is $R^4$ and $R^4$ is selected from the group consisting of all of the preceding structures depicted in this paragraph. Also provided are embodiments in any one or more hydrogen atom(s) in any of the preceding structures depicted in this paragraph is/are enriched, e.g., replaced with deuterium atom(s) or tritium atom(s). For example, in some embodiments, each hydrogen bonded to a ring carbon in the forgoing groups is replaced with a corresponding isotope, e.g., deuterium or tritium. Each hydrogen bonded to an acyclic carbon in the forgoing groups, e.g., methyl or methoxy carbons, is replaced with a corresponding isotope, e.g., deuterium or tritium. Further, for example, the forgoing groups are perdeuterated, in which every hydrogen is replaced with deuterium, or pertritiated, in which every hydrogen is replaced with tritium. In some embodiments, one or more ring carbons in the forgoing groups is/are replaced with $^{13}C$. For example, in polycyclic rings among the forgoing groups, one or more ring carbons in the ring directly bonded to the rest of the compound is/are replaced with $^{13}C$. In polycyclic rings among the forgoing groups, one or more ring carbons is/are replaced with $^{13}C$ in the ring that substitutes or is fused to the ring bonded to the rest of the compound. Further, for example, every ring carbon in the forgoing groups is replaced with $^{13}C$.

Also provided is a compound of formula (I), or a salt thereof, wherein G is selected from the group consisting of:

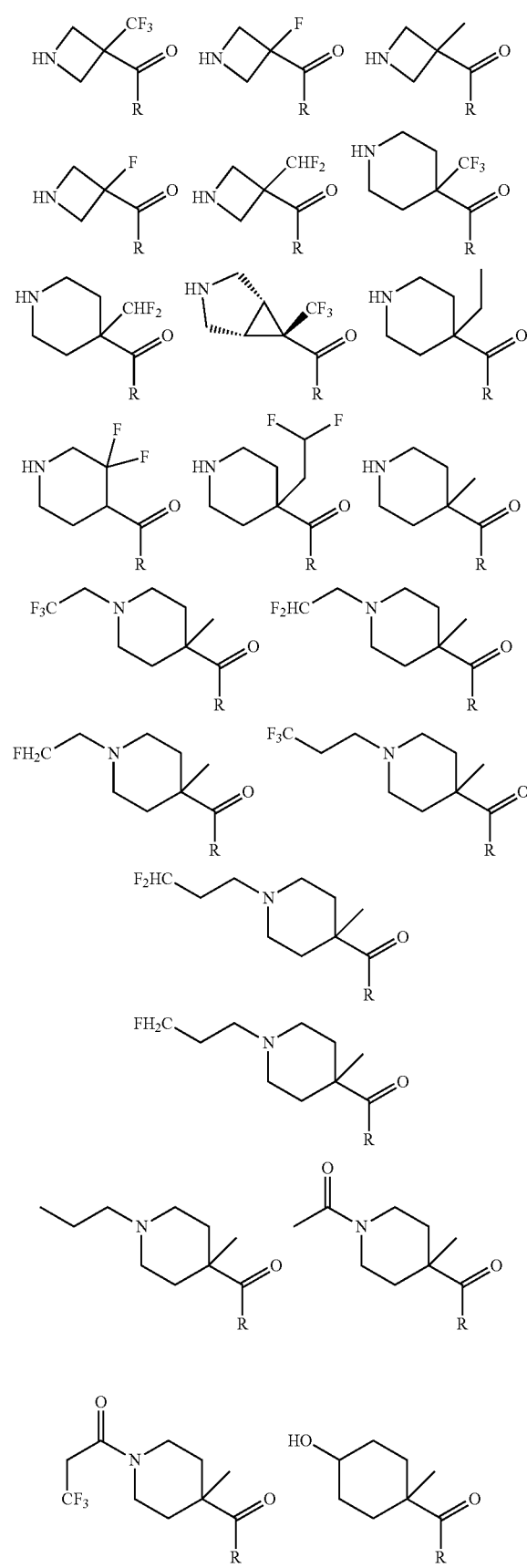
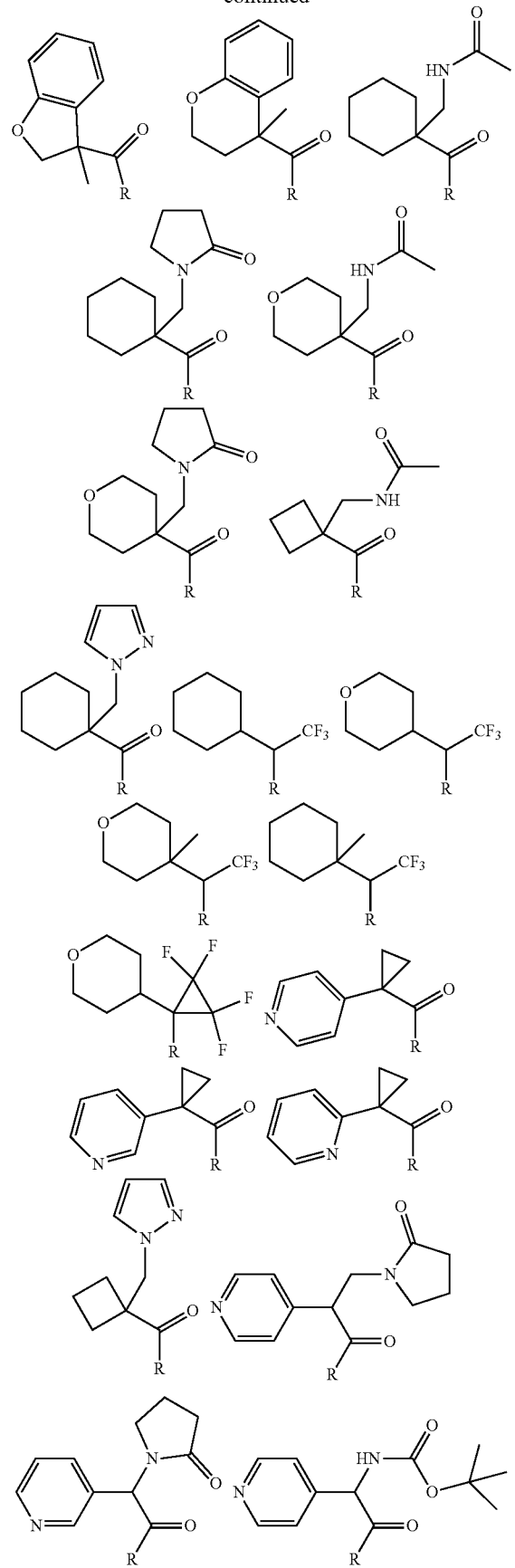

-continued
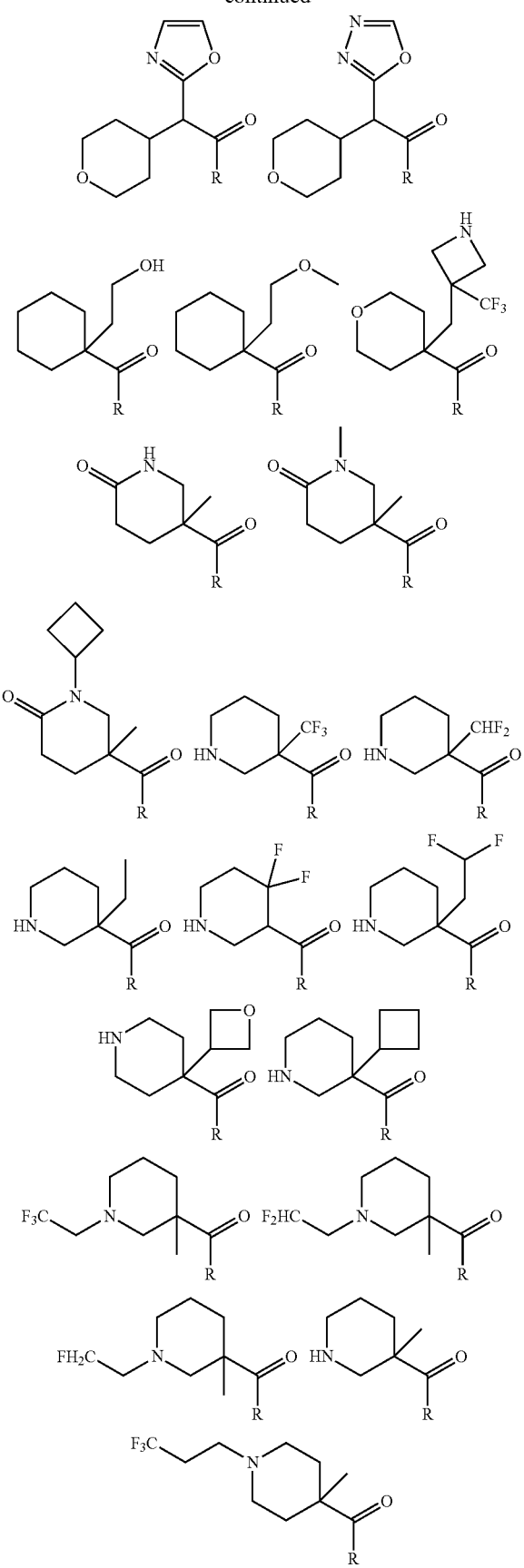
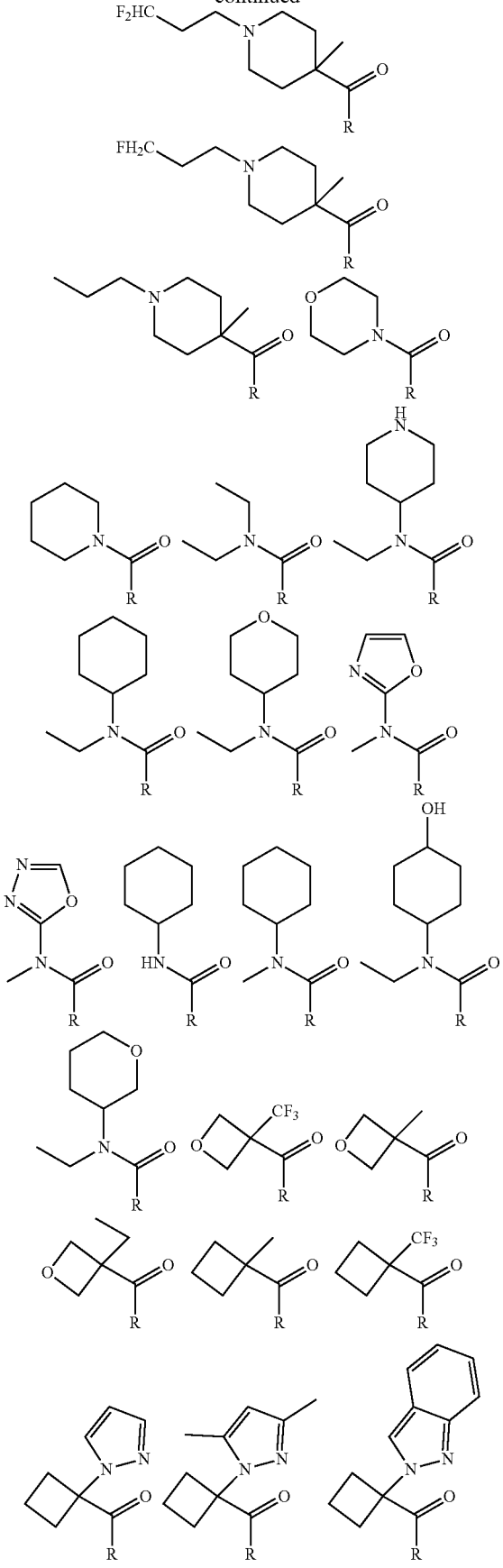

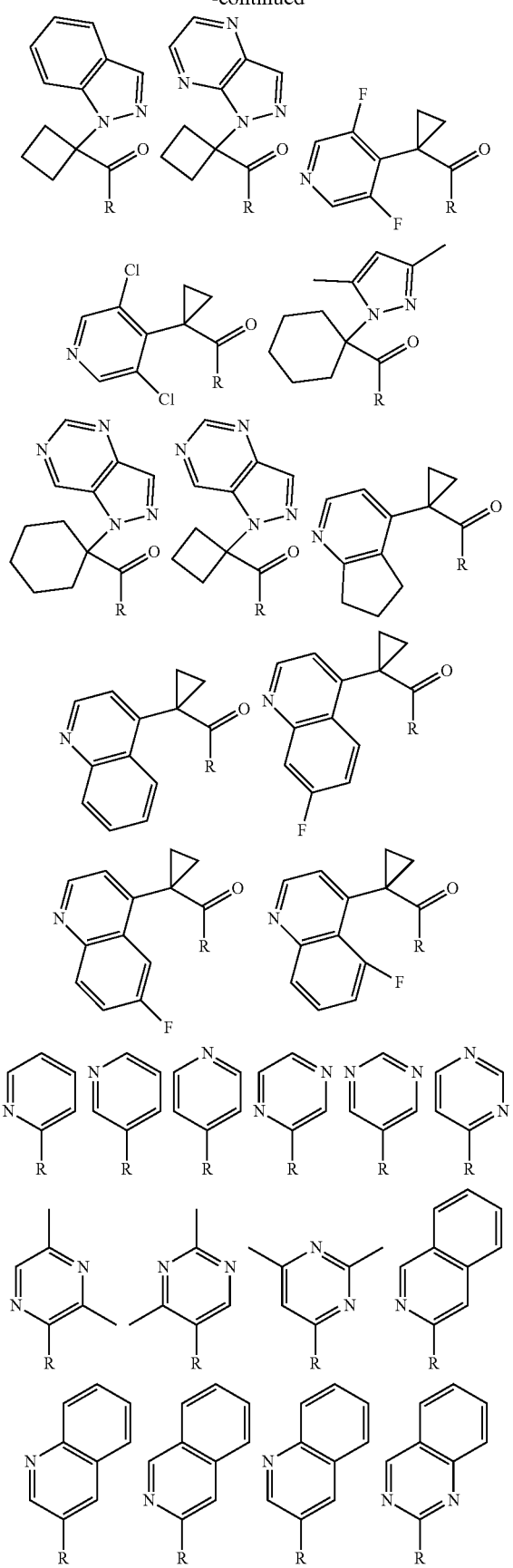
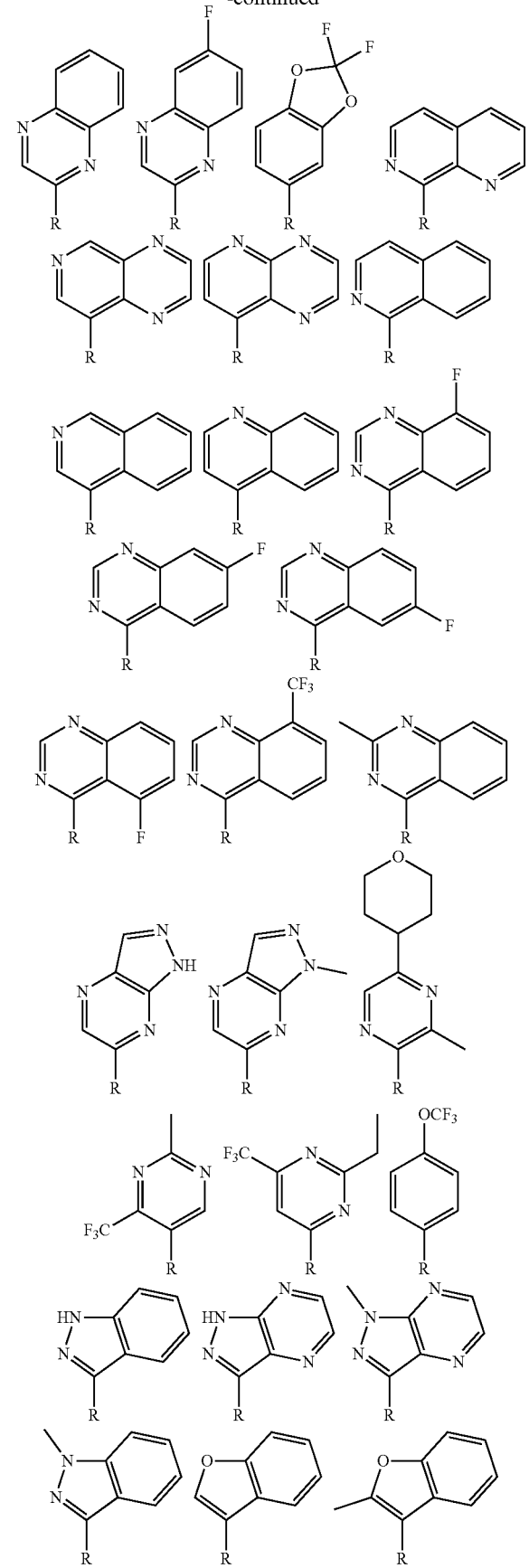

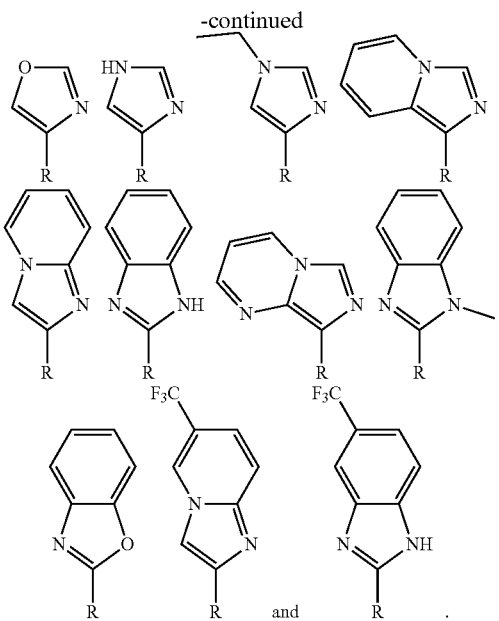

In the moieties listed above, R indicates the point of attachment to the N of the parent molecule. The description above of embodiments for formula (I) also apply equally to formula (A) to provide the corresponding embodiments of formula (A). Also provided are embodiments in any one or more hydrogen atom(s) in any of the preceding structures depicted in this paragraph is/are enriched, e.g., replaced with deuterium atom(s) or tritium atom(s). For example, in some embodiments, each hydrogen bonded to a ring carbon in the forgoing groups is replaced with a corresponding isotope, e.g., deuterium or tritium. Each hydrogen bonded to an acyclic carbon in the forgoing groups, e.g., methyl or methoxy carbons, is replaced with a corresponding isotope, e.g., deuterium or tritium. Further, for example, the forgoing groups are perdeuterated, in which every hydrogen is replaced with deuterium, or pertritiated, in which every hydrogen is replaced with tritium. In some embodiments, one or more ring carbons in the forgoing groups is/are replaced with $^{13}C$. For example, in polycyclic rings among the forgoing groups, one or more ring carbons in the ring directly bonded to the rest of the compound is/are replaced with $^{13}C$. In polycyclic rings among the forgoing groups, one or more ring carbons is/are replaced with $^{13}C$ in the ring that substitutes or is fused to the ring bonded to the rest of the compound. Further, for example, every ring carbon in the forgoing groups is replaced with $^{13}C$.

Representative compounds are listed in Table 1, FIG. 1.

Representative compounds are listed in Table 1, FIG. 1, for example, in various embodiments, Compound Nos. 1-77, Compound Nos. 78-124, and Compound Nos. 1-124.

In some embodiments, provided is a compound selected from Compound Nos. 1-77 in Table 1, FIG. 1, or a stereoisomer thereof (including a mixture of two or more stereoisomers thereof), or a salt thereof. In some embodiments, the compound is a salt of a compound selected from Compound Nos. 1-77 in Table 1, FIG. 1, or a stereoisomer thereof.

In some embodiments, provided is a compound selected from Compound Nos. 1-77 in Table 1, FIG. 1, or a stereoisomer thereof (including a mixture of two or more stereoisomers thereof), or a salt thereof. In some embodiments, the compound is a salt of a compound selected from Compound Nos. 1-77 in Table 1, FIG. 1, or a stereoisomer thereof. In some embodiments, provided is a compound selected from Compound Nos. 1-124 in Table 1, FIG. 1, or a stereoisomer thereof (including a mixture of two or more stereoisomers thereof), or a salt thereof. In some embodiments, the compound is a salt of a compound selected from Compound Nos. 1-124 in Table 1, FIG. 1, or a stereoisomer thereof.

In one variation, the compound detailed herein is selected from the group consisting of: (2-pivalamido-9-(5,6,7,8-tetrahydro-1,8-naphthyridin-2-yl)nonanoic acid; 2-(1-(pyridin-2-yl)pyrrolidine-2-carboxamido)-9-(5,6,7,8-tetrahydro-1,8-naphthyridin-2-yl)nonanoic acid; 2-(2-methyl-2-(pyridin-3-yl)propanamido)-9-(5,6,7,8-tetrahydro-1,8-naphthyridin-2-yl)nonanoic acid; 2-(2-ethylbutanamido)-9-(5,6,7,8-tetrahydro-1,8-naphthyridin-2-yl)nonanoic acid; 2-(morpholine-4-carboxamido)-9-(5,6,7,8-tetrahydro-1,8-naphthyridin-2-yl)nonanoic acid; 2-(4-methyltetrahydro-2H-pyran-4-carboxamido)-9-(5,6,7,8-tetrahydro-1,8-naphthyridin-2-yl)nonanoic acid; 2-(1-phenylpyrrolidine-2-carboxamido)-9-(5,6,7,8-tetrahydro-1,8-naphthyridin-2-yl) nonanoic acid; 2-(1-benzylpyrrolidine-2-carboxamido)-9-(5,6,7,8-tetrahydro-1,8-naphthyridin-2-yl)nonanoic acid; 2-(2-methyl-2-phenylpropanamido)-9-(5,6,7,8-tetrahydro-1,8-naphthyridin-2-yl)nonanoic acid; 2-(1-(pyrimidin-2-ylmethyl)pyrrolidine-2-carboxamido)-9-(5,6,7,8-tetrahydro-1,8-naphthyridin-2-yl)nonanoic acid; 2-(1-(2-(Pyridin-4-yl)acetyl)pyrrolidine-2-carboxamido)-9-(5,6,7,8-tetrahydro-1, 8-naphthyridin-2-yl)nonanoic acid; 2-(1-(pyrimidin-4-ylmethyl)pyrrolidine-2-carboxamido)-9-(5,6,7,8-tetrahydro-1,8-naphthyridin-2-yl)nonanoic acid; 2-(1-(pyridin-3-ylmethyl)pyrrolidine-2-carboxamido)-9-(5,6,7, 8-tetrahydro-1,8-naphthyridin-2-yl)nonanoic acid; 2-(1-(tert-butoxycarbonyl)piperidine-2-carboxamido)-9-(5,6,7,8-tetrahydro-1,8-naphthyridin-2-yl)nonanoic acid; 2-(2-(2-chlorophenyl)acetamido)-9-(5,6,7,8-tetrahydro-1,8-naphthyridin-2-yl)nonanoic acid; 2-(1-(tert-butoxycarbonyl)-3-methylpiperidine-4-carboxamido)-9-(5, 6,7,8-tetrahydro-1,8-naphthyridin-2-yl)nonanoic acid; 2-(1-(tert-butoxycarbonyl)piperidine-4-carboxamido)-9-(5,6,7,8-tetrahydro-1,8-naphthyridin-2-yl)nonanoic acid; 2-(2-(1-(tert-butoxycarbonyl)pyrrolidin-2-yl)acetamido)-9-(5,6,7,8-tetrahydro-1,8-naphthyridin-2-yl)nonanoic acid; 2-(1-benzylazetidine-2-carboxamido)-9-(5,6,7,8-tetrahydro-1,8-naphthyridin-2-yl)nonanoic acid; 2-(1-(3-methoxypropanoyl)-3-methylpyrrolidine-2-carboxamido)-9-(5,6,7,8-tetrahydro-1,8-naphthyridin-2-yl)nonanoic acid; 2-(1-(3-methoxypropanoyl)piperidine-3-carboxamido)-9-(5,6,7,8-tetrahydro-1,8-naphthyridin-2-yl)nonanoic acid; 2-(4-(methylsulfonyl)butanamido)-9-(5,6,7,8-tetrahydro-1, 8-naphthyridin-2-yl)nonanoic acid; 2-(2-hydroxy-2-phenylacetamido)-9-(5,6,7,8-tetrahydro-1,8-naphthyridin-2-yl) nonanoic acid; 2-(3-hydroxy-2-phenylpropanamido)-9-(5,6, 7,8-tetrahydro-1,8-naphthyridin-2-yl)nonanoic acid; 2-(3,3-diethylureido)-9-(5,6,7,8-tetrahydro-1,8-naphthyridin-2-yl) nonanoic acid; 2-(4-methoxybutanamido)-9-(5,6,7,8-tetrahydro-1,8-naphthyridin-2-yl)nonanoic acid; 9-(5,6,7,8-tetrahydro-1,8-naphthyridin-2-yl)-2-(tetrahydrofuran-3-carboxamido)nonanoic acid; 2-((((1-(tert-butoxycarbonyl)-3-methylazetidin-3-yl)oxy)carbonyl)amino)-9-(5,6,7,8-tetrahydro-1,8-naphthyridin-2-yl)nonanoic acid; 2-[(1-tert-butoxycarbonylazetidin-3-yl)oxycarbonylamino]-9-(5,6,7, 8-tetrahydro-1,8-naphthyridin-2-yl)nonanoic acid; 2-(piperidine-4-carboxamido)-9-(5,6,7,8-tetrahydro-1,8-naphthyridin-2-yl)nonanoic acid; 9-(5,6,7,8-tetrahydro-1,8-naphthyridin-2-yl)-2-(tetrahydro-2H-pyran-4-carboxamido) nonanoic acid; 2-(1-acetylpiperidine-4-carboxamido)-9-(5, 6,7,8-tetrahydro-1,8-naphthyridin-2-yl)nonanoic acid; 2-(1-(methylsulfonyl)piperidine-3-carboxamido)-9-(5,6,7,8- tetrahydro-1,8-naphthyridin-2-yl)nonanoic acid; 2-(3-sulfamoylpropanamido)-9-(5,6,7,8-tetrahydro-1,8-naphthyridin-2-yl)nonanoic acid; 2-(1-(methylsulfonyl)piperidine-4-carboxamido)-9-(5,6,7,8-tetrahydro-1,8-naphthyridin-2-yl)nonanoic acid; 2-(3-(methylsulfonamido)propanamido)-9-(5,6,7,8-tetrahydro-1,8-naphthyridin-2-yl)nonanoic acid; 2-(3-methyltetrahydrofuran-3-carboxamido)-9-(5,6,7,8-tetrahydro-1,8-naphthyridin-2-yl)nonanoic acid; 9-(5,6,7,8-tetrahydro-1,8-naphthyridin-2-yl)-2-(4-(trifluoromethyl)tetrahydro-2H-pyran-4-carboxamido)nonanoic acid; 2-(8-oxabicyclo[3.2.1]octane-3-carboxamido)-9-(5,6,7,8-tetrahydro-1,8-naphthyridin-2-yl)nonanoic acid; 2-(1-methylcyclohexanecarboxamido)-9-(5,6,7,8-tetrahydro-1,8-naphthyridin-2-yl)nonanoic acid; 2-(bicyclo[1.1.1]pentane-1-carboxamido)-9-(5,6,7,8-tetrahydro-1,8-naphthyridin-2-yl)nonanoic acid; 2-(chromane-4-carboxamido)-9-(5,6,7,8-tetrahydro-1,8-naphthyridin-2-yl)nonanoic acid; 2-(3-methyltetrahydro-2H-pyran-3-carboxamido)-9-(5,6,7,8-tetrahydro-1,8-naphthyridin-2-yl)nonanoic acid; 2-(4-(((tert-butoxycarbonyl)amino)methyl)tetrahydro-2H-pyran-4-carboxamido)-9-(5,6,7,8-tetrahydro-1,8-naphthyridin-2-yl)nonanoic acid; 2-(4-Phenyltetrahydro-2H-pyran-4-carboxamido)-9-(5,6,7,8-tetrahydro-1,8-naphthyridin-2-yl)nonanoic acid; 2-(4-(aminomethyl)tetrahydro-2H-pyran-4-carboxamido)-9-(5,6,7,8-tetrahydro-1,8-naphthyridin-2-yl)nonanoic acid; 2-(4-methylpiperidine-4-carboxamido)-9-(5,6,7,8-tetrahydro-1,8-naphthyridin-2-yl)nonanoic acid; 2-(4-fluorotetrahydro-2H-pyran-4-carboxamido)-9-(5,6,7,8-tetrahydro-1,8-naphthyridin-2-yl)nonanoic acid; 2-((6-(propylsulfonyl)pyrimidin-4-yl)amino)-9-(5,6,7,8-tetrahydro-1,8-naphthyridin-2-yl)nonanoic acid; 2-((1-methyl-1H-pyrazolo[4,3-d]pyrimidin-7-yl)amino)-9-(5,6,7,8-tetrahydro-1,8-naphthyridin-2-yl)nonanoic acid; 2-((5-(pyridin-3-yl)pyrimidin-2-yl)amino)-9-(5,6,7,8-tetrahydro-1,8-naphthyridin-2-yl)nonanoic acid; 2-((1H-pyrazolo[4,3-d]pyrimidin-7-yl)amino)-9-(5,6,7,8-tetrahydro-1,8-naphthyridin-2-yl)nonanoic acid; 2-((6-(difluoromethyl)pyrimidin-4-yl)amino)-9-(5,6,7,8-tetrahydro-1,8-naphthyridin-2-yl)nonanoic acid; 2-((5-(pyridin-4-yl)pyrimidin-2-yl)amino)-9-(5,6,7,8-tetrahydro-1,8-naphthyridin-2-yl)nonanoic acid; 2-((6-morpholinopyrimidin-4-yl)amino)-9-(5,6,7,8-tetrahydro-1,8-naphthyridin-2-yl)nonanoic acid; 2-((6-(pyrrolidin-1-yl)pyrimidin-4-yl)amino)-9-(5,6,7,8-tetrahydro-1,8-naphthyridin-2-yl)nonanoic acid; 2-((1-methyl-1H-pyrazolo[3,4-d]pyrimidin-4-yl)amino)-9-(5,6,7,8-tetrahydro-1,8-naphthyridin-2-yl)nonanoic acid; 2-((1H-pyrazolo[3,4-d]pyrimidin-4-yl)amino)-9-(5,6,7,8-tetrahydro-1,8-naphthyridin-2-yl)nonanoic acid; 2-((1H-pyrazolo[3,4-d]pyrimidin-6-yl)amino)-9-(5,6,7,8-tetrahydro-1,8-naphthyridin-2-yl)nonanoic acid; 2-((6-(4,4-difluoropiperidin-1-yl)pyrimidin-4-yl)amino)-9-(5,6,7,8-tetrahydro-1,8-naphthyridin-2-yl)nonanoic acid; 2-((6-(dimethylamino)pyrimidin-4-yl)amino)-9-(5,6,7,8-tetrahydro-1,8-naphthyridin-2-yl)nonanoic acid; 2-(pyrimidin-4-ylamino)-9-(5,6,7,8-tetrahydro-1,8-naphthyridin-2-yl)nonanoic acid; 2-((8-bromoquinazolin-4-yl)amino)-9-(5,6,7,8-tetrahydro-1,8-naphthyridin-2-yl)nonanoic acid; 2-(quinazolin-4-ylamino)-9-(5,6,7,8-tetrahydro-1,8-naphthyridin-2-yl)nonanoic acid; 2-(((2,3-dihydrobenzo[b][1,4]dioxin-6-yl)methyl)amino)-9-(5,6,7,8-tetrahydro-1,8-naphthyridin-2-yl)nonanoic acid; 2-(benzylamino)-9-(5,6,7,8-tetrahydro-1,8-naphthyridin-2-yl)nonanoic acid; 2-((quinolin-4-ylmethyl)amino)-9-(5,6,7,8-tetrahydro-1,8-naphthyridin-2-yl)nonanoic acid; 2-((quinolin-6-ylmethyl)amino)-9-(5,6,7,8-tetrahydro-1,8-naphthyridin-2-yl)nonanoic acid; 2-((quinolin-8-ylmethyl)amino)-9-(5,6,7,8-tetrahydro-1,8-naphthyridin-2-yl)nonanoic acid; 2-((1-phenylethyl)amino)-9-(5,6,7,8-tetrahydro-1,8-naphthyridin-2-yl)nonanoic acid; 2-(((1H-pyrrolo[2,3-b]pyridin-3-yl)methyl)amino)-9-(5,6,7,8-tetrahydro-1,8-naphthyridin-2-yl)nonanoic acid; 2-(4-(tert-butoxycarbonyl)morpholine-3-carboxamido)-9-(5,6,7,8-tetrahydro-1,8-naphthyridin-2-yl)nonanoic acid; 2-(7-oxabicyclo[2.2.1]heptane-2-carboxamido)-9-(5,6,7,8-tetrahydro-1,8-naphthyridin-2-yl)nonanoic acid; 2-(2-methyl-2-(tetrahydro-2H-pyran-4-yl)propanamido)-9-(5,6,7,8-tetrahydro-1,8-naphthyridin-2-yl)nonanoic acid; 2-(1-(tert-butoxycarbonyl)-3,3-difluoropiperidine-4-carboxamido)-9-(5,6,7,8-tetrahydro-1,8-naphthyridin-2-yl)nonanoic acid; 2-(2,6-dimethyltetrahydro-2H-pyran-4-carboxamido)-9-(5,6,7,8-tetrahydro-1,8-naphthyridin-2-yl)nonanoic acid; 2-(2,2-dimethyltetrahydro-2H-pyran-4-carboxamido)-9-(5,6,7,8-tetrahydro-1,8-naphthyridin-2-yl)nonanoic acid; 2-(1-(tert-butoxycarbonyl)-4-(trifluoromethyl)piperidine-4-carboxamido)-9-(5,6,7,8-tetrahydro-1,8-naphthyridin-2-yl)nonanoic acid; 9-(5,6,7,8-tetrahydro-1,8-naphthyridin-2-yl)-2-(2,2,6,6-tetramethyltetrahydro-2H-pyran-4-carboxamido)nonanoic acid; 2-(1-(tert-butoxycarbonyl)-4-(2,2-difluoroethyl)piperidine-4-carboxamido)-9-(5,6,7,8-tetrahydro-1,8-naphthyridin-2-yl)nonanoic acid; 9-(5,6,7,8-tetrahydro-1,8-naphthyridin-2-yl)-2-(3,4,5,6-tetrahydro-[1,1'-biphenyl]-2-ylcarboxamido)nonanoic acid; 2-(2-(pyridin-4-yl)acetamido)-9-(5,6,7,8-tetrahydro-1,8-naphthyridin-2-yl)nonanoic acid; 2-(1-(phenylsulfonyl)pyrrolidine-2-carboxamido)-9-(5,6,7,8-tetrahydro-1,8-naphthyridin-2-yl)nonanoic acid; 2-(((4-methyltetrahydro-2H-pyran-4-yl)methyl)amino)-9-(5,6,7,8-tetrahydro-1,8-naphthyridin-2-yl)nonanoic acid; 2-(((1-(pyridin-3-yl)ethyl)amino)-9-(5,6,7,8-tetrahydro-1,8-naphthyridin-2-yl)nonanoic acid; 9-(5,6,7,8-tetrahydro-1,8-naphthyridin-2-yl)-2-(((1,3,5-trimethyl-1H-pyrazol-4-yl)methyl)amino)nonanoic acid; 2-(2,6-Dimethylpiperidine-1-carboxamido)-9-(5,6,7,8-tetrahydro-1,8-naphthyridin-2-yl)nonanoic acid; 2-(2,5-dimethylpyrrolidine-1-carboxamido)-9-(5,6,7,8-tetrahydro-1,8-naphthyridin-2-yl)nonanoic acid; 2-(3,5-dimethylmorpholine-4-carboxamido)-9-(5,6,7,8-tetrahydro-1,8-naphthyridin-2-yl)nonanoic acid; 9-(5,6,7,8-tetrahydro-1,8-naphthyridin-2-yl)-2-(2,4,6-trimethylpiperazine-1-carboxamido)nonanoic acid; 2-(3-azabicyclo[3.3.1]nonane-9-carboxamido)-9-(5,6,7,8-tetrahydro-1,8-naphthyridin-2-yl)nonanoic acid; 2-(3-acetyl-3-azabicyclo[3.3.1]nonane-9-carboxamido)-9-(5,6,7,8-tetrahydro-1,8-naphthyridin-2-yl)nonanoic acid; 2-(4-methyl-1-((1-methyl-1H-pyrazol-4-yl)methyl)piperidine-4-carboxamido)-9-(5,6,7,8-tetrahydro-1,8-naphthyridin-2-yl)nonanoic acid; 2-(4-((tert-butoxycarbonyl)amino)bicyclo[2.2.2]octane-1-carboxamido)-9-(5,6,7,8-tetrahydro-1,8-naphthyridin-2-yl)nonanoic acid; 2-(adamantane-1-carbonylamino)-9-(5,6,7,8-tetrahydro-1,8-naphthyridin-2-yl)nonanoic acid; 2-(4-((tert-butoxycarbonyl)amino)-1-methylcyclohexane-1-carboxamido)-9-(5,6,7,8-tetrahydro-1,8-naphthyridin-2-yl)nonanoic acid; 2-(4-amino-1-methylcyclohexane-1-carboxamido)-9-(5,6,7,8-tetrahydro-1,8-naphthyridin-2-yl)nonanoic acid; 2-(4-aminobicyclo[2.2.2]octane-1-carboxamido)-9-(5,6,7,8-tetrahydro-1,8-naphthyridin-2-yl)nonanoic acid; 2-(4-acetamido-1-methylcyclohexane-1-carboxamido)-9-(5,6,7,8-tetrahydro-1,8-naphthyridin-2-yl)nonanoic acid; 2-(5,5-dimethyl-3-(phenylsulfonyl)thiazolidine-4-carboxamido)-9-(5,6,7,8-tetrahydro-1,8-naphthyridin-2-yl)nonanoic acid; 2-(4-methyl-1-(3,3,3-trifluoropropyl)piperidine-4-carboxamido)-9-(5,6,7,8- tetrahydro-1,8-naphthyridin-2-yl)nonanoic acid; 2-[(1-acetyl-4-methyl-piperidine-4-carbonyl)amino]-9-(5,6,7,8-tetrahydro-1,8-naphthyridin-2-yl)nonanoic acid; 2-(4-methyl-1-pivaloylpiperidine-4-carboxamido)-9-(5,6,7,8-tetrahydro-1,8-naphthyridin-2-yl)nonanoic acid; 2-(1-(3-fluoropropyl)-4-methylpiperidine-4-carboxamido)-9-(5,6,7,8-tetrahydro-1,8-naphthyridin-2-yl)nonanoic acid; 2-(4-(hydroxymethyl)tetrahydro-2H-pyran-4-carboxamido)-9-(5,6,7,8-tetrahydro-1,8-naphthyridin-2-yl)nonanoic acid; 5,5-difluoro-2-(4-methyltetrahydro-2H-pyran-4-carboxamido)-9-(5,6,7,8-tetrahydro-1,8-naphthyridin-2-yl)nonanoic acid; 5,5-difluoro-2-(quinazolin-4-ylamino)-9-(5,6,7,8-tetrahydro-1,8-naphthyridin-2-yl)nonanoic acid; 9-(5,6,7,8-tetrahydro-1,8-naphthyridin-2-yl)-2-[[2,2,2-trifluoro-1-tetrahydropyran-4-yl-ethyl]amino]nonanoic acid; and 2-(4-cyanotetrahydro-2H-pyran-4-carboxamido)-9-(5,6,7,8-tetrahydro-1,8-naphthyridin-2-yl)nonanoic acid; or a salt thereof.

In one variation, the compound detailed herein is selected from the group consisting of: (S)-2-pivalamido-9-(5,6,7,8-tetrahydro-1,8-naphthyridin-2-yl)nonanoic acid; (S)-2-((S)-1-(pyridin-2-yl)pyrrolidine-2-carboxamido)-9-(5,6,7,8-tetrahydro-1,8-naphthyridin-2-yl)nonanoic acid; (S)-2-((R)-1-(pyridin-2-yl)pyrrolidine-2-carboxamido)-9-(5,6,7,8-tetrahydro-1,8-naphthyridin-2-yl)nonanoic acid; (S)-2-(2-methyl-2-(pyridin-3-yl)propanamido)-9-(5,6,7,8-tetrahydro-1,8-naphthyridin-2-yl)nonanoic acid; (S)-2-(2-ethylbutanamido)-9-(5,6,7,8-tetrahydro-1,8-naphthyridin-2-yl)nonanoic acid; (S)-2-(morpholine-4-carboxamido)-9-(5,6,7,8-tetrahydro-1,8-naphthyridin-2-yl)nonanoic acid; (2S)-2-(2,2-dimethyltetrahydro-2H-pyran-4-carboxamido)-9-(5,6,7,8-tetrahydro-1,8-naphthyridin-2-yl)nonanoic acid; (S)-2-(4-methyltetrahydro-2H-pyran-4-carboxamido)-9-(5,6,7,8-tetrahydro-1,8-naphthyridin-2-yl)nonanoic acid; (S)-2-((S)-1-phenylpyrrolidine-2-carboxamido)-9-(5,6,7,8-tetrahydro-1,8-naphthyridin-2-yl)nonanoic acid; (S)-2-((S)-1-benzylpyrrolidine-2-carboxamido)-9-(5,6,7,8-tetrahydro-1,8-naphthyridin-2-yl)nonanoic acid; (S)-2-(2-methyl-2-phenylpropanamido)-9-(5,6,7,8-tetrahydro-1,8-naphthyridin-2-yl)nonanoic acid; (S)-2-((S)-1-(pyrimidin-2-ylmethyl)pyrrolidine-2-carboxamido)-9-(5,6,7,8-tetrahydro-1,8-naphthyridin-2-yl)nonanoic acid; (S)-2-((S)-1-(2-(Pyridin-4-yl)acetyl)pyrrolidine-2-carboxamido)-9-(5,6,7,8-tetrahydro-1,8-naphthyridin-2-yl)nonanoic acid; (S)-2-((S)-1-(pyrimidin-4-ylmethyl)pyrrolidine-2-carboxamido)-9-(5,6,7,8-tetrahydro-1,8-naphthyridin-2-yl)nonanoic acid; (S)-2-((S)-1-(pyridin-3-ylmethyl)pyrrolidine-2-carboxamido)-9-(5,6,7,8-tetrahydro-1,8-naphthyridin-2-yl)nonanoic acid; (S)-2-((S)-1-(tert-butoxycarbonyl)piperidine-2-carboxamido)-9-(5,6,7,8-tetrahydro-1,8-naphthyridin-2-yl)nonanoic acid; (S)-2-(2-(2-chlorophenyl)acetamido)-9-(5,6,7,8-tetrahydro-1,8-naphthyridin-2-yl)nonanoic acid; (S)-2-((3R,4R)-1-(tert-butoxycarbonyl)-3-methylpiperidine-4-carboxamido)-9-(5,6,7,8-tetrahydro-1,8-naphthyridin-2-yl)nonanoic acid; (S)-2-(1-(tert-butoxycarbonyl)piperidine-4-carboxamido)-9-(5,6,7,8-tetrahydro-1,8-naphthyridin-2-yl)nonanoic acid; (S)-2-(2-((S)-1-(tert-butoxycarbonyl)pyrrolidin-2-yl)acetamido)-9-(5,6,7,8-tetrahydro-1,8-naphthyridin-2-yl)nonanoic acid; (S)-2-((S)-1-benzylazetidine-2-carboxamido)-9-(5,6,7,8-tetrahydro-1,8-naphthyridin-2-yl)nonanoic acid; (S)-2-((2S,3S)-1-(3-methoxypropanoyl)-3-methylpyrrolidine-2-carboxamido)-9-(5,6,7,8-tetrahydro-1,8-naphthyridin-2-yl)nonanoic acid; (S)-2-((R)-1-(3-methoxypropanoyl)piperidine-3-carboxamido)-9-(5,6,7,8-tetrahydro-1,8-naphthyridin-2-yl)nonanoic acid; (S)-2-(4-(methylsulfonyl)butanamido)-9-(5,6,7,8-tetrahydro-1,8-naphthyridin-2-yl)nonanoic acid; (S)-2-((R)-2-hydroxy-2-phenylacetamido)-9-(5,6,7,8-tetrahydro-1,8-naphthyridin-2-yl)nonanoic acid; (S)-2-((S)-2-hydroxy-2-phenylacetamido)-9-(5,6,7,8-tetrahydro-1,8-naphthyridin-2-yl) nonanoic acid; (S)-2-((R)-3-hydroxy-2-phenylpropanamido)-9-(5,6,7,8-tetrahydro-1,8-naphthyridin-2-yl)nonanoic acid; (S)-2-((S)-3-hydroxy-2-phenylpropanamido)-9-(5,6,7,8-tetrahydro-1,8-naphthyridin-2-yl)nonanoic acid; (S)-2-(3,3-diethylureido)-9-(5,6,7,8-tetrahydro-1,8-naphthyridin-2-yl)nonanoic acid; (S)-2-(4-methoxybutanamido)-9-(5,6,7,8-tetrahydro-1,8-naphthyridin-2-yl)nonanoic acid; (S)-9-(5,6,7,8-tetrahydro-1,8-naphthyridin-2-yl)-2-((R)-tetrahydrofuran-3-carboxamido)nonanoic acid; (S)-9-(5,6,7,8-tetrahydro-1,8-naphthyridin-2-yl)-2-((S)-tetrahydrofuran-3-carboxamido)nonanoic acid; (S)-2-((((1-(tert-butoxycarbonyl)-3-methylazetidin-3-yl)oxy)carbonyl)amino)-9-(5,6,7,8-tetrahydro-1,8-naphthyridin-2-yl)nonanoic acid; (2S)-2-[(1-tert-butoxycarbonylazetidin-3-yl)oxycarbonylamino]-9-(5,6,7,8-tetrahydro-1,8-naphthyridin-2-yl)nonanoic acid; (S)-2-(piperidine-4-carboxamido)-9-(5,6,7,8-tetrahydro-1,8-naphthyridin-2-yl)nonanoic acid; (S)-9-(5,6,7,8-tetrahydro-1,8-naphthyridin-2-yl)-2-(tetrahydro-2H-pyran-4-carboxamido)nonanoic acid; (S)-2-(1-acetylpiperidine-4-carboxamido)-9-(5,6,7,8-tetrahydro-1,8-naphthyridin-2-yl)nonanoic acid; (S)-2-((R)-1-(methylsulfonyl)piperidine-3-carboxamido)-9-(5,6,7,8-tetrahydro-1,8-naphthyridin-2-yl)nonanoic acid; (S)-2-((S)-1-(methylsulfonyl)piperidine-3-carboxamido)-9-(5,6,7,8-tetrahydro-1,8-naphthyridin-2-yl)nonanoic acid; (S)-2-(3-sulfamoylpropanamido)-9-(5,6,7,8-tetrahydro-1,8-naphthyridin-2-yl)nonanoic acid; (S)-2-(1-(methylsulfonyl)piperidine-4-carboxamido)-9-(5,6,7,8-tetrahydro-1,8-naphthyridin-2-yl)nonanoic acid; (S)-2-(3-(methylsulfonamido)propanamido)-9-(5,6,7,8-tetrahydro-1,8-naphthyridin-2-yl)nonanoic acid; (S)-2-((R)-3-methyltetrahydrofuran-3-carboxamido)-9-(5,6,7,8-tetrahydro-1,8-naphthyridin-2-yl)nonanoic acid; (S)-2-((S)-3-methyltetrahydrofuran-3-carboxamido)-9-(5,6,7,8-tetrahydro-1,8-naphthyridin-2-yl)nonanoic acid; (S)-9-(5,6,7,8-tetrahydro-1,8-naphthyridin-2-yl)-2-(4-(trifluoromethyl)tetrahydro-2H-pyran-4-carboxamido)nonanoic acid; (S)-2-((1R,3s,5S)-8-oxabicyclo[3.2.1]octane-3-carboxamido)-9-(5,6,7,8-tetrahydro-1,8-naphthyridin-2-yl)nonanoic acid; (S)-2-((1R,3r,5S)-8-oxabicyclo[3.2.1]octane-3-carboxamido)-9-(5,6,7,8-tetrahydro-1,8-naphthyridin-2-yl)nonanoic acid; (S)-2-(1-methylcyclohexanecarboxamido)-9-(5,6,7,8-tetrahydro-1,8-naphthyridin-2-yl)nonanoic acid; (S)-2-(bicyclo[1.1.1]pentane-1-carboxamido)-9-(5,6,7,8-tetrahydro-1,8-naphthyridin-2-yl)nonanoic acid; (S)-2-((S)-chromane-4-carboxamido)-9-(5,6,7,8-tetrahydro-1,8-naphthyridin-2-yl)nonanoic acid; (S)-2-((R)-chromane-4-carboxamido)-9-(5,6,7,8-tetrahydro-1,8-naphthyridin-2-yl)nonanoic acid; (S)-2-((R)-3-methyltetrahydro-2H-pyran-3-carboxamido)-9-(5,6,7,8-tetrahydro-1,8-naphthyridin-2-yl)nonanoic acid; (S)-2-((S)-3-methyltetrahydro-2H-pyran-3-carboxamido)-9-(5,6,7,8-tetrahydro-1,8-naphthyridin-2-yl)nonanoic acid; (S)-2-(4-(((tert-butoxycarbonyl)amino)methyl)tetrahydro-2H-pyran-4-carboxamido)-9-(5,6,7,8-tetrahydro-1,8-naphthyridin-2-yl)nonanoic acid; (S)-2-(4-Phenyltetrahydro-2H-pyran-4-carboxamido)-9-(5,6,7,8-tetrahydro-1,8-naphthyridin-2-yl)nonanoic acid; (S)-2-(4-(aminomethyl)tetrahydro-2H-pyran-4-carboxamido)-9-(5,6,7,8-tetrahydro-1,8-naphthyridin-2-yl)nonanoic acid; (R)-2-(4-methyltetrahydro-2H-pyran-4-carboxamido)-9-(5,6,7,8-tetrahydro-1,8-naphthyridin-2-yl)nonanoic acid; (S)-2-(4-methylpiperidine-4-carboxamido)-9-(5,6,7,8-tetrahydro-1, 8-naphthyridin-2-yl)nonanoic acid; (S)-2-(4-fluorotetrahydro-2H-pyran-4-carboxamido)-9-(5,6,7,8-tetrahydro-1,8-naphthyridin-2-yl)nonanoic acid; (S)-2-((6-(propylsulfonyl)pyrimidin-4-yl)amino)-9-(5,6,7,8-tetrahydro-1,8-naphthyridin-2-yl)nonanoic acid; (S)-2-((1-methyl-1H-pyrazolo[4,3-d]pyrimidin-7-yl)amino)-9-(5,6,7,8-tetrahydro-1,8-naphthyridin-2-yl)nonanoic acid; (S)-2-((5-(pyridin-3-yl)pyrimidin-2-yl)amino)-9-(5,6,7,8-tetrahydro-1,8-naphthyridin-2-yl)nonanoic acid; (S)-2-((1H-pyrazolo[4,3-d]pyrimidin-7-yl)amino)-9-(5,6,7,8-tetrahydro-1,8-naphthyridin-2-yl)nonanoic acid; (S)-2-((6-(difluoromethyl)pyrimidin-4-yl)amino)-9-(5,6,7,8-tetrahydro-1,8-naphthyridin-2-yl)nonanoic acid; (S)-2-((5-(pyridin-4-yl)pyrimidin-2-yl)amino)-9-(5,6,7,8-tetrahydro-1,8-naphthyridin-2-yl)nonanoic acid; (S)-2-((6-morpholinopyrimidin-4-yl)amino)-9-(5,6,7,8-tetrahydro-1,8-naphthyridin-2-yl)nonanoic acid; (S)-2-((6-(pyrrolidin-1-yl)pyrimidin-4-yl)amino)-9-(5,6,7,8-tetrahydro-1,8-naphthyridin-2-yl)nonanoic acid; (S)-2-((1-methyl-1H-pyrazolo[3,4-d]pyrimidin-4-yl)amino)-9-(5,6,7,8-tetrahydro-1,8-naphthyridin-2-yl)nonanoic acid; (S)-2-((1H-pyrazolo[3,4-d]pyrimidin-4-yl)amino)-9-(5,6,7,8-tetrahydro-1,8-naphthyridin-2-yl)nonanoic acid; (S)-2-((1H-pyrazolo[3,4-d]pyrimidin-6-yl)amino)-9-(5,6,7,8-tetrahydro-1,8-naphthyridin-2-yl)nonanoic acid; (S)-2-((6-(4,4-difluoropiperidin-1-yl)pyrimidin-4-yl)amino)-9-(5,6,7,8-tetrahydro-1,8-naphthyridin-2-yl)nonanoic acid; (S)-2-((6-(dimethylamino)pyrimidin-4-yl)amino)-9-(5,6,7,8-tetrahydro-1,8-naphthyridin-2-yl)nonanoic acid; (S)-2-(pyrimidin-4-ylamino)-9-(5,6,7,8-tetrahydro-1,8-naphthyridin-2-yl)nonanoic acid; (S)-2-((8-bromoquinazolin-4-yl)amino)-9-(5,6,7,8-tetrahydro-1,8-naphthyridin-2-yl)nonanoic acid; (S)-2-(quinazolin-4-ylamino)-9-(5,6,7,8-tetrahydro-1,8-naphthyridin-2-yl)nonanoic acid; (S)-2-(((2,3-dihydrobenzo[b][1,4]dioxin-6-yl)methyl)amino)-9-(5,6,7,8-tetrahydro-1,8-naphthyridin-2-yl)nonanoic acid; (S)-2-(benzylamino)-9-(5,6,7,8-tetrahydro-1,8-naphthyridin-2-yl)nonanoic acid; (S)-2-((quinolin-4-ylmethyl)amino)-9-(5,6,7,8-tetrahydro-1,8-naphthyridin-2-yl)nonanoic acid; (S)-2-((quinolin-6-ylmethyl)amino)-9-(5,6,7,8-tetrahydro-1,8-naphthyridin-2-yl)nonanoic acid; (S)-2-((quinolin-8-ylmethyl)amino)-9-(5,6,7,8-tetrahydro-1,8-naphthyridin-2-yl)nonanoic acid; (S)-2-(((R)-1-phenylethyl)amino)-9-(5,6,7,8-tetrahydro-1,8-naphthyridin-2-yl)nonanoic acid; (S)-2-(((S)-1-phenylethyl)amino)-9-(5,6,7,8-tetrahydro-1,8-naphthyridin-2-yl)nonanoic acid; (S)-2-(((1H-pyrrolo[2,3-b]pyridin-3-yl)methyl)amino)-9-(5,6,7,8-tetrahydro-1,8-naphthyridin-2-yl)nonanoic acid; (S)-2-((S)-4-(tert-butoxycarbonyl)morpholine-3-carboxamido)-9-(5,6,7,8-tetrahydro-1,8-naphthyridin-2-yl)nonanoic acid; (2S)-2-(7-oxabicyclo[2.2.1]heptane-2-carboxamido)-9-(5,6,7,8-tetrahydro-1,8-naphthyridin-2-yl)nonanoic acid; (2S)-2-((2R)-7-oxabicyclo[2.2.1]heptane-2-carboxamido)-9-(5,6,7,8-tetrahydro-1,8-naphthyridin-2-yl)nonanoic acid; (2S)-2-((2S)-7-oxabicyclo[2.2.1]heptane-2-carboxamido)-9-(5,6,7,8-tetrahydro-1,8-naphthyridin-2-yl)nonanoic acid; (S)-2-(2-methyl-2-(tetrahydro-2H-pyran-4-yl)propanamido)-9-(5,6,7,8-tetrahydro-1,8-naphthyridin-2-yl)nonanoic acid; (2S)-2-(1-(tert-butoxycarbonyl)-3,3-difluoropiperidine-4-carboxamido)-9-(5,6,7,8-tetrahydro-1,8-naphthyridin-2-yl)nonanoic acid; (2S)-2-((2R,6S)-2,6-dimethyltetrahydro-2H-pyran-4-carboxamido)-9-(5,6,7,8-tetrahydro-1,8-naphthyridin-2-yl)nonanoic acid; (S)-2-((S)-2,2-dimethyltetrahydro-2H-pyran-4-carboxamido)-9-(5,6,7,8-tetrahydro-1,8-naphthyridin-2-yl)nonanoic acid; (S)-2-((R)-2,2-dimethyltetrahydro-2H-pyran-4-carboxamido)-9-(5,6,7,8-tetrahydro-1,8-naphthyridin-2-yl)nonanoic acid; (S)-2-(1-(tert-butoxycarbonyl)-4-(trifluoromethyl)piperidine-4-carboxamido)-9-(5,6,7,8-tetrahydro-1,8-naphthyridin-2-yl)nonanoic acid; (S)-9-(5,6,7,8-tetrahydro-1,8-naphthyridin-2-yl)-2-(2,2,6,6-tetramethyltetrahydro-2H-pyran-4-carboxamido)nonanoic acid; (S)-2-(1-(tert-butoxycarbonyl)-4-(2,2-difluoroethyl)piperidine-4-carboxamido)-9-(5,6,7,8-tetrahydro-1,8-naphthyridin-2-yl)nonanoic acid; (S)-9-(5,6,7,8-tetrahydro-1,8-naphthyridin-2-yl)-2-(3,4,5,6-tetrahydro-[1,1'-biphenyl]-2-ylcarboxamido)nonanoic acid; (S)-2-(2-(pyridin-4-yl)acetamido)-9-(5,6,7,8-tetrahydro-1,8-naphthyridin-2-yl)nonanoic acid; (S)-2-((S)-1-(phenylsulfonyl)pyrrolidine-2-carboxamido)-9-(5,6,7,8-tetrahydro-1,8-naphthyridin-2-yl)nonanoic acid; (S)-2-(((4-methyltetrahydro-2H-pyran-4-yl)methyl)amino)-9-(5,6,7,8-tetrahydro-1,8-naphthyridin-2-yl)nonanoic acid; (S)-2-(((R)-1-(pyridin-3-yl)ethyl)amino)-9-(5,6,7,8-tetrahydro-1,8-naphthyridin-2-yl)nonanoic acid; (S)-2-(((S)-1-(pyridin-3-yl)ethyl)amino)-9-(5,6,7,8-tetrahydro-1,8-naphthyridin-2-yl)nonanoic acid; (S)-9-(5,6,7,8-tetrahydro-1,8-naphthyridin-2-yl)-2-(((1,3,5-trimethyl-1H-pyrazol-4-yl)methyl)amino)nonanoic acid; (S)-2-((2S,6R)-2,6-Dimethylpiperidine-1-carboxamido)-9-(5,6,7,8-tetrahydro-1,8-naphthyridin-2-yl)nonanoic acid; (S)-2-((2S,5R)-2,5-dimethylpyrrolidine-1-carboxamido)-9-(5,6,7,8-tetrahydro-1,8-naphthyridin-2-yl)nonanoic acid; (S)-2-((2R,5R)-2,5-dimethylpyrrolidine-1-carboxamido)-9-(5,6,7,8-tetrahydro-1,8-naphthyridin-2-yl)nonanoic acid; (S)-2-((3R,5R)-3,5-dimethylmorpholine-4-carboxamido)-9-(5,6,7,8-tetrahydro-1,8-naphthyridin-2-yl)nonanoic acid; (S)-2-((3R,5 S)-3,5-dimethylmorpholine-4-carboxamido)-9-(5,6,7,8-tetrahydro-1,8-naphthyridin-2-yl)nonanoic acid; (S)-9-(5,6,7,8-tetrahydro-1,8-naphthyridin-2-yl)-2-((2R,6S)-2,4,6-trimethylpiperazine-1-carboxamido)nonanoic acid; (2S)-2-(3-azabicyclo[3.3.1]nonane-9-carboxamido)-9-(5,6,7,8-tetrahydro-1,8-naphthyridin-2-yl)nonanoic acid; (S)-2-((1R,5 S,9S)-3-acetyl-3-azabicyclo[3.3.1]nonane-9-carboxamido)-9-(5,6,7,8-tetrahydro-1,8-naphthyridin-2-yl)nonanoic acid; (S)-2-((1R,5 S,9R)-3-acetyl-3-azabicyclo[3.3.1]nonane-9-carboxamido)-9-(5,6,7,8-tetrahydro-1,8-naphthyridin-2-yl)nonanoic acid; (S)-2-(4-methyl-1-((1-methyl-1H-pyrazol-4-yl)methyl)piperidine-4-carboxamido)-9-(5,6,7,8-tetrahydro-1,8-naphthyridin-2-yl)nonanoic acid; (S)-2-(4-((tert-butoxycarbonyl)amino)bicyclo[2.2.2]octane-1-carboxamido)-9-(5,6,7,8-tetrahydro-1,8-naphthyridin-2-yl)nonanoic acid; (2S)-2-(adamantane-1-carbonylamino)-9-(5,6,7,8-tetrahydro-1,8-naphthyridin-2-yl)nonanoic acid; (S)-2-(4-((tert-butoxycarbonyl)amino)-1-methylcyclohexane-1-carboxamido)-9-(5,6,7,8-tetrahydro-1,8-naphthyridin-2-yl)nonanoic acid; (S)-2-(4-amino-1-methylcyclohexane-1-carboxamido)-9-(5,6,7,8-tetrahydro-1,8-naphthyridin-2-yl)nonanoic acid; (S)-2-(4-aminobicyclo[2.2.2]octane-1-carboxamido)-9-(5,6,7,8-tetrahydro-1,8-naphthyridin-2-yl)nonanoic acid; (S)-2-(4-acetamido-1-methylcyclohexane-1-carboxamido)-9-(5,6,7,8-tetrahydro-1,8-naphthyridin-2-yl)nonanoic acid; (S)-2-((S)-5,5-dimethyl-3-(phenylsulfonyl)thiazolidine-4-carboxamido)-9-(5,6,7,8-tetrahydro-1,8-naphthyridin-2-yl)nonanoic acid; (R)-2-((S)-1-(phenylsulfonyl)pyrrolidine-2-carboxamido)-9-(5,6,7,8-tetrahydro-1,8-naphthyridin-2-yl)nonanoic acid; (S)-2-(4-methyl-1-(3,3,3-trifluoropropyl)piperidine-4-carboxamido)-9-(5,6,7,8-tetrahydro-1,8-naphthyridin-2-yl)nonanoic acid; (2S)-2-[(1-acetyl-4-methyl-piperidine-4-carbonyl)amino]-9-(5,6,7,8-tetrahydro-1,8-naphthyridin-2-yl)nonanoic acid; (S)-2-(4-methyl-1-pivaloylpiperidine-4-carboxamido)-9-(5,6,7,8-tetrahydro-1,8-naphthyridin-2-yl)nonanoic acid; (S)-2-(1-

(3-fluoropropyl)-4-methylpiperidine-4-carboxamido)-9-(5,6,7,8-tetrahydro-1,8-naphthyridin-2-yl)nonanoic acid; (S)-2-(4-(hydroxymethyl)tetrahydro-2H-pyran-4-carboxamido)-9-(5,6,7,8-tetrahydro-1,8-naphthyridin-2-yl) nonanoic acid; (S)-5,5-difluoro-2-(4-methyltetrahydro-2H-pyran-4-carboxamido)-9-(5,6,7,8-tetrahydro-1,8-naphthyridin-2-yl)nonanoic acid; (R)-5,5-difluoro-2-(4-methyltetrahydro-2H-pyran-4-carboxamido)-9-(5,6,7,8-tetrahydro-1,8-naphthyridin-2-yl)nonanoic acid; (S)-5,5-difluoro-2-(quinazolin-4-ylamino)-9-(5,6,7,8-tetrahydro-1,8-naphthyridin-2-yl)nonanoic acid; (2S)-9-(5,6,7,8-tetrahydro-1,8-naphthyridin-2-yl)-2-[[(1S)-2,2,2-trifluoro-1-tetrahydropyran-4-yl-ethyl]amino]nonanoic acid; (2S)-9-(5,6,7,8-tetrahydro-1,8-naphthyridin-2-yl)-2-[[(1R)-2,2,2-trifluoro-1-tetrahydropyran-4-yl-ethyl]amino]nonanoic acid; and (S)-2-(4-cyanotetrahydro-2H-pyran-4-carboxamido)-9-(5,6,7,8-tetrahydro-1,8-naphthyridin-2-yl) nonanoic acid; or a salt thereof.

In some embodiments, a composition, such as a pharmaceutical composition, is provided wherein the composition comprises a compound selected from the group consisting of one or more of Compound Nos. 1-77 in Table 1, FIG. 1, or a stereoisomer thereof (including a mixture of two or more stereoisomers thereof), or a salt thereof. In some embodiments, the composition comprises a compound selected from the group consisting of a salt of one or more of Compound Nos 1-77. In one aspect, the composition is a pharmaceutical composition that further comprises a pharmaceutically acceptable carrier.

In some embodiments, a composition, such as a pharmaceutical composition, is provided wherein the composition comprises a compound selected from the group consisting of one or more of Compound Nos. 1-77 in Table 1, FIG. 1, or a stereoisomer thereof (including a mixture of two or more stereoisomers thereof), or a salt thereof. In some embodiments, the composition comprises a compound selected from the group consisting of a salt of one or more of Compound Nos. 1-77, FIG. 1. In some embodiments, a composition, such as a pharmaceutical composition, is provided wherein the composition comprises a compound selected from the group consisting of one or more of Compound Nos. 1-124 in Table 1, FIG. 1, or a stereoisomer thereof (including a mixture of two or more stereoisomers thereof), or a salt thereof. In some embodiments, the composition comprises a compound selected from the group consisting of a salt of one or more of Compound Nos. 1-124 in Table 1, FIG. 1. In one aspect, the composition is a pharmaceutical composition that further comprises a pharmaceutically acceptable carrier.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also described and embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced. Where one or more tertiary amine moiety is present in the compound, the N-oxides are also provided and described. A chemical structure which can be depicted as different tautomers is considered aromatic if either tautomer would be considered aromatic. For example, the structure pyridin-2(1H)-one,

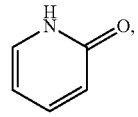

is considered aromatic due to its tautomer 2-hydroxypyridine,

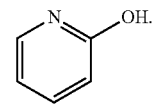

Compounds described herein are $\alpha_v\beta_6$ integrin inhibitors. In some instances, it is desirable for the compound to inhibit other integrins in addition to $\alpha_v\beta_6$ integrin. In some embodiments, the compound inhibits $\alpha_v\beta_6$ integrin and one or more of $\alpha_v\beta_1$, $\alpha_v\beta_3$, $\alpha_v\beta_5$, $\alpha_2\beta_1$, $\alpha_3\beta_1$, $\alpha_6\beta_1$ integrin, $\alpha_7\beta_1$ and $\alpha_{11}\beta_1$. In some embodiments, the compound inhibits $\alpha_v\beta_6$ integrin and $\alpha_v\beta_1$ integrin. In some embodiments, the compound inhibits $\alpha_v\beta_6$ integrin, $\alpha_v\beta_3$ integrin and $\alpha_v\beta_5$ integrin. In some embodiments, the compound inhibits $\alpha_v\beta_6$ integrin and $\alpha_2\beta_1$ integrin. In some embodiments, the compound inhibits $\alpha_v\beta_6$ integrin, $\alpha_2\beta_1$ integrin and $\alpha_3\beta_1$ integrin. In some embodiments, the compound inhibits $\alpha_v\beta_6$ integrin and $\alpha_6\beta_1$ integrin. In some embodiments, the compound inhibits $\alpha_v\beta_6$ integrin and $\alpha_7\beta_1$ integrin. In some embodiments, the compound inhibits $\alpha_v\beta_6$ integrin and $\alpha_{11}\beta_1$ integrin.

In some instances, it is desirable to avoid inhibition of other integrins. In some embodiments, the compound is a selective $\alpha_v\beta_6$ integrin inhibitor. In some embodiments, the compound does not inhibit substantially $\alpha_4\beta_1$, $\alpha_v\beta_8$ and/or $\alpha_2\beta_3$ integrin. In some embodiments, the compound inhibits $\alpha_v\beta_6$ integrin but does not inhibit substantially $\alpha_4\beta_1$ integrin. In some embodiments, the compound inhibits $\alpha_v\beta_6$ integrin but does not inhibit substantially $\alpha_v\beta_8$ integrin. In some embodiments, the compound inhibits $\alpha_v\beta_6$ integrin but does not inhibit substantially $\alpha_2\beta_3$ integrin. In some embodiments, the compound inhibits $\alpha_v\beta_6$ integrin but does not inhibit substantially the $\alpha_v\beta_8$ integrin and the $\alpha_4\beta_1$ integrin.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$ $^{13}N$, $^{15}O$, $^{17}O$, $^{32}P$, $^{35}S$, $^{18}F$, $^{36}Cl$. Incorporation of heavier isotopes such as deuterium ($^2H$ or D) can afford certain therapeutic advantages resulting from greater metabolic stability, for example, increased in vivo half-life, or reduced dosage requirements and, hence may be preferred in some instances. The description above of embodiments for formula (I) also apply equally to formula (A) to provide the corresponding embodiments of formula (A).

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound.

Articles of manufacture comprising a compound of the invention, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms.

General Synthetic Methods

The compounds of the invention may be prepared by a number of processes as generally described below and more specifically in the Examples hereinafter (such as the Schemes provides in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds provided herein may be prepared according to Schemes, Procedures, and Examples. Reaction conditions for the transformations of Schemes listed below are provided in the Procedures that follow. The final product depicted below can be prepared according to Scheme A, wherein $R^x$ is a carboxylic protecting group and R is $R^3$ as defined for formula (I).

Scheme A

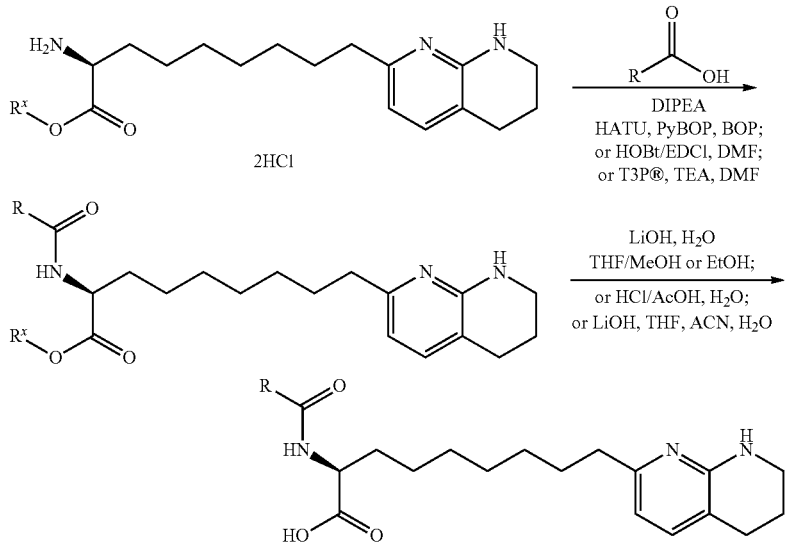

The final product depicted below can be prepared according to Scheme B, wherein $R^x$ is a carboxylic protecting group and R is $R^4$ as defined for formula (I).

Scheme B

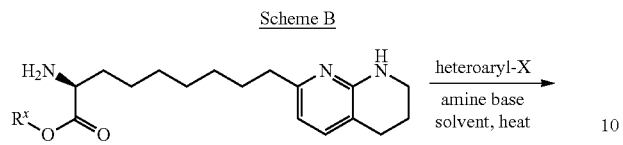

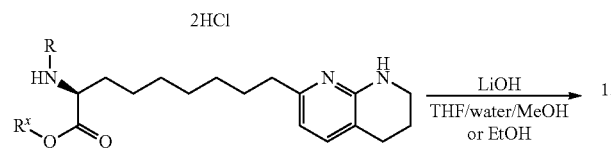

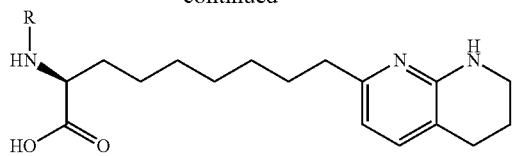

The final product depicted below can be prepared according to Scheme C, wherein $R^x$ is a carboxylic protecting group and Y refers to the portion of the molecule that links the —C(O)N(H)— portion of the molecule with the remainder of the $R^3$ moiety.

Scheme C

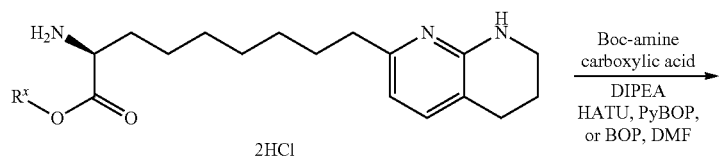

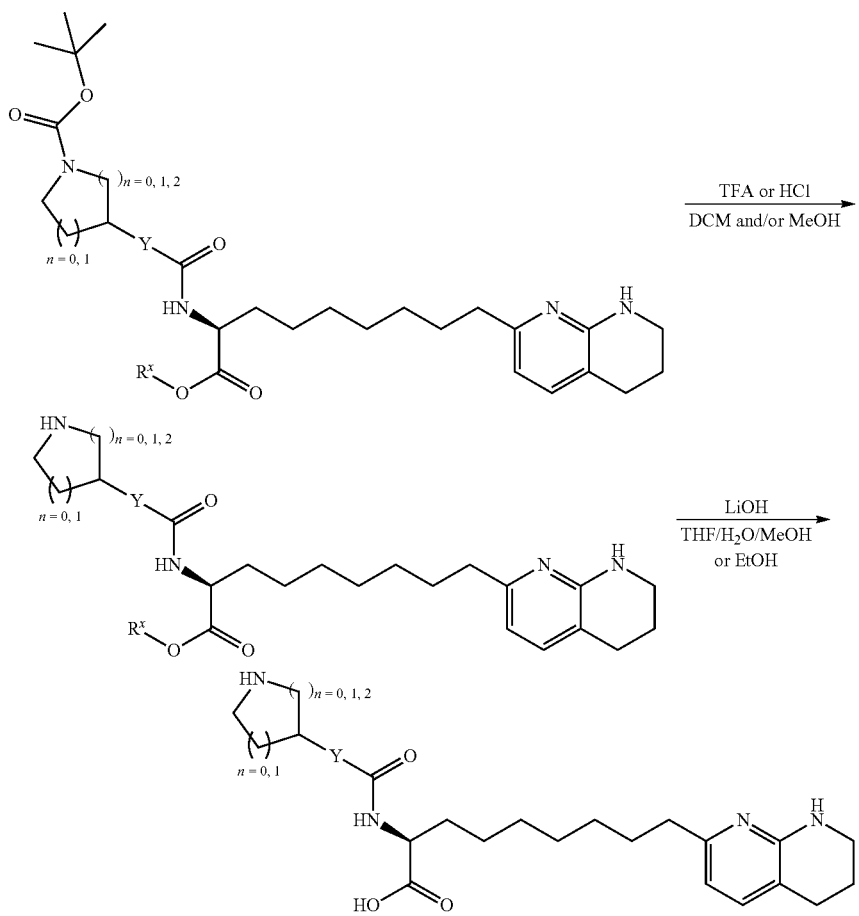

The final product depicted below can be prepared according to Scheme D, wherein X is a halide and $R^x$ is a carboxylic protecting group. It is understood the ring bearing the Het description can be any heteroaromatic ring.

Scheme D

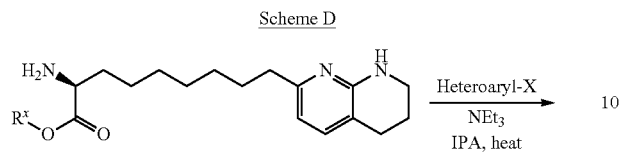

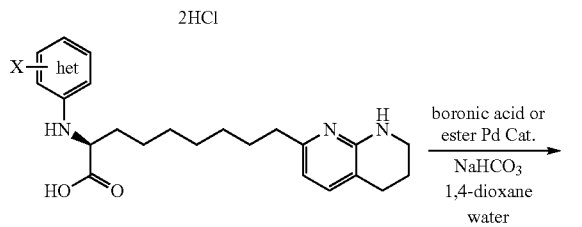

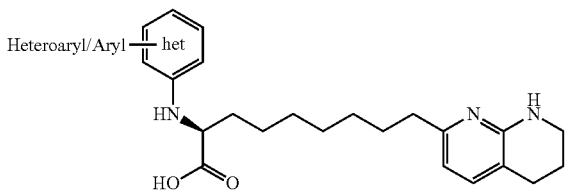

The final product depicted below can be prepared according to Scheme E, wherein Y refers to the portion of the molecule that links the —C(O)N(H)— portion of the molecule with the remainder of the $R^3$ moiety and $R^x$ is a carboxylic protecting group.

Scheme E

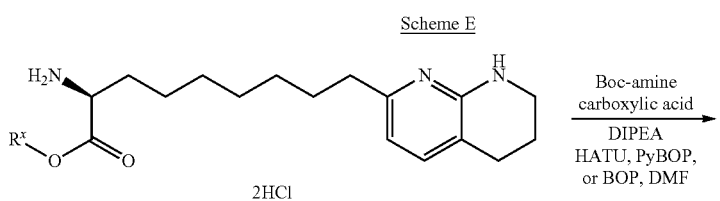

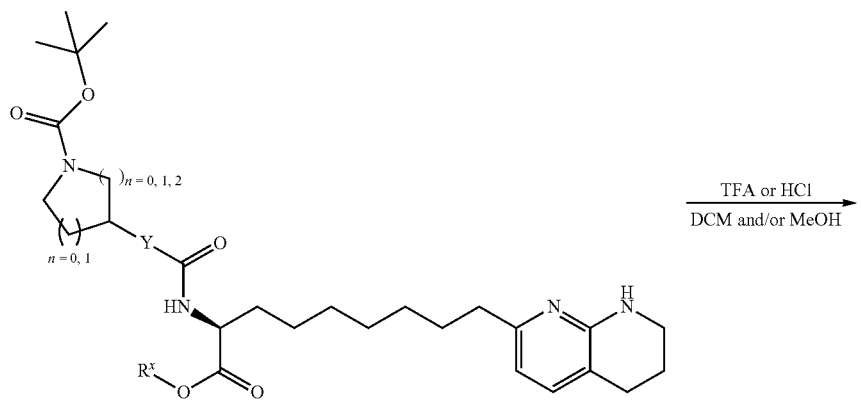

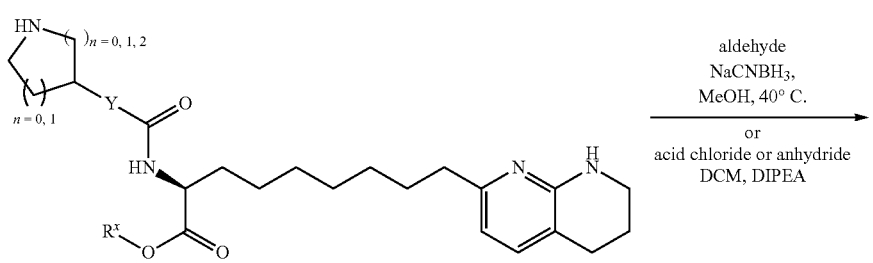

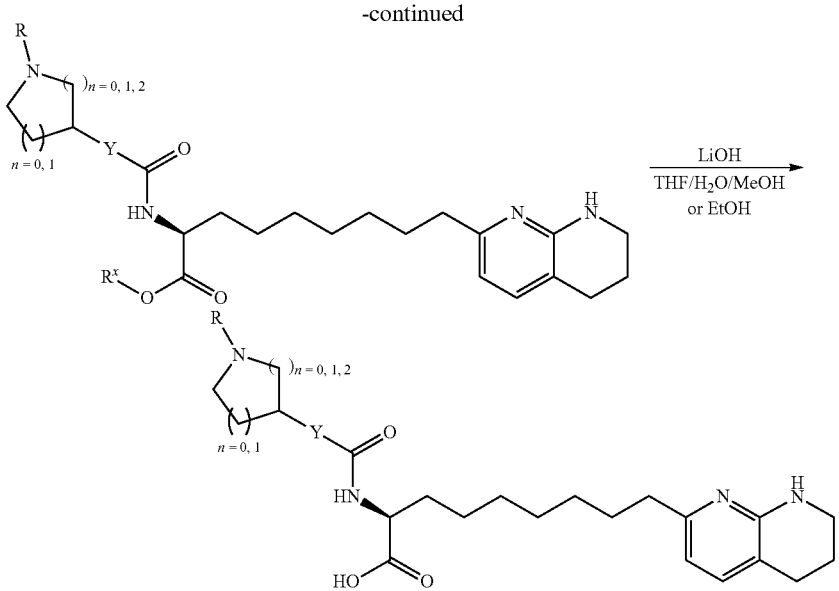

The final product depicted below can be prepared according to Scheme F, wherein X is a halide, $R^x$ is a carboxylic protecting group, and R is $R^{4e}$ as defined for formula (I), or any applicable variations detailed herein. It is understood the ring bearing the Het description can be any heteroaromatic ring.

The final product depicted below can be prepared according to Scheme G, wherein $R^x$ is a carboxylic protecting group and R is $R^{4a}$ as defined for formula (I), or any applicable variations detailed herein.

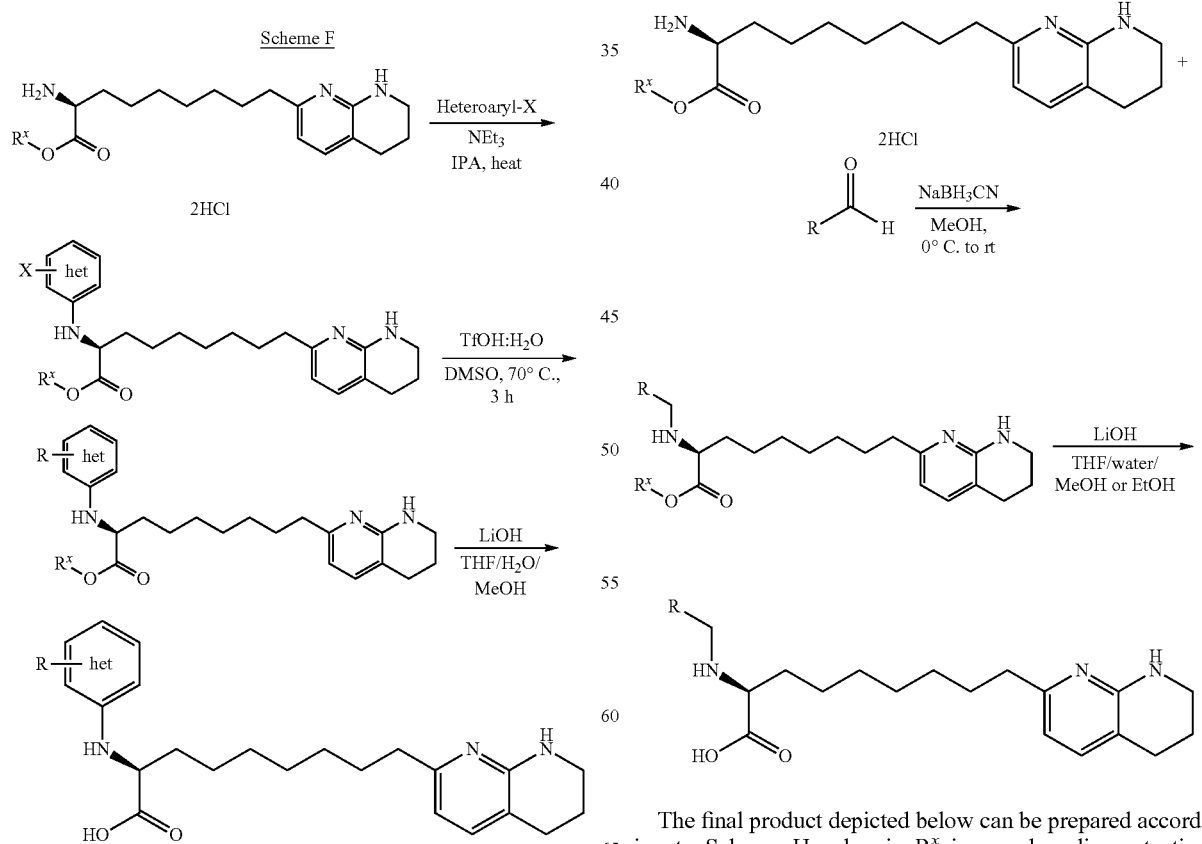

The final product depicted below can be prepared according to Scheme H, wherein $R^x$ is a carboxylic protecting group and R is $R^{4a}$ as defined for formula (I), or any applicable variations detailed herein.

Scheme H

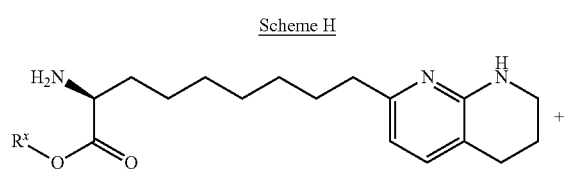

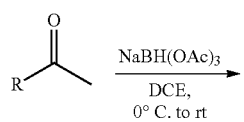

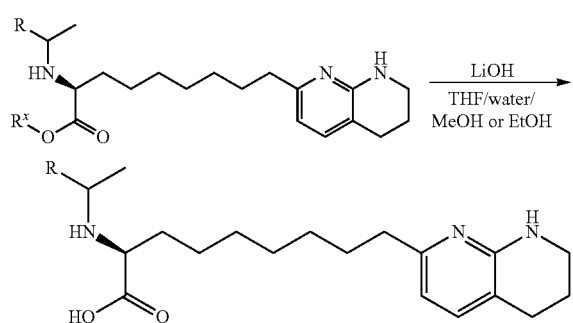

The final product depicted below can be prepared according to Scheme I, wherein $R^x$ is a carboxylic protecting group and R is $R^3$ as defined for formula (I), or any applicable variations detailed herein.

Scheme I

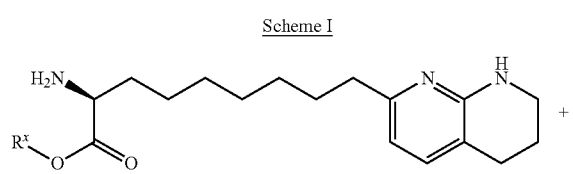

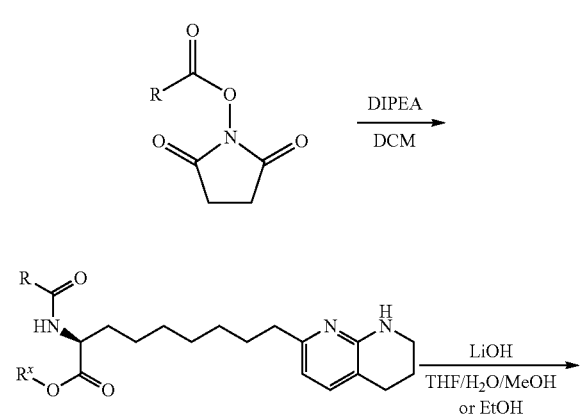

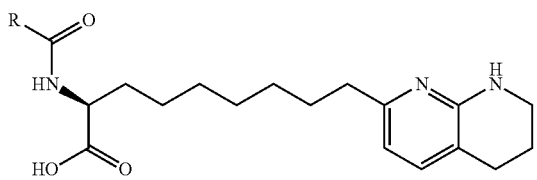

The final product depicted below can be prepared according to Scheme J.

Scheme J

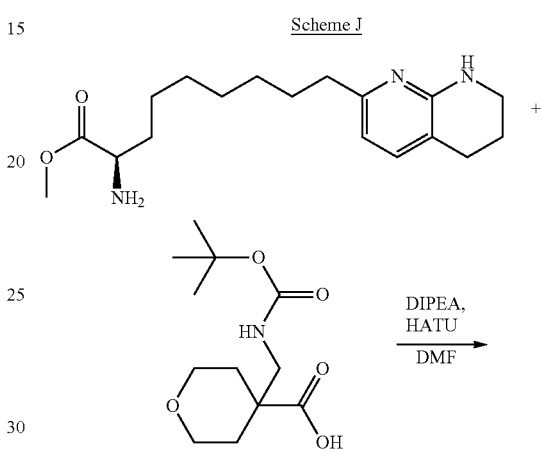

The final product depicted below can be prepared according to Scheme K.

Scheme K

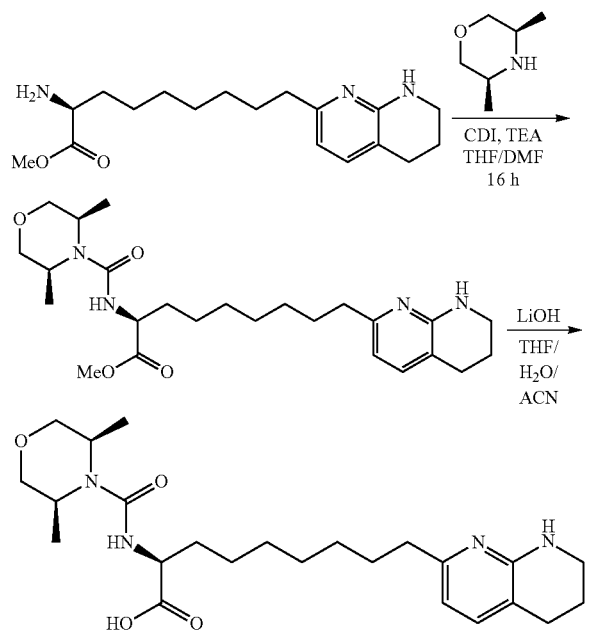

It is understood that the Schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4$^{th}$ edition, Wiley-Interscience, New York, 2006.

Additional methods of preparing compounds according to formula (I), and salts thereof, are provided in the Examples. As a skilled artisan would recognize, the methods of preparation taught herein may be adapted to provide additional compounds within the scope of formula (I), for example, by selecting starting materials which would provide a desired compound. The syntheses of the products depicted above in Schemes A-K for formula (I) can also be carried out for formula (A).

Pharmaceutical Compositions and Formulations

Pharmaceutical compositions of any of the compounds detailed herein, including compounds of the formula (I), (I-A), (II), (II-A), (II-A-1), and (II-B), or a salt thereof, or any of compounds of Table 1, FIG. 1, or a salt thereof, or mixtures thereof, are embraced by this invention. Pharmaceutical compositions of any of the compounds detailed herein, including compounds of the formula (A), (I), (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), or a salt thereof, or any of compounds of Table 1, FIG. 1, or a salt thereof, or mixtures thereof, are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation. In one embodiment, the pharmaceutical composition is a composition for controlled release of any of the compounds detailed herein.

A compound as detailed herein may in one aspect be in a purified form and compositions comprising a compound in purified forms are detailed herein. In one embodiment, compositions may have no more than 35% impurity, wherein the impurity denotes a compound other than the compound comprising the majority of the composition or a salt thereof, for example, a composition of a compound selected from a compound of Table 1, FIG. 1, may contains no more than 35% impurity, wherein the impurity denotes a compound other than the compound of Table 1, FIG. 1, or a salt thereof. In one embodiment, compositions may contain no more than 25% impurity. In one embodiment, compositions may contains no more than 20% impurity. In still further embodiments, compositions comprising a compound as detailed herein or a salt thereof are provided as compositions of substantially pure compounds. "Substantially pure" compositions comprise no more than 10% impurity, such as a composition comprising less than 9%, 7%, 5%, 3%, 1%, or 0.5% impurity. In some embodiments, a composition containing a compound as detailed herein or a salt thereof is in substantially pure form. In still another variation, a composition of substantially pure compound or a salt thereof is provided wherein the composition contains or no more than 10% impurity. In a further variation, a composition of substantially pure compound or a salt thereof is provided wherein the composition contains or no more than 9% impurity. In a further variation, a composition of substantially pure compound or a salt thereof is provided wherein the composition contains or no more than 7% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 10% or preferably no more than 5% or more preferably no more than 3% or even more preferably no more than 1% impurity or most preferably no more than 0.5% impurity, which impurity may be the compound in a different stereochemical form. For instance, a composition of substantially pure (S) compound means that the composition contains no more than 10% or no more than 5% or no more than 3% or no more than 1% or no more than 0.5% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (I), or any variation thereof, e.g., a compound of formula (I-A), (II), (II-A), (II-A-1), or (II-B), a compound selected from Compound Nos. 1-77 in Table 1, FIG. 1, or a stereoisomer thereof, or a pharmaceutically acceptable salt thereof. In one aspect, provided is a method of treating a fibrotic disease in an individual in need thereof comprising administering to the individual a therapeutically effective amount of a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof. In one aspect, the individual is a human. The individual, such as human, may be in need of treatment, such as a human who has or is suspected of having a fibrotic disease.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease. In some embodiments, the individual at risk for developing a fibrotic disease is an individual who has or is suspected of having NAFLD, NASH, CKD, scleroderma, Crohn's Disease, NSIP, PSC, PBC, or is an individual who has had or is suspected of having had a myocardial infarction.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In some embodiments, the fibrotic disease is a pulmonary fibrosis, e.g., idiopathic pulmonary fibrosis (IPF).

In some embodiments, the fibrotic disease is a primary sclerosing cholangitis, or biliary fibrosis.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic steatosis induced liver fibrosis, and cirrhosis.

In some embodiments, the fibrotic disease is biliary tract fibrosis.

In some embodiments, the fibrotic disease is renal fibrosis, e.g., diabetic nephrosclerosis, hypertensive nephrosclerosis, focal segmental glomerulosclerosis ("FSGS"), and acute kidney injury from contrast induced nephropathy.

In some embodiments, the fibrotic disease is systemic and local sclerosis or scleroderma, keloids and hypertrophic scars, or post surgical adhesions.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In one aspect, provided is a compound of formula (I), or any variation thereof, e.g., a compound of formula (I-A), (II), (II-A), (II-A-1), or (II-B), a compound selected from Compound Nos. 1-77 in Table 1, FIG. 1, or a stereoisomer thereof, or a pharmaceutically acceptable salt thereof, for use in the treatment of a fibrotic disease. In one aspect, provided is a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof, for use in the treatment of a fibrotic disease.

Also provided is use of a compound of formula (I), or any variation thereof, e.g., a compound of formula (I-A), (II), (II-A), (II-A-1), or (II-B), a compound selected from Compound Nos. 1-77 in Table 1, FIG. 1, or a stereoisomer thereof, or a pharmaceutically acceptable salt thereof, in the manufacture of a medicament for the treatment of a fibrotic disease. Also provided is use of a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof, in the manufacture of a medicament for the treatment of a fibrotic disease.

In another aspect, provided is a method of inhibiting $\alpha_v\beta_6$ integrin in an individual comprising administering a compound of formula (I), or any variation thereof, e.g., a compound of formula (I-A), (II), (II-A), (II-A-1), or (II-B), a stereoisomer thereof, or a compound selected from Compound Nos. 1-77 in Table 1, FIG. 1, or a pharmaceutically acceptable salt thereof. In another aspect, provided is a method of inhibiting $\alpha_v\beta_6$ integrin in an individual comprising administering a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof.

Also provided is a method of inhibiting TGFβ activation in a cell comprising administering to the cell a compound of formula (I), or any variation thereof, e.g., a compound of formula (I-A), (II), (II-A), (II-A-1), or (II-B), a compound selected from Compound Nos. 1-77 in Table 1, FIG. 1, or a stereoisomer thereof, or a pharmaceutically acceptable salt thereof. Also provided is a method of inhibiting TGFβ activation in a cell comprising administering to the cell a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof.

Also provided is a method of inhibiting $\alpha_v\beta_6$ integrin in an individual in need thereof, comprising administering to the individual a compound of formula (I), or any variation thereof, e.g., a compound of formula (I-A), (II), (II-A), (II-A-1), or (II-B), a compound selected from Compound Nos. 1-77, FIG. 1, in Table 1, or a stereoisomer thereof, or a pharmaceutically acceptable salt thereof. Also provided is a method of inhibiting $\alpha_v\beta_6$ integrin in an individual in need thereof, comprising administering to the individual a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof. In one such method, the compound is a selective $\alpha_v\beta_6$ integrin inhibitor. In another such method, the compound does not inhibit substantially $\alpha_4\beta_1$, $\alpha_v\beta_8$ and/or $\alpha_2\beta_3$ integrin. In yet another such method, the compound inhibits $\alpha_v\beta_6$ integrin but does not inhibit substantially $\alpha_4\beta_1$ integrin. In still another such method, the compound inhibits $\alpha_v\beta_6$ integrin but does not inhibit substantially $\alpha_v\beta_8$ integrin. In a further such method, the compound inhibits $\alpha_v\beta_6$ integrin but does not inhibit substantially $\alpha_2\beta_3$ integrin. In one embodiment is provided a method of inhibiting $\alpha_v\beta_6$ integrin and one or more of $\alpha_v\beta_1$, $\alpha_v\beta_3$, $\alpha_v\beta_5$, $\alpha_2\beta_1$, $\alpha_3\beta_1$, $\alpha_6\beta_1$ integrin, $\alpha_7\beta_1$ and $\alpha_{11}\beta_1$ in an individual in need thereof. In another embodiment is provided a method of inhibiting $\alpha_v\beta_6$ integrin and $\alpha_v\beta_1$ integrin. In another embodiment is provided a method of inhibiting $\alpha_v\beta_6$ integrin, $\alpha_v\beta_3$ integrin and $\alpha_v\beta_5$ integrin. In another embodiment is provided a method of inhibiting $\alpha_v\beta_6$ integrin and $\alpha_2\beta_1$ integrin. In another embodiment is provided a method of inhibiting $\alpha_v\beta_6$ integrin, $\alpha_2\beta_1$ integrin and $\alpha_3\beta_1$ integrin. In another embodiment is provided a method of inhibiting $\alpha_v\beta_6$ integrin and $\alpha_6\beta_1$ integrin. In another embodiment is provided a method of inhibiting $\alpha_v\beta_6$ integrin and $\alpha_7\beta_1$ integrin. In another embodiment is provided a method of inhibiting $\alpha_v\beta_6$ integrin and $\alpha_{11}\beta_1$ integrin. In all such embodiments, in one aspect the method of inhibition is for an individual in need thereof, such as an individual who has or is suspected of having a fibrotic disease, and wherein the method comprises administering to the individual a compound of formula (I), or any variation thereof, e.g., a compound of formula (I-A), (II), (II-A), (II-A-1), or (II-B), a compound selected from Compound Nos. 1-77 in Table 1, FIG. 1, or a stereoisomer thereof, or a pharmaceutically acceptable salt thereof. In all such embodiments, in one aspect the method of inhibition is for an individual in need thereof, such as an individual who has or is suspected of having a fibrotic disease, and wherein the method comprises administering to the individual a compound of formula (A), or (I), or any variation thereof, e.g., a compound of formula (I-A), (II), (II-A), (II-A-1, 2, 3, or 4), (II-A-1a), (II-A-2a), (II-A-3a), (II-A-4a, 4b, or 4c), (II-A-5a, 5b, 5c, 5d, or 5e), (II-A-6a, 6b, 6c, 6d, 6e, 6f, 6g, 6h, 6i, 6j, 6k, 6l, or 6m), (II-B), (II-B-1a or 1b), (II-B-2a or 2b), (II-B-3a or 3b), (II-B-4a, 4b, 4c, 4d, or 4e), or (II-B-5a or 5b), a compound selected from Compound Nos. 1-124 in Table 1, FIG. 1, or a stereoisomer thereof, or a pharmaceutically acceptable salt thereof.

In any of the described methods, in one aspect the individual is a human, such as a human in need of the method. The individual may be a human who has been diagnosed with or is suspected of having a fibrotic disease. The individual may be a human who does not have detectable disease but who has one or more risk factors for developing a fibrotic disease.

Kits

The invention further provides kits for carrying out the methods of the invention, which comprises one or more compounds described herein, or a salt thereof, or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or subunit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

Procedures

Compounds provided herein may be prepared according to Schemes, as exemplified by the Procedures and Examples. Minor variations in temperatures, concentrations, reaction times, and other parameters can be made when following the Procedures, which do not substantially affect the results of the Procedures.

Procedure A

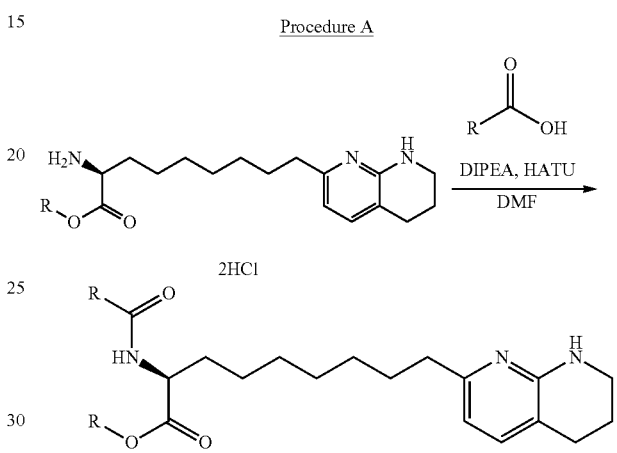

To a solution of methyl (S)-2-amino-9-(5,6,7,8-tetrahydro-1,8-naphthyridin-2-yl)nonanoate in DMF was added DIPEA (10 equiv) followed by carboxylic acid (1.1 equiv) and HATU (1.1 equiv). The reaction was allowed to stir at rt while monitoring reaction progress by LCMS. When the starting material had been consumed, the reaction was diluted with 1 N NaOH and extracted with EA, washed with brine, dried over sodium sulfate, and concd. The crude residue was purified by silica gel chromatography to afford the depicted compound. In some embodiment, the R group attached to the amide moiety of the reaction product is $R^3$ as defined for formula (A). In some embodiments, the R group attached to the ester moiety of the starting material and reaction product is a carboxylic acid protecting group.

Procedure B

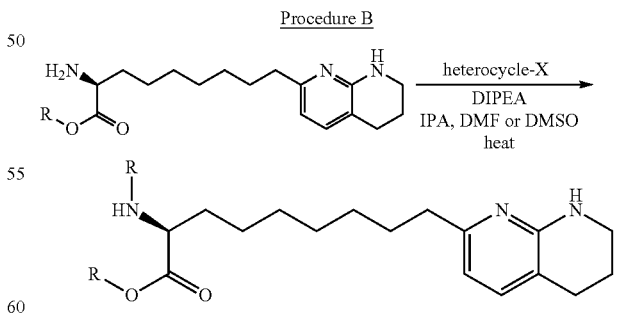

To a solution of methyl (S)-2-amino-9-(5,6,7,8-tetrahydro-1,8-naphthyridin-2-yl)nonanoate in a solvent such as IPA, DMF, or DMSO was added halogenated heteroarene and an excess of amine base such as triethylamine or diisopropylethylamine. The reaction mixture was then heated until completion as determined by LCMS. The reaction mixture was coned or used directly in the next step. Halogenated heterocyclyls can also be used to add a corresponding heterocyclic R group on the amine. In some embodiment, the R group attached to the amine moiety of the reaction product is $R^4$ as defined for formula (A). In some embodiments, the R group attached to the ester moiety of the starting material and reaction product is a carboxylic acid protecting group.

Procedure C

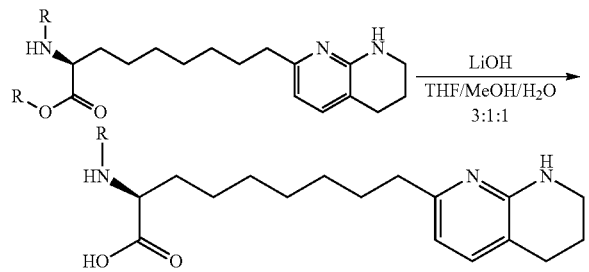

To a solution of the depicted ester in an appropriate solvent mixture such as THF/MeOH/H$_2$O or THF/EtOH/H$_2$O was added LiOH (3-5 equiv). The reaction was allowed to stir at rt while monitoring reaction progress by LCMS. Upon completion, the reaction was coned and purified by reverse phase preparative HPLC to afford the depicted carboxylic acid as the TFA salt. In some embodiment, the R group attached to the amine moiety of the starting material and reaction product is $R^4$ as defined for formula (A). In some embodiments, the R group attached to the ester moiety of the starting material is a carboxylic acid protecting group.

Procedure D

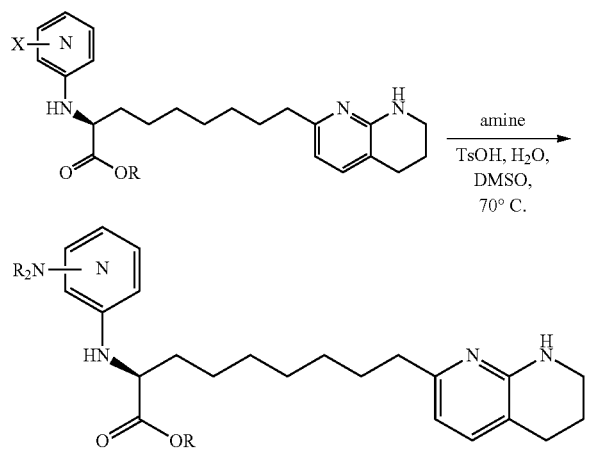

To a solution of the depicted halogenated heterocycle in DMSO was added tosic acid monohydrate and the depicted amine. The reaction mixture was heated at 70° C. until the starting material had been consumed as determined by LCMS. The reaction was poured into water and extracted with EA. The organic layers were combined, washed with brine, dried over sodium sulfate, and coned by rotary evaporation to afford the depicted product as a crude mixture, which was used directly in the next reaction. In some embodiment, X is a halide. It is understood that the ring bearing the N description is any heteroaromatic ring containing at least one nitrogen atom. In some embodiments, the ring bearing the N description is $R^4$ as defined for formula (A). In some embodiments, one of the two R groups attached to nitrogen atom of the reaction product is $R^{14}$, and the other R group attached to the nitrogen atom of the reaction product is $R^{15}$, wherein $R^{14}$ and $R^{15}$ are as defined for formula (A). In some embodiments, the two R groups attached to the nitrogen atom are taken together with the nitrogen atom to which they are attached to form $R^{12}$, wherein $R^{12}$ is a 3- to 12-membered heterocyclyl optionally substituted by $R^{12a}$, wherein $R^{12a}$ is as defined for formula (A). In some embodiments, the R group attached to the ester moiety of the starting material and reaction product is a carboxylic acid protecting group.

Procedure E

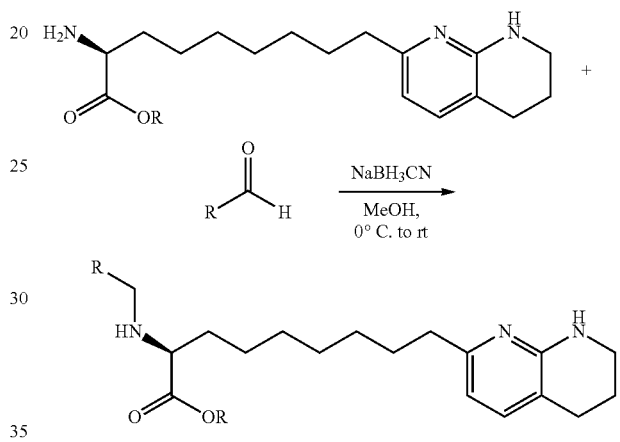

To a solution of the depicted amine (1 equiv) in MeOH was added aldehyde (1.3 equiv), NaBH$_3$CN (2.5 equiv), and acetic acid (1 equiv) at 0° C. The mixture was allowed to warm to rt and was stirred for 18 h or until LCMS indicated product formation was complete. The reaction mixture was then treated with sat aq sodium carbonate and extracted with DCM. The combined organic layers were washed with brine and coned by rotary evaporation to afford a crude residue, which was purified by reverse phase preparative TLC (PE: EA 1:1) to afford the depicted product.

In some embodiments, the R group attached to the methylene moiety of the reaction product is $R^{4a}$ as defined for formula (A). In some embodiments, the R group attached to the ester moiety of the starting material and reaction product is a carboxylic acid protecting group.

Procedure F

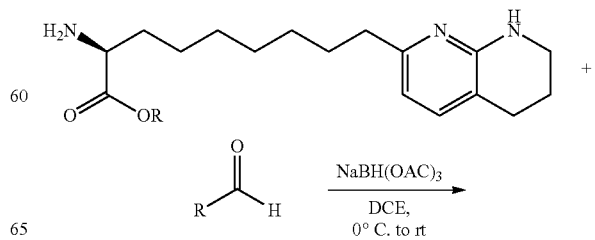

-continued

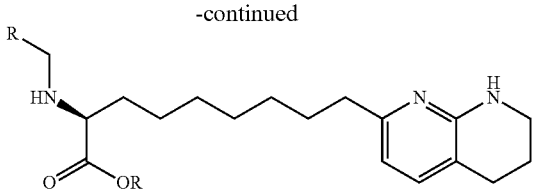

A solution of the depicted amine (1 equiv) was prepared in DCE, and the reaction mixture was adjusted to pH 6 by the addition of AcOH before adding sodium triacetoxyborohydride (2.5 equiv). The reaction mixture was cooled to 0° C. before adding ketone (1.5 equiv). The reaction was allowed to warm to rt and stirred for 16 h, at which time LCMS indicated the presence of the depicted product. The reaction mixture was treated with sat aq sodium bicarbonate and extracted with DCM. The organic layer was washed with brine, dried over sodium sulfate, and coned to afford the crude residue, which was purified by preparative TLC (PE:EA, 1:1) to afford the depicted product. In some embodiments, the R group attached to the methylene moiety of the reaction product is $R^{4a}$ as defined for formula (A). In some embodiments, the R group attached to the ester moiety of the starting material and reaction product is a carboxylic acid protecting group.

Procedure G

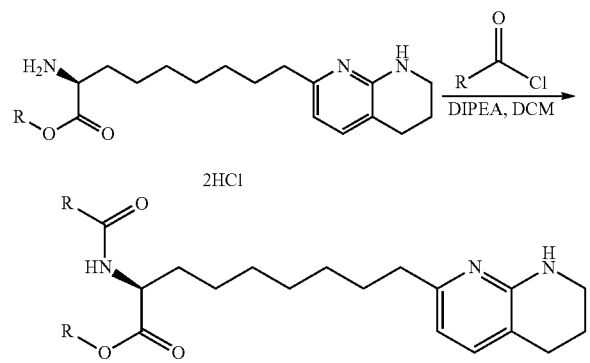

To a solution of the depicted amine (1 equiv) in DCM was added DIPEA (10 equiv) followed by acid chloride (4 equiv). The reaction was stirred at rt for 1 h, coned, and used directly in the next step. In some embodiments, the R group attached to the amide moiety of the reaction product is $R^3$ as defined for formula (A). In some embodiments, the R group attached to the ester moiety of the starting material and reaction product is a carboxylic acid protecting group.

Procedure H

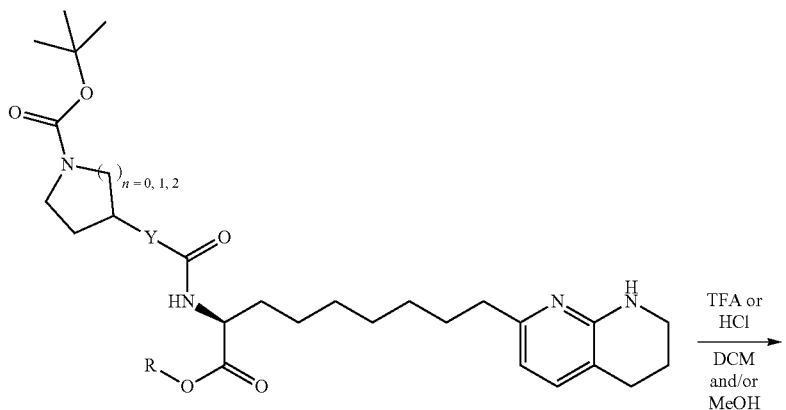

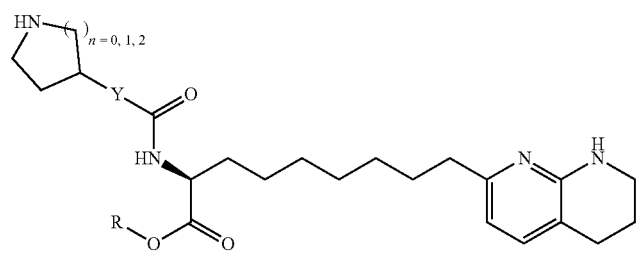

To a solution of the depicted BOC-protected amine in DCM or MeOH was added either TFA or HCl in 1,4-dioxane or diethyl ether in excess. The reaction was stirred at rt until LCMS indicated the starting material had been consumed. The reaction was then coned by rotary evaporation to afford the depicted product as a salt, which was used directly in the next reaction. In some embodiments, Y refers to the portion of the molecule that links the —C(O)N(H)— portion of the compound with the remainder of the $R^3$ moiety. In some embodiments, the R group attached to the ester moiety of the starting material and reaction product is a carboxylic acid protecting group.

Procedure I

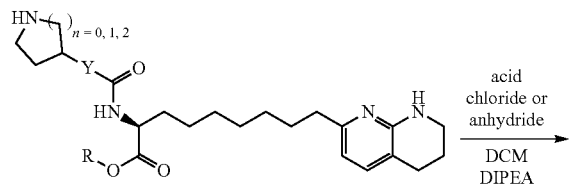

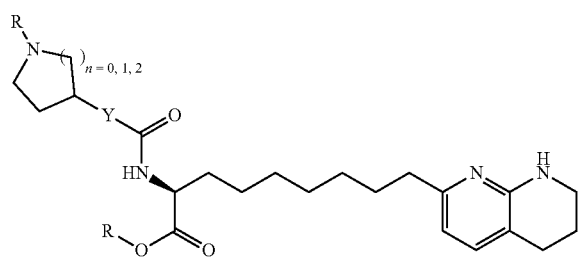

To a solution of the depicted amine (1.0 equiv) in DCM was added DIPEA (4 equiv) followed by acid chloride or anhydride (2 equiv). The reaction was stirred at rt and monitored by LCMS for the consumption of starting material. The reaction mixture was then coned and purified by reverse phase preparatory HPLC to afford the depicted product. In some embodiments, Y refers to the portion of the molecule that links the —C(O)N(H)— portion of the compound with the remainder of the $R^3$ moiety. In some embodiments, the R group attached to the nitrogen atom of the heterocyclyl moiety is $R^{3f}$ as defined for formula (A). In some embodiments, the R group attached to the nitrogen atom of the heterocyclyl moiety is $R^{12a}$ as defined for formula (A). In some embodiments, the R group attached to the ester moiety of the starting material and reaction product is a carboxylic acid protecting group.

Procedure J

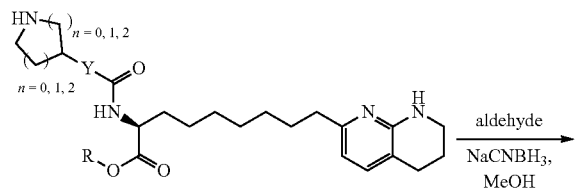

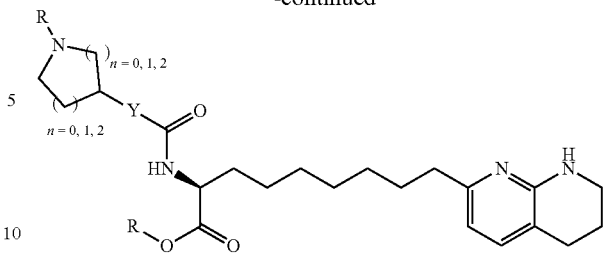

A mixture of amine (1 equiv), aldehyde (1.5 equiv), and NaBH$_3$CN (5 equiv) in MeOH was stirred at rt for 12 h until starting material had been consumed as determined by LCMS. The reaction mixture was diluted with EA and washed with brine, dried over sodium sulfate, filtered, and concd to afford the crude residue, which was purified by preparative TLC or column chromatography on silica gel to afford the depicted product. In some embodiments, Y refers to the portion of the molecule that links the —C(O)N(H)— portion of the compound with the remainder of the $R^3$ moiety. In some embodiments, the R group attached to the nitrogen atom of the heterocyclyl moiety is $R^{3f}$ as defined for formula (A). In some embodiments, the R group attached to the nitrogen atom of the heterocyclyl moiety is $R^{12a}$ as defined for formula (A). In some embodiments, the R group attached to the ester moiety of the starting material and reaction product is a carboxylic acid protecting group.

Procedure K

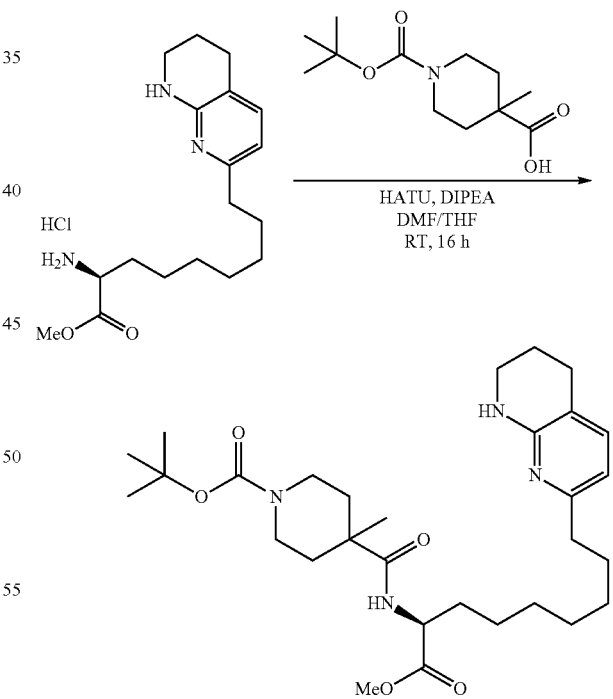

tert-Butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate To a solution of methyl (S)-2-amino-9-(5,6,7,8-tetrahydro-1,8-naphthyridin-2-yl)nonanoate hydrochloride (390 mg, 1.22 mmol) in DMF (1 mL) and THF (3 mL) was added 1-(tert-butoxycarbonyl)-4-methylpiperidine-4-carboxylic acid (326 mg, 1.34 mmol), diisopropylethylamine (0.85 mL, 4.9 mmol), and HATU (510 mg, 1.34 mmol). The reaction was allowed to stir at rt for 16 h before diluting with water, extracting with EtOAc, washing with brine, drying over sodium sulfate, and concentrating. The crude residue was purified by FCC eluting with 0-15% MeOH in DCM to afford tert-Butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate (614 mg, 92% yield). LCMS theoretical m/z=545.4 [M+H]$^+$, found 545.4.

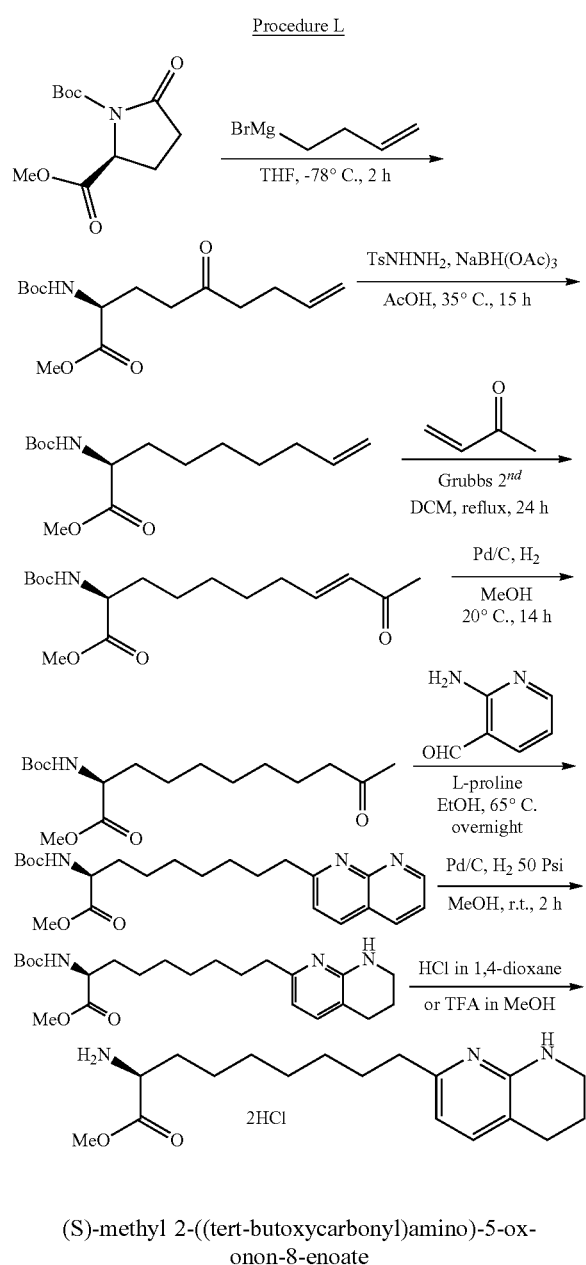

Procedure L (S)-methyl 2-((tert-butoxycarbonyl)amino)-5-oxonon-8-enoate

To a solution of (S)-1-tert-butyl 2-methyl 5-oxopyrrolidine-1,2-dicarboxylate (250 g, 1.0 mol, 1.0 equiv) in THF (2500 mL) was added but-3-en-1-ylmagnesium bromide (1.0 M, 1.2 L, 1.2 equiv) dropwise at −78° C. for 30 min, and then the solution was stirred at −78° C. for 1.5 h. TLC (PE:EA=5:1) showed that a new spot appeared. The mixture was quenched with sat NH$_4$Cl (500 mL) and separated. The aqueous layer was extracted with EA. The combined organic layers were dried over Na$_2$SO$_4$ and coned. The residue was purified by column chromatography (SiO$_2$, PE:EA=15:1) to yield the title compound (180 g, 0.63 mol, 61% yield) as colorless oil. LCMS (ESI+): m/z=300.1 (M+H)$^+$. $^1$H NMR (400 MHz, CDCl$_3$): δ ppm 5.74-5.84 (m, 1H) 4.88-5.21 (m, 3H) 4.27 (br d, J=4.63 Hz, 1H) 3.74 (s, 3H) 2.42-2.62 (m, 4H) 2.32 (q, J=7.06 Hz, 2H) 2.08-2.20 (m, 1H) 1.82-1.97 (m, 1H) 1.44 (s, 9H).

(S)-methyl 2-((tert-butoxycarbonyl)amino)non-8-enoate

To a solution of (S)-methyl 2-((tert-butoxycarbonyl)amino)-5-oxonon-8-enoate (200 g, 670 mmol, 1.0 equiv) in AcOH (2 L) was added 4-methylbenzenesulfonohydrazide (147 g, 788 mmol, 1.18 equiv). The mixture was stirred at 15° C. for 2 h, then NaBH(OAc)$_3$ (566 g, 2.67 mol, 4.00 equiv) was added. The solution was stirred 15 h at 35° C. TLC (PE:EA=5:1) showed that a new spot had appeared and that the starting material was consumed. The mixture was concd and poured into cold water (12 L) and extracted with EA. The combined organic phases were washed with sat aq NaHCO$_3$ (1.2 L) and brine (1.2 L), dried over Na$_2$SO$_4$, filtered, and coned to afford a crude residue. The crude residue was purified by column chromatography (SiO$_2$, PE:EA=15:1) to afford the title compound (105 g, 368 mmol, 55.1% yield) as a colorless oil. $^1$H NMR (400 MHz, CDCl$_3$): δ ppm 5.72-5.82 (m, 1H) 4.87-5.07 (m, 3H) 4.17-4.38 (m, 1H) 3.72 (s, 3H) 1.95-2.08 (m, 2H) 1.69-1.86 (m, 1H) 1.53-1.66 (m, 1H) 1.21-1.50 (m, 15H).

(S,E)-methyl 2-((tert-butoxycarbonyl)amino)-10-xoundec-8-enoate

To a solution of but-3-en-2-one (62.6 g, 893 mmol, 74.5 mL, 3.00 equiv) and Grubbs catalyst 2$^{nd}$ Generation (12.6 g, 14.9 mmol, 0.0500 equiv) in DCM (800 mL) was added (S)-methyl 2-((tert-butoxycarbonyl)amino)non-8-enoate (85.0 g, 297 mmol, 1.00 equiv) at 40° C., and the mixture was stirred for 24 h. TLC (PE:EA=5:1) showed that a new spot appeared, and LCMS indicated that the starting material had been completely consumed. The solution was coned to give a crude residue. The crude residue was purified by column chromatography (SiO$_2$, PE:EA=15:1) to afford the title compound (62.9 g, 192 mmol, 64.5% yield) as a colorless oil. LCMS (ESI+): m/z=228.4 (M+H-BOC)$^+$; $^1$H NMR (400 MHz, CDCl$_3$): δ ppm 6.67-6.90 (m, 1H) 6.07 (dt, J=15.99, 1.38 Hz, 1H) 5.00 (br d, J=7.72 Hz, 1H) 4.22-4.37 (m, 1H) 3.75 (s, 3H) 2.15-2.28 (m, 5H) 1.75-1.85 (m, 1H) 1.57-1.66 (m, 1H) 1.43-1.50 (m, 11H) 1.31-1.39 (m, 4H); Chiral SFC method: column: Daicel CHIRALPAK® AD-3 (Chiral Technologies, Inc., West Chester, Pa.), 3 µm, 0.46× 10 cm, 4.0 mL/min, 220 nm, phase A=CO$_2$, Phase B=MeOH (0.05% IPA), Rt1=1.14 min, Rt2=1.29 min, 100% ee.

(S)-methyl 2-((tert-butoxycarbonyl)amino)-10-oxoundecanoate

To a solution of (S,E)-methyl 2-((tert-butoxycarbonyl)amino)-10-oxoundec-8-enoate (100 g, 305 mmol, 1.00 equiv) in MeOH (400 mL) was added Pd/C (30 g, 10% purity), and the flask was evacuated and purged with H$_2$ gas (15 psi). The reaction flask was left under a H$_2$ balloon (15 psi) atmosphere for 14 h at 20° C. TLC (PE:EA=5:1) showed that starting material had been consumed and a new spot was detected. The solution was filtered through Celite and concd to afford (the title compound (300 g, 911 mmol, 99.4% yield) as a colorless oil. $^1$H NMR (400 MHz, CDCl$_3$): δ ppm 4.89-5.07 (m, 1H) 4.22-4.37 (m, 1H) 3.74 (s, 3H) 2.41 (t, J=7.40 Hz, 2H) 2.13 (s, 3H) 1.78 (br dd, J=12.96, 5.14 Hz, 1H) 1.51-1.66 (m, 3H) 1.45 (s, 9H) 1.23-1.36 (m, 8H).

(S)-methyl 2-((tert-butoxycarbonyl)amino)-9-(1,8-naphthyridin-2-yl)nonanoate

To a solution of (S)-methyl 2-((tert-butoxycarbonyl)amino)-10-oxoundecanoate (20.0 g, 60.7 mmol, 1.00 equiv) in EtOH (200 mL) was added L-proline (3.49 g, 30.4 mmol, 0.500 equiv) and 2-aminonicotinaldehyde (7.41 g, 60.7 mmol, 1.00 equiv). The mixture was stirred at 65° C. for 13 h. TLC (PE:EA, 1:1) showed a new spot was detected with R$_f$=0.16. The reaction mixture was concd under reduced pressure to remove solvent. The residue was diluted with H$_2$O (2000 mL) and extracted with EA. The combined organic layers were washed with brine (2000 mL), dried over anhyd Na$_2$SO$_4$, filtered, and concd under reduced pressure to give the crude residue. The residue was purified by column chromatography (SiO$_2$, PE:EA=3:1 to 1:1) to afford the title compound (120 g, 289 mmol, 31.7% yield) as a yellow oil. LCMS (ESI+): m/z=416.2 (M+H)$^+$; $^1$H NMR (400 MHz, CDCl$_3$): δ ppm 9.08 (dd, J=4.19, 1.98 Hz, 1H) 8.16 (dd, J=8.16, 1.98 Hz, 1H) 8.09 (d, J=8.38 Hz, 1H) 7.44 (dd, J=8.05, 4.30 Hz, 1H) 7.39 (d, J=8.38 Hz, 1H) 4.90-5.14 (m, 1H) 4.21-4.35 (m, 1H) 3.73 (s, 3H) 2.98-3.10 (m, 2H) 1.88 (quin, J=7.50 Hz, 2H) 1.70-1.82 (m, 1H) 1.53-1.67 (m, 1H) 1.44 (s, 9H) 1.29-1.48 (m, 8H); Chiral SFC method: column: Daicel CHIRALPAK® AD-3 (Chiral Technologies, Inc., West Chester, Pa.), 3 μm, 0.46×10 cm, 2.5 mL/min, 220 nm, phase A=CO$_2$, Phase B=MeOH (0.05% IPA), Rt1=3.25 min, Rt2=3.45 min, 99.6% ee.

(S)-methyl 2-((tert-butoxycarbonyl)amino)-9-(5,6,7,8-tetrahydro-1,8-naphthyridin-2-yl)nonanoate To a solution of (S)-methyl 2-((tert-butoxycarbonyl)amino)-9-(1,8-naphthyridin-2-yl)nonanoate (22.0 g, 52.9 mmol, 1.00 equiv) in MeOH (200 mL) was added Pd/C (6 g, 10% purity). The flask was evacuated and back-filled with H$_2$ (50 Psi), and held for 5 h at 25° C. LCMS showed that starting material had been completely consumed, and one main peak with the product mass was detected. The solution was coned to give a residue. The residue was purified by prep-HPLC (column: XTIMATE® (Welch Materials, Hurst, Tex.); C18 10 μm 250 mm×50 mm; mobile phase: [water (10 mM NH$_4$HCO$_3$)—I]; B %: 50%-73%, 20 min) to afford the title compound (77.9 g, 179 mmol, 48.3% yield) as a white solid. LCMS (ESI+): m/z=420.2 (M+H)$^+$; $^1$H NMR (400 MHz, CDCl$_3$): δ ppm 7.05 (d, J=7.45 Hz, 1H) 6.34 (d, J=7.45 Hz, 1H) 5.01 (br d, J=8.33 Hz, 1H) 4.79 (br s, 1H) 4.21-4.36 (m, 1H) 3.73 (s, 3H) 3.35-3.46 (m, 2H) 2.69 (t, J=6.36 Hz, 2H) 2.42-2.59 (m, 2H) 1.86-1.95 (m, 2H) 1.72-1.84 (m, 1H) 1.55-1.67 (m, 3H) 1.44 (s, 9H) 1.30 (br s, 8H); Chiral SFC method: Daicel CHIRALPAK® AD-3 (Chiral Technologies, Inc., West Chester, Pa.), 3 μm, 0.46×10 cm, 2.5 mL/min, 220 nm, phase A=CO$_2$, Phase B=MeOH (0.05% IPA), Rt1=3.04 min, Rt2=3.32 min, 99.5% ee.

Methyl (S)-2-amino-9-(5,6,7,8-tetrahydro-1,8-naphthyridin-2-yl)nonanoate

To a solution of methyl (S)-2-((tert-butoxycarbonyl)amino)-9-(5,6,7,8-tetrahydro-1,8-naphthyridin-2-yl)nonanoate (1.6 g, 3.8 mmol, 1.0 equiv) in 10 mL of DCM was added 4 N HCl in 1,4-dioxane (7.6 mL, 30 mmol, 8.0 equiv). The solution was stirred for 1 h until LCMS showed the starting material had been consumed. The reaction solution was coned via rotary evaporation to afford the title compound as a sticky, yellow solid, which was used without further purification.

Procedure M

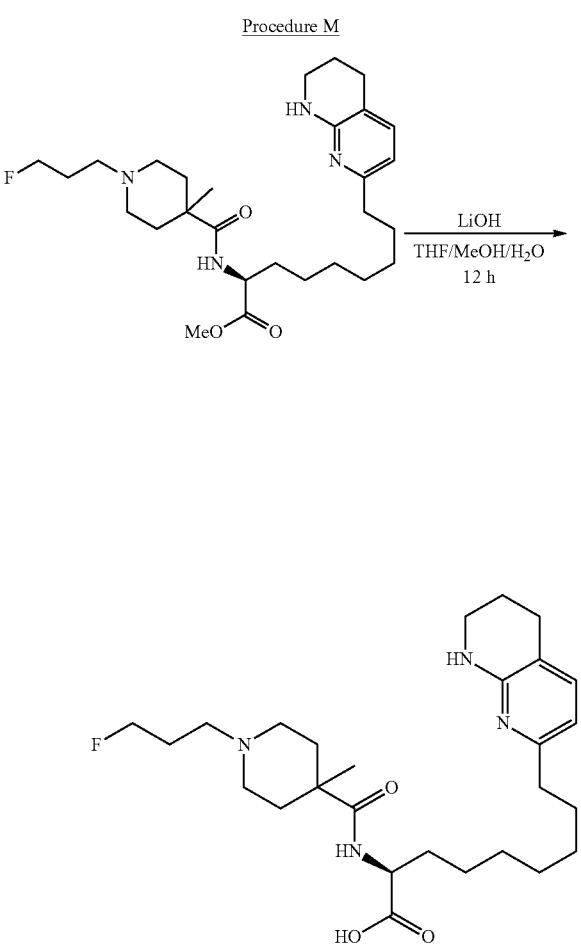

(S)-2-(1-(3-fluoropropyl)-4-methylpiperidine-4-carboxamido)-9-(5,6,7,8-tetrahydro-1,8-naphthyridin-2-yl)nonanoic Acid To a solution of methyl (S)-2-(1-(3-fluoropropyl)-4-methylpiperidine-4-carboxamido)-9-(5,6,7,8-tetrahydro-1,8-naphthyridin-2-yl)nonanoate (113 mg, 0.225 mmol) in THF:MeOH:H$_2$O (3:1:1) was added lithium hydroxide (22 mg, 0.90 mmol). The reaction mixture was stirred at RT for 12 h. The reaction mixture was diluted with AcOH:H$_2$O (1:1) and purified by reverse phase prep HPLC to afford the title compound (44 mg, 40% yield) as a thin film. LCMS theoretical m/z=491.3 [M+H]$^+$, found 491.3.

Procedure N

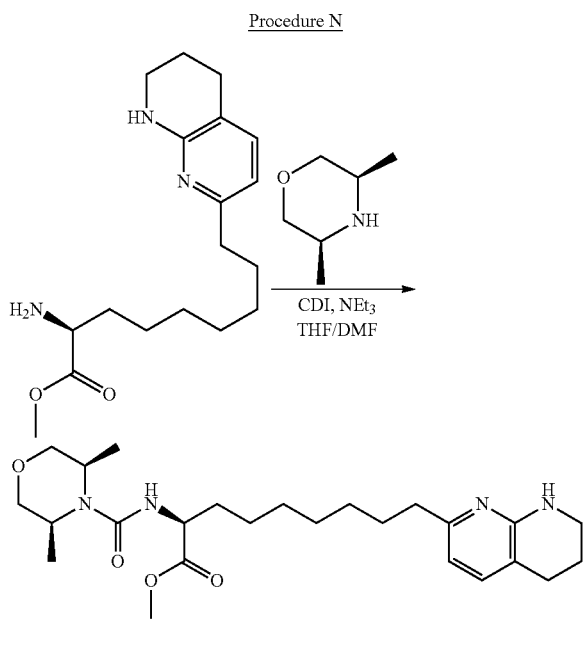

(S)-methyl 2-((3R,5S)-3,5-dimethylmorpholine-4-carboxamido)-9-(5,6,7,8-tetrahydro-1,8-naphthyridin-2-yl)nonanoate Et₃N (220 mg, 2.18 mmol) was added to a solution of methyl (S)-2-amino-9-(5,6,7,8-tetrahydro-1,8-naphthyridin-2-yl)nonanoate (250 mg, 702 µmol, HCl) and CDI (125 mg, 772 µmol) in dry DMF (2.5 mL) and THF (5 mL) at 0° C., which was stirred for 30 min. A solution of (3R,5S)-3,5-dimethylmorpholine (117 mg, 772 µmol, HCl) in DMF (2.5 mL) was added to the mixture. The mixture was allowed to warm to 25° C. and stirred for 12 h. LCMS showed that the desired mass was detected. The mixture was diluted with H₂O (5 mL), and extracted with EA (5 mL×3). The combined organic layers were washed with H₂O (5 mL), dried and coned. The residue was purified by prep-TLC (SiO₂, PE:EA=0:1) to yield the title compd (150 mg, 326 µmol, 46.4% yield) as yellow liquid. LCMS theoretical m/z=461.3 [M+H]⁺, found 461.2. 400 MHz ¹H NMR, CDCl₃, δ ppm 6.99 (d, J=7.06 Hz, 1H), 6.26 (d, J=7.28 Hz, 1H), 4.81 (br d, J=7.50 Hz, 1H), 4.39-4.55 (m, 1H), 3.72-3.89 (m, 2H), 3.61-3.70 (m, 5H), 3.48-3.57 (m, 2H), 3.32 (br d, J=4.41 Hz, 2H), 2.62 (t, J=6.17 Hz, 2H), 2.40-2.49 (m, 2H), 1.65-1.87 (m, 4H), 1.49-1.56 (m, 2H), 1.17-1.35 (m, 14H).

Procedure O

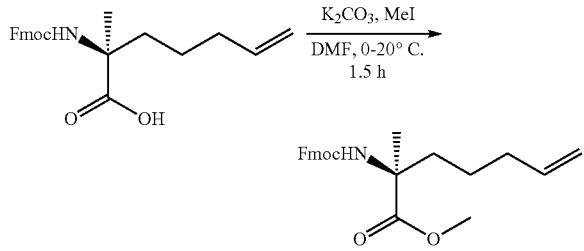

Methyl (S)-2-((((9H-fluoren-9-yl)methoxy)carbonyl)amino)-2-methylhept-6-enoate To a solution of (S)-2-((((9H-fluoren-9-yl)methoxy)carbonyl)amino)-2-methylhept-6-enoic acid (9.00 g, 23.7 mmol) in DMF (90 mL) was added K₂CO₃ (6.56 g, 47.4 mmol) and MeI (6.73 g, 47.4 mmol) at 0° C., then the reaction mixture was stirred at 20° C. for 2 h. The reaction mixture was poured into H₂O (30 mL) and extracted with EA. The combined organic layers were dried over Na₂SO₄, filtered, and coned under reduced pressure to give a residue. The residue was purified by FCC (2% to 12% pet-ether in EA) to afford 8.6 g of title compd (92% yield) as a colorless oil. 400 MHz ¹H NMR, CDCl₃, δ ppm 7.78 (d, J=7.58 Hz, 2H) 7.61 (d, J=7.34 Hz, 2H) 7.37-7.46 (m, 2H) 7.30-7.37 (m, 2H) 5.53-5.86 (m, 2H) 4.88-5.08 (m, 2H) 4.39 (br s, 2H) 4.20-4.27 (m, 1H) 3.77 (br s, 3H) 2.17 (br s, 1H) 2.04 (br s, 1H) 1.70-1.91 (m, 1H) 1.59 (br s, 3H) 1.31-1.47 (m, 1H) 1.07-1.24 (m, 1H).

Procedure P

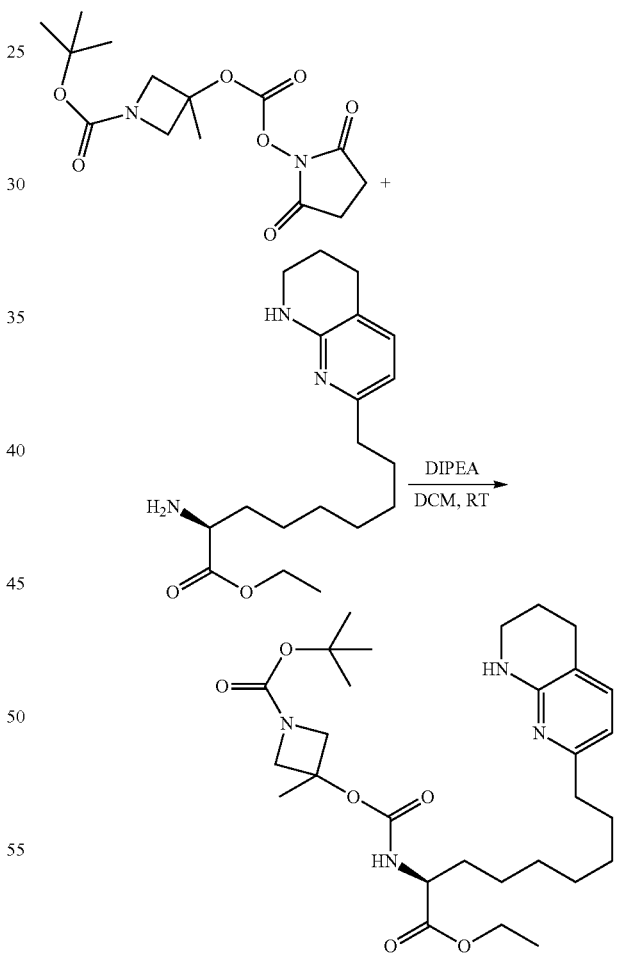

tert-butyl (S)-3-(((1-ethoxy-1-oxo-9-(5,6,7,8-tetrahydro-1,8-naphthyridin-2-yl)nonan-2-yl)carbamoyl)oxy)-3-methylazetidine-1-carboxylate To a solution of tert-butyl 3-(2,5-dioxopyrrolidin-1-yl)oxycarbonyloxy-3-methyl-azetidine-1-carboxylate (120 mg, 0.38 mmol) and DIPEA (0.22 mL, 1.3 mmol) in DCM (10 mL) was added ethyl (S)-2-amino-9-(5,6,7,8-tetrahydro-1,8-naphthyridin-2-yl)nonanoate (120 mg, 0.38 mmol). The reaction was stirred at RT for 1 h and concentrated. The crude product was used without further purification.

pane-2-sulfinamide (35 mg, 82 µmol) in 1,4-dioxane:H$_2$O (1:1, 1 mL) was added H$_2$SO$_4$ (45 µL, 0.82 mmol) at rt. The reaction mixture was refluxed for 20 h. Prep-reverse phase HPLC purification afforded (S)-2-amino-5,5-difluoro-9-(5,6,7,8-tetrahydro-1,8-naphthyridin-2-yl)nonanoic acid. LCMS (ESI+): m/z=342.1 [M+H]$^+$.

Procedure Q

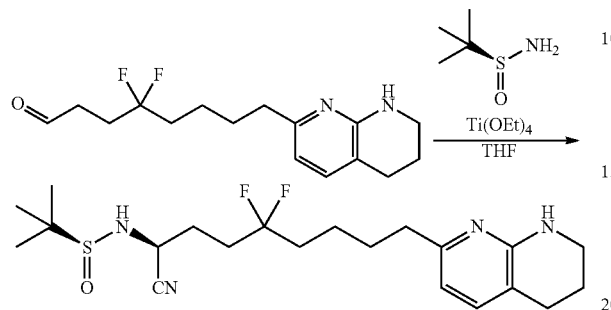

(S)—N—((S)-1-cyano-4,4-difluoro-8-(5,6,7,8-tetrahydro-1,8-naphthyridin-2-yl)octyl)-2-methylpropane-2-sulfinamide To a solution of 4,4-difluoro-8-(5,6,7,8-tetrahydro-1,8-naphthyridin-2-yl)octanal (128 mg, 0.43 mmol) in THF (3 mL) was added (S)-2-methylpropane-2-sulfinamide (63 mg, 0.52 mmol) followed by Titanium(IV) ethoxide (247 mg, 1.085 mmol) at rt. The reaction mixture was refluxed for 30 h in which (S)—N-(4,4-difluoro-8-(5,6,7,8-tetrahydro-1,8-naphthyridin-2-yl)octylidene)-2-methylpropane-2-sulfinamide was generated and used directly. In a separate reaction flask, diethylaluminium (1 M in toluene, 0.645 mL, 0.645 mmol) was added to a solution of i-PrOH (33 µL, 0.43 mmol) in THF (2 mL). After stirring for 10 min, the reaction mixture was cooled to −78° C., the previously generated intermediate in THF was added to the reaction mixture. The reaction mixture was allowed to warm up to rt slowly and stirred at ambient temperature for 10 h. The reaction was quenched with sat aq NH$_4$Cl. The reaction mixture was diluted with EA and H$_2$O, and filtered through a Celite pad. The aq phase was separated and extracted with EA, dried over Na$_2$SO$_4$, filtered, coned, and purified by prep-reverse phase HPLC to give (S)—N—((S)-1-cyano-4,4-difluoro-8-(5,6,7,8-tetrahydro-1,8-naphthyridin-2-yl)octyl)-2-methylpropane-2-sulfinamide. LCMS (ESI+): m/z=427.2 [M+H]$^+$.

Procedure R

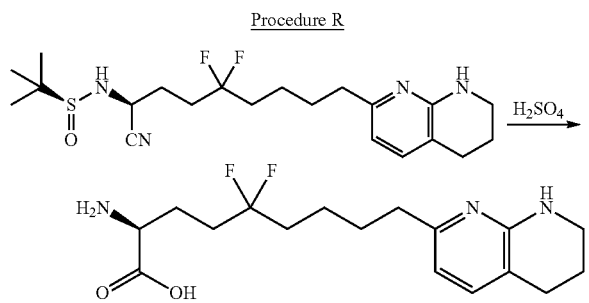

(S)-2-amino-5,5-difluoro-9-(5,6,7,8-tetrahydro-1,8-naphthyridin-2-yl)nonanoic Acid To a solution of (S)—N—((S)-1-cyano-4,4-difluoro-8-(5,6,7,8-tetrahydro-1,8-naphthyridin-2-yl)octyl)-2-methylpro- Procedure S

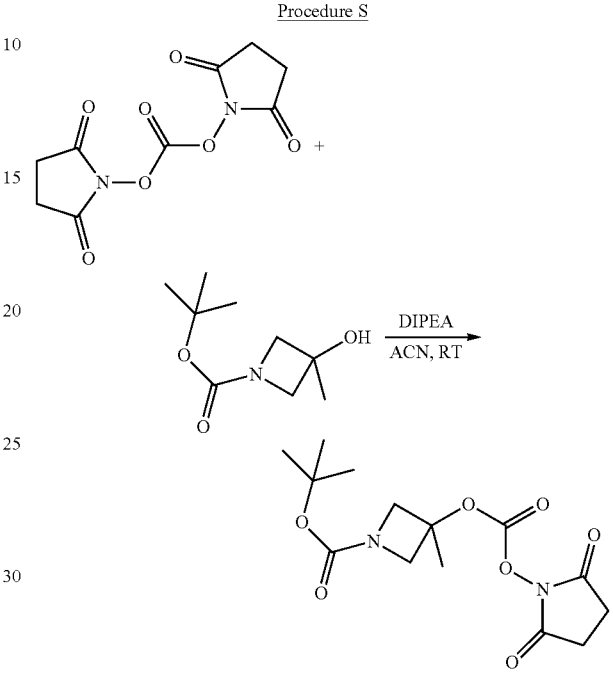

tert-butyl 3-((((2,5-dioxopyrrolidin-1-yl)oxy)carbonyl)oxy)-3-methylazetidine-1-carboxylate A solution of tert-butyl 3-hydroxy-3-methylazetidine-1-carboxylate (1.09 g, 5.81 mmol) in ACN (50 mL) was added bis(2,5-dioxopyrrolidin-1-yl) carbonate (2.98 g, 11.6 mmol) and DIPEA (2.02 mL, 11.6 mmol). The reaction was allowed to stir at rt for 18 h and was then concentrated and used without further purification.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Compound 1: (S)-2-pivalamido-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)

nonanoate and pivalic acid using Procedures A and C. LCMS theoretical m/z=390.3 [M+H]+, found 390.1.

Compound 2: (S)-2-((S)-1-(pyridin-2-yl)pyrrolidine-2-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate using Procedure A with pyridin-2-yl-L-proline and Procedure C. LCMS theoretical m/z=480.3 [M+H]+, found 480.3.

Compound 3: (S)-2-((R)-1-(pyridin-2-yl)pyrrolidine-2-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate using Procedure A with pyridin-2-yl-D-proline, followed by Procedure C. LCMS theoretical m/z=480.3 [M+H]+, found 480.3.

Compound 4: (S)-2-(2-methyl-2-(pyridin-3-yl)propanamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate using Procedure A with 2-methyl-2-(pyridin-3-yl)propanoic acid, followed by Procedure C. LCMS theoretical m/z=453.3 [M+H]+, found 453.0.

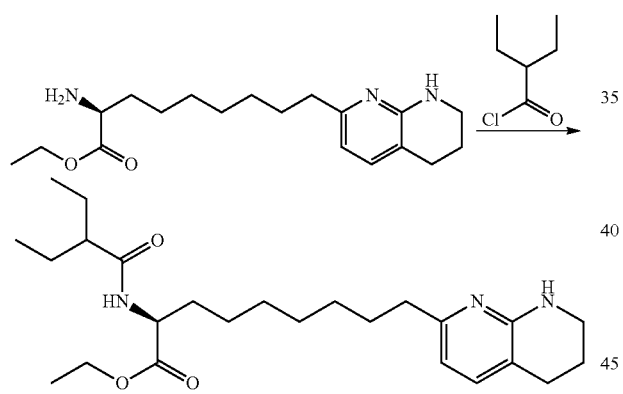

Ethyl (S)-2-(2-ethylbutanamido)-9-(5,6,7,8-tetrahydro-1,8-naphthyridin-2-yl)nonanoate To a mixture of ethyl (2S)-2-amino-9-(5,6,7,8-tetrahydro-1,8-naphthyridin-2-yl)nonanoate bis hydrochloride salt (70 mg, 0.2 mmol, 1 equiv) in DCM (0.5 mL) at rt was added DIPEA (0.21 mL, 1.2 mmol, 6 equiv). The mixture was sonicated to aid dissolution. The mixture was treated by slowly adding 2-ethylbutanoyl chloride (0.04 mL, 0.3 mmol). The resulting mixture was stirred at rt for 2 d. LCMS of the reaction mixture showed the product mass, and the reaction was coned and used directly in the next reaction.

Compound 5: (S)-2-(2-ethylbutanamido)-9-(5,6,7,8-tetrahydro-1,8-naphthyridin-2-yl)nonanoic Acid Prepared using Scheme I and Procedure C beginning with ethyl (S)-2-(2-ethylbutanamido)-9-(5,6,7,8-tetrahydro-1,8-naphthyridin-2-yl)nonanoate. LCMS theoretical m/z=404.3 [M+H]+, found 404.3.

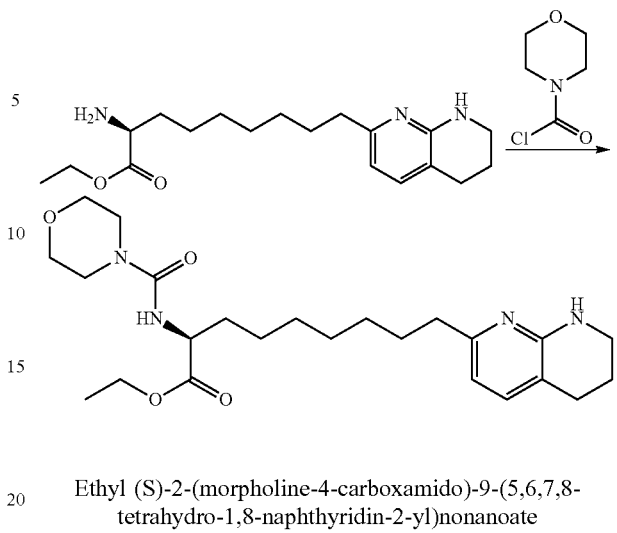

Ethyl (S)-2-(morpholine-4-carboxamido)-9-(5,6,7,8-tetrahydro-1,8-naphthyridin-2-yl)nonanoate To a mixture of ethyl (S)-2-amino-9-(5,6,7,8-tetrahydro-1,8-naphthyridin-2-yl)nonanoate bis hydrochloride (60 mg, 0.17 mmol, 1 equiv) in DCM (0.5 mL) at rt was added DIPEA (0.18 mL, 1.0 mmol, 6 equiv). The mixture was sonicated to aid dissolution. To the mixture was added morpholine-4-carbonyl chloride (0.03 mL, 0.26 mmol). The reaction was stirred at rt for 2 d until LCMS showed the mass of the title compound. The reaction mixture was coned and used directly in the next reaction.

Compound 6: (S)-2-(morpholine-4-carboxamido)-9-(5,6,7,8-tetrahydro-1,8-naphthyridin-2-yl)nonanoic Acid Prepared using Scheme I with Procedure C starting with ethyl (S)-2-(morpholine-4-carboxamido)-9-(5,6,7,8-tetrahydro-1,8-naphthyridin-2-yl)nonanoate. LCMS theoretical m/z=419.3 [M+H]+, found 419.3.

Compound 7: (2S)-2-(2,2-dimethyltetrahydro-2H-pyran-4-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate and 2,2-dimethyltetrahydropyran-4-carboxylic acid using Procedures A and C. LCMS theoretical m/z=446.3 [M+H]+, found 446.3.

Compound 8: (S)-2-(4-methyltetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 4-methyltetrahydro-2H-pyran-4-carboxylic acid using Procedures A and C. LCMS theoretical m/z=432.2 [M+H]+, found 432.3.

Compound 9: (S)-2-((S)-1-phenylpyrrolidine-2-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)

nonanoate using Procedure A with (S)-1-phenylpyrrolidine-2-carboxylic acid and Procedure C. LCMS theoretical m/z=479.3 [M+H]+, found 479.3.

Compound 10: (S)-2-((S)-1-benzylpyrrolidine-2-carboxamido)-9-(5,6,7,8-tetrahydro-1,8-naphthyridin-2-yl)nonanoic Acid Prepared according to Scheme A beginning with (S)-methyl 2-amino-9-(5,6,7,8-tetrahydro-1,8-naphthyridin-2-yl)nonanoate and (S)-1-benzylpyrrolidine-2-carboxylic acid using Procedures A and C. LCMS theoretical m/z=493.3 [M+H]+, found 493.0.

Compound 11: (S)-2-(2-methyl-2-phenylpropanamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate using Procedure A with 2-methyl-2-phenylpropanoic acid, followed by Procedure C. LCMS theoretical m/z=452.3 [M+H]+, found 452.3.

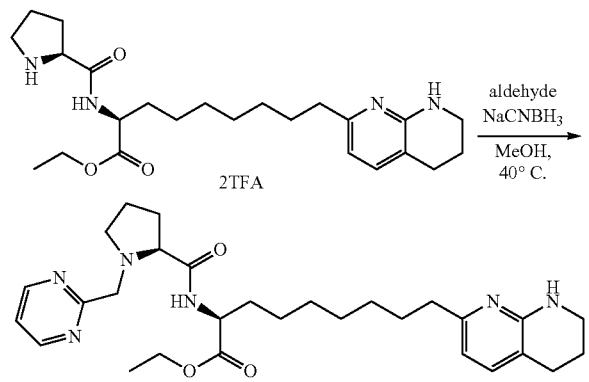

Ethyl (S)-2-((S)-1-(pyrimidin-2-ylmethyl)pyrrolidine-2-carboxamido)-9-(5,6,7,8-tetrahydro-1,8-naphthyridin-2-yl)nonanoate To a solution of ethyl (S)-2-((S)-pyrrolidine-2-carboxamido)-9-(5,6,7,8-tetrahydro-1,8-naphthyridin-2-yl)nonanoate (50 mg, 0.08 mmol, 1 equiv) in 0.5 mL MeOH was added pyrimidine-2-carbaldehyde (0.018 mL, 0.19 mol, 2.5 equiv). The mixture was heated at 40° C. for 10 min before adding sodium cyanoborohydride (12 mg, 0.19 mmol, 2.5 equiv) and continuing to heat for an additional 2 h. The crude mixture was used directly in the next step.

Compound 12: (S)-2-((S)-1-(pyrimidin-2-ylmethyl)pyrrolidine-2-carboxamido)-9-(5,6,7,8-tetrahydro-1,8-naphthyridin-2-yl)nonanoic Acid Prepared using Scheme E with Procedure C employing a crude mixture of ethyl (S)-2-((S)-1-(pyrimidin-2-ylmethyl)pyrrolidine-2-carboxamido)-9-(5,6,7,8-tetrahydro-1,8-naphthyridin-2-yl)nonanoate. LCMS theoretical m/z=495.3 [M+H]+, found 495.3.

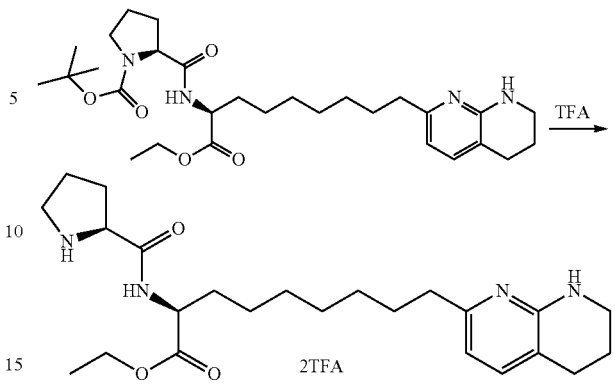

Ethyl (S)-2-((S)-pyrrolidine-2-carboxamido)-9-(5,6,7,8-tetrahydro-1,8-naphthyridin-2-yl)nonanoate (S)-2-((S)-1-(tert-butoxycarbonyl)pyrrolidine-2-carboxamido)-9-(5,6,7,8-tetrahydro-1,8-naphthyridin-2-yl) nonanoic acid was prepared using Procedure A. (S)-2-((S)-1-(tert-butoxycarbonyl)pyrrolidine-2-carboxamido)-9-(5,6,7,8-tetrahydro-1,8-naphthyridin-2-yl)nonanoic acid (334 mg, 0.63 mmol, 1.0 equiv) was treated with 4 N HCl in 1,4-dioxane (2.0 mL) at rt for 30 min. The reaction was coned and then azeotroped with EA and frozen to afford a yellow paste. The material was then purified by RP-HPLC to afford 201 mg (48% yield) of the title compound as the TFA salt, a yellowish, viscous oil, which was used directly in the next step.

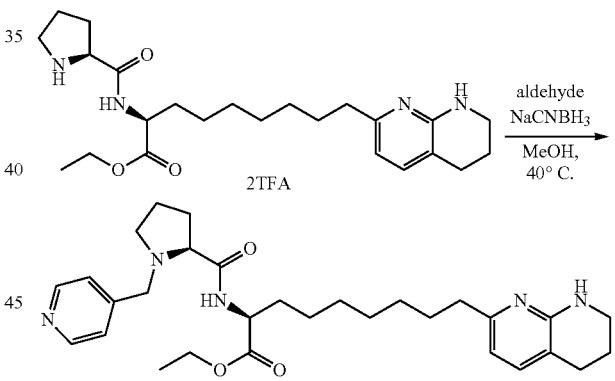

Ethyl (S)-2-((S)-1-(2-(Pyridin-4-yl)acetyl)pyrrolidine-2-carboxamido)-9-(5,6,7,8-tetrahydro-1,8-naphthyridin-2-yl)nonanoate To a solution of ethyl (S)-2-((S)-pyrrolidine-2-carboxamido)-9-(5,6,7,8-tetrahydro-1,8-naphthyridin-2-yl)nonanoate (50 mg, 0.08 mmol, 1 equiv) in 0.5 mL MeOH was added isonicotinaldehyde (0.01 mL, 0.15 mol, 2 equiv). The mixture was heated at 40° C. for 10 min before adding sodium cyanoborohydride (9.5 mg, 0.15 mmol, 2 equiv) and continuing to heat for an additional h. The crude mixture was used directly in the next step.

Compound 13: (S)-2-((S)-1-(2-(Pyridin-4-yl)acetyl) pyrrolidine-2-carbamido)-9-(5,6,7,8-tetrahydro-1,8-naphthyridin-2-yl)nonanoic Acid Prepared using Scheme E with Procedure C employing a crude mixture of ethyl (S)-2-((S)-1-(pyridin-4-ylmethyl)pyrrolidine-2-carboxamido)-9-(5,6,7,8-tetrahydro-1,8-naphthyridin-2-yl)nonanoate. LCMS theoretical m/z=494.3 [M+H]+, found 494.3.

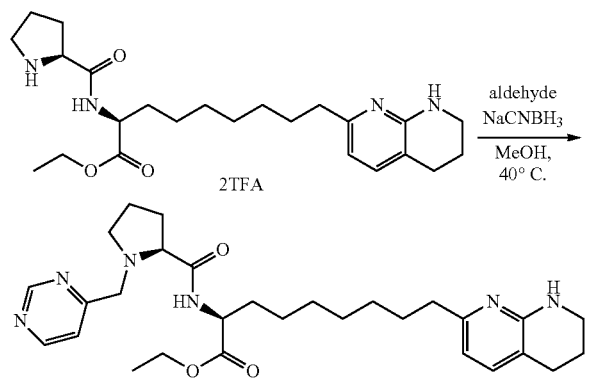

Ethyl (S)-2-((S)-1-(pyrimidin-4-ylmethyl)pyrrolidine-2-carboxamido)-9-(5,6,7,8-tetrahydro-1,8-naphthyridin-2-yl)nonanoate To a solution of ethyl (S)-2-((S)-pyrrolidine-2-carboxamido)-9-(5,6,7,8-tetrahydro-1,8-naphthyridin-2-yl) nonanoate (50 mg, 0.08 mmol, 1 equiv) in 0.5 mL MeOH was added pyrimidine-4-carbaldehyde (0.018 mL, 0.19 mol, 2.5 equiv). The mixture was heated at 40° C. for 10 min before adding sodium cyanoborohydride (12 mg, 0.19 mmol, 2.5 equiv) and continuing to heat for an additional 2 h. The crude mixture was used directly in the next step.

Compound 14: (S)-2-((S)-1-(pyrimidin-4-ylmethyl) pyrrolidine-2-carboxamido)-9-(5,6,7,8-tetrahydro-1, 8-naphthyridin-2-yl)nonanoic Acid Prepared using Scheme E with Procedure C employing a crude mixture of (S)-2-((S)-1-(pyrimidin-2-ylmethyl)pyrrolidine-2-carboxamido)-9-(5,6,7,8-tetrahydro-1,8-naphthyridin-2-yl)nonanoic acid. LCMS theoretical m/z=495.3 [M+H]+, found 495.3.

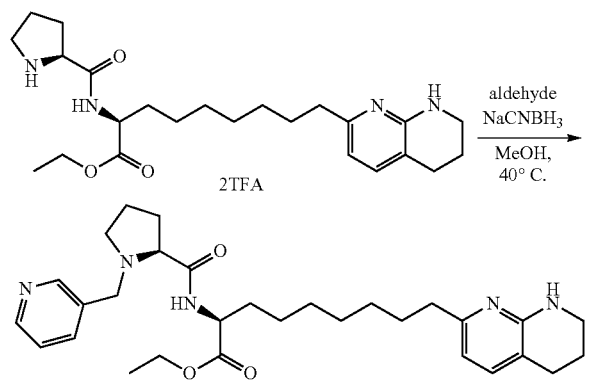

Ethyl (S)-2-((S)-1-(pyridin-3-ylmethyl)pyrrolidine-2-carboxamido)-9-(5,6,7,8-tetrahydro-1,8-naphthyridin-2-yl)nonanoate To a solution of ethyl (S)-2-((S)-pyrrolidine-2-carboxamido)-9-(5,6,7,8-tetrahydro-1,8-naphthyridin-2-yl) nonanoate (50 mg, 0.08 mmol, 1 equiv) in 0.5 mL MeOH was added 3-pyridinecarboxaldehyde (0.018 mL, 0.19 mol, 2.5 equiv). The mixture was heated at 40° C. for 10 min before adding sodium cyanoborohydride (12 mg, 0.19 mmol, 2.5 equiv) and continuing to heat for an additional 2 h. The crude mixture was used directly in the next step.

Compound 15: (S)-2-((S)-1-(pyridin-3-ylmethyl) pyrrolidine-2-carboxamido)-9-(5,6,7,8-tetrahydro-1, 8-naphthyridin-2-yl)nonanoic Acid Prepared using Scheme E with Procedure C employing a crude mixture of ethyl (S)-2-((S)-1-(pyridin-3-ylmethyl)pyrrolidine-2-carboxamido)-9-(5,6,7,8-tetrahydro-1,8-naphthyridin-2-yl)nonanoate. LCMS theoretical m/z=494.3 [M+H]+, found 494.3.

Compound 16: (S)-2-((S)-1-(tert-butoxycarbonyl) piperidine-2-carboxamido)-9-(5,6,7,8-tetrahydro-1, 8-naphthyridin-2-yl)nonanoic Acid Prepared with Scheme A beginning with ethyl (S)-2-amino-9-(5,6,7,8-tetrahydro-1,8-naphthyridin-2-yl)nonanoate and (S)-1-(tert-butoxycarbonyl)piperidine-2-carboxylic acid using Procedures A and C. LCMS theoretical m/z=517.3 [M+H]+, found 517.3.

Compound 17: (S)-2-(2-(2-chlorophenyl)acetamido)-9-(5,6,7,8-tetrahydro-1,8-naphthyridin-2-yl) nonanoic Acid Prepared with Scheme A beginning with ethyl (S)-2-amino-9-(5,6,7,8-tetrahydro-1,8-naphthyridin-2-yl)nonanoate and 2-chlorophenylacetic acid using Procedures A and C. LCMS theoretical m/z=458.2 [M+H]+, found 458.2.

Compound 18: (S)-2-((3R,4R)-1-(tert-butoxycarbonyl)-3-methylpiperidine-4-carboxamido)-9-(5,6,7,8-tetrahydro-1,8-naphthyridin-2-yl)nonanoic Acid Prepared with Scheme A beginning with ethyl (S)-2-amino-9-(5,6,7,8-tetrahydro-1,8-naphthyridin-2-yl)nonanoate and (3 S,4S)-1-tert-butoxycarbonyl-3-methyl-piperidine-4-carboxylic acid using Procedures A and C. LCMS theoretical m/z=531.3 [M+H]+, found 531.4.

Compound 19: (S)-2-(1-(tert-butoxycarbonyl)piperidine-4-carboxamido)-9-(5,6,7,8-tetrahydro-1,8-naphthyridin-2-yl)nonanoic Acid Prepared with Scheme A beginning with ethyl (S)-2-amino-9-(5,6,7,8-tetrahydro-1,8-naphthyridin-2-yl)nonanoate and 1-(tert-butoxycarbonyl)piperidine-4-carboxylic acid using Procedures A and C. LCMS theoretical m/z=517.3 [M+H]+, found 517.3.

Compound 20: (S)-2-(2-((S)-1-(tert-butoxycarbonyl) pyrrolidin-2-yl)acetamido)-9-(5,6,7,8-tetrahydro-1,8-naphthyridin-2-yl)nonanoic Acid Prepared with Scheme A beginning with ethyl (S)-2-amino-9-(5,6,7,8-tetrahydro-1,8-naphthyridin-2-yl)nonanoate 2-[(2S)-1-tert-butoxycarbonylpyrrolidin-2-yl]acetic acid using Procedures A and C. LCMS theoretical m/z=517.3 [M+H]+, found 517.3.

Compound 21: (S)-2-((S)-1-benzylazetidine-2-carboxamido)-9-(5,6,7,8-tetrahydro-1,8-naphthyridin-2-yl)nonanoic Acid Prepared using Scheme E with Procedure A employing ethyl (S)-2-amino-9-(5,6,7,8-tetrahydro-1,8-naphthyridin-2-yl)nonanoate and (S)-1-(tert-butoxycarbonyl)azetidine-2-carboxylic acid, Procedures H, J, and C. LCMS theoretical m/z=479.3 [M+H]+, found 479.2.

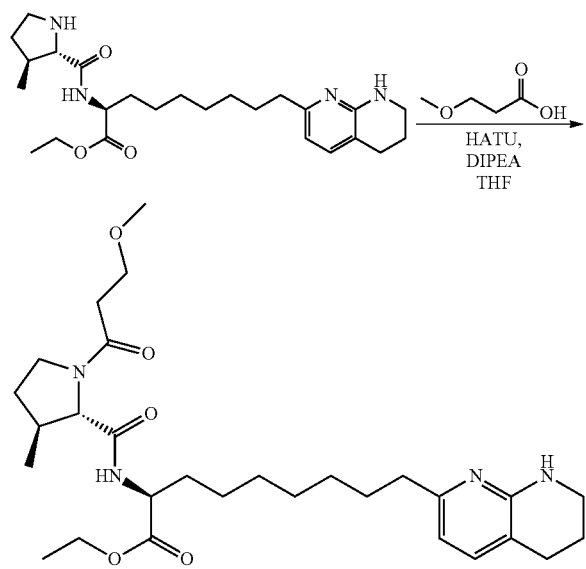

Ethyl (S)-2-((2S,3S)-1-(3-methoxypropanoyl)-3-methylpyrrolidine-2-carboxamido)-9-(5,6,7,8-tetrahydro-1,8-naphthyridin-2-yl)nonanoate Ethyl (S)-2-((2S,3S)-3-methylpyrrolidine-2-carboxamido)-9-(5,6,7,8-tetrahydro-1,8-naphthyridin-2-yl)nonanoate was synthesized according to Procedure A using ethyl (S)-2-amino-9-(5,6,7,8-tetrahydro-1,8-naphthyridin-2-yl)nonanoate and (2S,3S)-1-tert-butoxycarbonyl-3-methylpyrrolidine-2-carboxylic acid. To a mixture of ethyl (S)-2-((2S,3S)-3-methylpyrrolidine-2-carboxamido)-9-(5,6,7,8-tetrahydro-1,8-naphthyridin-2-yl)nonanoate (17 mg, 0.038 mmol, 1 equiv) and 3-methoxypropionic acid (5 mg, 0.5 mmol, 1.2 equiv) in THF (0.5 mL) was added HATU (17 mg, 0.05 mmol, 1.2 equiv) followed by DIPEA (0.04 mL, 0.2 mmol, 6 equiv). The reaction was stirred at rt for 1 h before concentrating and purifying by reverse phase chromatography to afford the title compound as a white solid, which was used directly in the next reaction.

Compound 22: (S)-2-((2S,3S)-1-(3-methoxypropanoyl)-3-methylpyrrolidine-2-carboxamido)-9-(5,6,7,8-tetrahydro-1,8-naphthyridin-2-yl)nonanoic Acid Prepared with Scheme A beginning with ethyl (S)-2-amino-9-(5,6,7,8-tetrahydro-1,8-naphthyridin-2-yl)nonanoate and 2-[(2S)-1-tert-butoxycarbonylpyrrolidin-2-yl]acetic acid using Procedure C. LCMS theoretical m/z=503.3 [M+H]+, found 503.3.

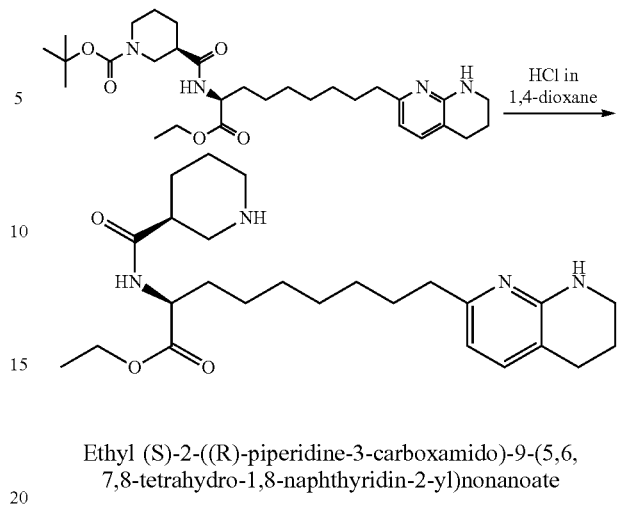

Ethyl (S)-2-((R)-piperidine-3-carboxamido)-9-(5,6,7,8-tetrahydro-1,8-naphthyridin-2-yl)nonanoate Ethyl (S)-2-((R)-piperidine-3-carboxamido)-9-(5,6,7,8-tetrahydro-1,8-naphthyridin-2-yl)nonanoate was synthesized according to Procedure A employing ethyl (S)-2-amino-9-(5,6,7,8-tetrahydro-1,8-naphthyridin-2-yl)nonanoate and (R)-1-(tert-butoxycarbonyl)piperidine-3-carboxylic acid. To a solution of ethyl (S)-2-((R)-piperidine-3-carboxamido)-9-(5,6,7,8-tetrahydro-1,8-naphthyridin-2-yl)nonanoate (72 mg, 0.12 mmol) was added 4 N HCl in 1,4-dioxane (0.5 mL). The reaction was stirred for 1 h at rt before concentrating. The crude residue was used directly in the next reaction.

Compound 23: (S)-2-((R)-1-(3-methoxypropanoyl)piperidine-3-carboxamido)-9-(5,6,7,8-tetrahydro-1,8-naphthyridin-2-yl)nonanoic Acid Prepared according to Scheme E and the above description as well as Procedure C, employing ethyl (S)-2-((R)-1-(3-methoxypropanoyl)piperidine-3-carboxamido)-9-(5,6,7,8-tetrahydro-1,8-naphthyridin-2-yl)nonanoate. LCMS theoretical m/z=503.3 [M+H]+, found 503.3.

Compound 24: (S)-2-(4-(methylsulfonyl)butanamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate and 4-methylsulfonylbutanoic acid using Procedures A and C. LCMS theoretical m/z=454.2 [M+H]+, found 454.3.

Compound 25: (S)-2-((R)-2-hydroxy-2-phenylacetamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate and (R)-(−)-mandelic acid using Procedures A and C. LCMS theoretical m/z=440.2 [M+H]+, found 440.3.

Compound 26: (S)-2-((S)-2-hydroxy-2-phenylacetamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)

nonanoate and (S)-(−)-mandelic acid using Procedures A and C. LCMS theoretical m/z=440.2 [M+H]+, found 440.3.

Compound 27: (S)-2-((R)-3-hydroxy-2-phenylpropanamido)-9-(5,6,7,8-tetrahydro-1,8-naphthyridin-2-yl)nonanoic Acid Prepared according to Scheme A using Procedure C employing ethyl (2S)-2-(3-hydroxy-2-phenylpropanamido)-9-(5,6,7,8-tetrahydro-1,8-naphthyridin-2-yl)nonanoate to afford one of the (R)- and (S)-enantiomers by reverse phase column chromatography as the first eluting peak. Absolute stereochemistry at the benzylic center was unassigned, as indicated by the wavy bond for Compound 27 in FIG. 1. LCMS theoretical m/z=454.3 [M+H]+, found 454.3.

Compound 28: (S)-2-((S)-3-hydroxy-2-phenylpropanamido)-9-(5,6,7,8-tetrahydro-1,8-naphthyridin-2-yl)nonanoic Acid Prepared according to Scheme A using Procedure C employing ethyl (2S)-2-(3-hydroxy-2-phenylpropanamido)-9-(5,6,7,8-tetrahydro-1,8-naphthyridin-2-yl)nonanoate to afford, compared to Compound 27, the other of the (R)- and (S)-enantiomers by reverse phase column chromatography as the second eluting peak. Absolute stereochemistry at the benzylic center was unassigned, as indicated by the wavy bond for Compound 28 in FIG. 1. LCMS theoretical m/z=454.3 [M+H]+, found 454.3.

Compound 29: (S)-2-(3,3-diethylureido)-9-(5,6,7,8-tetrahydro-1,8-naphthyridin-2-yl)nonanoic Acid Prepared according to Scheme I using Procedure G with methyl (S)-2-amino-9-(5,6,7,8-tetrahydro-1,8-naphthyridin-2-yl)nonanoate and diethylcarbamic chloride followed by Procedure C. LCMS theoretical m/z=405.3, [M+H]+, found 405.3.

Compound 30: (S)-2-(4-methoxybutanamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 4-methoxybutanoic acid using Procedures A and C. LCMS theoretical m/z=405.5. [M+H]+, found 406.4.

Compound 31: (S)-9-(5,6,7,8-tetrahydro-1,8-naphthyridin-2-yl)-2-((R)-tetrahydrofuran-3-carboxamido)nonanoic acid and (S)-9-(5,6,7,8-tetrahydro-1,8-naphthyridin-2-yl)-2-((S)-tetrahydrofuran-3-carboxamido)nonanoic Acid Prepared according to Scheme A beginning with methyl (S)-2-amino-9-(5,6,7,8-tetrahydro-1,8-naphthyridin-2-yl)nonanoate and tetrahydrofuran-3-carboxylic acid using Procedures A and C. LCMS theoretical m/z=403.5. [M+H]+, found 404.3.

Compound 32: (S)-2-((((1-(tert-butoxycarbonyl)-3-methylazetidin-3-yl)oxy)carbonyl)amino)-9-(5,6,7,8-tetrahydro-1,8-naphthyridin-2-yl)nonanoic Acid Prepared according to Scheme I beginning with methyl (S)-2-amino-9-(5,6,7,8-tetrahydro-1,8-naphthyridin-2-yl)nonanoate, then generating tert-butyl 3-(2,5-dioxopyrrolidin-1-yl)oxycarbonyloxy-3-methyl-azetidine-1-carboxylate according to Procedure R using tert-butyl 3-(carboxyoxy)-3-methylazetidine-1-carboxylate, followed by Procedure C. LCMS theoretical m/z=519.3. [M+H]+, found 519.3.

Compound 33: (2S)-2-[(1-tert-butoxycarbonylazetidin-3-yl)oxycarbonylamino]-9-(5,6,7,8-tetrahydro-1,8-naphthyridin-2-yl)nonanoic Acid Prepared according to Scheme I beginning with methyl (S)-2-amino-9-(5,6,7,8-tetrahydro-1,8-naphthyridin-2-yl)nonanoate then generating tert-butyl 3-(2,5-dioxopyrrolidin-1-yl)oxycarbonyloxy-3-methyl-azetidine-1-carboxylate according to Procedure R using tert-butyl 3-(carboxyoxy)-3-methylazetidine-1-carboxylate, followed by Procedure C. LCMS theoretical m/z=505.3. [M+H]+, found 505.3.

Compound 34: (S)-2-(piperidine-4-carboxamido)-9-(5,6,7,8-tetrahydro-1,8-naphthyridin-2-yl)nonanoic Acid Prepared according to Scheme C beginning with methyl (S)-2-amino-9-(5,6,7,8-tetrahydro-1,8-naphthyridin-2-yl)nonanoate and 1-(tert-butoxycarbonyl)piperidine-4-carboxylic acid using Procedure A, followed by Procedures H and C. LCMS theoretical m/z=417.3. [M+H]+, found 417.3.

Compound 35: (S)-9-(5,6,7,8-tetrahydro-1,8-naphthyridin-2-yl)-2-(tetrahydro-2H-pyran-4-carboxamido)nonanoic Acid Prepared according to Scheme A beginning with methyl (S)-2-amino-9-(5,6,7,8-tetrahydro-1,8-naphthyridin-2-yl)nonanoate and tetrahydro-2H-pyran-4-carboxylic acid using Procedures A and C. LCMS theoretical m/z=418.3. [M+H]+, found 418.3.

Compound 36: (S)-2-(1-acetylpiperidine-4-carboxamido)-9-(5,6,7,8-tetrahydro-1,8-naphthyridin-2-yl)nonanoic Acid Prepared according to Scheme E beginning with methyl (S)-2-amino-9-(5,6,7,8-tetrahydro-1,8-naphthyridin-2-yl)nonanoate and 1-(tert-butoxycarbonyl)piperidine-4-carboxylic acid using Procedures A, H, I, and C. LCMS theoretical m/z=459.3. [M+H]+, found 459.2.

Compound 37: (S)-2-((R)-1-(methylsulfonyl)piperidine-3-carboxamido)-9-(5,6,7,8-tetrahydro-1,8-naphthyridin-2-yl)nonanoic acid and (S)-2-((S)-1-(methylsulfonyl)piperidine-3-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 1-(methylsulfonyl)piperidine-3-carboxylic acid using Procedures A and C. LCMS theoretical m/z=494.3. [M+H]+, found 495.3.

Compound 38: (S)-2-(3-sulfamoylpropanamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)

nonanoate and 3-sulfamoylpropanoic acid using Procedures A and C. LCMS theoretical m/z=441.2. [M+H]+, found 441.2.

Compound 39: (S)-2-(1-(methylsulfonyl)piperidine-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 1-(methylsulfonyl) piperidine-4-carboxylic acid using Procedures A and C. LCMS theoretical m/z=495.3. [M+H]+, found 495.3.

Compound 40: (S)-2-(3-(methylsulfonamido)propanamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 3-(methylsulfonamido)propanoic acid using Procedures A and C. LCMS theoretical m/z=455.2. [M+H]+, found 455.3.

Compound 41: (S)-2-((R)-3-methyltetrahydrofuran-3-carboxamido)-9-(5,6,7,8-tetrahydro-1,8-naphthyridin-2-yl)nonanoic acid and (S)-2-((S)-3-methyltetrahydrofuran-3-carboxamido)-9-(5,6,7,8-tetrahydro-1, 8-naphthyridin-2-yl)nonanoic Acid Prepared according to Scheme A beginning with ethyl (S)-2-amino-9-(5,6,7,8-tetrahydro-1,8-naphthyridin-2-yl) nonanoate and 3-methyltetrahydrofuran-3-carboxylic acid using Procedures A and C to afford a 1:1 mixture of diastereomers. LCMS theoretical m/z=418.3 [M+H]+, found 418.3.

Compound 42: (S)-9-(5,6,7,8-tetrahydro-1,8-naphthyridin-2-yl)-2-(4-(trifluoromethyl)tetrahydro-2H-pyran-4-carboxamido)nonanoic Acid Prepared according to Scheme A beginning with ethyl (S)-2-amino-9-(5,6,7,8-tetrahydro-1,8-naphthyridin-2-yl) nonanoate and 4-(trifluoromethyl)tetrahydropyran-4-carboxylic acid using Procedures A and C. LCMS theoretical m/z=486.3 [M+H]+, found 486.3.

Compound 43: (S)-2-((1R,3s,5S)-8-oxabicyclo [3.2.1]octane-3-carboxamido)-9-(5,6,7,8-tetrahydro-1,8-naphthyridin-2-yl)nonanoic acid and (S)-2-((1R, 3r,5S)-8-oxabicyclo[3.2.1]octane-3-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl) nonanoate and 8-oxabicyclo[3.2.1]octane-3-carboxylic acid using Procedures A and C to afford a mixture of diastereomers. LCMS theoretical m/z=444.3 [M+H]+, found 444.3.

Compound 44: (S)-2-(1-methylcyclohexanecarboxamido)-9-(5,6,7,8-tetrahydro-1,8-naphthyridin-2-yl) nonanoic Acid Prepared according to Scheme A beginning with ethyl (S)-2-amino-9-(5,6,7,8-tetrahydro-1,8-naphthyridin-2-yl) nonanoate and 1-methylcyclohexane-1-carboxylic acid using Procedures A and C. Also prepared according to Scheme A beginning with methyl (S)-2-amino-9-(5,6,7,8-tetrahydro-1,8-naphthyridin-2-yl)nonanoate and 1-methylcyclohexanecarboxylic acid using Procedures K and M with methyl (S)-2-(1-methylcyclohexane-1-carboxamido)-9-(5,6,7,8-tetrahydro-1,8-naphthyridin-2-yl)nonanoate. LCMS theoretical m/z=430.2 [M+H]+, found 430.3.

Compound 45: (S)-2-(bicyclo[1.1.1]pentane-1-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and bicyclo[1.1.1]pentane-1-carboxylic acid using Procedures A and C. Also prepared according to Scheme A beginning with methyl (S)-2-amino-9-(5,6,7,8-tetrahydro-1,8-naphthyridin-2-yl)nonanoate and bicyclo [1.1.1]pentane-1-carboxylic acid using Procedures K and M. LCMS theoretical m/z=400.2 [M+H]+, found 400.2.

Compound 46: (S)-2-((S)-chromane-4-carboxamido)-9-(5,6,7,8-tetrahydro-1,8-naphthyridin-2-yl) nonanoic Acid and (S)-2-((R)-chromane-4-carboxamido)-9-(5,6,7,8-tetrahydro-1,8-naphthyridin-2-yl) nonanoic Acid Prepared according to Scheme A beginning with ethyl (S)-2-amino-9-(5,6,7,8-tetrahydro-1,8-naphthyridin-2-yl) nonanoate and chromane-4-carboxylic acid using Procedures A and C to afford a 1:1 mixture of diastereomers. LCMS theoretical m/z=466.3 [M+H]+, found 466.3.

Compound 47: (S)-2-((R)-3-methyltetrahydro-2H-pyran-3-carboxamido)-9-(5,6,7,8-tetrahydro-1,8-naphthyridin-2-yl)nonanoic Acid and (S)-2-((S)-3-methyltetrahydro-2H-pyran-3-carboxamido)-9-(5,6, 7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl) nonanoate and 3-methyltetrahydropyran-3-carboxylic acid using Procedures A and C to afford a 1:1 mixture of diastereomers. LCMS theoretical m/z=432.3 [M+H]+, found 432.3.

Compound 48: (S)-2-(4-(((tert-butoxycarbonyl) amino)methyl)tetrahydro-2H-pyran-4-carboxamido)-9-(5,6,7,8-tetrahydro-1,8-naphthyridin-2-yl)nonanoic Acid Prepared according to Scheme J using Procedure A with methyl (S)-2-amino-9-(5,6,7,8-tetrahydro-1,8-naphthyridin-2-yl)nonanoate and 4-(((tert-butoxycarbonyl)amino)methyl) tetrahydro-2H-pyran-4-carboxylic acid, followed by Procedure C. LCMS theoretical m/z=547.3. [M+H]+, found 547.4.

Compound 49: (S)-2-(4-Phenyltetrahydro-2H-pyran-4-carboxamido)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl) nonanoate and 3-methyltetrahydropyran-3-carboxylic acid using Procedures A and C. LCMS theoretical m/z=494.3 [M+H]+, found 494.3.

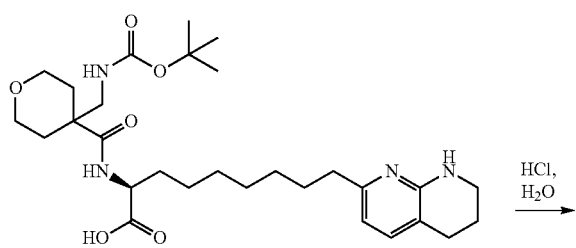

HCl, H₂O

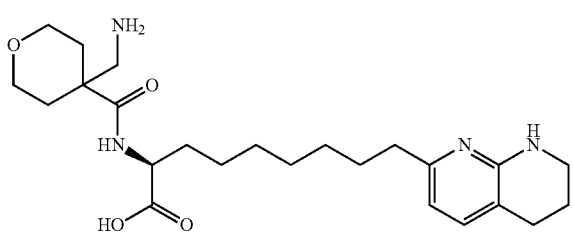

Compound 50: (S)-2-(4-(aminomethyl)tetrahydro-2H-pyran-4-carboxamido)-9-(5,6,7,8-tetrahydro-1,8-naphthyridin-2-yl)nonanoic Acid Prepared according to Scheme J using Procedure A with methyl (S)-2-amino-9-(5,6,7,8-tetrahydro-1,8-naphthyridin-2-yl)nonanoate and 4-(((tert-butoxycarbonyl)amino)methyl)tetrahydro-2H-pyran-4-carboxylic acid. Final BOC removal was achieved using the following: (S)-2-(4-(((tert-butoxycarbonyl)amino)methyl)tetrahydro-2H-pyran-4-carboxamido)-9-(5,6,7,8-tetrahydro-1,8-naphthyridin-2-yl)nonanoic acid (280 mg, 0.51 mmol, 1 equiv) was diluted with 1 mL DCM and treated with 2.55 mL of 2 M HCl in water (10 equiv) for 18 h. The reaction mixture was coned and azeotroped with hexanes. The product was then diluted in 1:1 ACN:H₂O and placed under lyophilization to afford the title compound as a white foam (190 mg, 83% yield). LCMS theoretical m/z=447.3. [M+H]+, found 447.3.

Compound 51: (R)-2-(4-methyltetrahydro-2H-pyran-4-carboxamido)-9-(5,6,7,8-tetrahydro-1,8-naphthyridin-2-yl)nonanoic Acid Prepared according to Procedure L for the synthesis of (S)-methyl 2-((tert-butoxycarbonyl)amino)-9-(5,6,7,8-tetrahydro-1,8-naphthyridin-2-yl)nonanoate except substituting 1-(tert-butyl) 2-methyl (R)-5-oxopyrrolidine-1,2-dicarboxylate for 1-(tert-butyl) 2-methyl (S)-5-oxopyrrolidine-1,2-dicarboxylate to afford methyl (R)-2-amino-9-(5,6,7,8-tetrahydro-1,8-naphthyridin-2-yl)nonanoate dihydrochloride salt. The title compound was prepared according to Scheme A using Procedure B with methyl (R)-2-amino-9-(5,6,7,8-tetrahydro-1,8-naphthyridin-2-yl)nonanoate and 4-methyltetrahydro-2H-pyran-4-carboxylic acid and Procedure C. LCMS theoretical m/z=432.3, [M+H]+, found 432.3.

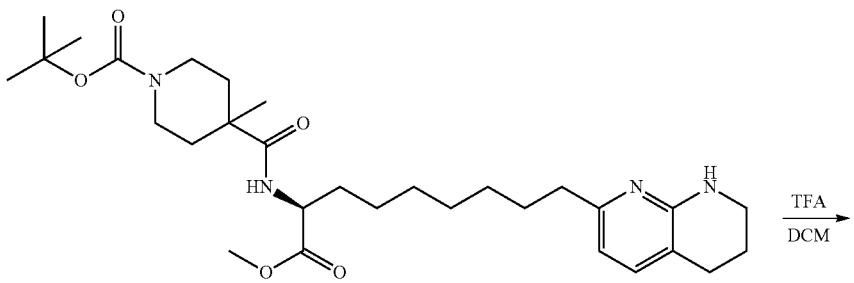

TFA
DCM

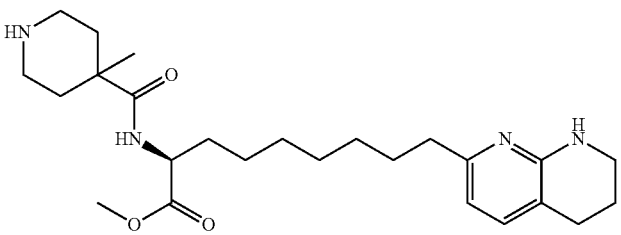

Methyl (S)-2-(4-methylpiperidine-4-carboxamido)-9-(5,6,7,8-tetrahydro-1,8-naphthyridin-2-yl)nonanoate Tert-Butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate was synthesized according to Procedure A employing 1-tert-butoxycarbonyl-4-methylpiperidine-4-carboxylic acid. To a crude solution of tert-butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate (410 mg, 0.76 mmol, 1.0 equiv) in DCM (1.5 mL) was added TFA (1 mL). The reaction was stirred at rt for 12 h. LCMS showed no remaining starting material. The reaction was coned and purified by reverse phase preparative HPLC to afford 304 mg of the title compound as the TFA adduct (71% yield).

Compound 52: (S)-2-(4-methylpiperidine-4-carbox-amido)-9-(5,6,7,8-tetrahydro-1,8-naphthyridin-2-yl) nonanoic Acid Prepared according to Scheme C beginning with ethyl (S)-2-amino-9-(5,6,7,8-tetrahydro-1,8-naphthyridin-2-yl)nonanoate and 1-tert-butoxycarbonyl-4-methyl-piperidine-4-carboxylic acid using Procedure A. Procedure C was employed using used methyl (S)-2-(4-methylpiperidine-4-carboxamido)-9-(5,6,7,8-tetrahydro-1,8-naphthyridin-2-yl)nonanoate. LCMS theoretical m/z=431.3 [M+H]+, found 431.3.

Compound 53: (S)-2-(4-fluorotetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 4-fluorotetrahydro-2H-pyran-4-carboxylic acid using Procedures A and C. Also prepared according to Scheme A beginning with methyl (S)-2-amino-9-(5,6,7,8-tetrahydro-1,8-naphthyridin-2-yl)nonanoate and 4-fluorotetrahydro-2H-pyran-4-carboxylic acid using Procedures K and M. LCMS theoretical m/z=436.2 [M+H]$^+$, found 436.2.

Compound 54: (S)-2-((6-(propylsulfonyl)pyrimidin-4-yl)amino)-9-(5,6,7,8-tetrahydro-1,8-naphthyridin-2-yl)nonanoic Acid Prepared according to Scheme A beginning with ethyl (S)-2-amino-9-(5,6,7,8-tetrahydro-1,8-naphthyridin-2-yl)nonanoate and 4-chloro-6-(propylsulfonyl)pyrimidine using Procedures A and C. LCMS theoretical m/z=490.2 [M+H]$^+$, found 490.0.

Compound 55: (S)-2-((1-methyl-1H-pyrazolo[4,3-d]pyrimidin-7-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate then using Procedure B with 7-chloro-1-methyl-1H-pyrazolo[4,3-d]pyrimidine and Procedure C with ethyl (S)-2-((1-methyl-1H-pyrazolo[4,3-d]pyrimidin-7-yl)amino)-9-(5,6,7,8-tetrahydro-1,8-naphthyridin-2-yl)nonanoate. LCMS theoretical m/z=438.3 [M+H]+, found 438.0.

Compound 56: (S)-2-((5-(pyridin-3-yl)pyrimidin-2-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate, followed by Procedure B using 2-chloro-5-(pyridin-3-yl)pyrimidine and Procedure C using ethyl (S)-2-((5-(pyridin-3-yl)pyrimidin-2-yl)amino)-9-(5,6,7,8-tetrahydro-1,8-naphthyridin-2-yl)nonanoate. LCMS theoretical m/z=461.3 [M+H]+, found 461.0.

Compound 57: (S)-2-((1H-pyrazolo[4,3-d]pyrimidin-7-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate then using Procedure B with 7-chloro-1H-pyrazolo[4,3-d]pyrimidine and Procedure C with ethyl (S)-2-((1H-pyrazolo[4,3-d]pyrimidin-7-yl)amino)-9-(5,6,7,8-tetrahydro-1,8-naphthyridin-2-yl)nonanoate. LCMS theoretical m/z=424.2 [M+H]+, found 424.0.

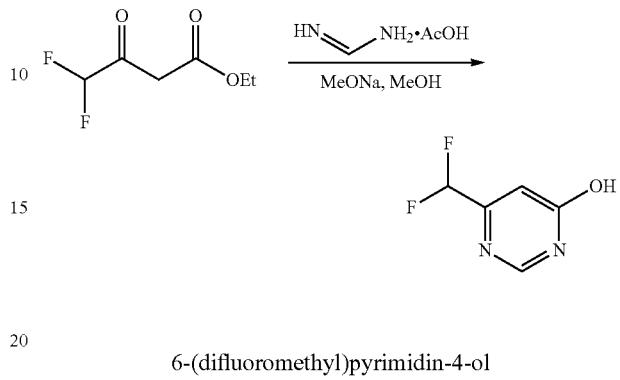

6-(difluoromethyl)pyrimidin-4-ol

To a mixture of ethyl 4,4-difluoro-3-oxobutanoate (5.00 g, 30.1 mmol), acetic acid (3.13 g, 30.1 mmol), and metha-nimidamide in MeOH (15.0 mL) was added MeONa (2.80 g, 71.9 mmol, 2.39 equiv) in one portion at 25° C. The mixture was stirred at 25° C. for 12 h until LCMS showed the consumption of starting material. The reaction mixture was diluted with acetic acid and H$_2$O (90 mL, V:V=1:2) and extracted with EA (100 mL). The organic layer was washed with water (100 mL), dried over Na$_2$SO$_4$, and filtered. The filtrate was coned by rotary evaporation to afford 6-(difluoromethyl)pyrimidin-4-ol (2.75 g, 18.8 mmol, 62.5% yield) as yellow oil. The product was used to next step without further purification.

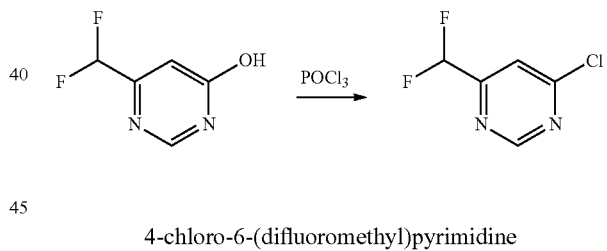

4-chloro-6-(difluoromethyl)pyrimidine

A mixture of 6-(difluoromethyl)pyrimidin-4-ol (2.57 g, 17.6 mmol) in POCl$_3$ (25.0 mL) was degassed and purged with N$_2$, and then the mixture was stirred at 120° C. for 12 h under N$_2$. TLC (PE:EA, 10:1, R$_f$=0.53) showed that the starting material had been consumed. The mixture was concd by rotary evaporation to remove POCl$_3$. The mixture was diluted with dichloromethane and washed with aqueous NaHCO$_3$), water, and aq NaCl. The organic layer was dried with Na$_2$SO$_4$ and filtered, and the filtrate was coned by rotary evaporation to afford the title compound (800 mg, 4.86 mmol, 27.6% yield) as a brown oil. The product was used to next step without further purification.

Compound 58: (S)-2-((6-(difluoromethyl)pyrimidin-4-yl)amino)-9-(5,6,7,8-tetrahydro-1,8-naphthyridin-2-yl)nonanoic Acid Prepared according to Scheme B using Procedure B with ethyl (S)-2-amino-9-(5,6,7,8-tetrahydro-1,8-naphthyridin-2- yl)nonanoate and 4-chloro-6-(difluoromethyl)pyrimidine and Procedure C. LCMS theoretical m/z=434.2 [M+H]+, found 434.2.

Compound 59: (S)-2-((5-(pyridin-4-yl)pyrimidin-2-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate then using Procedure B with 2-chloro-5-(pyridin-4-yl)pyrimidine and Procedure C with ethyl (S)-2-((5-(pyridin-4-yl)pyrimidin-2-yl)amino)-9-(5,6,7,8-tetrahydro-1,8-naphthyridin-2-yl)nonanoate. LCMS theoretical m/z=461.3 [M+H]+, found 461.0.

Compound 60: (S)-2-((6-morpholinopyrimidin-4-yl)amino)-9-(5,6,7,8-tetrahydro-1,8-naphthyridin-2-yl)nonanoic Acid Prepared according to Scheme F beginning with ethyl (S)-2-amino-9-(5,6,7,8-tetrahydro-1,8-naphthyridin-2-yl)nonanoate and 4,6-dichloropyrimidine in Procedure B, using morpholine in Procedure D, and Procedure C to afford the title compound. LCMS theoretical m/z=469.3 [M+H]+, found 469.1.

Compound 61: (S)-2-((6-(pyrrolidin-1-yl)pyrimidin-4-yl)amino)-9-(5,6,7,8-tetrahydro-1,8-naphthyridin-2-yl)nonanoic Acid Prepared according to Scheme F beginning with ethyl (S)-2-amino-9-(5,6,7,8-tetrahydro-1,8-naphthyridin-2-yl)nonanoate and 4,6-dichloropyrimidine in Procedure B, using pyrrolidine in Procedure D, followed by Procedure C to afford the title compound. LCMS theoretical m/z=453.3 [M+H]+, found 453.2.

Compound 62: (S)-2-((1-methyl-1H-pyrazolo[3,4-d]pyrimidin-4-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate and then using Procedure B with 4-chloro-1-methyl-1H-pyrazolo[3,4-d]pyrimidine and Procedure C. LCMS theoretical m/z=438.3 [M+H]+, found 438.2.

Compound 63: (S)-2-((1H-pyrazolo[3,4-d]pyrimidin-4-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate, then Procedure B using 4-chloro-1H-pyrazolo[3,4-d]pyrimidine, followed by Procedure C. LCMS theoretical m/z=424.2 [M+H]+, found 424.2.

Compound 64: (S)-2-((1H-pyrazolo[3,4-d]pyrimidin-6-yl)amino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl)nonanoate, then Procedure B using 7-chloro-1H-pyrazolo[4,3-d]pyrimidine, followed by Procedure C. LCMS theoretical m/z=424.2 [M+H]+, found 424.2.

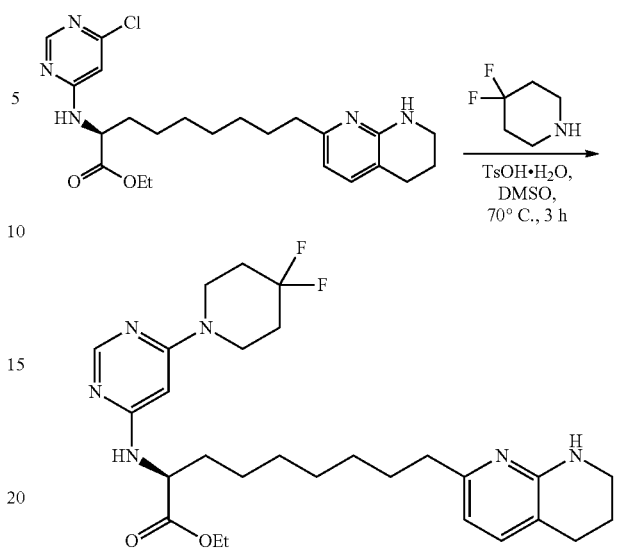

(S)-ethyl 2-((6-(4,4-difluoropiperidin-1-yl)pyrimidin-4-yl)amino)-9-(5,6,7,8-tetrahydro-1,8-naphthyridin-2-yl)nonanoate A solution of (S)-ethyl 2-((6-chloropyrimidin-4-yl)amino)-9-(5,6,7,8-tetrahydro-1,8-naphthyridin-2-yl)nonanoate (200.00 mg, 448.45 μmol, 1.00 equiv), 4,4-difluoropiperidine (706.71 mg, 4.48 mmol, 10.00 equiv, HCl) and TsOH·H$_2$O (8.53 mg, 44.85 μmol, 0.10 equiv) in DMSO (2.00 mL) was stirred at 70° C. for 12 h. LCMS showed that the desired MS was detected. The reaction mixture was poured into water (15 mL), and extracted with EA. The organic layers were combined, washed with brine (30 mL), dried over sodium sulfate and evaporated under reduced pressure to yield the title compound (180.00 mg, 339.21 μmol, 75.64% yield) as yellow oil. LCMS theoretical m/z=531.3. [M+H]+, found 531.1.

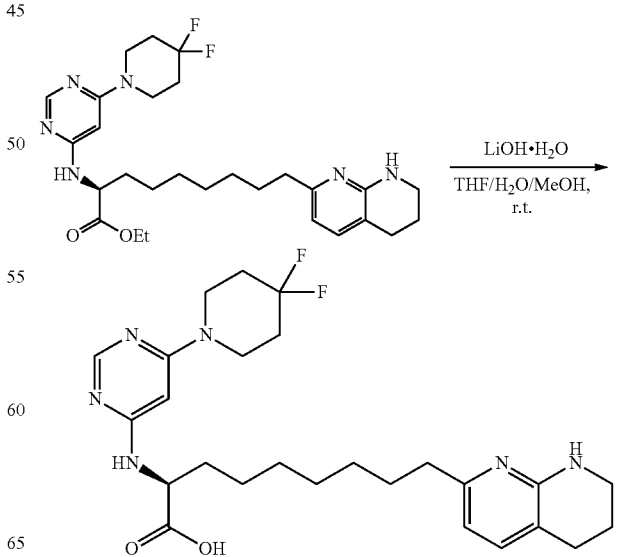

Compound 65: (S)-2-((6-(4,4-difluoropiperidin-1-yl) pyrimidin-4-yl)amino)-9-(5,6,7,8-tetrahydro-1,8-naphthyridin-2-yl)nonanoic Acid Prepared according to Scheme F beginning with ethyl (S)-2-amino-9-(5,6,7,8-tetrahydro-1,8-naphthyridin-2-yl) nonanoate and 4,6-dichloropyrimidine in Procedure B, using the above description to afford (S)-ethyl 2-((6-(4,4-difluoropiperidin-1-yl)pyrimidin-4-yl)amino)-9-(5,6,7,8-tetrahydro-1,8-naphthyridin-2-yl)nonanoate, which was converted to the title compound by the following method: A solution of (S)-ethyl 2-((6-(4,4-difluoropiperidin-1-yl)pyrimidin-4-yl)amino)-9-(5,6,7,8-tetrahydro-1,8-naphthyridin-2-yl)nonanoate (180 mg, 339 µmol, 1.00 equiv), HCl (12 M, 121 µL, 10.0 equiv), AcOH (20.4 mg, 0.339 mmol, 19.4 µL, 1.00 equiv) in ACN (5 mL) and H$_2$O (5 mL) was stirred at 70° C. for 3 h. LCMS showed that the desired mass was detected. The solvent was removed in vacuo. The crude residue was purified by prep-HPLC (column: YMC-Actus Triart (YMC Co., Ltd., Kyoto, Japan) C18 150×30 mm 5 µm; mobile phase: [water (10 mM NH$_4$HCO$_3$)—I]; B %: 30%-50%, 12 min) to yield (S)-2-((6-(4,4-difluoropiperidin-1-yl)pyrimidin-4-yl)amino)-9-(5,6,7,8-tetrahydro-1,8-naphthyridin-2-yl)nonanoic acid (2 mg, 0.004 mmol, 1% yield) as a yellow oil. LCMS theoretical m/z=503.3 [M+H]+, found 503.2.

Compound 66: (S)-2-((6-(dimethylamino)pyrimidin-4-yl)amino)-9-(5,6,7,8-tetrahydro-1,8-naphthyridin-2-yl)nonanoic Acid Prepared according to Scheme F beginning with ethyl (S)-2-amino-9-(5,6,7,8-tetrahydro-1,8-naphthyridin-2-yl) nonanoate and 4,6-dichloropyrimidine in Procedure B, using dimethylamine in Procedure D, and Procedure C to afford the title compound. LCMS theoretical m/z=427.3. [M+H]+, found 427.2.

Compound 67: (S)-2-(pyrimidin-4-ylamino)-9-(5,6,7,8-tetrahydro-1,8-naphthyridin-2-yl)nonanoic Acid Prepared according to Scheme B beginning with ethyl (S)-2-amino-9-(5,6,7,8-tetrahydro-1,8-naphthyridin-2-yl) nonanoate then using Procedure B with 3-chloropyrimidine and Procedure C. LCMS theoretical m/z=384.2 [M+H]+, found 384.2.

Compound 68: (S)-2-((8-bromoquinazolin-4-yl)amino)-9-(5,6,7,8-tetrahydro-1,8-naphthyridin-2-yl)nonanoic Acid Prepared according to Scheme B using Procedure B with methyl (S)-2-amino-9-(5,6,7,8-tetrahydro-1,8-naphthyridin-2-yl)nonanoate and 8-bromo-4-chloroquinazoline followed by Procedure C. LCMS theoretical m/z=512.2, [M+H]+, found 513.2.

Compound 69: (S)-2-(quinazolin-4-ylamino)-9-(5,6,7,8-tetrahydro-1,8-naphthyridin-2-yl)nonanoic Acid Prepared according to Scheme B using Procedure B with methyl (S)-2-amino-9-(5,6,7,8-tetrahydro-1,8-naphthyridin-2-yl)nonanoate and 4-chloroquinazoline followed by Procedure C. LCMS theoretical m/z=434.3, [M+H]+, found 434.3.

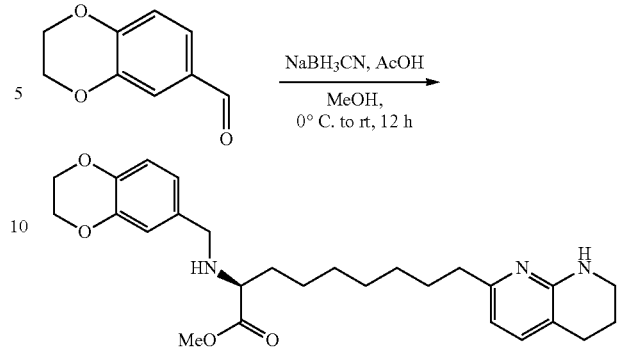

(S)-methyl 2-(((2,3-dihydrobenzo[b][1,4]dioxin-6-yl)methyl)amino)-9-(5,6,7,8-tetrahydro-1,8-naphthyridin-2-yl)nonanoate To a mixture of (S)-methyl 2-amino-9-(5,6,7,8-tetrahydro-1,8-naphthyridin-2-yl)nonanoate hydrochloride (150 mg, 0.421 mmol, 1.00 equiv) in MeOH (3 mL) was added AcOH (25 mg, 0.42 mmol, 24 µL, 1.0 equiv), NaBH$_3$CN (66 mg, 1.0 mmol, 2.5 equiv) at 0° C. under nitrogen. 2,3-Dihydrobenzo[b][1,4]dioxine-6-carbaldehyde (90 mg, 0.55, 55 µL, 1.3 equiv) was added into the mixture. The mixture was stirred at 20° C. for 18 h. LCMS showed the mass of the title compound. The mixture was treated with 6 mL NaHCO$_3$ solution and was extracted with DCM. The organic layer was washed with brine and Na$_2$SO$_4$ and coned by rotary evaporation to give the crude residue, which was purified by preparative TLC (PE:EA, 1:1) to obtain (S)-methyl 2-(((2,3-dihydrobenzo[b][1,4]dioxin-6-yl)methyl) amino)-9-(5,6,7,8-tetrahydro-1,8-naphthyridin-2-yl) nonanoate (130 mg, 0.23 mmol, 55% yield, 83% purity by HPLC) as a colorless oil. LCMS theoretical m/z=468.3 [M+H]+, found 468.5.

Compound 70: (S)-2-(((2,3-dihydrobenzo[b][1,4] dioxin-6-yl)methyl)amino)-9-(5,6,7,8-tetrahydro-1, 8-naphthyridin-2-yl)nonanoic Acid Prepared according to Scheme G beginning with methyl (S)-2-amino-9-(5,6,7,8-tetrahydro-1,8-naphthyridin-2-yl) nonanoate and 2,3-dihydrobenzo[b][1,4]dioxine-6-carbaldehyde using Procedures E and C. Also prepared according to Scheme G using Procedure E with methyl (S)-2-amino-9-(5,6,7,8-tetrahydro-1,8-naphthyridin-2-yl)nonanoate and 2,3-dihydrobenzo[b][1,4]dioxine-6-carbaldehyde and Procedure M with methyl (S)-2-(((2,3-dihydrobenzo[b][1,4] dioxin-6-yl)methyl)amino)-9-(5,6,7,8-tetrahydro-1,8-naphthyridin-2-yl)nonanoate to afford the title compd as a colorless oil. LCMS theoretical m/z=454.3 [M+H]+, found 454.2. 400 MHz $^1$H NMR, methanol-d$_4$, δ ppm 7.59 (d, J=7.28 Hz, 1H) 7.02 (s, 1H) 6.93-6.98 (m, 1H) 6.86-6.92 (m, 1H) 6.61 (d, J=7.50 Hz, 1H) 4.26 (s, 4H) 4.08-4.18 (m, 2H) 3.93 (t, J=6.06 Hz, 1H) 3.51 (t, J=5.62 Hz, 2H) 2.82 (t, J=6.17 Hz, 2H) 2.70 (t, J=7.83 Hz, 2H) 1.95 (dt, J=11.36, 5.79 Hz, 4H) 1.70 (br d, J=7.28 Hz, 2H) 1.39 (br s, 8H).

Compound 71: (S)-2-(benzylamino)-9-(5,6,7,8-tetrahydro-1,8-naphthyridin-2-yl)nonanoic Acid Prepared according to Scheme G beginning with (S)-methyl 2-amino-9-(5,6,7,8-tetrahydro-1,8-naphthyridin-2- yl)nonanoate and benzaldehyde using Procedures E and C. Also prepared according to Scheme G beginning with Procedure E using methyl (S)-2-amino-9-(5,6,7,8-tetrahydro-1,8-naphthyridin-2-yl)nonanoate and benzaldehyde using Procedures F and B. LCMS theoretical m/z=396.2 [M+H]+, found 396.2.

Compound 72: (S)-2-((quinolin-4-ylmethyl)amino)-9-(5,6,7,8-tetrahydro-1,8-naphthyridin-2-yl)nonanoic Acid Prepared according to Scheme H beginning with (S)-methyl 2-amino-9-(5,6,7,8-tetrahydro-1,8-naphthyridin-2-yl)nonanoate and quinoline-4-carbaldehyde using Procedures E and C. Also prepared according to Scheme G beginning with Procedure E using methyl (S)-2-amino-9-(5,6,7,8-tetrahydro-1,8-naphthyridin-2-yl)nonanoate and quinoline-4-carbaldehyde and Procedure M with methyl (S)-2-((quinolin-4-ylmethyl)amino)-9-(5,6,7,8-tetrahydro-1,8-naphthyridin-2-yl)nonanoate. LCMS theoretical m/z=447.2 [M+H]+, found 447.2.

Compound 73: (S)-2-((quinolin-6-ylmethyl)amino)-9-(5,6,7,8-tetrahydro-1,8-naphthyridin-2-yl)nonanoic Acid Prepared according to Scheme G beginning with (S)-methyl 2-amino-9-(5,6,7,8-tetrahydro-1,8-naphthyridin-2-yl)nonanoate and quinoline-6-carbaldehyde using Procedures E and C. Also prepared according to Scheme G beginning with Procedure E using methyl (S)-2-amino-9-(5,6,7,8-tetrahydro-1,8-naphthyridin-2-yl)nonanoate and quinoline-6-carbaldehyde using Procedure M with methyl (S)-2-((quinolin-6-ylmethyl)amino)-9-(5,6,7,8-tetrahydro-1,8-naphthyridin-2-yl)nonanoate. LCMS theoretical m/z=447.2 [M+H]+, found 447.2.

Compound 74: (S)-2-((quinolin-8-ylmethyl)amino)-9-(5,6,7,8-tetrahydro-1,8-naphthyridin-2-yl)nonanoic Acid Prepared according to Scheme G beginning with (S)-methyl 2-amino-9-(5,6,7,8-tetrahydro-1,8-naphthyridin-2-yl)nonanoate and quinoline-8-carbaldehyde using Procedures E and C. Also prepared according to Scheme G beginning with Procedure E using methyl (S)-2-amino-9-(5,6,7,8-tetrahydro-1,8-naphthyridin-2-yl)nonanoate and quinoline-8-carbaldehyde and Procedure M with methyl (S)-2-((quinolin-8-ylmethyl)amino)-9-(5,6,7,8-tetrahydro-1,8-naphthyridin-2-yl)nonanoate. LCMS theoretical m/z=447.2 [M+H]+, found 447.2.

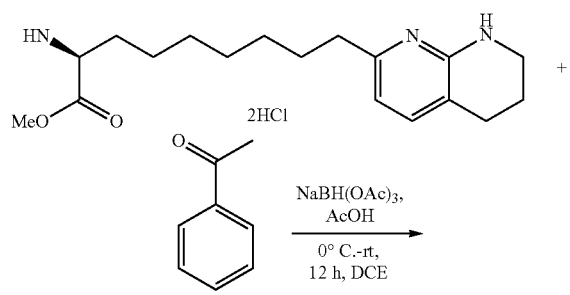

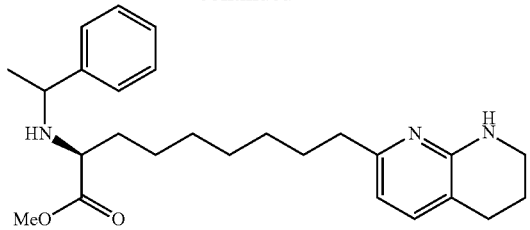

(2S)-methyl 2-((1-phenylethyl)amino)-9-(5,6,7,8-tetrahydro-1,8-naphthyridin-2-yl)nonanoate To a mixture of (S)-methyl 2-amino-9-(5,6,7,8-tetrahydro-1,8-naphthyridin-2-yl)nonanoate (300 mg, 939.14 μmol, 1 equiv) in DCE (3 mL) was adjusted to pH=6 by AcOH. NaBH(OAc)$_3$ (497.61 mg, 2.35 mmol, 2.5 equiv) was added into the mixture at 0° C. under N$_2$. Acetophenone (169.25 mg, 1.41 mmol, 164.32 μL, 1.5 equiv) was added into the mixture with stirring for 16 h at 20° C. LCMS indicated desired MS was detected. The mixture was quenched using NaHCO$_3$ solution and was extracted by DCM. The organic layer was dried by brine and Na$_2$SO$_4$, and coned under reduced pressure to give a residue. The crude product was purified by prep-TLC (PE:EA=0:1) to obtain the title compound (110 mg, 236.31 μmol, 25.16% yield, 91% purity) as a colorless oil. LCMS theoretical m/z=424.2 [M+H]+, found 424.2. Chiral purity: 41:58.

Compound 75: (S)-2-(((R)-1-phenylethyl)amino)-9-(5,6,7,8-tetrahydro-1,8-naphthyridin-2-yl)nonanoic Acid and (S)-2-(((S)-1-phenylethyl)amino)-9-(5,6,7,8-tetrahydro-1,8-naphthyridin-2-yl)nonanoic Acid Prepared according to Scheme H beginning with (S)-methyl 2-amino-9-(5,6,7,8-tetrahydro-1,8-naphthyridin-2-yl)nonanoate and acetophenone using Procedures I and C. Also prepared according to Scheme G beginning with Procedure E using methyl (S)-2-amino-9-(5,6,7,8-tetrahydro-1,8-naphthyridin-2-yl)nonanoate and acetophenone and Procedure M methyl (2S)-2-((1-phenylethyl)amino)-9-(5,6,7,8-tetrahydro-1,8-naphthyridin-2-yl)nonanoate to afford a mixture of diastereomers at the benzylic position. LCMS theoretical m/z=410.2 [M+H]+, found 410.2.

Compound 76: (S)-2-(((1H-pyrrolo[2,3-b]pyridin-3-pyridyl)methyl)amino)-9-(5,6,7,8-tetrahydro-1,8-naphthyridin-2-yl)nonanoic Acid Prepared according to Scheme G beginning with (S)-methyl 2-amino-9-(5,6,7,8-tetrahydro-1,8-naphthyridin-2-yl)nonanoate and 1H-pyrrolo[2,3-b]pyridine-3-carbaldehyde using Procedures E and C. Also prepared according to Scheme G beginning with Procedure E with methyl (S)-2-amino-9-(5,6,7,8-tetrahydro-1,8-naphthyridin-2-yl)nonanoate and 1H-pyrrolo[2,3-b]pyridine-3-carbaldehyde using Procedure M with methyl (S)-2-(((1H-pyrrolo[2,3-b]pyridin-3-yl)methyl)amino)-9-(5,6,7,8-tetrahydro-1,8-naphthyridin-2-yl)nonanoate. LCMS theoretical m/z=436.2 [M+H]+, found 436.2.

Compound 77: (S)-2-((S)-4-(tert-butoxycarbonyl)morpholine-3-carboxamido)-9-(5,6,7,8-tetrahydro-1,8-naphthyridin-2-yl)nonanoic Acid May be prepared starting with methyl (S)-2-amino-9-(5,6,7,8-tetrahydro-1,8-naphthyridin-2-yl)nonanoate and (S)-

4-(tert-butoxycarbonyl)morpholine-3-carboxylic acid, employing an amide coupling reagent such as HATU in the presence of an amine base such as diisopropylethylamine to afford tert-butyl (S)-3-(((S)-1-methoxy-1-oxo-9-(5,6,7,8-tetrahydro-1,8-naphthyridin-2-yl)nonan-2-yl)carbamoyl) morpholine-4-carboxylate. tert-Butyl (S)-3-(((S)-1-methoxy-1-oxo-9-(5,6,7,8-tetrahydro-1,8-naphthyridin-2-yl)nonan-2-yl)carbamoyl)morpholine-4-carboxylate may then be converted to (S)-2-((S)-4-(tert-butoxycarbonyl)morpholine-3-carboxamido)-9-(5,6,7,8-tetrahydro-1,8-naphthyridin-2-yl)nonanoic acid by treatment with lithium hydroxide in a mixture of THF:MeOH:water 3:1:1 and purification by reverse-phase preparatory HPLC.

Compound 78: (2S)-2-(7-oxabicyclo[2.2.1]heptane-2-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 7-oxabicyclo[2.2.1]heptane-2-carboxylic acid using Procedure K, methyl (2S)-2-(7-oxabicyclo[2.2.1] heptane-2-carboxamido)-9-(5,6,7,8-tetrahydro-1,8-naphthyridin-2-yl)nonanoate using Procedure M to afford a mixture of isomers. LCMS theoretical m/z=430.3 [M+H]⁺, found 430.4.

Compound 79: (2S)-2-((2R)-7-oxabicyclo[2.2.1] heptane-2-carboxamido)-9-(5,6,7,8-tetrahydro-1,8-naphthyridin-2-yl)nonanoic Acid Prepared according to Compound 78 and separated by chiral SFC as follows: separation (column: Daicel CHIRAL-PAK® IC, Chiral Technologies, Inc., West Chester, Pa. (250 mm*30 mm, 5 μm); mobile phase: [0.1% NH₃H₂O ETOH]; B %: 42%-42%, 10 min) and prep-HPLC (neutral condition, column: XTIMATE® (Welch Materials, Hurst, Tex.); C18 150*25 mm*5 μm; mobile phase: [water (10 mM NH₄HCO₃)-ACN]; B %: 15%-40%, 10 min. column: HUAPU C8 Extreme BDS 150*30 5 μm (Dalian Institute of Chemical Physics, CAS 457, Zhongshan, China); mobile phase: [water (10 mM NH₄HCO₃)-ACN]; B %: 20%-40%, 10 min) to obtain the title compd as a white solid (6.74 mg, 15.7 μmol, 5.80% yield, 100% purity) as a 62:37 mixture of isomers of unassigned absolute stereochemistry at the oxobicycloheptane, as indicated by the wavy bond for Compound 79 in FIG. 1. LCMS theoretical m/z=430.3 [M+H]⁺, found 430.4.

Compound 80: (2S)-2-((2S)-7-oxabicyclo[2.2.1] heptane-2-carboxamido)-9-(5,6,7,8-tetrahydro-1,8-naphthyridin-2-yl)nonanoic Acid Prepared according to Compound 79, and isolated as a 47:53 mixture of isomers of unassigned absolute stereochemistry at the oxobicycloheptane, as indicated by the wavy bond for Compound 80 in FIG. 1. LCMS theoretical m/z=430.3 [M+H]⁺, found 430.2.

Compound 81: (S)-2-(2-methyl-2-(tetrahydro-2H-pyran-4-yl)propanamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 2-methyl-2-(tetrahydro-2H-pyran-4-yl)propanoic acid using Procedures K and M with methyl (S)-2-(2-methyl-2-(tetrahydro-2H-pyran-4-yl)propanamido)-9-(5,6,7,8-tetrahydro-1,8-naphthyridin-2-yl)nonanoate. LCMS theoretical m/z=460.3 [M+H]⁺, found 460.3.

Compound 82: (2S)-2-(1-(tert-butoxycarbonyl)-3,3-difluoropiperidine-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 1-(tert-butoxycarbonyl)-3,3-difluoropiperidine-4-carboxylic acid using Procedures K and M with tert-butyl 3,3-difluoro-4-(((S)-1-methoxy-1-oxo-9-(5,6,7,8-tetrahydro-1,8-naphthyridin-2-yl)nonan-2-yl)carbamoyl)piperidine-1-carboxylate. LCMS theoretical m/z=553.3 [M+H]⁺, found 553.3.

Compound 83: (2S)-2-((2R,6S)-2,6-dimethyltetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and (2R,6S)-2,6-dimethyltetrahydro-2H-pyran-4-carboxylic acid using Procedures A and O with methyl (2S)-2-((2R,6S)-2,6-dimethyltetrahydro-2H-pyran-4-carboxamido)-9-(5,6,7,8-tetrahydro-1,8-naphthyridin-2-yl) nonanoate. LCMS theoretical m/z=446.3 [M+H]⁺, found 446.3.

Compound 84: (S)-2-((S)-2,2-dimethyltetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 2,2-dimethyltetrahydro-2H-pyran-4-carboxylic acid using Procedures K and M with methyl (2S)-2-(2,2-dimethyltetrahydro-2H-pyran-4-carboxamido)-9-(5,6,7,8-tetrahydro-1,8-naphthyridin-2-yl)nonanoate to afford the title compd as the first eluting isomer of unassigned absolute stereochemistry at the 4-position of the 2,2-dimethyltetrahydro-2H-pyran, as indicated by the wavy bond for Compound 84 in FIG. 1. LCMS theoretical m/z=446.3. [M+H]⁺, found 446.3.

Compound 85: (S)-2-((R)-2,2-dimethyltetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl) nonanoate and 2,2-dimethyltetrahydro-2H-pyran-4-carboxylic acid using Procedures K and M with methyl (2S)-2-(2,2-dimethyltetrahydro-2H-pyran-4-carboxamido)-9-(5,6,7,8-tetrahydro-1,8-naphthyridin-2-yl)nonanoate to afford the title compd as the second eluting isomer of unassigned absolute stereochemistry at the 4-position of the 2,2-dimethyltetrahydro-2H-pyran, as indicated by the wavy bond for Compound 85 in FIG. 1. LCMS theoretical m/z=446.3. [M+H]⁺, found 446.3.

Compound 86: (S)-2-(1-(tert-butoxycarbonyl)-4-(trifluoromethyl)piperidine-4-carboxamido)-9-(5,6,7, 8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)

nonanoate and 1-(tert-butoxycarbonyl)-4-(trifluoromethyl) piperidine-4-carboxylic acid using Procedures K and M with tert-butyl (S)-4-((1-methoxy-1-oxo-9-(5,6,7,8-tetrahydro-1,8-naphthyridin-2-yl)nonan-2-yl)carbamoyl)-4-(trifluoromethyl)piperidine-1-carboxylate. LCMS theoretical m/z=585.3. [M+H]$^+$, found 585.3.

Compound 87: (S)-9-(5,6,7,8-tetrahydro-1,8-naphthyridin-2-yl)-2-(2,2,6,6-tetramethyltetrahydro-2H-pyran-4-carboxamido)nonanoic Acid Prepared according to Scheme A beginning with methyl (S)-2-amino-9-(5,6,7,8-tetrahydro-1,8-naphthyridin-2-yl)nonanoate and 2,2,6,6-tetramethyltetrahydro-2H-pyran-4-carboxylic acid using Procedures K and M with methyl (S)-9-(5,6,7,8-tetrahydro-1,8-naphthyridin-2-yl)-2-(2,2,6,6-tetramethyltetrahydro-2H-pyran-4-carboxamido)nonanoate. LCMS theoretical m/z=474.3. [M+H]$^+$, found 474.6.

Compound 88: (S)-2-(1-(tert-butoxycarbonyl)-4-(2,2-difluoroethyl)piperidine-4-carboxamido)-9-(5,6,7,8-tetrahydro-1,8-naphthyridin-2-yl)nonanoic Acid Prepared according to Scheme A beginning with 1-(tert-butoxycarbonyl)-4-(2,2-difluoroethyl)piperidine-4-carboxylic acid and methyl (S)-2-amino-9-(5,6,7,8-tetrahydro-1,8-naphthyridin-2-yl)nonanoate using Procedures K and M and tert-butyl (S)-4-(2,2-difluoroethyl)-4-((1-methoxy-1-oxo-9-(5,6,7,8-tetrahydro-1,8-naphthyridin-2-yl)nonan-2-yl)carbamoyl)piperidine-1-carboxylate. LCMS theoretical m/z=581.3 [M+H]$^+$, found 581.3.

Compound 89: (S)-9-(5,6,7,8-tetrahydro-1,8-naphthyridin-2-yl)-2-(3,4,5,6-tetrahydro-[1,1'-biphenyl]-2-ylcarboxamido)nonanoic Acid Prepared according to Scheme A beginning with 3,4,5,6-tetrahydro-[1,1'-biphenyl]-2-carboxylic acid and methyl (S)-2-amino-9-(5,6,7,8-tetrahydro-1,8-naphthyridin-2-yl)nonanoate using Procedures K and M with methyl (S)-9-(5,6,7,8-tetrahydro-1,8-naphthyridin-2-yl)-2-(3,4,5,6-tetrahydro-[1,1'-biphenyl]-2-carboxamido)nonanoate. LCMS theoretical m/z=490.3 [M+H]$^+$, found 490.3.

Compound 90: (S)-2-(2-(pyridin-4-yl)acetamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 2-(pyridin-4-yl)acetic acid using Procedures K and M with methyl (S)-2-(2-(pyridin-4-yl)acetamido)-9-(5,6,7,8-tetrahydro-1,8-naphthyridin-2-yl)nonanoate. LCMS theoretical m/z=425.2 [M+H]$^+$, found 425.2.

Compound 91: (S)-2-((S)-1-(phenylsulfonyl)pyrrolidine-2-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and (S)-1-(phenylsulfonyl)pyrrolidine-2-carboxylic acid using Procedures K and M with methyl (S)-2-((S)-1-(phenylsulfonyl)pyrrolidine-2-carboxamido)-9-(5,6,7,8-tetrahydro-1,8-naphthyridin-2-yl)nonanoate. LCMS theoretical m/z=543.3. [M+H]+, found 543.3.

Compound 92: (S)-2-(((4-methyltetrahydro-2H-pyran-4-yl)methyl)amino)-9-(5,6,7,8-tetrahydro-1,8-naphthyridin-2-yl)nonanoic Acid Prepared according to Scheme G beginning with Procedure E using methyl (S)-2-amino-9-(5,6,7,8-tetrahydro-1,8-naphthyridin-2-yl)nonanoate and 4-methyltetrahydro-2H-pyran-4-carbaldehyde and Procedure M with methyl (S)-2-(((4-methyltetrahydro-2H-pyran-4-yl)methyl)amino)-9-(5,6,7,8-tetrahydro-1,8-naphthyridin-2-yl)nonanoate. LCMS theoretical m/z=418.3 [M+H]$^+$, found 418.3.

Compound 93: (S)-2-(((R)-1-(pyridin-3-yl)ethyl)amino)-9-(5,6,7,8-tetrahydro-1,8-naphthyridin-2-yl)nonanoic Acid Prepared according to Scheme G beginning with Procedure E using methyl (S)-2-amino-9-(5,6,7,8-tetrahydro-1,8-naphthyridin-2-yl)nonanoate and 1-(pyridin-3-yl)ethanone and Procedure M with methyl (2S)-2-((1-(pyridin-3-yl)ethyl)amino)-9-(5,6,7,8-tetrahydro-1,8-naphthyridin-2-yl)nonanoate to afford the title compd as a 74:26 mixture of diastereomers of unassigned absolute stereochemistry at the alpha-methyl pyridyl center, as indicated by the wavy bond for Compound 93 in FIG. 1. LCMS theoretical m/z=411.3 [M+H]$^+$, found 411.2.

Compound 94: (S)-2-(((S)-1-(pyridin-3-yl)ethyl)amino)-9-(5,6,7,8-tetrahydro-1,8-naphthyridin-2-yl)nonanoic Acid Prepared according to Compound 93 to afford the title compd as a 35:65 mixture of diastereomers of unassigned absolute stereochemistry at the alpha-methyl pyridyl center, as indicated by the wavy bond for Compound 94 in FIG. 1. LCMS theoretical m/z=411.3 [M+H]$^+$, found 411.2.

Compound 95: (S)-9-(5,6,7,8-tetrahydro-1,8-naphthyridin-2-yl)-2-(((1,3,5-trimethyl-1H-pyrazol-4-yl)methyl)amino)nonanoic Acid Prepared according to Scheme G beginning with Procedure E using methyl (S)-2-amino-9-(5,6,7,8-tetrahydro-1,8-naphthyridin-2-yl)nonanoate and 1,3,5-trimethyl-1H-pyrazole-4-carbaldehyde and Procedure M using methyl (S)-9-(5,6,7,8-tetrahydro-1,8-naphthyridin-2-yl)-2-(((1,3,5-trimethyl-1H-pyrazol-4-yl)methyl)amino)nonanoate. LCMS theoretical m/z=428.3 [M+H]$^+$, found 428.2.

Compound 96: (S)-2-((2S,6R)-2,6-Dimethylpiperidine-1-carboxamido)-9-(5,6,7,8-tetrahydro-1,8-naphthyridin-2-yl)nonanoic Acid Prepared according to Scheme K beginning with methyl (S)-2-amino-9-(5,6,7,8-tetrahydro-1,8-naphthyridin-2-yl)nonanoate and (2S,6R)-2,6-dimethylpiperidine using Procedures N and M with methyl (S)-2-((2S,6R)-2,6-dimethylpiperidine-1-carboxamido)-9-(5,6,7,8-tetrahydro-1,8-naphthyridin-2-yl)nonanoate. LCMS theoretical m/z=445.3 [M+H]$^+$, found 445.2.

Compound 97: (S)-2-((2S,5R)-2,5-dimethylpyrrolidine-1-carboxamido)-9-(5,6,7,8-tetrahydro-1,8-naphthyridin-2-yl)nonanoic Acid Prepared according to Scheme K beginning with methyl (S)-2-amino-9-(5,6,7,8-tetrahydro-1,8-naphthyridin-2-yl)

nonanoate and (2S,5R)-2,5-dimethylpyrrolidine in Procedures N and M with methyl (S)-2-((2S,5R)-2,5-dimethylpyrrolidine-1-carboxamido)-9-(5,6,7,8-tetrahydro-1,8-naphthyridin-2-yl)nonanoate. LCMS theoretical m/z=431.3. [M+H]⁺, found 431.2.

Compound 98: (S)-2-((2R,5R)-2,5-dimethylpyrrolidine-1-carboxamido)-9-(5,6,7,8-tetrahydro-1,8-naphthyridin-2-yl)nonanoic Acid Prepared according to Scheme K beginning with methyl (S)-2-amino-9-(5,6,7,8-tetrahydro-1,8-naphthyridin-2-yl)nonanoate and (2R,5R)-2,5-dimethylpyrrolidine using Procedures N and M with methyl (S)-2-((2R,5R)-2,5-dimethylpyrrolidine-1-carboxamido)-9-(5,6,7,8-tetrahydro-1,8-naphthyridin-2-yl)nonanoate. LCMS theoretical m/z=431.3. [M+H]⁺, found 431.3.

Compound 99: (S)-2-((3R,5R)-3,5-dimethylmorpholine-4-carboxamido)-9-(5,6,7,8-tetrahydro-1,8-naphthyridin-2-yl)nonanoic Acid Prepared according to Scheme K beginning with methyl (S)-2-amino-9-(5,6,7,8-tetrahydro-1,8-naphthyridin-2-yl)nonanoate and (3R,5R)-3,5-dimethylmorpholine in Procedures N and M with methyl (S)-2-((3R,5R)-3,5-dimethylmorpholine-4-carboxamido)-9-(5,6,7,8-tetrahydro-1,8-naphthyridin-2-yl)nonanoate. LCMS theoretical m/z=447.3 [M+H]⁺, found 447.3.

Compound 100: (S)-2-((3R,5S)-3,5-dimethylmorpholine-4-carboxamido)-9-(5,6,7,8-tetrahydro-1,8-naphthyridin-2-yl)nonanoic Acid Prepared according to Scheme K beginning with methyl (S)-2-amino-9-(5,6,7,8-tetrahydro-1,8-naphthyridin-2-yl)nonanoate and (3R,5R)-3,5-dimethylmorpholine in Procedures N and M with methyl (S)-2-((3R,5S)-3,5-dimethylmorpholine-4-carboxamido)-9-(5,6,7,8-tetrahydro-1,8-naphthyridin-2-yl)nonanoate. LCMS theoretical m/z=447.3 [M+H]+, found 447.3.

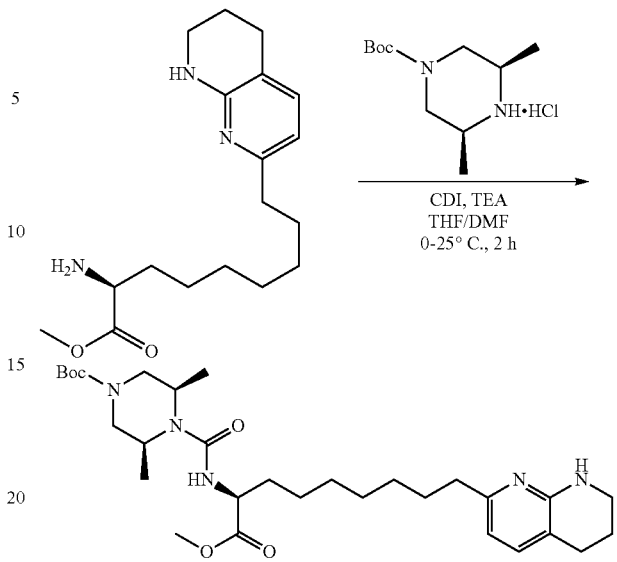

tert-butyl (3R,5S)-4-(((S)-1-methoxy-1-oxo-9-(5,6,7,8-tetrahydro-1,8-naphthyridin-2-yl)nonan-2-yl)carbamoyl)-3,5-dimethylpiperazine-1-carboxylate To a mixture of tert-butyl (3S,5R)-3,5-dimethylpiperazine-1-carboxylate; hydrochloride (200 mg, 800 μmol) in THF (2 mL) and DMF (2 mL) was added CDI (130 mg, 800 μmol) and TEA (250 mg, 2.4 mmol) at 0° C. The reaction mixture was stirred at 30° C. under N₂ for 3 h. Methyl (S)-2-amino-9-(5,6,7,8-tetrahydro-1,8-naphthyridin-2-yl)nonanoate (218 mg, 613 μmol) was added, and the reaction was stirred for 18 h. The aq phase was extracted with EA, dried over anhyd Na₂SO₄, coned, and purified by prep-TLC (EA:MeOH=10:1) to afford the title compd. LCMS theoretical m/z=560.4. [M+H]⁺, found 560.3.

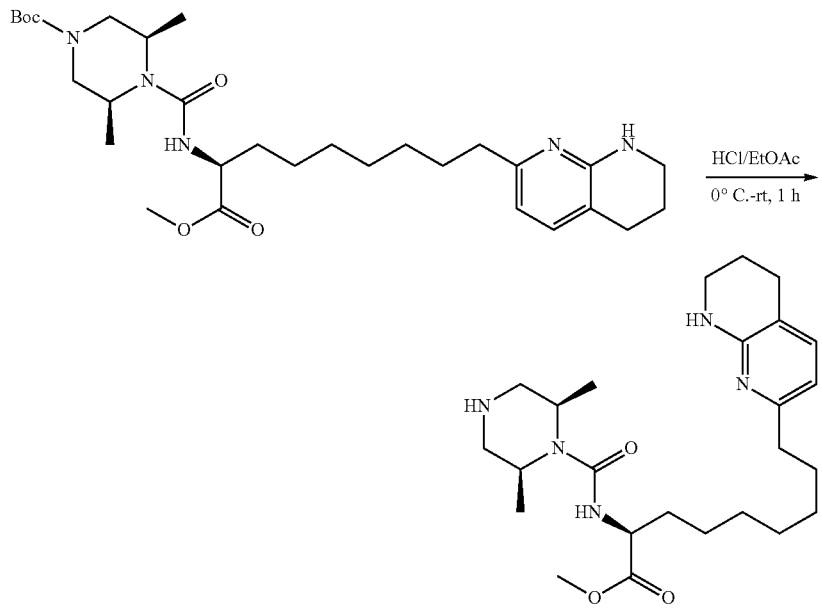

Methyl (S)-2-((2R,6S)-2,6-dimethylpiperazine-1-carboxamido)-9-(5,6,7,8-tetrahydro-1,8-naphthyridin-2-yl)nonanoate To a mixture of tert-butyl (3R,5S)-4-(((S)-1-methoxy-1-oxo-9-(5,6,7,8-tetrahydro-1,8-naphthyridin-2-yl)nonan-2-yl)carbamoyl)-3,5-dimethylpiperazine-1-carboxylate (247 mg, 441 µmol) in EA (1 mL) was added HCl/EA (4 M, 4.41 mL) at 0° C. The mixture was stirred at 0° C. for 1 h. The residue was coned in vacuum to yield 140 mg of the title compd as a crude yellow solid, which was used directly in the next reaction. LCMS theoretical m/z=460.3. [M+H]+, found 460.1.

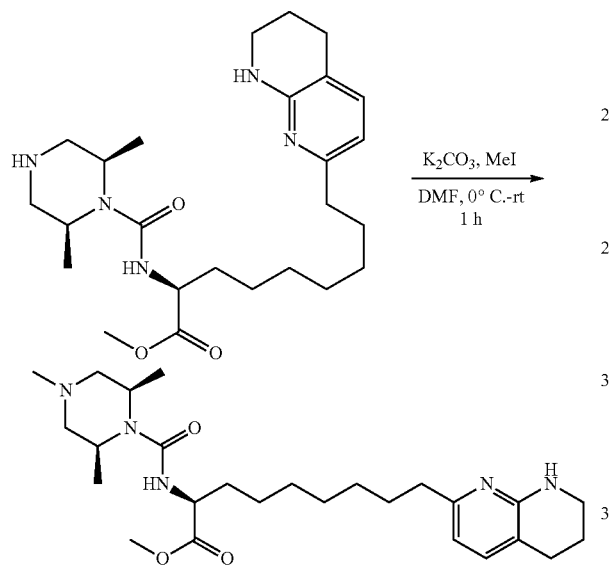

Methyl (S)-9-(5,6,7,8-tetrahydro-1,8-naphthyridin-2-yl)-2-((2R,6S)-2,4,6-trimethylpiperazine-1-carboxamido)nonanoate To a mixture of methyl (S)-2-((2R,6S)-2,6-dimethylpiperazine-1-carboxamido)-9-(5,6,7,8-tetrahydro-1,8-naphthyridin-2-yl)nonanoate (140 mg, 280 µmol, HCl) in DMF (2 mL) was added K$_2$CO$_3$ (78 mg, 560 µmol) and methyl iodide (60 mg, 420 µmol) at 0° C. under N$_2$. The mixture was stirred at 0° C. for 1 h. The aq phase was extracted with EA, dried with anhyd Na$_2$SO$_4$, filtered, and coned in vacuum. The residue was purified by prep-TLC (EA:MeOH=10:1) to afford 44 mg of the title compd as a colorless oil. LCMS theoretical m/z=474.3. [M+H]+, found 474.3.

Compound 101: (S)-9-(5,6,7,8-tetrahydro-1,8-naphthyridin-2-yl)-2-((2R,6S)-2,4,6-trimethylpiperazine-1-carboxamido)nonanoic Acid Prepared according to Procedure M using methyl (S)-9-(5,6,7,8-tetrahydro-1,8-naphthyridin-2-yl)-2-((2R,6S)-2,4,6-trimethylpiperazine-1-carboxamido)nonanoate to afford the title compd as a white solid. 400 MHz 1H NMR, methanol-d$_4$, δ ppm 7.43 (d, J=7.34 Hz, 1H) 6.49 (d, J=7.34 Hz, 1H) 4.23 (t, J=5.81 Hz, 1H) 4.04-4.16 (m, 2H) 3.40-3.51 (m, 2H) 2.70-2.82 (m, 4H) 2.64 (t, J=7.64 Hz, 2H) 2.31 (s, 3H) 2.10-2.20 (m, 2H) 1.88-1.98 (m, 2H) 1.71-1.87 (m, 2H) 1.67 (br d, J=6.60 Hz, 2H) 1.29-1.41 (m, 14H). LCMS theoretical m/z=460.3. [M+H]+, found 460.3.

Compound 102: (2S)-2-(3-azabicyclo[3.3.1]nonane-9-carboxamido)-9-(5,6,7,8-tetrahydro-1,8-naphthyridin-2-yl)nonanoic Acid Prepared according to Scheme E beginning with methyl (S)-2-amino-9-(5,6,7,8-tetrahydro-1,8-naphthyridin-2-yl) nonanoate and 3-azabicyclo[3.3.1]nonane-9-carboxylic acid using Procedures K and M with methyl (2S)-2-(3-azabicyclo [3.3.1]nonane-9-carboxamido)-9-(5,6,7,8-tetrahydro-1,8-naphthyridin-2-yl)nonanoate. LCMS theoretical m/z=457.6 [M+H]+, found 457.3.

Compound 103: (S)-2-((1R,5S,9S)-3-acetyl-3-azabicyclo[3.3.1]nonane-9-carboxamido)-9-(5,6,7,8-tetrahydro-1,8-naphthyridin-2-yl)nonanoic Acid Prepared using Procedure I using methyl (2S)-2-(3-azabicyclo[3.3.1]nonane-9-carboxamido)-9-(5,6,7,8-tetrahydro-1,8-naphthyridin-2-yl)nonanoate, and Procedure C with methyl (2S)-2-(3-acetyl-3-azabicyclo[3.3.1]nonane-9-carboxamido)-9-(5,6,7,8-tetrahydro-1,8-naphthyridin-2-yl) nonanoate to afford the title compd as the first eluting isomer; absolute stereochemistry at the amide carbon was not assigned, as indicated by the wavy bond for Compound 103 in FIG. 1. LCMS theoretical m/z=499.3 m/z [M+H]+, found 499.3. 400 MHz 1H NMR, methanol-d$_4$, δ ppm 7.40-7.48 (m, 1H) 6.52 (d, J=7.28 Hz, 1H) 4.54-4.64 (m, 1H) 4.30-4.40 (m, 1H) 4.02 (br d, J=13.45 Hz, 1H) 3.42-3.51 (m, 3H) 2.90-3.02 (m, 1H) 2.78 (t, J=6.17 Hz, 2H) 2.59-2.67 (m, 3H) 2.33 (br s, 2H) 2.12 (s, 3H) 2.10-2.14 (m, 1H) 1.55-2.03 (m, 11H) 1.55-2.03 (m, 1H) 1.30-1.46 (m, 9H).

Compound 104: (S)-2-((1R,5S,9R)-3-acetyl-3-azabicyclo[3.3.1]nonane-9-carboxamido)-9-(5,6,7,8-tetrahydro-1,8-naphthyridin-2-yl)nonanoic Acid Prepared according to Procedure C with methyl (2S)-2-(cis-3-acetyl-3-azabicyclo[3.3.1]nonane-9-carboxamido)-9-(5,6,7,8-tetrahydro-1,8-naphthyridin-2-yl)nonanoate afforded the title compd as the second eluting isomer; absolute stereochemistry at the amide carbon was not assigned, as indicated by the wavy bond for Compound 104 in FIG. 1. LCMS theoretical m/z=499.3 m/z [M+H]+, found 499.3. 400 MHz $^1$H NMR, methanol-d$_4$, δ ppm 7.45 (dd, J=7.28, 5.07 Hz, 1H) 6.51 (br d, J=4.63 Hz, 1H) 4.29 (br d, J=13.01 Hz, 2H) 3.67-3.85 (m, 2H) 3.42-3.50 (m, 2H) 3.13-3.28 (m, 1H) 2.78 (br t, J=6.06 Hz, 2H) 2.64 (br t, J=7.61 Hz, 2H) 2.57 (br s, 1H) 2.21-2.36 (m, 2H) 2.07 (d, J=2.65 Hz, 3H) 1.59-2.00 (m, 11H) 1.47-1.57 (m, 1H) 1.36 (br s, 8H).

Compound 105: (S)-2-(4-methyl-1-((1-methyl-H-pyrazol-4-yl)methyl)piperidine-4-carboxamido)-9-(5,6,7,8-tetrahydro-1,8-naphthyridin-2-yl)nonanoic Acid Prepared according to Scheme E using Procedure A with methyl (S)-2-amino-9-(5,6,7,8-tetrahydro-1,8-naphthyridin-2-yl)nonanoate and 1-(tert-butoxycarbonyl)-4-methylpiperidine-4-carboxylic acid, Procedure H with (S)-2-(1-(tert-butoxycarbonyl)-4-methylpiperidine-4-carboxamido)-9-(5,6,7,8-tetrahydro-1,8-naphthyridin-2-yl)nonanoic acid, Procedure J with (S)-2-(4-methylpiperidine-4-carboxamido)-9-(5,6,7,8-tetrahydro 1,8-naphthyridin-2-yl)

nonanoic acid and 1-methyl-1H-pyrazole-4-carbaldehyde, and Procedure C with methyl (S)-2-(4-methyl-1-((1-methyl-1H-pyrazol-4-yl)methyl)piperidine-4-carboxamido)-9-(5,6,7,8-tetrahydro-1,8-naphthyridin-2-yl)nonanoate. LCMS theoretical m/z=525.3 [M+H]+, found 525.4.

Compound 106: (S)-2-(4-((tert-butoxycarbonyl) amino)bicyclo[2.2.2]octane-1-carboxamido)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and 4-((tert-butoxycarbonyl)amino)bicyclo[2.2.2]octane-1-carboxylic acid, and Procedure C with methyl (S)-2-(4-((tert-butoxycarbonyl)amino)bicyclo[2.2.2]octane-1-carboxamido)-9-(5,6,7,8-tetrahydro-1,8-naphthyridin-2-yl)nonanoate. LCMS theoretical m/z=557.4 [M+H]+, found 557.3.

Compound 107: (2S)-2-(adamantane-1-carbonylamino)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and (3r,5r,7r)-adamantane-1-carboxylic acid, and Procedure C with methyl (S)-2-((3S,5S,7S)-adamantane-1-carboxamido)-9-(5,6,7,8-tetrahydro-1,8-naphthyridin-2-yl)nonanoate. LCMS theoretical m/z=468.3 [M+H]+, found 468.3.

Compound 108: (S)-2-(4-((tert-butoxycarbonyl) amino)-1-methylcyclohexane-1-carboxamido)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and 4-((tert-butoxycarbonyl)amino)-1-methylcyclohexane-1-carboxylic acid, and Procedure C with methyl (S)-2-(4-((tert-butoxycarbonyl)amino)-1-methylcyclohexane-1-carboxamido)-9-(5,6,7,8-tetrahydro-1,8-naphthyridin-2-yl)nonanoate. LCMS theoretical m/z=545.4 [M+H]+, found 545.3.

Compound 109: (S)-2-(4-amino-1-methylcyclohexane-1-carboxamido)-9-(5,6,7,8-tetrahydro-1,8-naphthyridin-2-yl)nonanoic Acid Prepared using Procedure H with (S)-2-(4-((tert-butoxycarbonyl)amino)-1-methylcyclohexane-1-carboxamido)-9-(5,6,7,8-tetrahydro-1,8-naphthyridin-2-yl)nonanoic acid. LCMS theoretical m/z=445.3 [M+H]+, found 445.3.

Compound 110: (S)-2-(4-aminobicyclo[2.2.2]octane-1-carboxamido)-9-(5,6,7,8-tetrahydro-1,8-naphthyridin-2-yl)nonanoic Acid Prepared using Procedure H with (S)-2-(4-((tert-butoxycarbonyl)amino)bicyclo[2.2.2]octane-1-carboxamido)-9-(5,6,7,8-tetrahydro-1,8-naphthyridin-2-yl)nonanoic acid. LCMS theoretical m/z=457.3 [M+H]+, found 457.3.

Compound 111: (S)-2-(4-acetamido-1-methylcyclohexane-1-carboxamido)-9-(5,6,7,8-tetrahydro-1,8-naphthyridin-2-yl)nonanoic Acid Prepared using Procedure I with (S)-2-(4-amino-1-methylcyclohexane-1-carboxamido)-9-(5,6,7,8-tetrahydro-1,8-naphthyridin-2-yl)nonanoic acid. LCMS theoretical m/z=487.3 [M+H]+, found 487.3.

Compound 112: (S)-2-((S)-5,5-dimethyl-3-(phenylsulfonyl)thiazolidine-4-carboxamido)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and (S)-5,5-dimethyl-3-(phenylsulfonyl)thiazolidine-4-carboxylic acid, and using Procedure C with methyl (S)-2-((S)-5,5-dimethyl-3-(phenylsulfonyl)thiazolidine-4-carboxamido)-9-(5,6,7,8-tetrahydro-1,8-naphthyridin-2-yl)nonanoate. LCMS theoretical m/z=589.2 [M+H]+, found 589.2.

Compound 113: (R)-2-((S)-1-(phenylsulfonyl)pyrrolidine-2-carboxamido)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and (phenylsulfonyl)-L-proline, and using Procedure C with methyl (S)-2-((S)-1-(phenylsulfonyl)pyrrolidine-2-carboxamido)-9-(5,6,7,8-tetrahydro-1,8-naphthyridin-2-yl)nonanoate. LCMS theoretical=543.3 [M+H]+, found 543.3.

Compound 114: (S)-2-(4-methyl-1-(3,3,3-trifluoropropyl)piperidine-4-carboxamido)-9-(5,6,7,8-tetrahydro-1,8-naphthyridin-2-yl)nonanoic Acid Prepared according to Scheme E using Procedure A with methyl (S)-2-amino-9-(5,6,7,8-tetrahydro-1,8-naphthyridin-2-yl)nonanoate and 1-(tert-butoxycarbonyl)-4-methylpiperidine-4-carboxylic acid, Procedure H using tert-butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate, Procedure J using methyl (S)-2-(4-methylpiperidine-4-carboxamido)-9-(5,6,7,8-tetrahydro-1,8-naphthyridin-2-yl)nonanoate and 3,3,3-trifluoropropanal, and Procedure C using methyl (S)-2-(4-methyl-1-(3,3,3-trifluoropropyl)piperidine-4-carboxamido)-9-(5,6,7,8-tetrahydro-1,8-naphthyridin-2-yl)nonanoate. LCMS theoretical m/z=527.3 [M+H]+, found 527.3.

Compound 115: (2S)-2-[(1-acetyl-4-methyl-piperidine-4-carbonyl)amino]-9-(5,6,7,8-tetrahydro-1,8-naphthyridin-2-yl)nonanoic Acid Prepared according to Scheme E using Procedure A with methyl (S)-2-amino-9-(5,6,7,8-tetrahydro-1,8-naphthyridin-2-yl)nonanoate and 1-(tert-butoxycarbonyl)-4-methylpiperidine-4-carboxylic acid, Procedure H using tert-butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate, Procedure I using methyl (S)-2-(4-methylpiperidine-4-carboxamido)-9-(5,6,7,8-tetrahydro-1,8-naphthyridin-2-yl)nonanoate and acetic anhydride, and Procedure C using methyl (S)-2-(1-acetyl-4-methylpiperidine-4-carboxamido)-9-(5,6,7,8-tetrahydro-1,8-naphthyridin-2-yl)nonanoate. LCMS theoretical m/z=473.3 [M+H]+, found 473.3.

Compound 116: (S)-2-(4-methyl-1-pivaloylpiperidine-4-carboxamido)-9-(5,6,7,8-tetrahydro-1,8-naphthyridin-2-yl)nonanoic Acid Prepared according to Scheme E using Procedure A with methyl (S)-2-amino-9-(5,6,7,8-tetrahydro-1,8-naphthyridin- 2-yl)nonanoate and 1-(tert-butoxycarbonyl)-4-methylpiperidine-4-carboxylic acid, Procedure H using tert-butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate, Procedure I using methyl (S)-2-(4-methylpiperidine-4-carboxamido)-9-(5,6,7,8-tetrahydro-1,8-naphthyridin-2-yl)nonanoate and pivaloyl chloride, and Procedure C using methyl (S)-2-(4-methyl-1-pivaloylpiperidine-4-carboxamido)-9-(5,6,7,8-tetrahydro-1,8-naphthyridin-2-yl)nonanoate. LCMS theoretical m/z=515.4 [M+H]+, found 515.3.

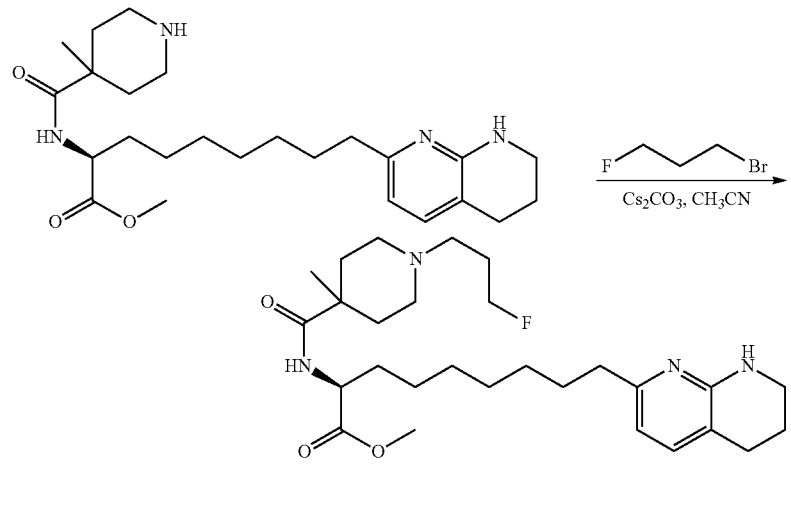

methyl (S)-2-(1-(3-fluoropropyl)-4-methylpiperidine-4-carboxamido)-9-(5,6,7,8-tetrahydro-1,8-naphthyridin-2-yl)nonanoate To a solution of methyl (S)-2-(4-methylpiperidine-4-carboxamido)-9-(5,6,7,8-tetrahydro-1,8-naphthyridin-2-yl)nonanoate (99.99 mg, 0.225 mmol, 1.0 equiv) in ACN (0.5 mL) was added cesium carbonate (146.56 mg, 0.450 mmol, 2 equiv) and 1-bromo-3-fluoropropane (30 µL, 0.337 mmol, 1.5 equiv). The solution was stirred at rt for 24 h, at which time LCMS showed partial conversion. The reaction was heated to 50° C. for 1 h, at which time LCMS showed complete conversion. The reaction was diluted in water (10 mL) and extracted with EA (3×10 mL). The combined organic layers were dried over Na$_2$SO$_4$, filtered, and coned. The crude material was used directly into next reaction.

Compound 117: (S)-2-(1-(3-fluoropropyl)-4-methylpiperidine-4-carboxamido)-9-(5,6,7,8-tetrahydro-1,8-naphthyridin-2-yl)nonanoic Acid Prepared according to Scheme E using Procedure A with methyl (S)-2-amino-9-(5,6,7,8-tetrahydro-1,8-naphthyridin-2-yl)nonanoate and 1-(tert-butoxycarbonyl)-4-methylpiperidine-4-carboxylic acid, Procedure H using tert-butyl (S)-4-((1-methoxy-1-oxo-9-(5,6,7,8-tetrahydro-1,8-naphthyridin-2-yl)nonan-2-yl)carbamoyl)-4-methylpiperidine-1-carboxylate, and Procedure C using methyl (S)-2-(1-(3-fluoropropyl)-4-methylpiperidine-4-carboxamido)-9-(5,6,7,8-tetrahydro-1,8-naphthyridin-2-yl)nonanoate. LCMS theoretical m/z=491.3 [M+H]+, found 491.3.

Compound 118: (S)-2-(4-(hydroxymethyl)tetrahydro-2H-pyran-4-carboxamido)-9-(5,6,7,8-tetrahydro-1,8-naphthyridin-2-yl)nonanoic Acid Prepared according to Scheme A using Procedure A with methyl (S)-2-amino-9-(5,6,7,8-tetrahydro-1,8-naphthyridin-2-yl)nonanoate and 4-(hydroxymethyl)tetrahydro-2H-pyran-4-carboxylic acid, and using Procedure C with methyl (S)-2-(4-(hydroxymethyl)tetrahydro-2H-pyran-4-carboxamido)-9-(5,6,7,8-tetrahydro-1,8-naphthyridin-2-yl)nonanoate. LCMS theoretical m/z=448.3 [M+H]+, found 448.2.

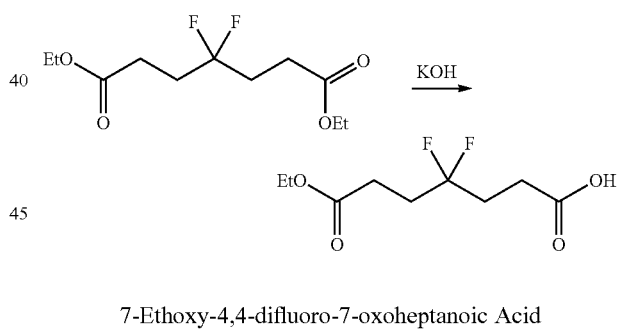

7-Ethoxy-4,4-difluoro-7-oxoheptanoic Acid

A solution of diester (5.00 g, 19.8 mmol) in ethanol was cooled to 0° C.; a solution of KOH (1.22 g, 21.8 mmol) in ethanol was added slowly to the reaction mixture. The resulting solution was warmed to rt and stirred for 10 h. The reaction mixture was coned, diluted with water, and extracted with hexanes:EA (3:1). The aq phase was acidified with 1N HCl and extracted by EA. The organic phases were combined and dried over Na$_2$SO$_4$, filtered, and coned to afford 2.88 g of the title compd as a white solid (65% yield). LCMS (ESI+): m/z=225.21 [M+H]+.

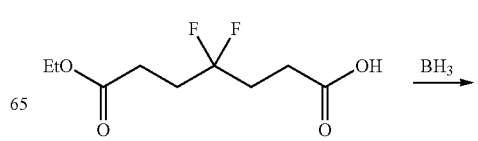

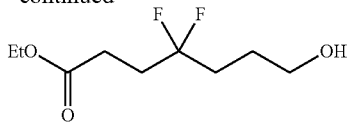

Ethyl 4,4-difluoro-7-hydroxyheptanoate

To a cooled solution of acid (2.88 g, 12.8 mmol) in THF in an ice bath was added BH₃/THF solution. After the addition, the reaction mixture was stirred at rt for 15 h. The reaction was treated with MeOH followed by water, extracted with EA, coned, and purified by FCC (hexanes: EA=2:1) to afford the title compd. LCMS (ESI+): m/z=211.127 [M+H]⁺.

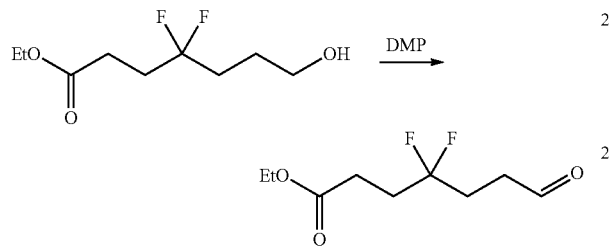

Ethyl 4,4-difluoro-7-oxoheptanoate

To a solution of alcohol (1.1 g, 5.2 mmol) in CH₂Cl₂ (20 mL) at rt was added Dess-Martin Periodinane (2.7 g, 6.3 mmol), and the resulting mixture was stirred for an additional 2 h at rt. The reaction mixture was treated with a sat aq Na₂S₂O₃ solution followed by slow addition of sat aq solution of NaHCO₃ solution. The organic phase was separated, and the aq phase was extracted by DCM. The combined organic layers were washed with brine, dried over Na₂SO₄, filtered through a silica pad, and coned in vacuo to give the title compd as a light-yellow oil, which was used directly in the next reaction. 400 MHz ¹H NMR, CDCl₃, δ 9.82 (t, J=1.0 Hz, 1H), 4.16 (q, J=7.2 Hz, 2H), 2.82-2.60 (m, 2H), 2.62-2.39 (m, 2H), 2.36-2.04 (m, 4H), 1.27 (t, J=7.1 Hz, 3H).

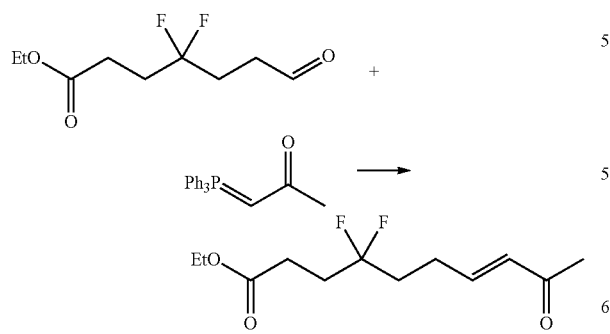

Ethyl (E)-4,4-difluoro-9-oxodec-7-enoate

A mixture of ethyl 4,4-difluoro-7-oxoheptanoate (1.08 g, 5.20 mmol) and 1-(triphenylphosphoranylidene)-2-propanone (1.99 g, 6.24 mmol) in DMF (10 mL) was heated to 80° C. for 10 h. After cooling to rt, the reaction mixture was diluted with H₂O and extracted with EA. The combined organic layers were washed with brine, dried with anhyd Na₂SO₄, filtered, and coned in vacuo. The residue was purified by FCC (hexanes:EA=3:1) to afford the title compd as a clear oil. LCMS (ESI+): m/z=249.2 [M+H]⁺. 400 MHz ¹H NMR, CDCl₃, δ 6.79 (dt, J=16.0, 6.8 Hz, 1H), 6.11 (dt, J=15.9, 1.6 Hz, 1H), 4.25-4.04 (m, 2H), 2.59-2.49 (m, 2H), 2.46 (dtd, J=9.8, 6.6, 1.6 Hz, 2H), 2.33-2.14 (m, 5H), 2.12-1.91 (m, 2H), 1.36-1.16 (m, 3H).

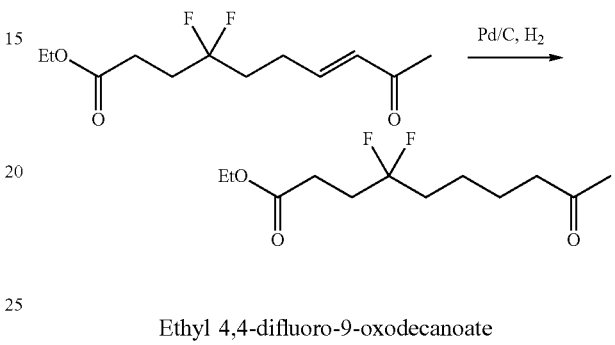

Ethyl 4,4-difluoro-9-oxodecanoate

A flask containing ethyl-4,4-difluoro-9-oxodec-7-enoate (2.17 g, 8.72 mmol) was charged 10 wt % Pd/C (244 mg), which was then diluted with MeOH (30 mL). The flask was evacuated and backfilled with H₂ for three cycles before stirring under an H₂ atmosphere overnight. The reaction mixture was filtered through a pad of Celite and coned in vacuo. The crude residue was purified by FCC to afford the title compd as a clear oil. LCMS (ESI+): m/z=251.1 [M+H]⁺. 400 MHz ¹H NMR, CDCl₃, δ 4.15 (d, J=7.2 Hz, 2H), 2.48 (dt, J=20.4, 7.4 Hz, 4H), 2.28-2.08 (m, 5H), 1.95-1.73 (m, 2H), 1.67-1.54 (m, 2H), 1.53-1.39 (m, 2H), 1.26 (t, J=7.2 Hz, 3H).

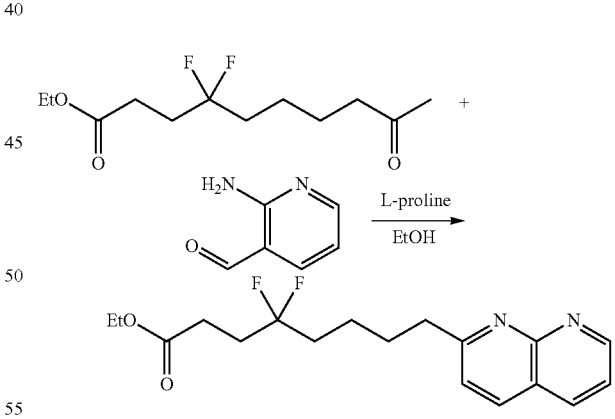

Ethyl 4,4-difluoro-8-(1,8-naphthyridin-2-yl)octanoate

To a mixture of ethyl 4,4-difluoro-9-oxodecanoate (2.18 g, 8.70 mmol) and 2-aminopyridine-3-carbaldehyde (1.17 g, 9.57 mmol) in EtOH (20 mL) was added L-proline (501 mg, 4.35 mmol). The mixture was refluxed at 85° C. for 12 h. The mixture was coned and purified by FCC (hexanes: EA=1:1 to 1:3) to give ethyl 4,4-difluoro-8-(1,8-naphthyridin-2-yl)octanoate (1.36 g, 46% yield) as a yellow solid.

LCMS (ESI+): m/z=337.1 [M+H]+. 400 MHz ¹H NMR, CDCl₃, δ 9.09 (dd, J=4.2, 2.0 Hz, 1H), 8.16 (dd, J=8.1, 2.0 Hz, 1H), 8.11 (d, J=8.3 Hz, 1H), 7.45 (dd, J=8.1, 4.2 Hz, 1H), 7.38 (d, J=8.2 Hz, 1H), 4.14 (q, J=7.2 Hz, 2H), 3.12-3.00 (m, 2H), 2.56-2.41 (m, 2H), 2.17 (tdd, J=16.6, 8.9, 6.8 Hz, 2H), 2.06-1.82 (m, 4H), 1.70-1.53 (m, 2H), 1.26 (t, J=7.1 Hz, 3H).

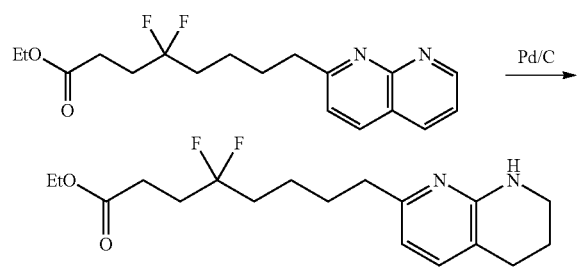

Ethyl 4,4-difluoro-8-(5,6,7,8-tetrahydro-1,8-naphthyridin-2-yl)octanoate

To a flask containing ethyl 4,4-difluoro-8-(1,8-naphthyridin-2-yl)octanoate (1.36 g, 4.04 mmol) was charged 20 wt % Pd(OH)₂/C (57 mg. 0.40 mmol), and the reaction mixture was treated with MeOH (15 mL). The flask was evacuated and backfilled with H₂ for three cycles then stirred under an H₂ atmosphere overnight. The reaction mixture was filtered through a pad of Celite and coned in vacuo. The crude residue was purified by FCC (hexanes:EA) to give ethyl 4,4-difluoro-8-(5,6,7,8-tetrahydro-1,8-naphthyridin-2-yl)octanoate as a clear oil. LCMS (ESI+): m/z=341.142 [M+H]+.

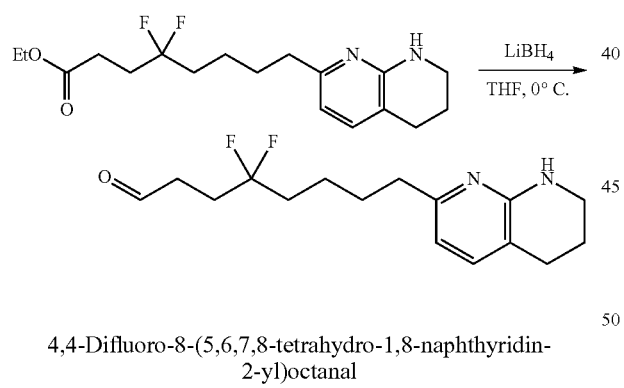

4,4-Difluoro-8-(5,6,7,8-tetrahydro-1,8-naphthyridin-2-yl)octanal

To a cooled solution of ethyl 8-(8-acetyl-5,6,7,8-tetrahydro-1,8-naphthyridin-2-yl)-4,4-difluorooctanoate (830 mg, 2.17 mmol) in THF (15 mL) in an ice bath was added LiBH₄/THF solution (4.34 mmol). After addition, the reaction mixture was allowed to stir at 0° C. for 2 h before treating with sat aq NH₄Cl. The mixture was filtered, and the filtrate was extracted with EA. The combined organic layers were dried over sodium sulfate and coned to provide the title compd. LCMS (ESI+): m/z=299.1 [M+H]+. 400 MHz 1H NMR, CDCl₃, δ 7.08 (d, J=7.3 Hz, 1H), 6.33 (d, J=7.2 Hz, 1H), 3.67 (t, J=6.3 Hz, 4H), 3.48-3.35 (m, 2H), 2.71 (dt, J=12.6, 6.5 Hz, 2H), 2.58 (t, J=7.7 Hz, 2H), 1.99-1.79 (m, 6H), 1.72 (tt, J=16.1, 7.1 Hz, 3H), 1.61-1.46 (m, 3H), 1.23 (s, 9H).

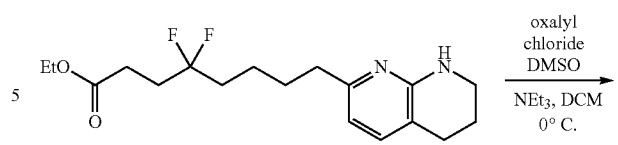

4,4-Difluoro-8-(5,6,7,8-tetrahydro-1,8-naphthyridin-2-yl)octanal

To a solution cooled to −78° C., of DMSO (116 μL, 1.63 mmol) in DCM (3 mL) was added oxalyl chloride (72 μL, 0.82 mmol) slowly, and the mixture was stirred for 15 min. Then a solution of 4,4-difluoro-8-(5,6,7,8-tetrahydro-1,8-naphthyridin-2-yl)octan-1-ol (163 mg, 0.550 mmol) in DCM (1 mL) was added followed by Et₃N (0.46 mL, 3.3 mmol). The reaction mixture was allowed to warm up to 0° C. and was treated with a sat aq NaHCO₃ solution. The organic phase was separated and the aq phase was extracted with EA. The combined organic layers were dried over sodium sulfate and coned to provide the title compd as a light yellow oil. 400 MHz ¹H NMR, CDCl₃, δ 9.81 (s, 1H), 7.10 (d, J=7.3 Hz, 1H), 6.31 (d, J=7.4 Hz, 1H), 3.49-3.33 (m, 3H), 2.76-2.52 (m, 4H), 1.88 (tt, J=16.3, 7.5 Hz, 5H), 1.70 (q, J=7.7 Hz, 2H), 1.33-1.07 (m, 2H).

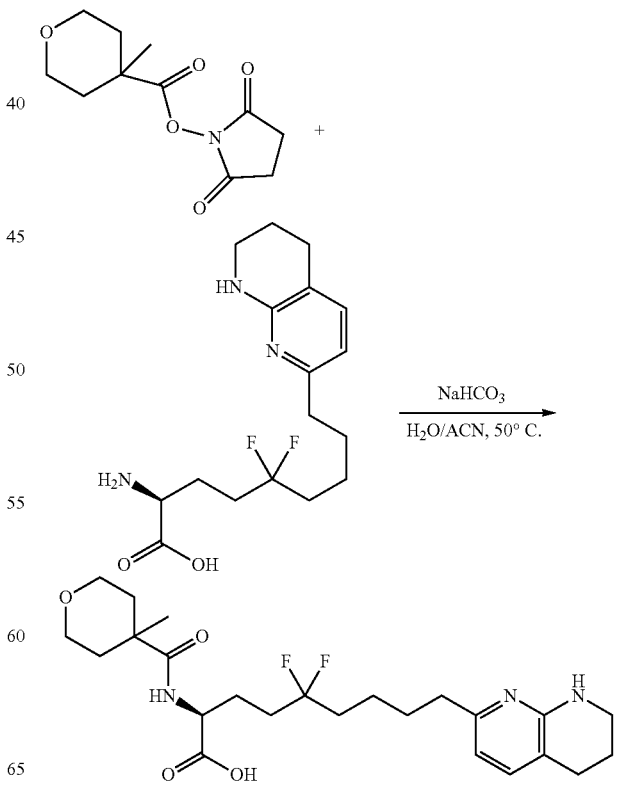

Compound 119: (S)-5,5-difluoro-2-(4-methyltetrahydro-2H-pyran-4-carboxamido)-9-(5,6,7,8-tetrahydro-1,8-naphthyridin-2-yl)nonanoic Acid A solution of 2,5-dioxopyrrolidin-1-yl 4-methyltetrahydro-2H-pyran-4-carboxylate (6.0 mg, 22 μmol) generated using Procedure S, (S)-2-amino-5,5-difluoro-9-(5,6,7,8-tetrahydro-1,8-naphthyridin-2-yl)nonanoic acid (5.0 mg, 15 μmol), and NaHCO$_3$ (7.0 mg, 73 μmol) in a mixed solvent of water:ACN (1:3, 1 mL) was heated to 50° C. for 2 h. The reaction mixture was cooled to rt and purified by prep-reverse phase HPLC to afford (S)-5,5-difluoro-2-(4-methyltetrahydro-2H-pyran-4-carboxamido)-9-(5,6,7,8-tetrahydro-1,8-naphthyridin-2-yl)nonanoic acid. LCMS (ESI+): m/z=468.2 [M+H]$^+$. 400 MHz $^1$H NMR, methanol-d$_4$, δ 7.84 (d, J=8.0 Hz, 1H), 7.61 (dt, J=7.3, 1.3 Hz, 1H), 6.65 (d, J=7.4 Hz, 1H), 4.45 (td, J=8.3, 7.7, 4.8 Hz, 1H), 3.77 (dt, J=11.9, 4.3 Hz, 2H), 3.66-3.45 (m, 4H), 2.84 (t, J=6.3 Hz, 2H), 2.74 (t, J=7.7 Hz, 2H), 2.06 (s, 4H), 2.02-1.83 (m, 6H), 1.76 (p, J=7.7 Hz, 2H), 1.67-1.44 (m, 4H), 1.25 (s, 3H).

m/z=468.3 [M+H]$^+$, found 468.3. 400 MHz $^1$H NMR, methanol-d$_4$, δ 7.83 (d, J=8.0 Hz, 1H), 7.61 (d, J=7.3 Hz, 1H), 6.64 (d, J=7.4 Hz, 1H), 4.45 (td, J=8.4, 7.8, 4.9 Hz, 1H), 3.77 (dt, J=11.7, 4.3 Hz, 2H), 3.66-3.45 (m, 4H), 2.84 (t, J=6.2 Hz, 2H), 2.74 (t, J=7.7 Hz, 2H), 2.20-2.04 (m, 4H), 1.95 (tq, J=14.6, 5.1, 3.7 Hz, 6H), 1.76 (p, J=7.7 Hz, 2H), 1.64-1.45 (m, 4H), 1.25 (s, 3H).

Compound 121: (S)-5,5-difluoro-2-(quinazolin-4-ylamino)-9-(5,6,7,8-tetrahydro-1,8-naphthyridin-2-yl)nonanoic Acid To a solution of (S)-2-amino-5,5-difluoro-9-(5,6,7,8-tetrahydro-1,8-naphthyridin-2-yl)nonanoic acid (5 mg, 0.01 mmol) in IPA (0.5 mL) was added 4-chloroquinazoline (4 mg, 0.02 mmol). The reaction was stirred at 50 C for 1 h, coned, and purified by prep-HPLC to afford the title compd. LCMS theoretical m/z=470.3 [M+H]$^+$, found 470.3.

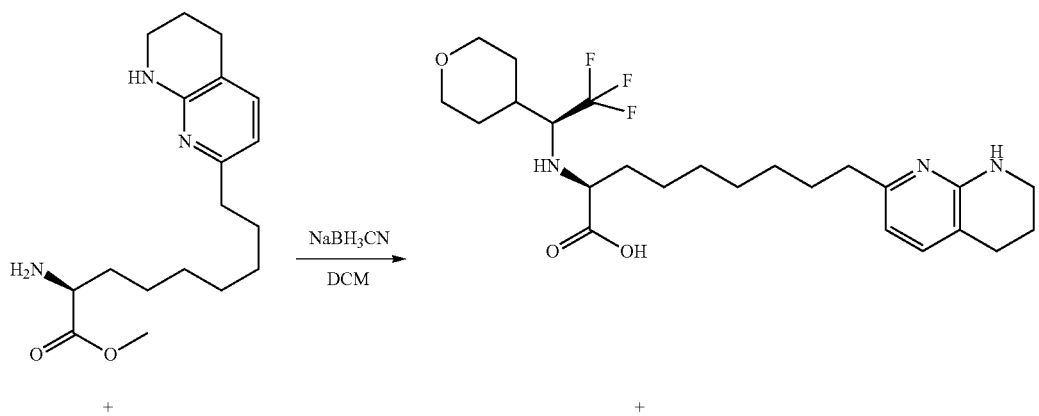

Compound 120: (R)-5,5-difluoro-2-(4-methyltetrahydro-2H-pyran-4-carboxamido)-9-(5,6,7,8-tetrahydro-1,8-naphthyridin-2-yl)nonanoic Acid Prepared according to Procedure Q with 4,4-difluoro-8-(5,6,7,8-tetrahydro-1,8-naphthyridin-2-yl)octanal, Procedure R with (R)—N—((R)-1-cyano-4,4-difluoro-8-(5,6,7,8-tetrahydro-1,8-naphthyridin-2-yl)octyl)-2-methylpropane-2-sulfinamide, and Procedure P with (S)-2-amino-5,5-difluoro-9-(5,6,7,8-tetrahydro-1,8-naphthyridin-2-yl)nonanoic acid and 2,5-dioxopyrrolidin-1-yl 4-methyltetrahydro-2H-pyran-4-carboxylate generated from Procedure S using 4-methyltetrahydro-2H-pyran-4-carboxylic acid to afford the title compd. LCMS theoretical

Compound 122 and 123:

To a solution of methyl (S)-2-amino-9-(5,6,7,8-tetrahydro-1,8-naphthyridin-2-yl)nonanoate (66 mg, 0.21 mmol) and 2,2,2-trifluoro-1-(tetrahydro-2H-pyran-4-yl)ethan-1-one (45 mg, 0.25 mmol) in DCM (1 mL) was added NaBH$_3$CN (16 mg, 0.25 mmol), and the reaction mixture was stirred overnight.

Compound 122: (2S)-9-(5,6,7,8-tetrahydro-1,8-naphthyridin-2-yl)-2-[[(1S)-2,2,2-trifluoro-1-tetrahydropyran-4-yl-ethyl]amino]nonanoic Acid The above reaction mixture was coned and purified by reverse phase prep-HPLC to afford the title compd as the

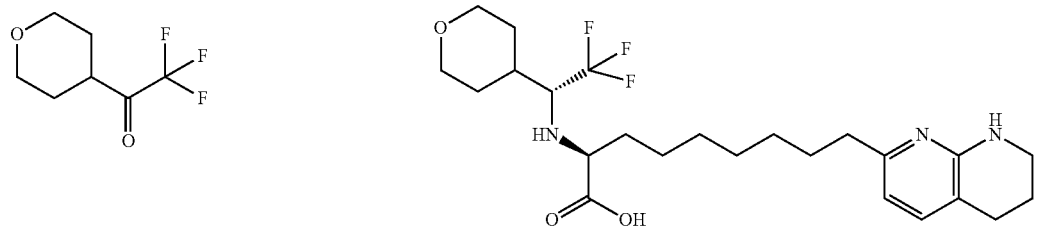

first eluting isomer; absolute stereochemistry at the trifluoromethyl stereocenter was not assigned, as indicated by the wavy bond for compound 123 in FIG. 1. LCMS theoretical m/z=472.3 [M+H]$^+$, found 472.3.

Compound 123: (2S)-9-(5,6,7,8-tetrahydro-1,8-naphthyridin-2-yl)-2-[[(1R)-2,2,2-trifluoro-1-tetrahydropyran-4-yl-ethyl]amino]nonanoic Acid The above reaction mixture was coned and purified by reverse phase prep-HPLC to afford the title compd as the second eluting isomer; absolute stereochemistry at the trifluoromethyl stereocenter was not assigned, as indicated by the wavy bond for compound 123 in FIG. 1. LCMS theoretical m/z=472.3 [M+H]$^+$, found 472.3.

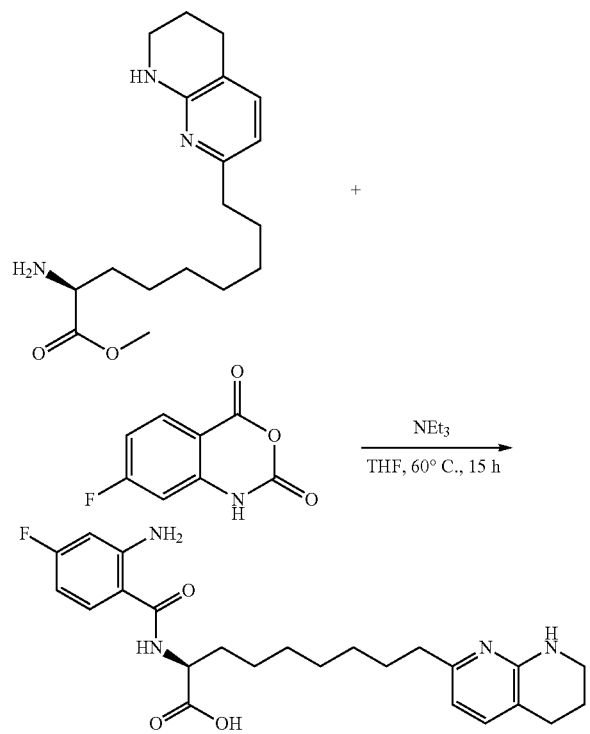

Compound 124: (S)-2-(4-cyanotetrahydro-2H-pyran-4-carboxamido)-9-(5,6,7,8-tetrahydro-1,8-naphthyridin-2-yl)nonanoic Acid Prepared according to Scheme A beginning with methyl (S)-2-amino-9-(5,6,7,8-tetrahydro-1,8-naphthyridin-2-yl)nonanoate and 4-cyanotetrahydro-2H-pyran-4-carboxylic acid using Procedures A and C. LCMS theoretical m/z=442.3. [M+H]+, found 443.2.

BIOLOGICAL EXAMPLES

Example B1—Solid Phase Integrin $\alpha_v\beta_6$ Binding Assay

Microplates were coated with recombinant human integrin $\alpha_v\beta_6$ (2 μg/mL) in PBS (100 μL/well 25 OC, overnight). The coating solution was removed, washed with wash buffer (0.05% Tween 20; 0.5 mM MnCl$_2$; in 1×TBS). Plate was blocked with 200 μL/well of Block Buffer (1% BSA; 5% sucrose; 0.5 mM MnCl$_2$; in 1×TBS) at 37° C. for 2 h. Dilutions of testing compounds and recombinant TGFβ1 LAP (0.67 μg/mL) in binding buffer (0.05% BSA; 2.5% sucrose; 0.5 mM MnCl$_2$; in 1×TBS) were added. The plate was incubated for 2 hours at 25° C., washed, and incubated for 1 hour with Biotin-Anti-hLAP. Bound antibody was detected by peroxidase-conjugated streptavidin. The IC$_{50}$ values for testing compounds were calculated by a four-parameter logistic regression.

The IC$_{50}$ values obtained for $\alpha_v\beta_6$ integrin inhibition for a first series of exemplary compounds are shown in Table B-1. The compounds tested were compound samples prepared according to procedures described in the Synthetic Examples section, with the stereochemical purity as indicated in the Examples.

TABLE B-1

| Compound No. | $\alpha_v\beta_6$ Inhibition IC$_{50}$ (nM) - range |
| --- | --- |
| 8 | <50 |
| 24 | 251-1000 |
| 30 | 251-1000 |
| 32 | <50 |
| 34 | 50-250 |
| 36 | 50-250 |
| 37 | <50 |
| 38 | 251-1000 |
| 39 | <50 |
| 42 | <50 |
| 43 | <50 |
| 44 | <50 |
| 45 | <50 |
| 46 | 50-250 |
| 47 | 50-250 |

Example B2—the Disclosed Compounds Potently Inhibit $\alpha_v\beta_6$ in a Solid Phase Assay A second series of exemplary compounds was selected for testing in the solid phase integrin $\alpha_v\beta_6$ binding assay. The compounds tested were compound samples prepared according to procedures described in the Synthetic Examples section, with the stereochemical purity as indicated in the Examples. As in Example B1, microplates were coated with recombinant human integrin $\alpha_v\beta_6$ (2 μg/mL) in PBS (100 μL/well 25° C., overnight). The coating solution was removed, washed with wash buffer (0.05% Tween 20; 0.5 mM MnCl$_2$; in 1×TBS). The plate was blocked with 200 μL/well of Block Buffer (1% BSA; 5% sucrose; 0.5 mM MnCl$_2$; in 1×TBS) at 37° C. for 2 h. Dilutions of testing compounds and recombinant TGFβ$_1$ LAP (0.67 μg/mL) in binding buffer (0.05% BSA; 2.5% sucrose; 0.5 mM MnCl$_2$; in 1×TBS) were added. The plate was incubated for 2 hours at 25° C., washed, and incubated for 1 hour with Biotin-Anti-hLAP. Bound antibody was detected by peroxidase-conjugated streptavidin. The IC$_{50}$ values for tested compounds were calculated by a four-parameter logistic regression.

Example B3—The Disclosed Compounds Potently Inhibit $\alpha_v\beta_1$ in a Solid Phase Assay The first and second series of exemplary compounds were tested in a solid phase integrin $\alpha_v\beta_1$ binding assay. The compounds tested were compound samples prepared according to procedures described in the Synthetic Examples section, with the stereochemical purity as indicated in the Examples. Similar to Examples B1 and B2, microplates were coated with recombinant human integrin $\alpha_v\beta_1$ (2 µg/mL) in PBS (100 L/well 25° C., overnight). The coating solution was removed, washed with wash buffer (0.05% Tween 20; 0.5 mM MnCl$_2$; in 1×TBS). The plate was blocked with 200 µL/well of Block Buffer (1% BSA; 5% sucrose; 0.5 mM MnCl$_2$; in 1×TBS) at 37° C. for 2 h. Dilutions of testing compounds and recombinant TGFβ$_1$ LAP (0.67 µg/mL) in binding buffer (0.05% BSA; 2.5% sucrose; 0.5 mM MnCl$_2$; in 1×TBS) were added. The plate was incubated for 2 hours at 25° C., washed, and incubated for 1 hour with Biotin-Anti-hLAP. Bound antibody was detected by peroxidase-conjugated streptavidin. The IC$_{50}$ values for tested compounds were calculated by a four-parameter logistic regression.

Example B4—The Disclosed Compounds Potently Inhibit Human $\alpha_v\beta_6$ Integrin The first and second series of exemplary compounds were tested for $\alpha_v\beta_6$ integrin biochemical potency using the ALPHASCREEN® (Perkin Elmer, Waltham, Mass.) proximity-based assay (a bead-based, non-radioactive Amplified Luminescent Proximity Homogeneous Assay) as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994). To gauge the potency of inhibitors of binding to human integrin $\alpha_v\beta_6$, inhibitor compounds and integrin were incubated together with recombinant TGFβ$_1$ LAP and biotinylated anti-LAP antibody plus acceptor and donor beads, following the manufacturer's recommendations. The donor beads were coated with streptavidin. The acceptor beads had a nitrilotriacetic acid Ni chelator, for binding to a 6×His-tag on human integrin $\alpha_v\beta_6$. All incubations occurred at room temperatures in 50 mM Tris-HCl, pH 7.5, 0.1% BSA supplemented with 1 mM each CaCl$_2$ and MgCl$_2$. The order of reagent addition was as follows: 1. $\alpha_v\beta_6$ integrin, test inhibitor compound, LAP, biotinylated anti-LAP antibody and acceptor beads were all added together. 2. After 2 hours, donor beads were added. After another 30 min incubation, samples were read.

Integrin binding was evaluated by exciting donor beads at 680 nm, and measuring the fluorescent signal produced, between 520-620 nm, using a Biotek Instruments (Winooski, Vt., USA) SynergyNeo2 multimode plate reader. Compound potency was assessed by determining inhibitor concentrations required to reduce fluorescent light output by 50%. Data analysis for IC$_{50}$ determinations was carried out by nonlinear four parameter logistic regression analysis using Dotmatics ELN Software (Core Informatics Inc., Branford, Conn.).

Example B5—The Disclosed Compounds Potently Inhibit Human $\alpha_v\beta_1$ Integrin The first and second series of exemplary compounds were tested for $\alpha_v\beta_1$ integrin biochemical potency using the ALPHASCREEN® proximity-based assay as described in Example B4. To gauge the potency of inhibitors of binding to human integrin $\alpha_v\beta_1$, inhibitor compounds and integrin were incubated together with biotinylated, purified human fibronectin plus acceptor and donor beads, following the manufacturer's recommendations. The donor beads were coated with streptavidin. The acceptor beads had a nitrilotriacetic acid Ni chelator, for binding to a 6×His-tag on human integrin $\alpha_v\beta_1$. All incubations occurred at room temperatures in 50 mM Tris-HCl, pH 7.5, 0.1% BSA supplemented with 1 mM each CaCl$_2$ and MgCl$_2$. The order of reagent addition was as follows: 1. $\alpha_v\beta_1$ integrin, test inhibitor compound, fibronectin-biotinylated and acceptor beads were all added together. 2. After 2 hours, donor beads were added. After another 30 min incubation, samples were read.

Integrin binding was evaluated by exciting donor beads at 680 nm, and measuring the fluorescent signal produced, between 520-620 nm, using a Biotek Instruments (Winooski, Vt., USA) SynergyNeo2 multimode plate reader. Compound potency was assessed by determining inhibitor concentrations required to reduce fluorescent light output by 50%. Data analysis for IC$_{50}$ determinations was carried out by nonlinear four parameter logistic regression analysis using Dotmatics ELN Software (Core Informatics Inc., Branford, Conn.).

Combined Inhibition Results of Examples B1, B2, B3, B4, and B5

Table B-2, FIG. 2, shows IC$_{50}$ data from Examples B1, B2, B3, B4, and B5 for inhibition of $\alpha_v\beta_1$ and $\alpha_v\beta_6$ integrin in the solid phase assays and inhibition of human $\alpha_v\beta_1$ and $\alpha_v\beta_6$ integrin in the proximity-based ALPHASCREEN® assays. The IC$_{50}$ data is shown in four ranges: below 50 nM; from 50 nM to below 250 nM; from above 250 nM to below 1000 nM; and 1000 nM and above.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:
1. A compound of formula (A):

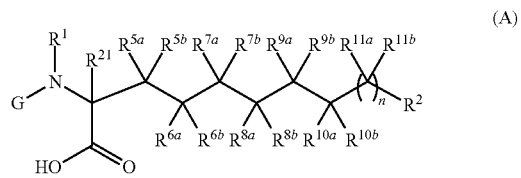

or a salt thereof, wherein:
  R$^1$ is hydrogen;
  R$^2$ is 5,6,7,8-tetrahydro-1,8-naphthyridin-2-yl optionally substituted by R$^{12}$;
  G is —C(O)R$^3$;
  R$^3$ is tetrahydropyranyl optionally substituted by R$^{3f}$;
  R$^{5a}$, R$^{5b}$, R$^{6a}$, R$^{6b}$, R$^{7a}$, R$^{7b}$, R$^{8a}$, R$^{8b}$, R$^{9a}$, R$^{9b}$, R$^{10a}$, and R$^{10b}$ are each independently hydrogen, deuterium, or halogen;
  each R$^{11a}$ and R$^{11b}$ are independently hydrogen, deuterium, or halogen;
  n is 0, 1, or 2;
  each R$^{3f}$ is independently oxo or R$^{12}$;
  each R$^{12}$ is independently C$_1$-C$_6$ alkyl, C$_2$-C$_6$ alkenyl, C$_2$-C$_6$ alkynyl, C$_3$-C$_8$ cycloalkyl, C$_6$-C$_{14}$ aryl, halogen, deuterium, —CN, —OR$^{13}$, —SR$^{13}$, —NR$^{14}$R$^{15}$, —NO$_2$, —C=NH(OR$^{13}$), —C(O)R$^{13}$, —OC(O)R$^{13}$, —C(O)OR$^{13}$, —C(O)NR$^{14}$R$^{15}$, —NR$^{13}$C(O)R$^{14}$, —NR$^{13}$C(O)OR$^{14}$, —NR$^{13}$C(O)NR$^{14}$R$^{15}$, —S(O)R$^{13}$, —S(O)$_2$R$^{13}$, —NR$^{13}$S(O)R$^{14}$, —NR$^{13}$S(O)$_2$R$^{14}$, —S(O)NR$^{14}$R$^{15}$, —S(O)$_2$NR$^{14}$R$^{15}$, or —P(O)(OR$^{13}$)(OR$^{14}$), wherein the C$_1$-C$_6$ alkyl, C$_2$-C$_6$ alkenyl, C$_2$-C$_6$ alkynyl, C$_3$-C$_8$ cycloalkyl, and C$_6$-C$_{14}$ aryl of R$^{12}$ are independently optionally substituted by R$^{12a}$;

each R$^{12a}$ is independently deuterium, halogen, oxo, —OR$^{16}$, —NR$^{16}$R$^{17}$, —C(O)R$^{16}$, —C(O)OR$^{16}$, —NR$^{16}$C(O)OR$^{18}$, —CN, —S(O)R$^{16}$, —S(O)$_2$R$^{16}$, —P(O)(OR$^{16}$)(OR$^{17}$), C$_3$-C$_8$ cycloalkyl, C$_6$-C$_{14}$ aryl, or C$_1$-C$_6$ alkyl, wherein the C$_6$-C$_{14}$ aryl, and C$_1$-C$_6$ alkyl of R$^{12a}$ are independently optionally substituted by R$^{12b}$;

each R$^{12b}$ is independently deuterium, oxo, —OH, halogen, or C$_1$-C$_6$ alkyl;

each R$^{13}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, or C$_6$-C$_{14}$ aryl, wherein the C$_1$-C$_6$ alkyl, C$_2$-C$_6$ alkenyl, C$_2$-C$_6$ alkynyl, C$_3$-C$_6$ cycloalkyl, and C$_6$-C$_{14}$ aryl of R$^{13}$ are each independently optionally substituted by R$^{13a}$;

each R$^{13a}$ is independently halogen, deuterium, oxo, —CN, —NR$^{19}$R$^{20}$, —P(O)(OR$^{19}$)(OR$^{20}$), or C$_1$-C$_6$ alkyl optionally substituted by deuterium, halogen, —OH, or oxo;

each R$^{14}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, or C$_6$-C$_{14}$ aryl, wherein the C$_1$-C$_6$ alkyl, C$_2$-C$_6$ alkenyl, C$_2$-C$_6$ alkynyl, C$_3$-C$_6$ cycloalkyl, and C$_6$-C$_{14}$ aryl of R$^{14}$ are independently optionally substituted by deuterium, halogen, oxo, —CN, OR$^{18}$, —NR$^{19}$R$^{20}$, or C$_1$-C$_6$ alkyl optionally substituted by deuterium, halogen, —OH, or oxo;

each R$^{15}$ is independently hydrogen, deuterium, C$_1$-C$_6$ alkyl, C$_2$-C$_6$ alkenyl, C$_2$-C$_6$ alkynyl, C$_3$-C$_6$ cycloalkyl, or C$_6$-C$_{14}$ aryl, wherein the C$_1$-C$_6$ alkyl, C$_2$-C$_6$ alkenyl, C$_2$-C$_6$ alkynyl, C$_3$-C$_6$ cycloalkyl, and C$_6$-C$_{14}$ aryl of R$^{15}$ are independently optionally substituted by deuterium, halogen, oxo, —CN, OR$^{18}$, —NR$^{19}$R$^{20}$, or C$_1$-C$_6$ alkyl optionally substituted by deuterium, halogen, —OH, or oxo;

each R$^{16}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{17}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{18}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{19}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{20}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo; and R$^{21}$ is hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_3$-C$_6$ cycloalkyl optionally substituted by deuterium, halogen, or oxo.

2. The compound of claim 1, or a salt thereof, wherein R$^{21}$ is methyl, ethyl, 1-propyl, or 2-propyl, and the carbon to which R$^{21}$ is bonded is in the R configuration or the S configuration.

3. The compound of claim 1, or a salt thereof, wherein R$^{7a}$ and R$^{7b}$ are both: hydrogen, deuterium, or fluorine.

4. The compound of claim 1, or a salt thereof, wherein R$^{21}$ is hydrogen and the compound is represented by formula (I):

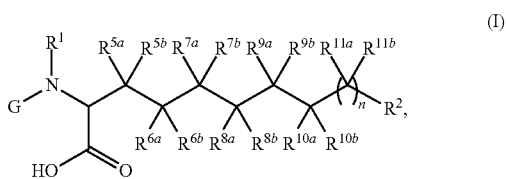

wherein each R$^{12b}$ is independently deuterium, oxo, —OH, or halogen.

5. The compound of claim 1, or a salt thereof, wherein n is 0 or 2.

6. The compound of claim 1, or a salt thereof, wherein n is 1.

7. The compound of claim 1, or a salt thereof, wherein R$_{5a}$, R$^{5b}$, R$^{6a}$, R$^{6b}$, R$^{7a}$, R$^{7b}$, R$^{8a}$, R$^{8b}$, R$^{9a}$, R$^{9b}$, R$^{10a}$, R$^{10b}$, R$^{11a}$, and R$^{11b}$ are each hydrogen.

8. The compound of claim 1, or a salt thereof, wherein R$^{5a}$, R$^{5b}$, R$^{6a}$, R$^{6b}$, R$^{7a}$, R$^{7b}$, R$^{8a}$, R$^{8b}$, R$^{9a}$, R$^{9b}$, R$^{10a}$, R$^{10b}$, R$^{11a}$, and R$^{11b}$ are each deuterium.

9. The compound of claim 1, or a salt thereof, wherein at least one of R$^{5a}$, R$^{5b}$, R$^{6a}$, R$^{6b}$, R$^{7a}$, R$^{7b}$, R$^{8a}$, R$^{8b}$, R$^{9a}$, R$^{9b}$, R$^{10a}$, R$^{10b}$ R$^{11a}$, R$^{11b}$, R$^{12}$, R$^{12a}$, R$^{12b}$, R$^{13}$, R$^{13a}$, R$^{14}$, R$^{15}$, R$^{16}$, R$^{17}$, R$^{18}$, R$^{19}$, or R$^{20}$ is deuterium.

10. The compound of claim 7, wherein R$^2$ is 5,6,7,8-tetrahydro-1,8-naphthyridin-2-yl and is represented by the compound of formula (II):

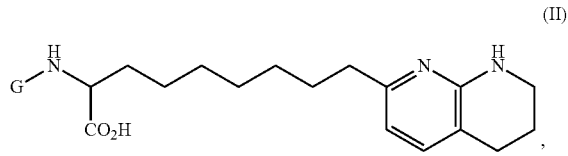

or a salt thereof.

11. The compound of claim 1, or a salt thereof, wherein G is —C(O)R$^3$ and R$^3$ is tetrahydropyran-4-yl optionally substituted by R$^{3f}$.

12. The compound of claim 1, or a salt thereof, wherein R$^3$ is tetrahydropyranyl substituted by 0-5 R$^{3f}$.

13. The compound of claim 12, or a salt thereof, wherein R$^3$ is tetrahydropyran-4-yl substituted by 0-5 R$^{3f}$.

14. The compound of claim 12, or a salt thereof, wherein R$^3$ is substituted by 1-5 R$^{3f}$, wherein at least one R$^{3f}$ is C$_1$-C$_6$ alkyl substituted by 0-5 moieties selected from the group consisting of halogen, —NR$^{16}$R$^{17}$, —NR$^{16}$C(O)OR$^{18}$, and C$_6$-C$_{14}$ aryl, wherein the C$_6$-C$_{14}$ aryl of R$^{3f}$ is independently substituted by 0-5 R$^{12b}$.

15. The compound of claim 14, or a salt thereof, wherein the at least one $R^{3f}$ is $C_1$-$C_2$ alkyl substituted by 0-5 fluoro, —$NH_2$, —NHC(O)O-t-butyl, or phenyl.

16. The compound of claim 12, or a salt thereof, wherein $R^3$ is substituted by:
   A) 1-5 $R^{3f}$, wherein at least one $R^{3f}$ is:
      I) unsubstituted $C_6$-$C_{14}$ aryl,
      II) $C_6$-$C_{14}$ aryl, which is independently substituted by 1-5 $R^{12a}$,
      III) phenyl which is independently substituted by 1-5 $R^{12a}$,
      IV) unsubstituted phenyl, or
      V) —C(O)$R^{13}$, —C(O)O$R^{13}$, or —S(O)$_2R^{13}$, wherein each $R^{13}$ is independently $C_1$-$C_6$ alkyl substituted by 0-5 —O$R^{18}$, wherein $R^{18}$ is $C_1$-$C_6$ alkyl substituted by 0-5 deuterium, halogen, or oxo; or
   B) two or more $R^{3f}$, wherein each $R^{3f}$ is independently selected from the group consisting of $C_1$-$C_6$ alkyl, —C(O)$R^{13}$, and —C(O)O$R^{13}$.

17. The compound of claim 1, or a salt thereof, wherein $R^3$ is selected from the group consisting of:

18. The compound of claim 1, or a salt thereof, wherein at least one of $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12}$, $R^{12a}$, $R^{12b}$, $R^{13}$, $R^{13a}$, $R^{14}$, $R^{15}$, $R^{16}$, $R^{17}$, $R^{18}$, $R^{19}$, $R^{20}$ or $R^{21}$ is deuterium.

19. The compound of claim 1, wherein the compound is represented by formula (I-B):

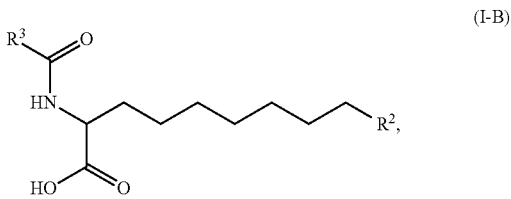

(I-B)

or a salt thereof.

20. The compound of claim 1, wherein the compound is represented by (II-A-6f):

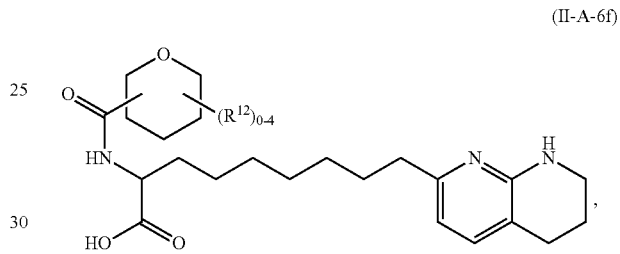

(II-A-6f)

or a salt thereof.

21. A pharmaceutical composition comprising a compound of claim 1, or a pharmaceutically acceptable salt thereof, and a pharmaceutically acceptable carrier or excipient.

22. A compound, or a pharmaceutically acceptable salt thereof, wherein the compound is selected from the group consisting of:

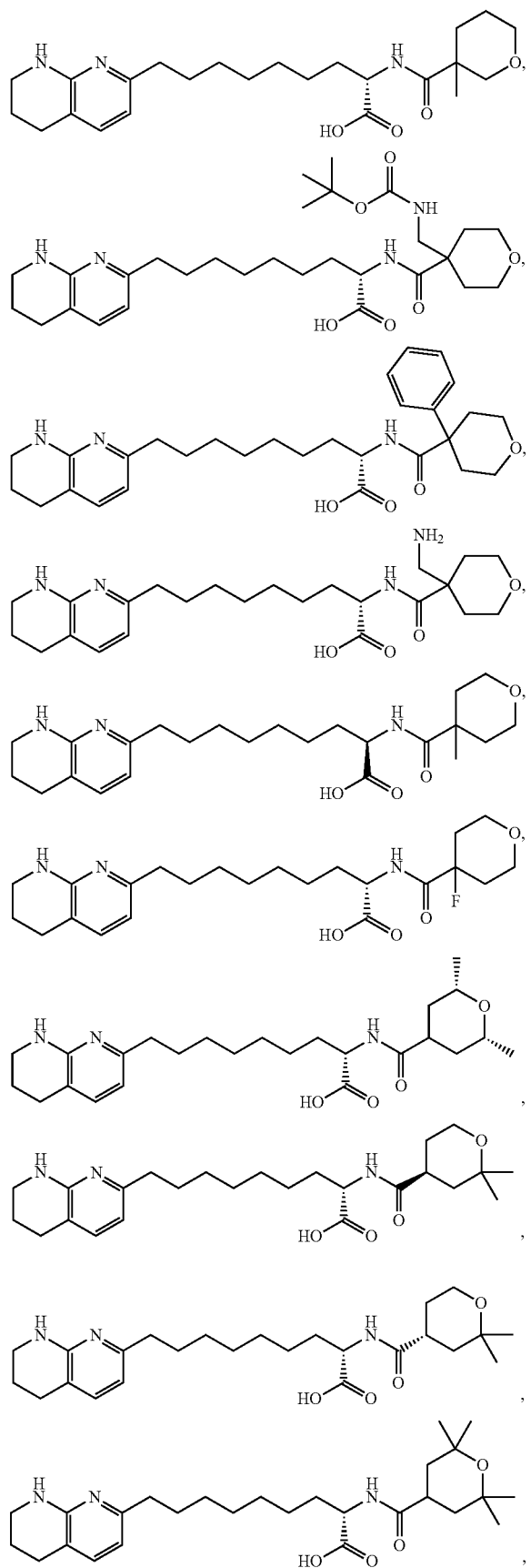

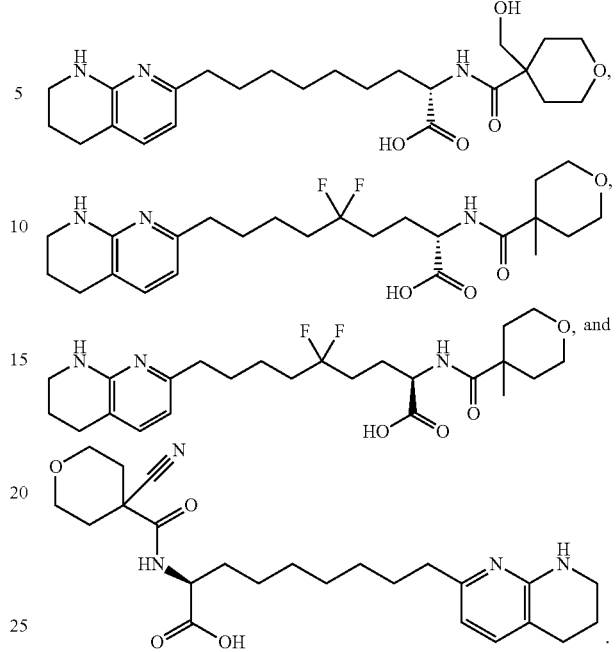

23. A compound, or a pharmaceutically acceptable salt thereof, selected from the group consisting of: 2-(4-methyltetrahydro-2H-pyran-4-carboxamido)-9-(5,6,7,8-tetrahydro-1,8-naphthyridin-2-yl)nonanoic acid; 9-(5,6,7,8-tetrahydro-1,8-naphthyridin-2-yl)-2-(tetrahydro-2H-pyran-4-carboxamido)nonanoic acid; 9-(5,6,7,8-tetrahydro-1,8-naphthyridin-2-yl)-2-(4-(trifluoromethyl)tetrahydro-2H-pyran-4-carboxamido)nonanoic acid; 2 (3 methyltetrahydro-2H-pyran-3-carboxamido)-9-(5,6,7,8-tetrahydro-1,8-naphthyridin-2-yl)nonanoic acid; 2-(4-(((tert-butoxycarbonyl)amino)methyl)tetrahydro-2H-pyran-4-carboxamido)-9-(5,6,7,8-tetrahydro-1,8-naphthyridin-2-yl) nonanoic acid; 2-(4-Phenyltetrahydro-2H-pyran-4-carboxamido)-9-(5,6,7,8-tetrahydro-1,8-naphthyridin-2-yl) nonanoic acid; 2-(4-(aminomethyl)tetrahydro-2H-pyran-4-carboxamido)-9-(5,6,7,8-tetrahydro-1,8-naphthyridin-2-yl) nonanoic acid; 2-(4-fluorotetrahydro-2H-pyran-4-carboxamido)-9-(5,6,7,8-tetrahydro-1,8-naphthyridin-2-yl) nonanoic acid; 2-(2,6-dimethyltetrahydro-2H-pyran-4-carboxamido)-9-(5,6,7,8-tetrahydro-1,8-naphthyridin-2-yl) nonanoic acid; 2-(2,2-dimethyltetrahydro-2H-pyran-4-carboxamido)-9-(5,6,7,8-tetrahydro-1,8-naphthyridin-2-yl) nonanoic acid; 9-(5,6,7,8-tetrahydro-1,8-naphthyridin-2-yl)-2-(2,2,6,6-tetramethyltetrahydro-2H-pyran-4-carboxamido) nonanoic acid; 2-(4-(hydroxymethyl)tetrahydro-2H-pyran-4-carboxamido)-9-(5,6,7,8-tetrahydro-1,8-naphthyridin-2-yl)nonanoic acid; 5,5-difluoro-2-(4-methyltetrahydro-2H-pyran-4-carboxamido)-9-(5,6,7,8-tetrahydro-1,8-naphthyridin-2-yl)nonanoic acid; and 2-(4-cyanotetrahydro-2H-pyran-4-carboxamido)-9-(5,6,7,8-tetrahydro-1,8-naphthyridin-2-yl)nonanoic acid.

24. The compound of claim 22, wherein the compound is

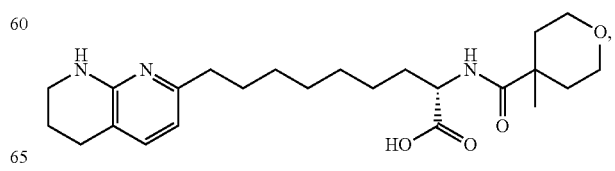

or a pharmaceutically acceptable salt thereof.

25. The compound of claim 22, wherein the compound is

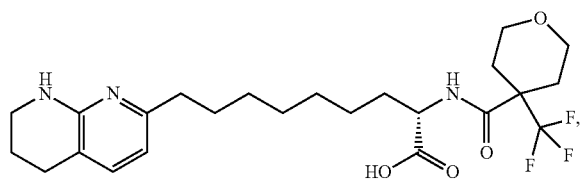 [SMILES: O=C(O)[C@H](CCCCCCCc1ccc2c(n1)NCCC2)NC(=O)C1(C(F)(F)F)CCOCC1]

or a pharmaceutically acceptable salt thereof.

26. The compound of claim 22, wherein the compound is

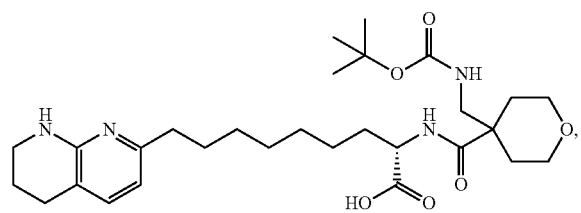 [SMILES: CC(C)(C)OC(=O)NCC1(C(=O)N[C@@H](CCCCCCCc2ccc3c(n2)NCCC3)C(=O)O)CCOCC1]

or a pharmaceutically acceptable salt thereof.

27. The compound of claim 22, wherein the compound is

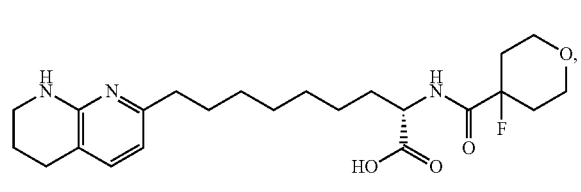

or a pharmaceutically acceptable salt thereof.

28. The compound of claim 22, wherein the compound is

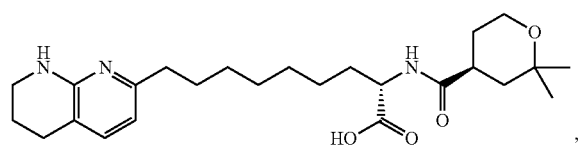 [SMILES: CC1(C)C[C@@H](C(=O)N[C@@H](CCCCCCCc2ccc3c(n2)NCCC3)C(=O)O)CCO1]

or a pharmaceutically acceptable salt thereof.

29. The compound of claim 22, wherein the compound is

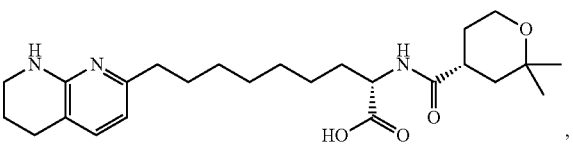 [SMILES: CC1(C)C[C@H](C(=O)N[C@@H](CCCCCCCc2ccc3c(n2)NCCC3)C(=O)O)CCO1]

or a pharmaceutically acceptable salt thereof.

30. The compound of claim 22, wherein the compound is

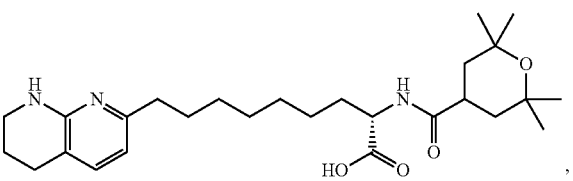 [SMILES: CC1(C)CC(C(=O)N[C@@H](CCCCCCCc2ccc3c(n2)NCCC3)C(=O)O)CC(C)(C)O1]

or a pharmaceutically acceptable salt thereof.

31. The compound of claim 22, wherein the compound is

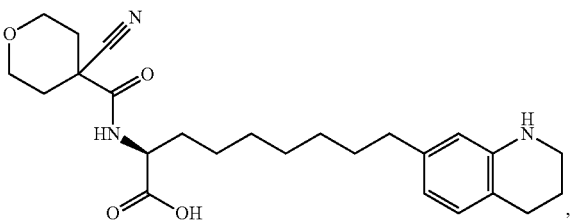 [SMILES: N#CC1(C(=O)N[C@@H](CCCCCCCc2ccc3c(c2)NCCC3)C(=O)O)CCOCC1]

or a pharmaceutically acceptable salt thereof.

32. A pharmaceutical composition comprising any one or more of the compounds of claim 22, or a pharmaceutically acceptable salt thereof, and a pharmaceutically acceptable carrier or excipient.

33. The compound of claim 10, or a salt thereof, wherein the carbon to which the —CO$_2$H group is bonded is in the S configuration.

* * * * *

UNITED STATES PATENT AND TRADEMARK OFFICE
CERTIFICATE OF CORRECTION

PATENT NO. : 11,396,506 B2
APPLICATION NO. : 16/455490
DATED : July 26, 2022
INVENTOR(S) : Katerina Leftheris It is certified that error appears in the above-identified patent and that said Letters Patent is hereby corrected as shown below:

On the Title Page (74): please replace:
"Morrison & Foerster LLP; Kraig Anderson; Johannes Hull"
With:
-- Morrison & Foerster LLP; Kraig Anderson and Johannes Hull, Pliant Therapeutics --

In the Drawings

At Figure 1, sheet 2, first row: please replace:

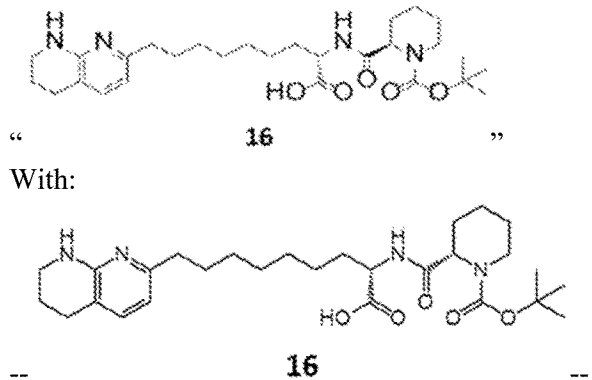

With:

" 16 "

-- 16 --

At Figure 1, sheet 2, second row: please replace:

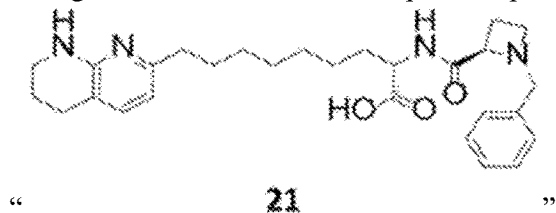

" 21 "

Signed and Sealed this
Eleventh Day of July, 2023

Katherine Kelly Vidal
*Director of the United States Patent and Trademark Office*

With:
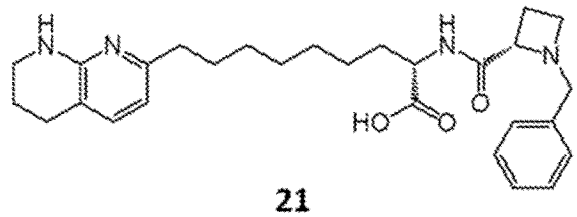
-- 21 --
At Figure 1, sheet 5, fourth row: please replace:
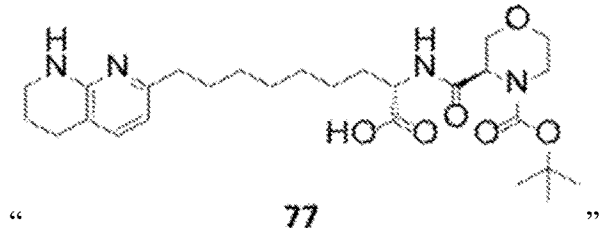
" 77 "
With:
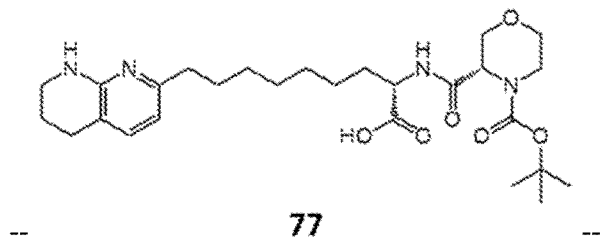
-- 77 --
At Figure 1, sheet 6, fourth row: please replace:
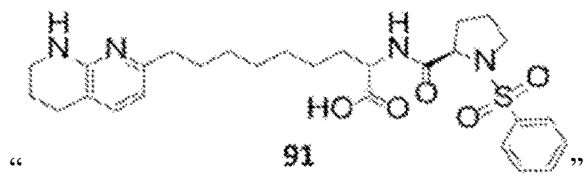
" 91 "
With:
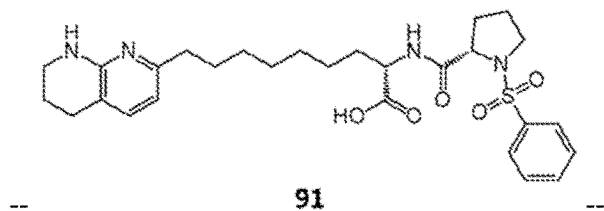
-- 91 --
At Figure 1, sheet 7, first row: please replace:
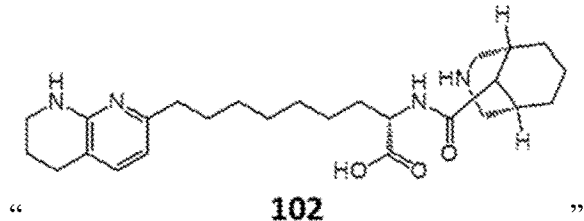
" 102 "

With:

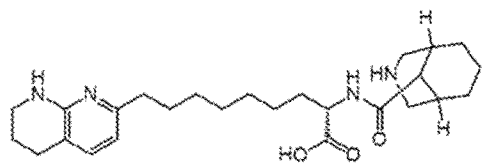

-- 102 --

In the Specification

At Column 9, Line number 52: please replace:
"coned,"
With:
-- concd, --

At Column 10, Line number 61: please replace:
"$R^{3c}$,"
With:
-- $R^{3e}$, --

At Column 12, Line number 25: please replace:
"Table IX"
With:
-- Table 1X --

At Column 13, Line number 10: please replace:
"$R_{4e}$;"
With:
-- $R^{4e}$; --

At Column 13, Line number 24: please replace:
"$R^{9b}$,"
With:
-- $R^{8b}$, --

At Column 14, Line number 55: please replace:
"Table IX"
With:
-- Table 1X --

At Column 15, Line number 62: please replace:
"Table IX"
With:
-- Table 1X --

At Column 17, Line number 49: please replace:
"$R^{2a}$."

CERTIFICATE OF CORRECTION (continued)
U.S. Pat. No. 11,396,506 B2

With:
-- $R^{12a}$. --

At Column 18, Line number 39: please replace:
"$R^{2a}$."
With:
-- $R^{12a}$. --

At Column 18, Line number 67: please replace:
"$R^{2a}$."
With:
-- $R^{12a}$ --

At Column 21, Line number 25: please replace:
"—C(O)OR$^3$,"
With:
-- —C(O)OR$^{13}$, --

At Column 31, Line number 15: please replace:
"—OR$^3$"
With:
-- —OR$^{13}$ --

At Column 31, Line number 26: please replace:
"—C(O)OR$^6$"
With:
-- —C(O)OR$^{16}$ --

At Column 31, Line number 27: please replace:
"—C(O)OR$^6$)."
With:
-- —C(O)OR$^{16}$). --

At Column 31, Line number 30: please replace:
"$R^3$"
With:
-- $R^{3d}$ --

At Column 31, Line number 31: please replace:
"—C(O)OR$^6$),"
With:
-- —C(O)OR$^{16}$), --

At Column 34, Line number 30-35: please insert:

-- , -- after " 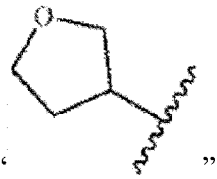 "

At Column 54, Line number 31: please replace:
"((3R,5 S)"
With:
-- ((3R,5S) --

At Column 54, Line number 37: please replace:
"((1R,5 S,9S)"
With:
-- ((1R,5S,9S) --

At Column 54, Line number 39: please replace:
"5 S,"
With:
-- 5S, --

At Column 57, Line number 1: please replace:
"$^{14}C$ $^{13}N$,"
With:
-- $^{14}C$, $^{13}N$, --

At Column 69, Line number 43: please replace:
"poly-ols,"
With:
-- polyols, --

At Column 75, Line number 1: please replace:
"coned"
With:
-- concd --

At Column 75, Line number 28: please replace:
"coned"
With:
-- concd --

At Column 75, Line number 44: please replace:
"TsOH, $H_2O$,"
With:
-- TsOH.$H_2O$, --

At Column 75, Line number 63: please replace:
"coned"
With:
-- concd --

At Column 76, Line number 44: please replace:
"coned"
With:
-- concd --

At Column 77, Line number 19: please replace:
"coned"
With:
-- concd --

At Column 78, Line number 21: please replace:
"coned"
With:
-- concd --

At Column 79, Line number 5: please replace:
"coned"
With:
-- concd --

At Column 79, Line number 22: please replace:
"DCM"
With:
-- DCM, --

At Column 79, Line number 43: please replace:
"coned"
With:
-- concd --

At Column 81, Line number 47: please replace:
"$H_2$"
With:
-- $H_2$, --

At Column 82, Line number 5: please replace:
"coned."
With:
-- concd. --

CERTIFICATE OF CORRECTION (continued)
U.S. Pat. No. 11,396,506 B2

At Column 82, Line number 28: please replace:
"coned"
With:
-- concd --

At Column 82, Line number 46: please replace:
"coned"
With:
-- concd --

At Column 83, Line number 53: please replace:
"coned"
With:
-- concd --

At Column 84, Line number 11: please replace:
"coned"
With:
-- concd --

At Column 85, Line number 44: please replace:
"coned"
With:
-- concd --

At Column 86, Line number 11: please replace:
"coned"
With:
-- concd --

At Column 87, Line number 44: please replace:
"coned"
With:
-- concd --

At Column 89, Line number 60: please replace:
"coned"
With:
-- concd --

At Column 90, Line number 30: please replace:
"coned"
With:
-- concd --

At Column 92, Line number 28: please replace:
"coned"
With:
-- concd --

At Column 94, Line number 44: please replace:
"(3 S,4S)"
With:
-- (3S,4S) --

At Column 101, Line number 65: please replace:
"coned"
With:
-- concd --

At Column 102, Line number 65: please replace:
"coned"
With:
-- concd --

At Column 104, Line number 32: please replace:
"coned"
With:
-- concd --

At Column 104, Line number 56: please replace:
"coned"
With:
-- concd --

At Column 108, Line number 32: please replace:
"coned"
With:
-- concd --

At Column 109, Line number 55-60: please replace:

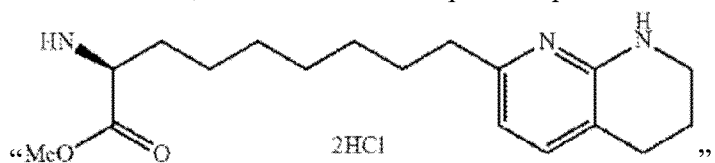

With:

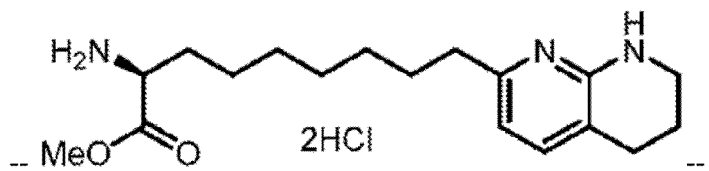

At Column 110, Line number 25: please replace:
"coned"
With:
-- concd --

At Column 116, Line number 38: please replace:
"coned"
With:
-- concd --

At Column 117, Line number 10: please replace:
"coned"
With:
-- concd --

At Column 117, Line number 51: please replace:
"coned"
With:
-- concd --

At Column 121, Line number 48: please replace:
"coned"
With:
-- concd --

At Column 122, Line number 54: please replace:
"coned"
With:
-- concd --

At Column 122, Line number 56: please replace:
"IN HCl"
With:
-- 1N HCl --

At Column 122, Line number 57: please replace:
"coned"
With:
-- concd --

At Column 123, Line number 15: please replace:
"coned"
With:
-- concd --

At Column 123, Line number 41: please replace:
"coned"
With:
-- concd --

At Column 124, Line number 5: please replace:
"coned"
With:
-- concd --

At Column 124, Line number 33: please replace:
"coned"
With:
-- concd --

At Column 124, Line number 65: please replace:
"coned"
With:
-- concd --

At Column 125, Line number 32: please replace:
"coned"
With:
-- concd --

At Column 125, Line number 61: please replace:
"coned"
With:
-- concd --

At Column 126, Line number 30: please replace:
"coned"
With:
-- concd --

At Column 128, Line number 21: please replace:
"coned"
With:
-- concd --

At Column 128, Line number 66: please replace:
"coned"
With:
-- concd --

At Column 129, Line number 10: please replace:
"coned"
With:
-- concd --

At Column 129, Line number 64: please replace:
"25 OC,"
With:
-- 25° C., --

At Column 130, Line number 36: please replace:
"the"
With:
-- The --

At Column 131, Line number 3: please replace:
"(100 L/"
With:
-- (100 µL/ --

In the Claims

At Column 133, Claim number 1, Line number 24: please insert:
-- —OR$^{18}$, -- after "—CN,"

At Column 134, Claim number 7, Line number 32: please replace:
"R$_{5a}$,"
With:
-- R$^{5a}$, --

At Column 134, Claim number 9, Line number 39: please replace:
"R$^{10b}$ R$^{11a}$"
With:
-- R$^{10b}$, R$^{11a}$ --

At Column 135, Claim number 17, Line number 24-30: please delete:

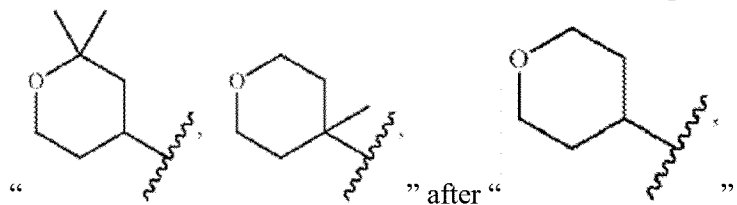

At Column 136, Claim number 18, Line number 1: please replace:
"R$^{10b}$R$^{11a}$,"
With:
-- R$^{10b}$, R$^{11a}$, --

CERTIFICATE OF CORRECTION (continued)
U.S. Pat. No. 11,396,506 B2

Page 12 of 12

At Column 136, Claim number 18, Line number 2: please replace:
"$R^{20}$"
With:
-- $R^{20}$, --

At Column 140, Claim number 31, Line number 26-37: please replace:

" 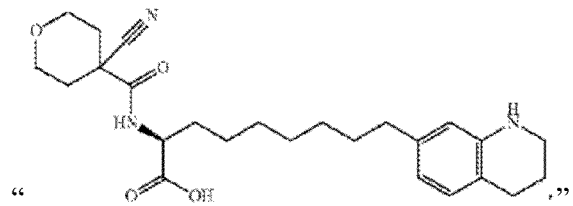 ,"

With:

-- 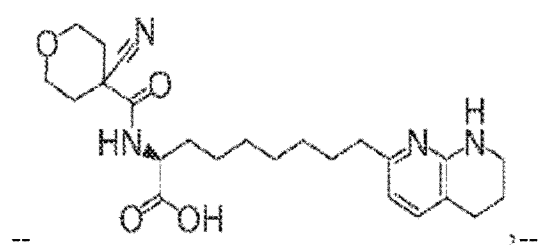 , --